US012590091B2

(12) United States Patent
Liu et al.

(10) Patent No.: US 12,590,091 B2
(45) Date of Patent: Mar. 31, 2026

(54) 1H-PYRROLO[3,2-C]PYRIDINE AND 1H-PYRROLO[2,3-C]PYRIDINE DERIVATIVES AS TLR9 INHIBITORS FOR THE TREATMENT OF FIBROSIS

(71) Applicant: BRISTOL-MYERS SQUIBB COMPANY, Princeton, NJ (US)

(72) Inventors: Chunjian Liu, Pennington, NJ (US); Alicia Regueiro-Ren, New Hope, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 475 days.

(21) Appl. No.: 18/042,069

(22) PCT Filed: Aug. 18, 2021

(86) PCT No.: PCT/US2021/046434
§ 371 (c)(1),
(2) Date: Feb. 17, 2023

(87) PCT Pub. No.: WO2022/040267
PCT Pub. Date: Feb. 24, 2022

(65) Prior Publication Data

US 2023/0312565 A1 Oct. 5, 2023

Related U.S. Application Data

(60) Provisional application No. 63/067,465, filed on Aug. 19, 2020.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC .................................................... C07D 471/04
See application file for complete search history.

(56) References Cited

U.S. PATENT DOCUMENTS 10,071,079 B2 9/2018 Dyckman et al.
10,478,424 B2 11/2019 Dyckman et al.
10,544,143 B2 1/2020 Dyckman et al.
10,660,877 B2 5/2020 Dyckman et al.
10,730,877 B2 8/2020 Dyckman et al.
10,912,766 B2 2/2021 Dyckman et al.
11,053,244 B1 7/2021 Dyckman et al.
11,130,756 B2 9/2021 Dyckman et al.
11,180,474 B2 11/2021 Dyckman et al.
11,299,501 B2 4/2022 Dyckman et al.
11,306,092 B2 4/2022 Dyckman et al.
11,420,958 B2 8/2022 Dyckman et al.
11,420,973 B2 8/2022 Dyckman et al.
11,427,580 B2 8/2022 Dyckman et al.
11,447,466 B2 9/2022 Dyckman et al.
2006/0235037 A1 10/2006 Purandare et al.
2009/0247504 A1 10/2009 Churcher et al.
2011/0275631 A1 11/2011 Abeywardane et al.
2013/0158049 A1 6/2013 Alam et al.
2013/0158066 A1 6/2013 Alam et al.
2017/0008885 A1 1/2017 Koul et al.
2020/0308172 A1 10/2020 Dyckman et al.
2021/0070751 A1 3/2021 Dyckman et al.
2021/0253593 A1 8/2021 Dyckman et al.

FOREIGN PATENT DOCUMENTS

EP 2738172 A1 6/2014
WO 2007115306 A2 10/2007
WO 2013156431 A1 10/2013
WO 2015088045 A1 6/2015
WO 17100594 A1 6/2017

(Continued)

OTHER PUBLICATIONS

Berge et al., (1977).*
Vippagunta et al. (2001).*
Banker et al. (1997).*
Wolff et al. (1995).*
Chattopadhyay, S. et al . . . , "Tyrosine phosphorylation in Toll-like Receptor signalling", Cytokine & Growth Factor Reviews, 25 (2014) 533-541.
Huestis, et al., Org Lett 11(6) 1357-1360 (2009).
International Preliminary Report on Patentability for PCT/US2021/046434 issued Feb. 16, 2023.

(Continued)

*Primary Examiner* — Paul V Ward
(74) *Attorney, Agent, or Firm* — Robert Kajubi; Gary Greenblatt; Mary Vanatten

(57) ABSTRACT

The present invention relates to 1H-pyrrolo[3,2-c]pyridine and 1H-pyrrolo[2,3-c]pyridine derivatives of formula (I) or a salt thereof. The present compounds are inhibitors of TLR9 and useful in treating preventing, or slowing fibrotic diseases, such as e.g. liver fibrosis, renal fibrosis, biliary fibrosis or pancreatic fibrosis, nonalcoholic steatohepatitis (NASH), non-alcoholic fatty liver disease (NAFLD), chronic kidney disease, diabetic kidney disease, primary sclerosing cholangitis (PSC) or primary biliary cirrhosis (PBC), or idiopathic pulmonary fibrosis (IPF).

(I)

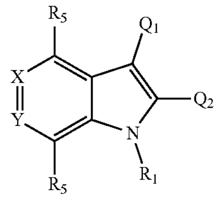

11 Claims, No Drawings

(56) References Cited

FOREIGN PATENT DOCUMENTS

| | | | |
|---|---|---|---|
| WO | 20180089695 | A1 | 5/2018 |
| WO | 19008072 | A1 | 1/2019 |
| WO | 2019125977 | A1 | 6/2019 |
| WO | 2019126082 | A1 | 6/2019 |
| WO | 2019126253 | A1 | 6/2019 |
| WO | 202033520 | A1 | 2/2020 |

OTHER PUBLICATIONS

Kawai, Taro, et al., "The role of pattern-recognition receptors in innate immunity: update on Toll-like receptors", Nature Immunology, 2010, vol. 11, No. 5, pp. 373-384.

Lamphier, M. et al., "Novel Small Molecule Inhibitors of TLR7 and TLR9: Mechanism of Action and Efficacy in Vivo", Mol Pharmacol, 2014, 85:429-440.

Patra, Mahesh Chandra, et al., "Recent Progress in the Development of Toll-like Receptor (TLR) antagonists", Exp. Opin. on Therapeutic Patents, 2016, vol. 26, No. 6, 719-730.

Roy, et al., "Design and developmen of benzoxazole derivatives with toll-like receptor 9 antagonism", Eur J Med Chem, 2017, vol. 134, 334-347.

Sims, et al., "The IL-1 Family: Regulators of Immunity", Nature Rev. Immunol., 2010, 10, 89-102.

Thwaites et al., Frontier in Immunology 5 1-8 (2014).

* cited by examiner

1H-PYRROLO[3,2-C]PYRIDINE AND 1H-PYRROLO[2,3-C]PYRIDINE DERIVATIVES AS TLR9 INHIBITORS FOR THE TREATMENT OF FIBROSIS

CROSS REFERENCE

This application is a national phase application under 35 U.S.C. § 371 of International Patent Application PCT/US2021/046434, filed Aug. 18, 2021, which claims priority to U.S. Provisional Application Ser. 63/067,465, filed Aug. 19, 2020, the contents of which are specifically incorporated fully herein by reference.

DESCRIPTION

The present invention generally relates to substituted heteroaryl compounds useful as inhibitors of signaling through Toll-like receptor 9 (TLR9). Provided herein are substituted heteroaryl compounds, compositions comprising such compounds, and methods of their use. The invention further pertains to pharmaceutical compositions containing at least one compound according to the invention that are useful for the treatment or prophylaxis of fibrotic diseases and other diseases, disorders, and conditions for which a TLR9 inhibitor is indicated.

Toll-like receptors (TLRs) are transmembrane proteins having the ability to initiate an inflammatory response upon recognition of pattern-associated molecular patterns (PAMPs) or microbe-associated molecular patterns (MAMPs). A total of 10 human TLRs have been identified and can be located in the cell surface or, as in the case of TLR7, 8 and 9, in the endolysosomes. TLR9 recognizes unmethylated single-stranded DNA containing cytosine-phosphate-guanine (CpG) motifs that are typically found in bacterial and mitochondrial DNA (mtDNA). TLR9 may contribute to fibrogenesis by promoting inflammation via the MyD88-dependent signalling pathway that ultimately mediates activation of IL-6, IFN-α, IL-1β, and TNF-α among others cytokines. (Barton G M, Kagan J C (2009) *Nat. Rev. Immunol.* 9(8), 535-42; Li X, Jiang S, Tapping R I (2010), *Cytokine* 49(1), 1-9).

TLR9 levels are higher in lung biopsies of rapid idiopathic pulmonary fibrosis (IPF) progressors than in the healthy or stable IPF progressors (Sci. Transl. Med. 2010, 2(57):57ra82). Circulating mtDNA, the ligand for TLR9 has recently been identified as a mechanism-based prognostic biomarker of IPF (Am J. Resp. and Crit. Care Med. 2017, 196(12), 1502). In addition, it has been observed that TLR9 is up-regulated in human and murine non-alcoholic steatohepatitis (NASH) (Clin. Sci. 2017, 131(16), 2145), while hepatocyte mitochondrial DNA drives NASH via activation of TLR9 (J. Clin. Inv. 2016, 126(3), 859. Accordingly, inhibitors/antagonists of TLR9 are predicted to have efficacy as novel therapeutic agents to treat fibrotic diseases.

TLR9 inhibition has been recognized as a potential route to therapies for fibrotic diseases including idiopathic pulmonary fibrosis (Trujillo et al. *Sci. Transl. Med.* 2010, 2(57):57ra82; Yoshizaki et al. *Ann Rheum Dis.* 2016 October; 75(10):1858-65), non-alcoholic steatohepatitis (Garcia-Martinez et al. *J Clin Invest* 2016, 126: 859-864; Gabele et al. *Biochem Biophys Res Commun.* 2008; 376:271-276), hepatic injury (Shaker et al. *Biochem Pharmacol.* 2016. 112:90-101; Hoeque et al. *J. Immun.* 2013, 190:4297-304), and scleroderma (systemic sclerosis or SSc) (Yoshizaki et al. *Ann Rheum Dis.* 2016 October; 75(10):1858-65); as well as heart failure (Oka et al. *Nature* 485, pages 251-255(2012)), and hypertension (McCarthy et al. *Cardiovascular Research,* 2015, Pages 119-130).

There remains a need for compounds useful as inhibitors of TLR9. Additionally, there remains a need for compounds useful as inhibitors of TLR9 that have selectivity over TLR7 or TLR8.

In view of the conditions that may benefit by treatment involving modulation of Toll-like receptors, it is immediately apparent that new compounds capable of inhibiting TLR9 and methods of using these compounds could provide substantial therapeutic benefits to a wide variety of patients.

Applicants have found potent compounds that have activity as TLR9 inhibitors. Further, applicants have found compounds that have activity as TLR9 inhibitors and are selective over TLR7 or TLR8. These compounds are provided to be useful as pharmaceuticals with desirable stability, bioavailability, therapeutic index, and toxicity values that are important to their druggability.

SUMMARY OF THE INVENTION

The present invention relates to a new class of substituted heteroaryl compounds found to be effective inhibitors of signaling through TLR9. These compounds are provided to be useful as pharmaceuticals with desirable stability, bioavailability, therapeutic index, and toxicity values that are important to their druggability.

The present invention provides compounds of Formula (I) that are useful as inhibitors of signaling through TLR9 and are useful for the treatment of fibrotic diseases, or stereoisomers, N-oxides, tautomers, pharmaceutically acceptable salts, solvates or prodrugs thereof.

The present invention also provides pharmaceutical compositions comprising a pharmaceutically acceptable carrier and at least one of the compounds of the present invention or stereoisomers, tautomers, pharmaceutically acceptable salts, solvates, or prodrugs thereof.

The present invention also provides a method for inhibition of Toll-like receptor 9 comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method for treating fibrotic diseases, comprising administering to a host in need of such treatment a therapeutically effective amount of at least one of the compounds of the present invention or stereoisomers, tautomers, pharmaceutically acceptable salts, solvates, or prodrugs thereof.

The present invention also provides a method of treating a disease or disorder associated with TLR9 activity, the method comprising administering to a mammal in need thereof, at least one of the compounds of Formula (I) or salts, solvates, and prodrugs thereof.

The present invention also provides processes and intermediates for making the compounds of Formula (I) including salts, solvates, and prodrugs thereof.

The present invention also provides at least one of the compounds of Formula (I) or salts, solvates, and prodrugs thereof, for use in therapy.

The present invention also provides the use of at least one of the compounds of Formula (I) or salts, solvates, and prodrugs thereof, for the manufacture of a medicament for the treatment of prophylaxis of TLR9 related conditions, such as fibrotic diseases, allergic diseases, autoimmune diseases, and inflammatory diseases.

The compound of Formula (I) and compositions comprising the compounds of Formula (I) may be used in treating, preventing, or curing various TLR9 related conditions. Pharmaceutical compositions comprising these compounds are useful for treating, preventing, or slowing the progression of diseases or disorders in a variety of therapeutic areas, such as fibrotic diseases, allergic diseases, autoimmune diseases, and inflammatory diseases.

These and other features of the invention will be set forth in expanded form as the disclosure continues.

DETAILED DESCRIPTION

The first aspect of the present invention provides at least one compound of Formula (I):

(I)

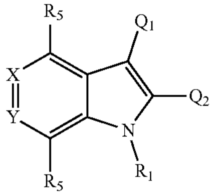

or stereoisomers, tautomer, solvates or salts thereof, wherein:

one of X and Y is N and the other of X and Y is C-A;

one of $Q_1$ and $Q_2$ is G and the other $Q_1$ and $Q_2$ is $R_3$;

G is:

(i) phenyl substituted with 1 to 3 substituents independently selected from $—OCH_3$, $—S(O)_2CH_3$, $—S(O)_2N(CH_3)_2$, $—S(O)_2$(cyclopropyl), and $—S(O)(NH)N(CH_3)_2$;

(ii)

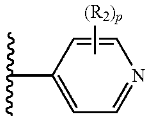 or 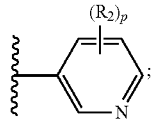

(iii)

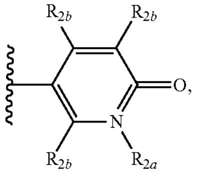 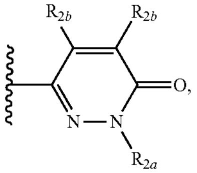 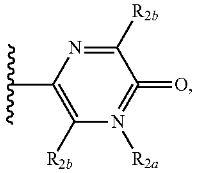 or 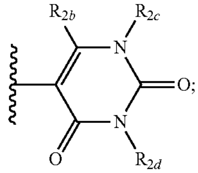

(iv) a 9-membered heterocyclic ring selected from:

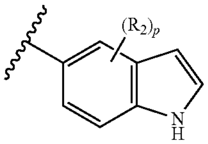 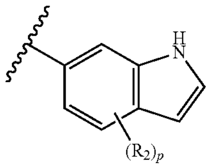

-continued

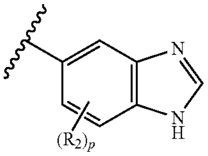 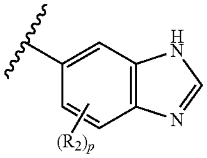

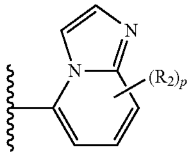 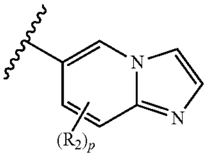

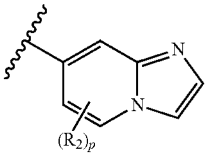 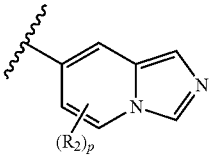

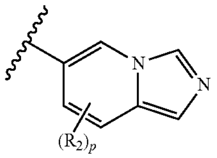 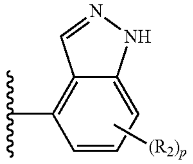

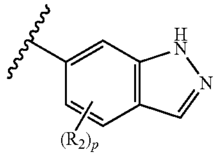 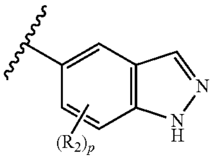

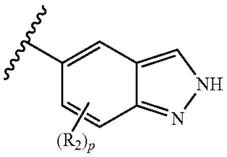 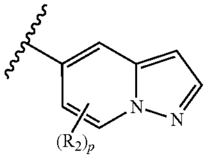

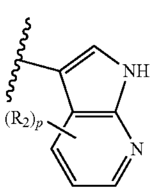 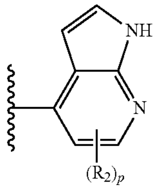 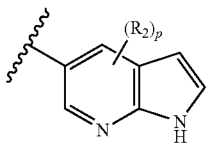

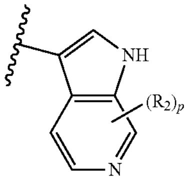 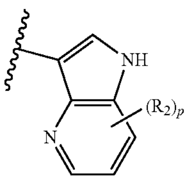 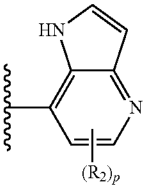

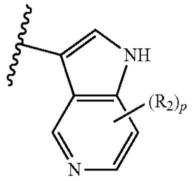 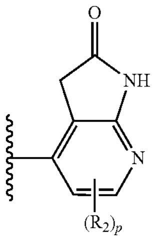

-continued
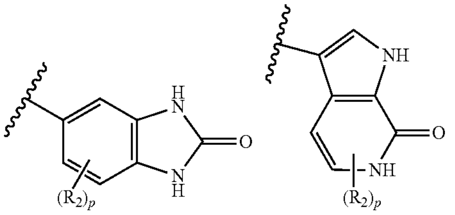
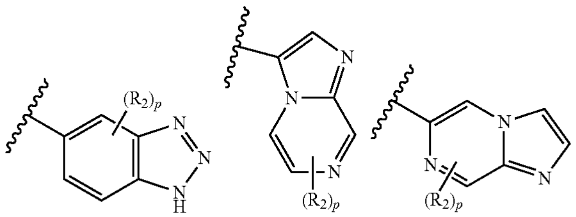
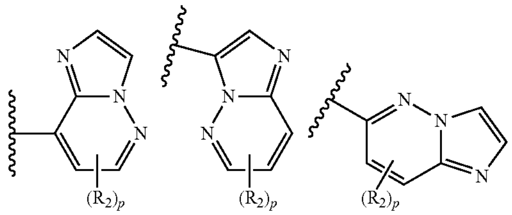
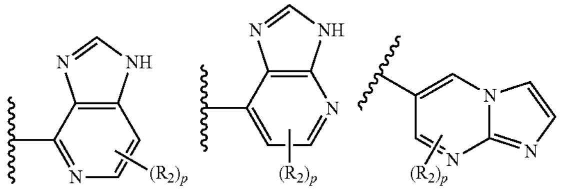
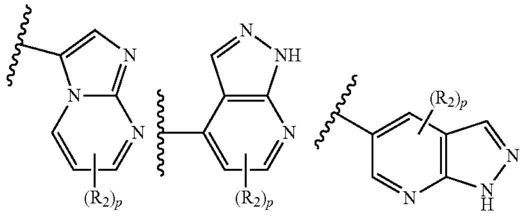
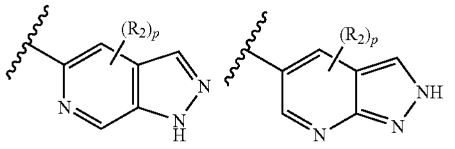
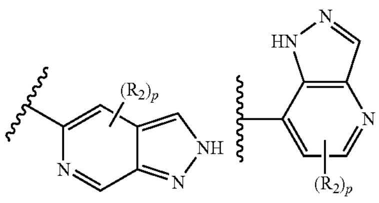
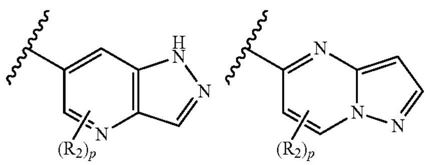
-continued
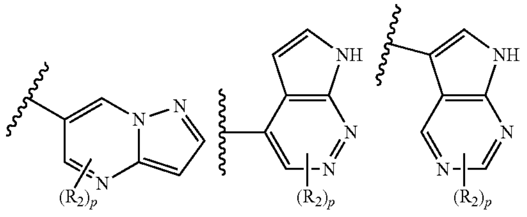
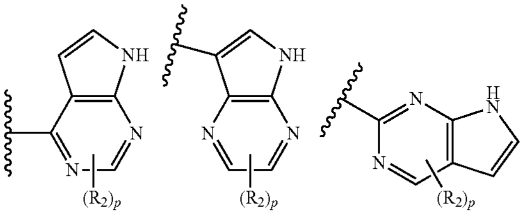
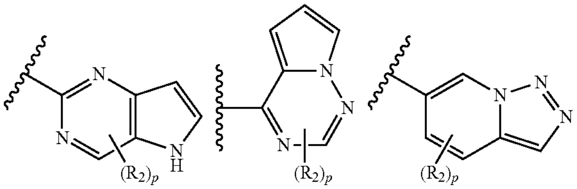
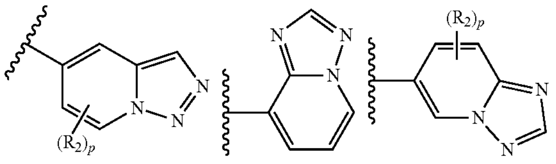
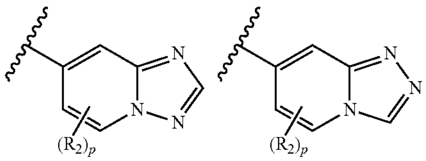
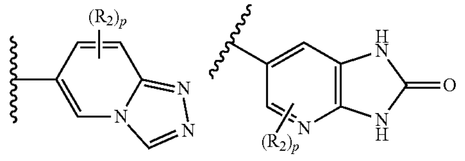
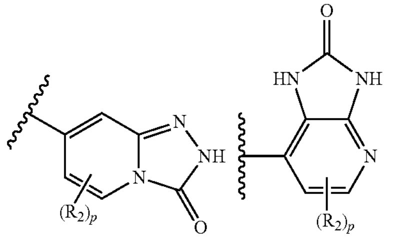
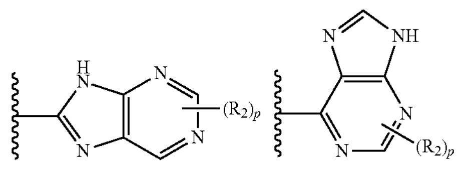
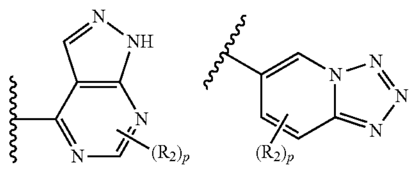

-continued
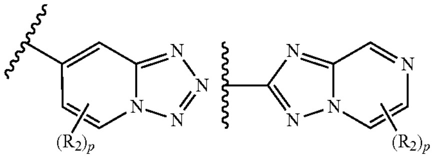
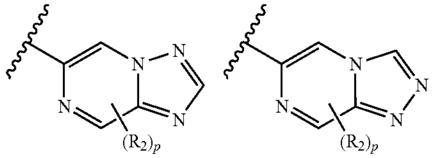
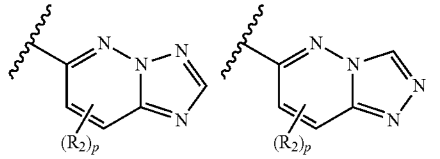
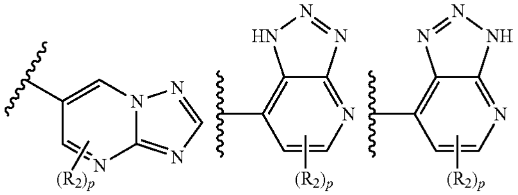
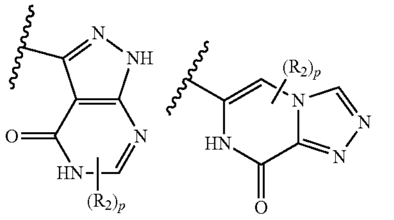
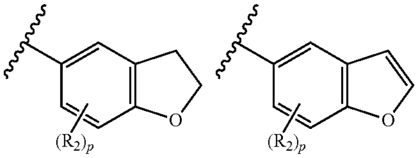
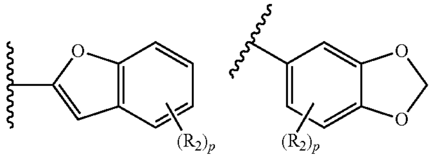
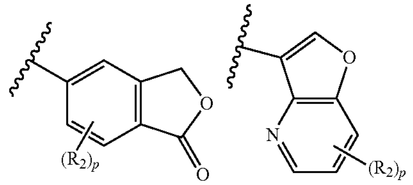
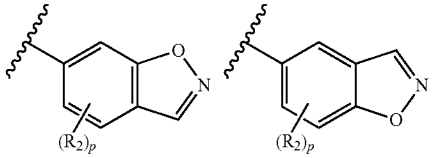
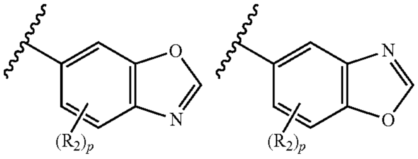
-continued
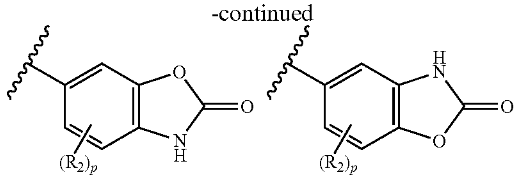
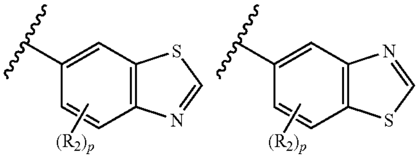
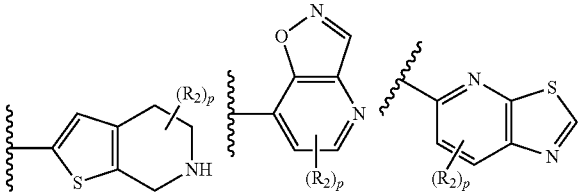
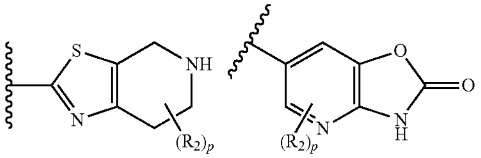
and
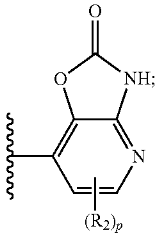
or
(v) 10-membered heterocyclic ring selected from:
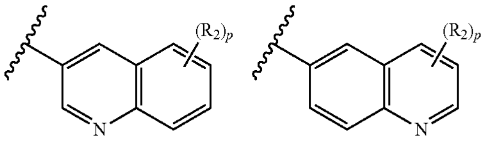
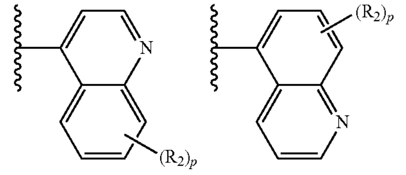
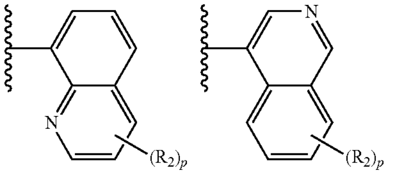
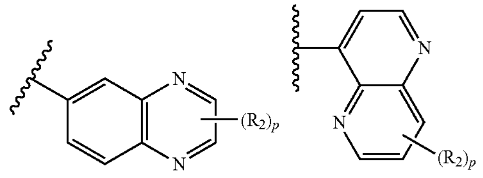

-continued

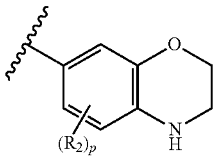

and

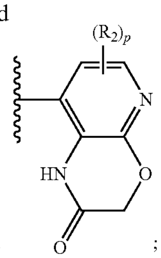

;

A is piperidinyl, phenyl, pyridinyl, pyrimidinyl, 6-azabicyclo[3.2.1]octanyl, or azabicyclo[3.2.1]octanyl, each substituted with $-L-R_4$ and zero to 2 $R_{4b}$;

L is a bond, $—CR_xR_x—$, or $—C(O)(CR_xR_x)_{0-2}—$;

$R_1$ is hydrogen, $C_{1-3}$ alkyl, $C_{1-2}$ fluoroalkyl, or $C_{3-4}$ cycloalkyl;

each $R_2$ is independently halo, —CN, —OH, $—NO_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, $—O(CH_2)_{1-2}OH$, $—(CH_2)_{0-4}O(C_{1-4}$ alkyl), $C_{1-3}$ fluoroalkoxy, $—(CH_2)_{1-4}O(C_{1-3}$ alkyl), $—O(CH_2)_{1-2}OC(O)(C_{1-3}$ alkyl), $—O(CH_2)_{1-2}NR_xR_x$, $—C(O)O(C_{1-3}$ alkyl), $—(CH_2)_{0-2}C(O)NR_yR_y$, $—C(O)NR_x(C_{1-5}$ hydroxyalkyl), $—C(O)NR_x(C_{2-6}$ alkoxyalkyl), $—C(O)NR_x(C_{3-6}$ cycloalkyl), $—NR_yR_y$, $—NR_y(C_{1-3}$ fluoroalkyl), $—NR_y(C_{1-4}$ hydroxyalkyl), $—NR_xCH_2$(phenyl), $—NR_xS(O)_2(C_{3-6}$ cycloalkyl), $—NR_xC(O)(C_{1-3}$ alkyl), $—NR_xCH_2(C_{3-6}$ cycloalkyl), $—S(O)_2(C_{1-3}$ alkyl), $—S(O)_2N(C_{1-3}$ alkyl$)_2$, $—S(O)(NH)N(C_{1-3}$ alkyl$)_2$, $—(CH_2)_{0-2}(C_{3-6}$ cycloalkyl), $—(CH_2)_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);

$R_{2a}$ is $C_{1-6}$ alkyl, $C_{1-3}$ fluoroalkyl, $C_{1-6}$ hydroxyalkyl, $C_{1-3}$ aminoalkyl, $—(CH_2)_{0-4}O(C_{1-3}$ alkyl), $C_{3-6}$ cycloalkyl, $—(CH_2)_{1-3}C(O)NR_xR_x$, $—CH_2(C_{3-6}$ cycloalkyl), $—CH_2$(phenyl), tetrahydrofuranyl, tetrahydropyranyl, or phenyl;

each $R_{2b}$ is independently H, halo, —CN, $—NR_xR_x$, $C_{1-6}$ alkyl, $C_{1-3}$ fluoroalkyl, $C_{1-3}$ hydroxyalkyl, $C_{1-3}$ fluoroalkoxy, $—(CH_2)_{0-2}O(C_{1-3}$ alkyl), $—(CH_2)_{0-3}C(O)NR_xR_x$, $—(CH_2)_{1-3}(C_{3-6}$ cycloalkyl), $—C(O)O(C_{1-3}$ alkyl), $—C(O)NR_x(C_{1-3}$ alkyl), $—CR_x{=}CR_xR_x$, or $—CR_x{=}CH(C_{3-6}$ cycloalkyl);

$R_{2c}$ is $R_{2a}$ or $R_{2b}$;

$R_{2d}$ is $R_{2a}$ or $R_{2b}$; provided that one of $R_{2c}$ and $R_{2d}$ is $R_{2a}$, and the other of $R_{2c}$ and $R_{2d}$ is $R_{2b}$;

$R_3$ is hydrogen, F, $C_{1-3}$ alkyl, or $C_{3-4}$ cycloalkyl;

$R_4$ is:

(i) $—N(CH_3)_2$;

(ii) morpholinyl, pyrrolidinyl, piperidinyl, piperazinyl, pyridinyl, dioxothiomorpholinyl, azaspiro[3.3]heptanyl, azabicyclo[3.2.1]octanyl, diazabicyclo[2.2.2]octanyl, or diazabicyclo[3.2.1]octanyl, each substituted with zero to 4 $R_{4a}$; or (iii)

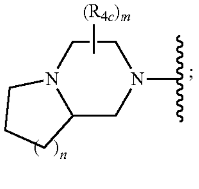

;

each $R_{4a}$ is independently —OH, $C_{1-6}$ alkyl, $C_{1-3}$ fluoroalkyl, $C_{3-6}$ cycloalkyl, $—CH_2(C_{3-6}$ cycloalkyl), $—C(O)(C_{1-4}$ alkyl), $—C(O)(C_{3-6}$ cycloalkyl), —C(O)(phenyl), $—C(O)CH_2(C_{3-6}$ cycloalkyl), $—C(O)CH_2$(phenyl), or $—C(O)O(C_{1-4}$ alkyl);

each $R_{4b}$ is independently F, Cl, or $—CH_3$;

each $R_{4c}$ is independently —OH, $C_{1-6}$ alkyl, $C_{1-3}$ fluoroalkyl, $—CH_2(C_{3-6}$ cycloalkyl), $—C(O)(C_{1-4}$ alkyl), —C(O)(phenyl), $—C(O)CH_2$(phenyl), $—C(O)OCH_2CH_3$, or $C_{3-6}$ cycloalkyl;

each $R_5$ is independently hydrogen, F, Cl, $C_{1-3}$ alkyl, $C_{1-3}$ hydroxyalkyl, $C_{1-3}$ alkoxy, cyclopropyl, or morpholinyl;

each $R_x$ is independently H or $—CH_3$;

each $R_y$ is independently H or $C_{1-6}$ alkyl;

m is zero, 1, or 2;

n is zero, 1, or 2; and p is zero, 1, 2, 3, or 4.

The second aspect of the present invention provides at least one compound of Formula (I):

(I)

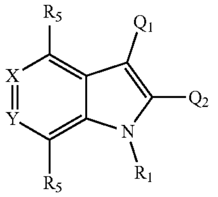

or a salt thereof, wherein:

one of X and Y is N and the other of X and Y is C-A;

one of $Q_1$ and $Q_2$ is G and the other $Q_1$ and $Q_2$ is $R_3$;

G is:

(i) phenyl substituted with 1 to 2 substituents independently selected from $—OCH_3$, $—S(O)_2CH_3$, $—S(O)_2N(CH_3)_2$, and $—S(O)(NH)N(CH_3)_2$;

(ii)

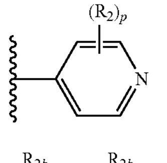

or

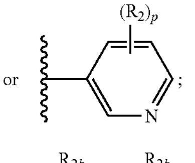

;

(iii)

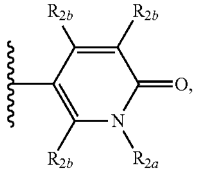

,

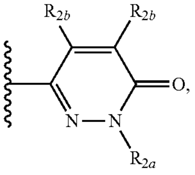

,

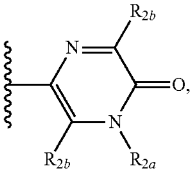

, or

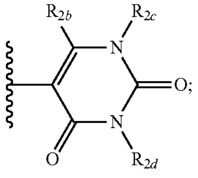

;

(iv) a 9-membered heterocyclic ring selected from:
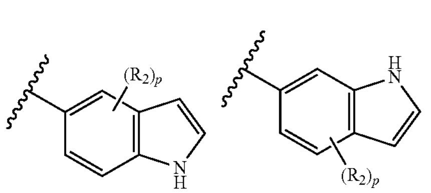
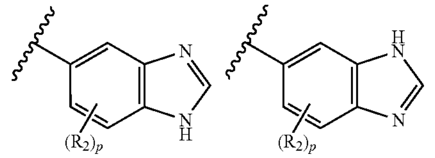
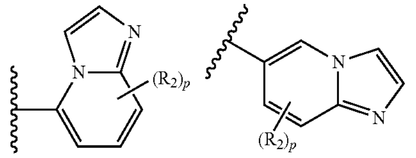
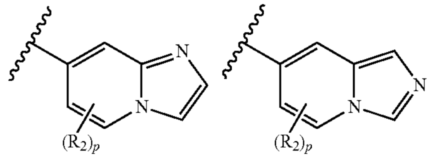
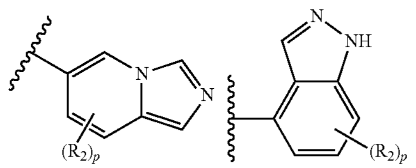
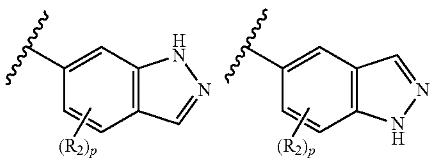
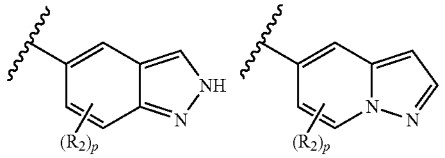
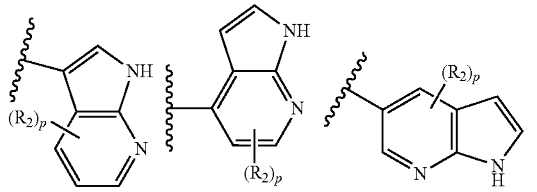
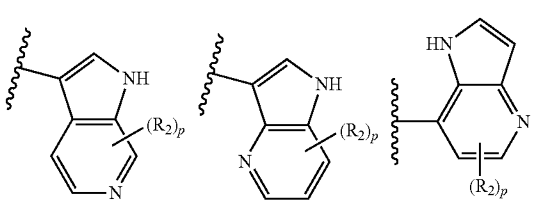
-continued
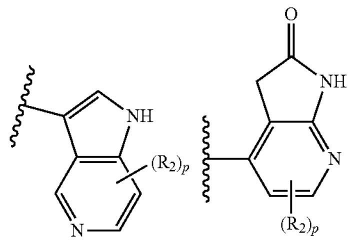
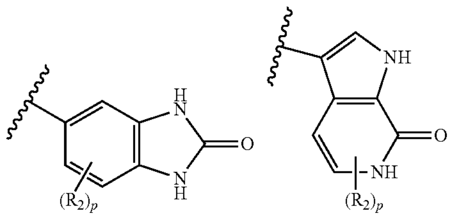
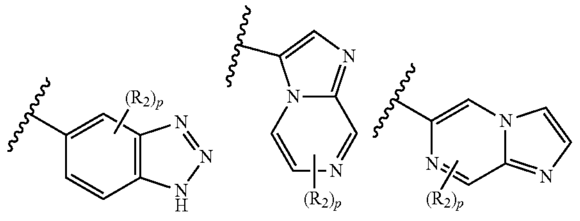
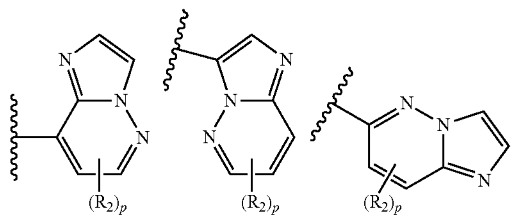
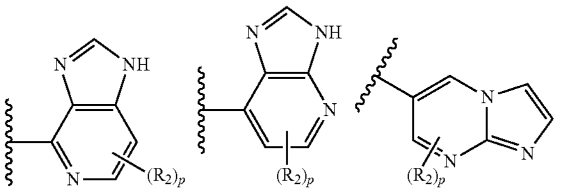
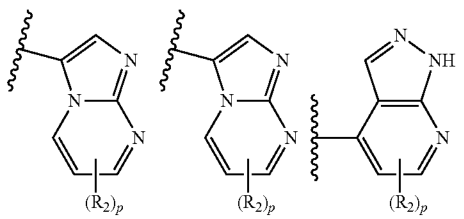
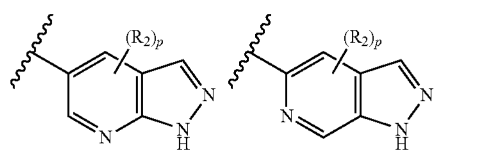
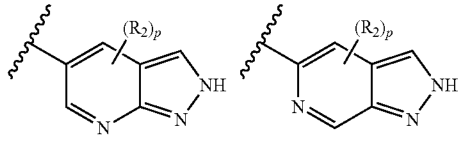

-continued
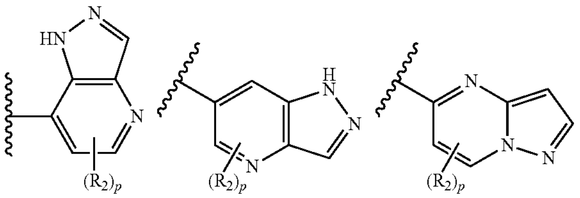
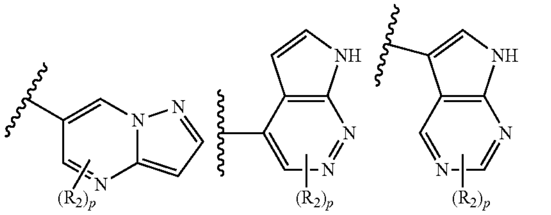
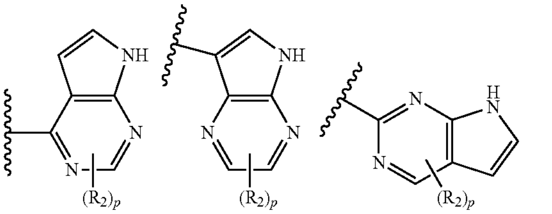
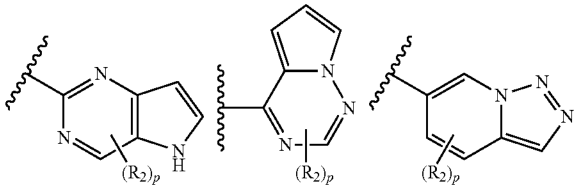
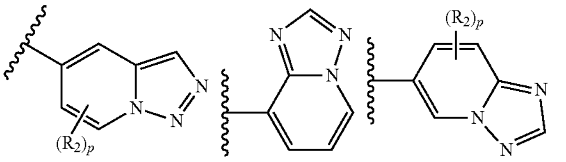
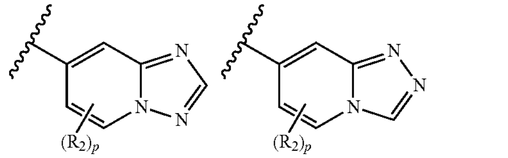
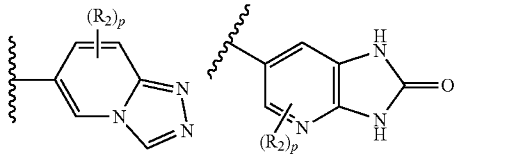
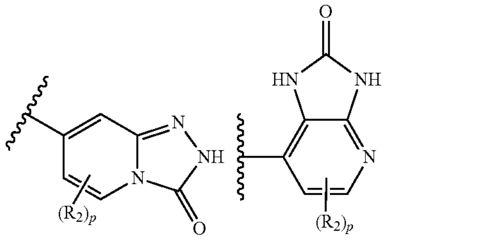
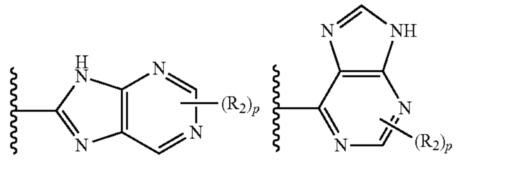
-continued
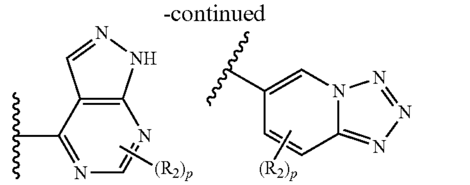
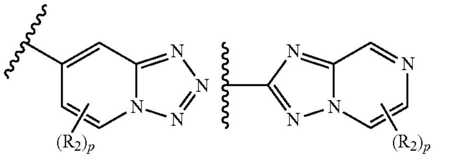
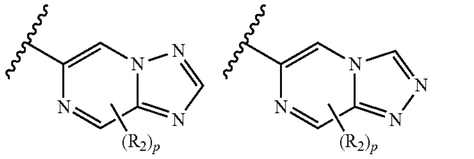
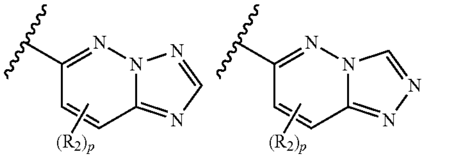
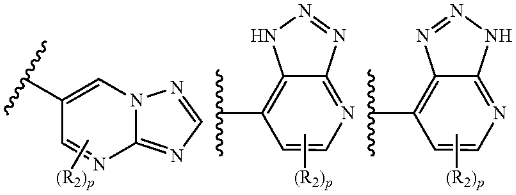
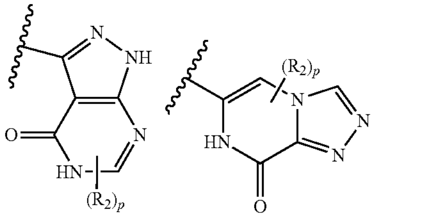
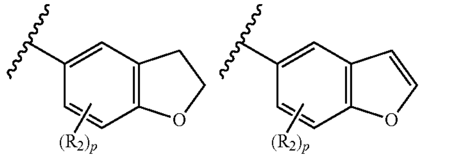
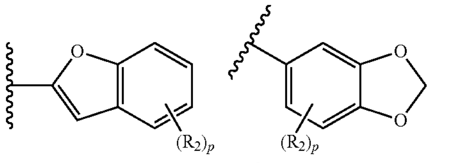
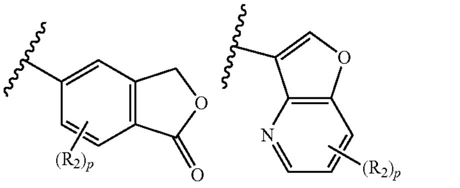
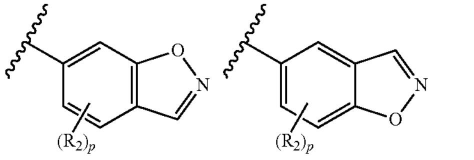

-continued

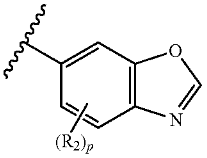 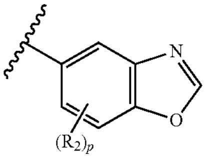

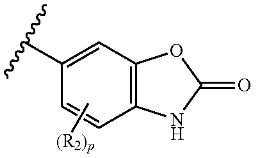 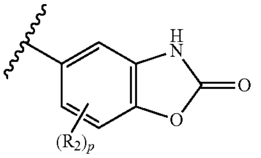

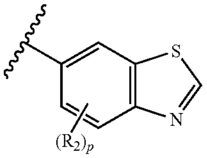 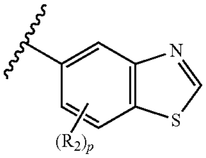

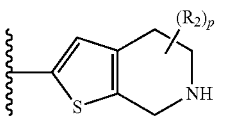 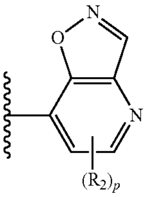 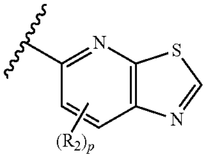

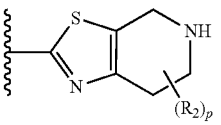 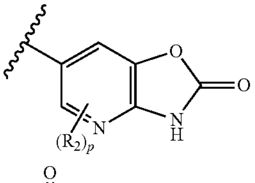 and

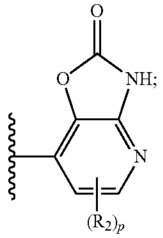

or (v) 10-membered heterocyclic ring selected from:

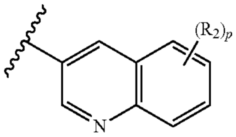 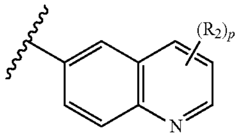

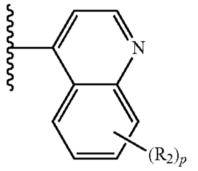 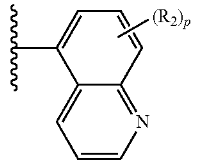

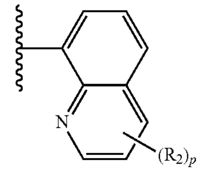 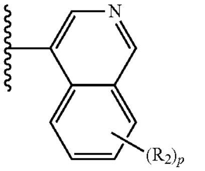

-continued

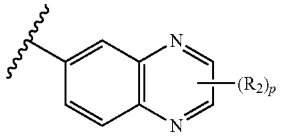 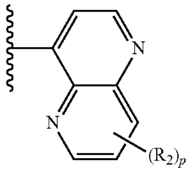

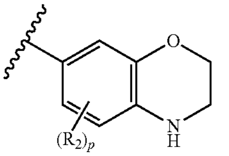 and 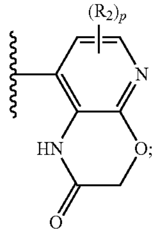

A is piperidinyl, phenyl, pyridinyl, pyrimidinyl, 6-azabicyclo[3.2.1]octanyl, or azabicyclo[3.2.1]octanyl, each substituted with -L-$R_4$ and zero to 1 $R_{4b}$;

L is a bond, —$CR_xR_x$— or —$C(O)(CR_xR_x)_{0-2}$—;

$R_1$ is hydrogen, $C_{1-3}$ alkyl, $C_{1-2}$ fluoroalkyl, or $C_{3-4}$ cycloalkyl;

each $R_2$ is independently halo, —CN, —OH, —$NO_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, —$O(CH_2)_{1-2}OH$, —$(CH_2)_{0-4}O(C_{1-4}$ alkyl), $C_{1-3}$ fluoroalkoxy, —$(CH_2)_{1-4}O(C_{1-3}$ alkyl), —$O(CH_2)_{1-2}OC(O)(C_{1-3}$ alkyl), —$O(CH_2)_{1-2}NR_xR_x$, —$C(O)O(C_{1-3}$ alkyl), —$(CH_2)_{0-2}C(O)NR_yR_y$, —$C(O)NR_x(C_{1-5}$ hydroxyalkyl), —$C(O)NR_x(C_{2-6}$ alkoxyalkyl), —$C(O)NR_x(C_{3-6}$ cycloalkyl), —$NR_yR_y$, —$NR_y(C_{1-3}$ fluoroalkyl), —$NR_y(C_{1-4}$ hydroxyalkyl), —$NR_xCH_2$(phenyl), —$NR_xS(O)_2(C_{3-6}$ cycloalkyl), —$NR_xC(O)(C_{1-3}$ alkyl), —$NR_xCH_2(C_{3-6}$ cycloalkyl), —$S(O)_2(C_{1-3}$ alkyl), —$S(O)_2N(C_{1-3}$ alkyl$)_2$, —$S(O)(NH)N(C_{1-3}$ alkyl$)_2$, —$(CH_2)_{0-2}(C_{3-6}$ cycloalkyl), —$(CH_2)_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);

$R_{2a}$ is $C_{1-6}$ alkyl, $C_{1-3}$ fluoroalkyl, $C_{1-6}$ hydroxyalkyl, $C_{1-3}$ aminoalkyl, —$(CH_2)_{0-4}O(C_{1-3}$ alkyl), $C_{3-6}$ cycloalkyl, —$(CH_2)_{1-3}C(O)NR_xR_x$, —$CH_2(C_{3-6}$ cycloalkyl), —$CH_2$(phenyl), tetrahydrofuranyl, tetrahydropyranyl, or phenyl;

each $R_{2b}$ is independently H, halo, —CN, —$NR_xR_x$, $C_{1-6}$ alkyl, $C_{1-3}$ fluoroalkyl, $C_{1-3}$ hydroxyalkyl, $C_{1-3}$ fluoroalkoxy, —$(CH_2)_{0-2}O(C_{1-3}$ alkyl), —$(CH_2)_{0-3}C(O)NR_xR_x$, —$(CH_2)_{1-3}(C_{3-6}$ cycloalkyl), —$C(O)O(C_{1-3}$ alkyl), —$C(O)NR_x(C_{1-3}$ alkyl), —$CR_x$=$CR_xR_x$, or —$CR_x$=$CH(C_{3-6}$ cycloalkyl);

$R_{2c}$ is $R_{2a}$ or $R_{2b}$;

$R_{2d}$ is $R_{2a}$ or $R_{2b}$; provided that one of $R_{2c}$ and $R_{2d}$ is $R_{2a}$, and the other of $R_{2c}$ and $R_{2d}$ is $R_{2b}$;

$R_3$ is hydrogen, $C_{1-3}$ alkyl, or $C_{3-4}$ cycloalkyl;

$R_4$ is:

(i) —$N(CH_3)_2$;

(ii) pyrrolidinyl, piperidinyl, piperazinyl, pyridinyl, azaspiro[3.3]heptanyl, or azabicyclo[3.2.1]octanyl, each substituted with zero to 2 $R_{4a}$; or (iii)

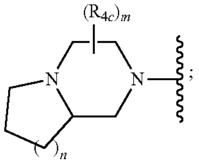

each $R_{4a}$ is independently $C_{1-6}$ alkyl, $C_{1-3}$ fluoroalkyl, $C_{3-6}$ cycloalkyl, $—CH_2(C_{3-6}$ cycloalkyl), $—C(O)(C_{1-4}$ alkyl), $—C(O)(C_{3-6}$ cycloalkyl), —C(O)(phenyl), $—C(O)CH_2(C_{3-6}$ cycloalkyl), $—C(O)CH_2$(phenyl), or $—C(O)O(C_{1-4}$ alkyl);

$R_{4b}$ is F, Cl, or $—CH_3$;

each $R_{4c}$ is independently $C_{1-6}$ alkyl, $C_{1-3}$ fluoroalkyl, $—CH_2(C_{3-6}$ cycloalkyl), $—C(O)(C_{1-4}$ alkyl), —C(O)(phenyl), $—C(O)CH_2$(phenyl), $—C(O)OCH_2CH_3$, or $C_{3-6}$ cycloalkyl;

each $R_5$ is independently hydrogen, F, Cl, $C_{1-2}$ alkyl, or cyclopropyl;

each $R_x$ is independently H or $—CH_3$;

each $R_y$ is independently H or $C_{1-6}$ alkyl;

m is zero, 1, or 2;

n is zero, 1, or 2; and p is zero, 1, 2, 3, or 4.

In one embodiment, a compound of Formula (I) or stereoisomers, tautomer, solvates or salts thereof is provided wherein X is C-A and Y is N. Compounds of this embodiment have the structure of Formula (II):

(II)

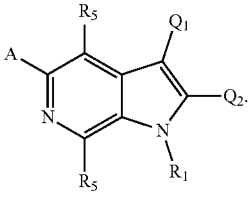

In one embodiment, a compound of Formula (I) or stereoisomers, tautomer, solvates or salts thereof is provided wherein X is C-A and Y is N; and $Q_1$ is G and $Q_2$ is $R_3$. Compounds of this embodiment have the structure of Formula (IIa):

(IIa)

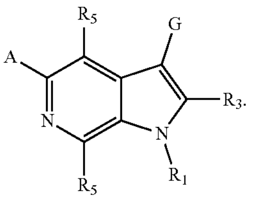

In one embodiment, a compound of Formula (I) or stereoisomers, tautomer, solvates or salts thereof is provided wherein X is C-A and Y is N; and $Q_1$ is $R_3$ and $Q_2$ is G. Compounds of this embodiment have the structure of Formula (IIb):

(IIb)

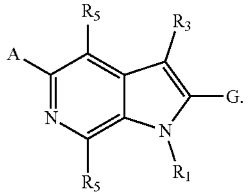

In one embodiment, a compound of Formula (I) or stereoisomers, tautomer, solvates or salts thereof is provided wherein X is N and Y is C-A. Compounds of this embodiment have the structure of Formula (III):

(III)

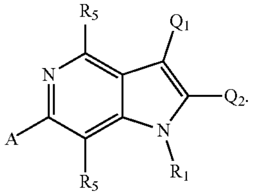

In one embodiment, a compound of Formula (I) or stereoisomers, tautomer, solvates or salts thereof is provided wherein X is N and Y is C-A; and $Q_1$ is G and $Q_2$ is $R_3$. Compounds of this embodiment have the structure of Formula (IIIa):

(IIIa)

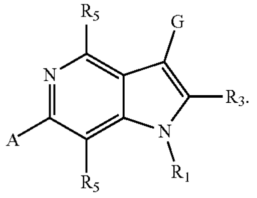

In one embodiment, a compound of Formula (I) or stereoisomers, tautomer, solvates or salts thereof is provided wherein X is N and Y is C-A; and $Q_1$ is $R_3$ and $Q_2$ is G. Compounds of this embodiment have the structure of Formula (IIIb):

(IIIb)

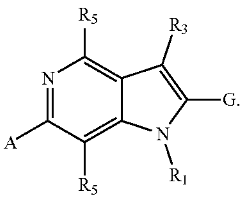

In one embodiment, a compound of Formula (I) or stereoisomers, tautomer, solvates or salts thereof is provided wherein G is phenyl substituted with 1 to 3 substituents independently selected from $—OCH_3$, $—S(O)_2CH_3$, $—S(O)_2N(CH_3)_2$, $—S(O)_2$(cyclopropyl), and —S(O)(NH)$N(CH_3)_2$. Included in this embodiment are compounds in which G is phenyl substituted with 1 to 2 substituents independently selected from $—OCH_3$, $—S(O)_2CH_3$, $—S(O)_2N(CH_3)_2$, and $—S(O)_2$(cyclopropyl). Also included in this embodiment are compounds in which G is:

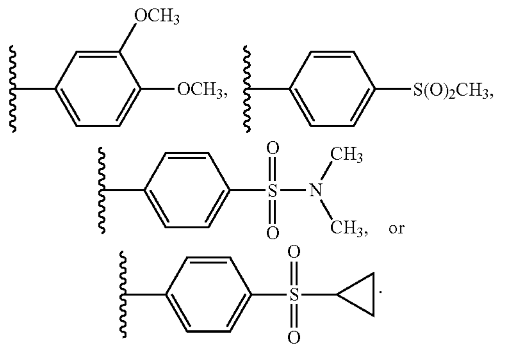

, , or .

In one embodiment, a compound of Formula (I) or stereoisomers, tautomer, solvates or salts thereof is provided wherein G is phenyl substituted with 1 to 2 substituents independently selected from $—OCH_3$, $—S(O)_2CH_3$, $—S(O)_2N(CH_3)_2$, and $—S(O)(NH)N(CH_3)_2$. Included in this embodiment are compounds in which G is phenyl substituted with 1 to 2 substituents independently selected from $—OCH_3$ and $—S(O)_2CH_3$. Also included in this embodiment are compounds in which G is:

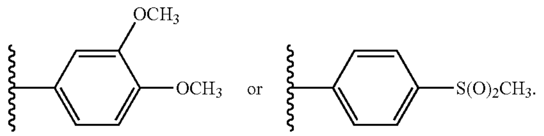

or .

In one embodiment, a compound of Formula (I) or stereoisomers, tautomer, solvates or salts thereof is provided wherein G is

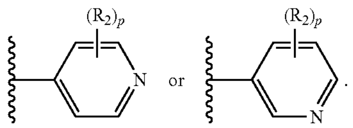

or .

Included in this embodiment are compounds in which each $R_2$ is independently F, Cl, Br, —CN, —OH, $—CH_3$, $—CH_2CH_3$, $—CF_3$, $—CH_2OH$, $—C(CH_3)_2OH$, $—CH_2NH_2$, $—OCH_3$, $—OCH_2CH_3$, $—OCH(CH_3)_2$, $—OCH_2CH_2OCH_3$, $—OCH_2CH_2N(CH_3)_2$, $—OCHF_2$, $—C(O)OCH_3$, $—C(O)NH_2$, $—C(O)NH(CH_2CH_3)$, —C(O)(thiazolyl), $—NH_2$, $—NH(CH_3)$, $—NH(CH_2CH_3)$, $—N(CH_3)_2$, $—NHC(O)CH_3$, $—NHC(O)C(CH_3)_3$, —NH($CH_2$-cyclopropyl), cyclopropyl, methylpiperidinyl, methylpiperazinyl, amino-oxadiazolyl, imidazolyl, or triazolyl. Also included in this embodiment are compounds in which each $R_2$ is independently F, Cl, —CN, $—CH_3$, $—OCH_3$, $—NH_2$, or cyclopropyl. Additionally, included in this embodiment are compounds in which p is 2; one $R_2$ is $—CH_3$; and the other $R_2$ is F, Cl, —CN, $—CH_3$, $—OCH_3$, $—NH_2$, or cyclopropyl.

In one embodiment, a compound of Formula (I) or stereoisomers, tautomer, solvates or salts thereof is provided wherein G is a 9-membered heterocyclic ring selected from:

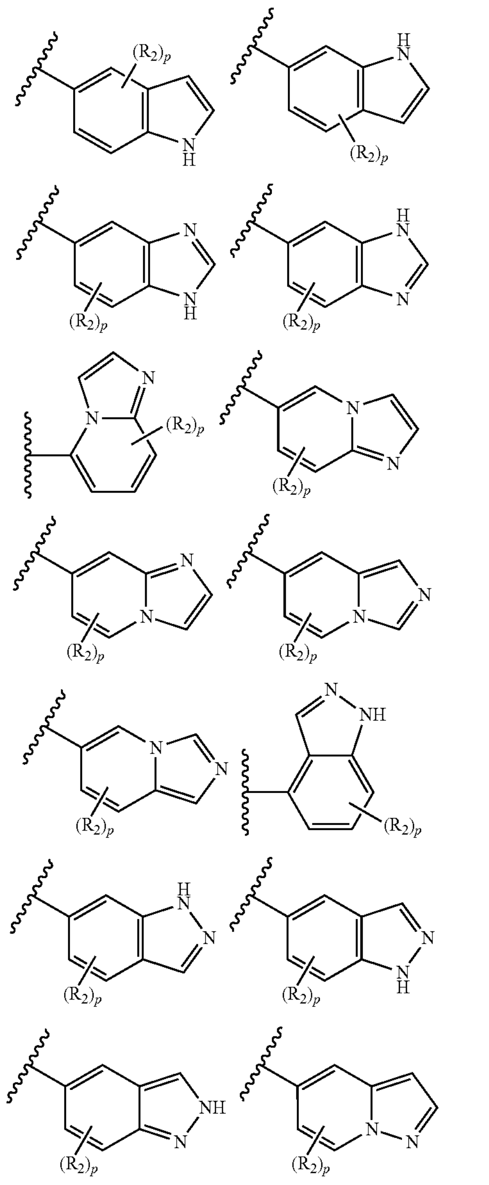

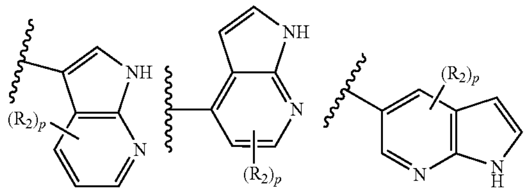

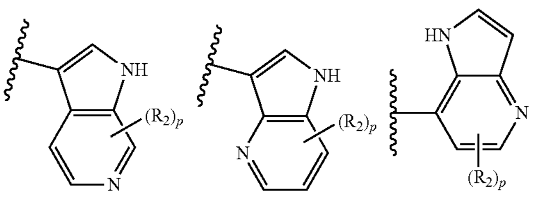

-continued
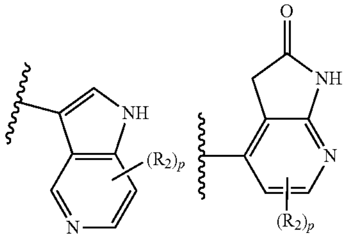
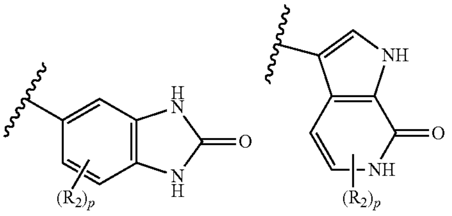
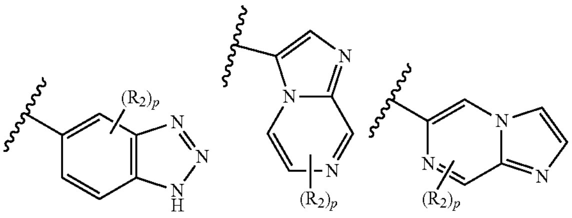
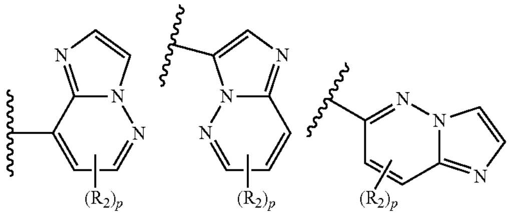
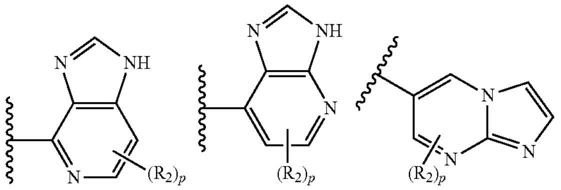
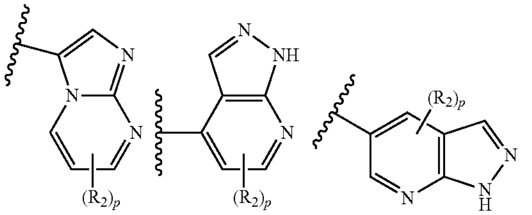
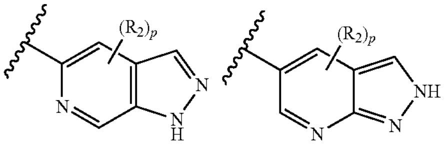
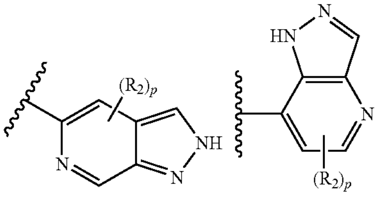
-continued
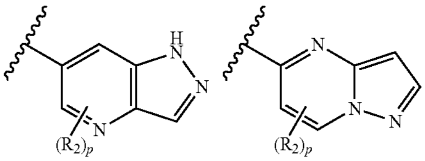
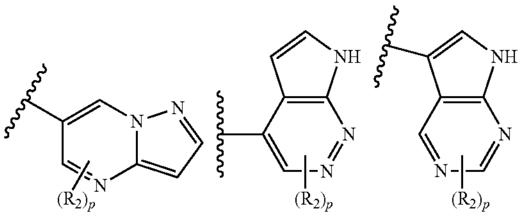
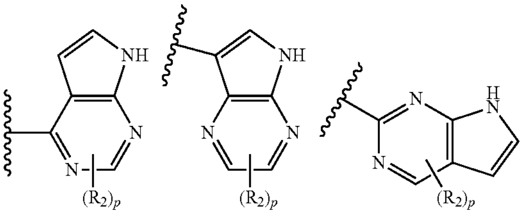
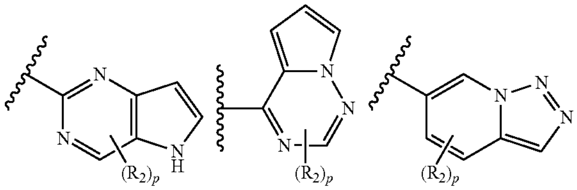
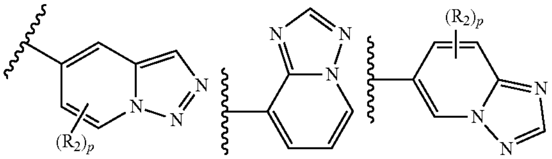
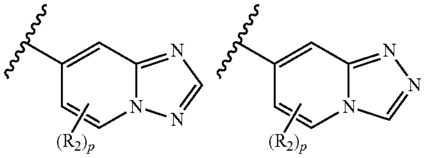
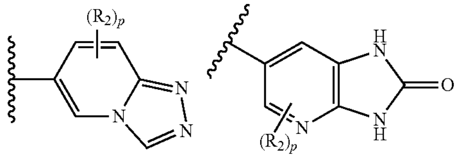
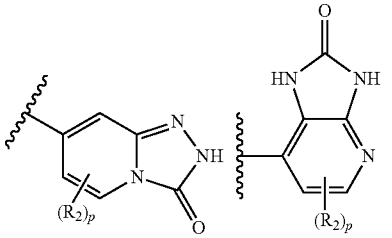
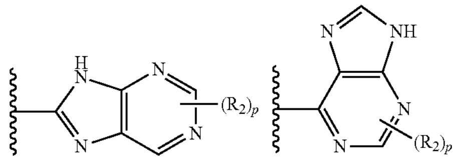

-continued
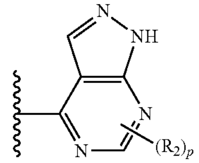
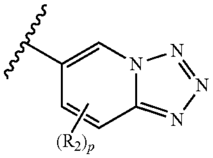
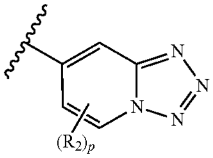
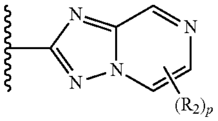
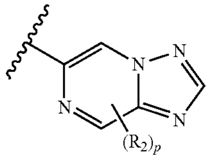
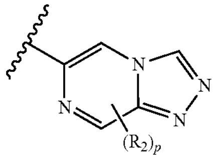
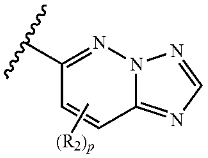
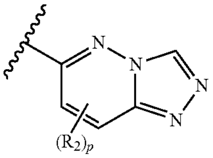
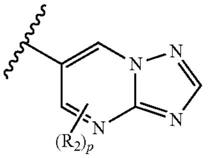
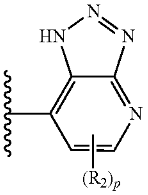
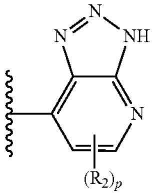
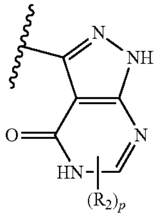
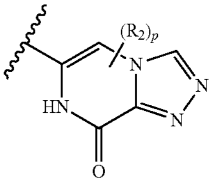
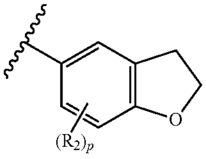
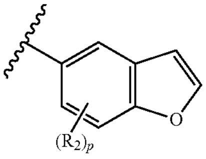
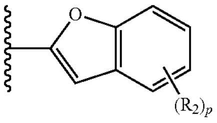
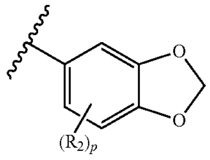
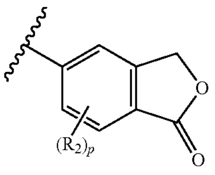
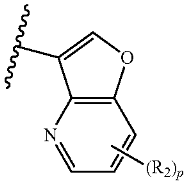
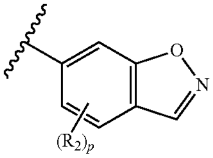
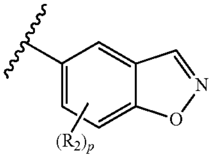
-continued
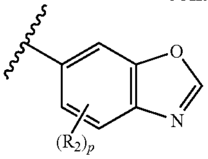
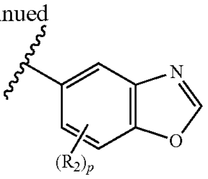
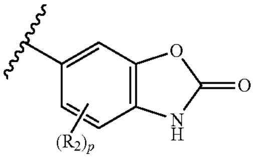
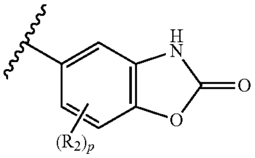
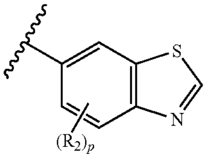
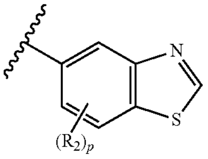
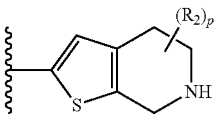
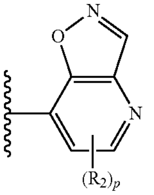
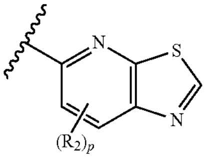
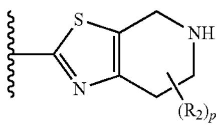
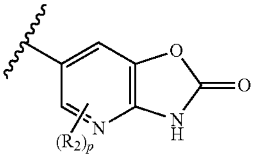
and
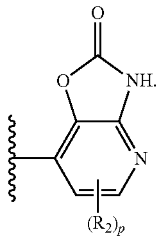
Included in this embodiment are compounds in which G is:
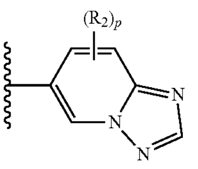
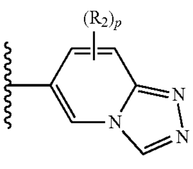
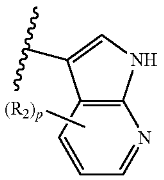
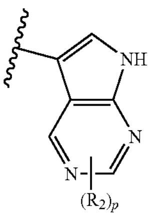
or
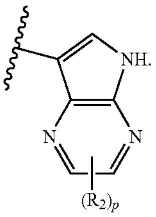
In one embodiment, a compound of Formula (I) or stereoisomers, tautomer, solvates or salts thereof is provided wherein G is a 10-membered heterocyclic ring selected from:

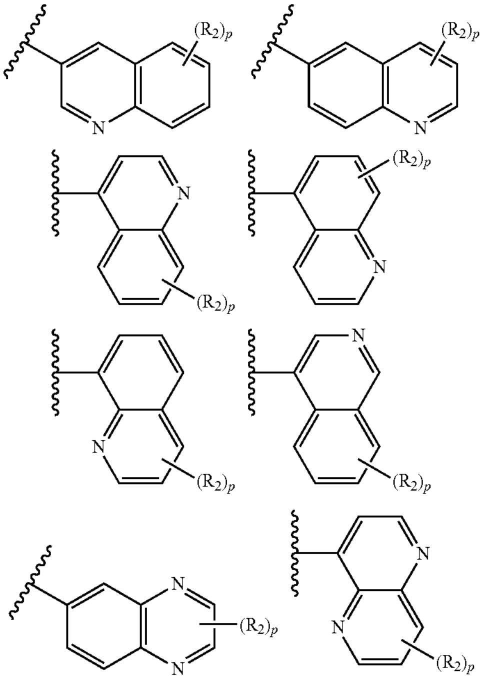

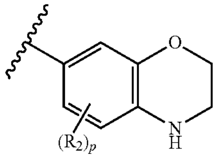

and

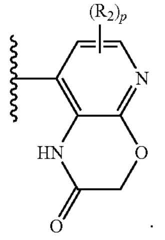

.

Included in this embodiment are compounds in which G is:

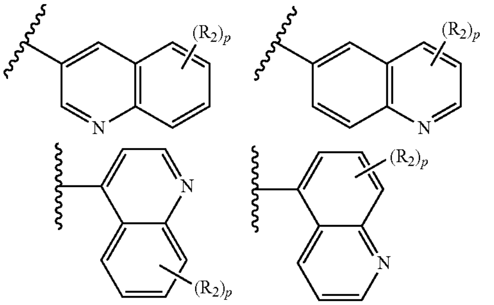

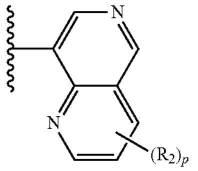

or

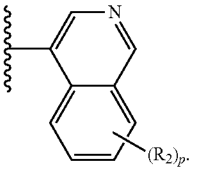

In one embodiment, a compound of Formula (I) or stereoisomers, tautomer, solvates or salts thereof is provided wherein G is:

(i) phenyl substituted with 1 to 2 substituents independently selected from —$OCH_3$, —$S(O)_2CH_3$, —$S(O)_2N(CH_3)_2$, and —$S(O)_2$(cyclopropyl);

(ii)

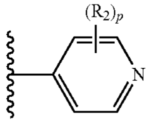

or

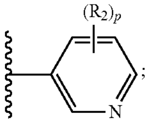

;

(iii)

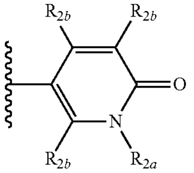

or

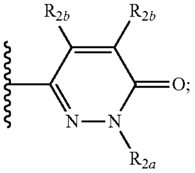

or (iv)

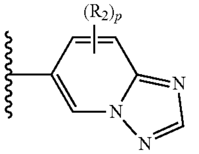

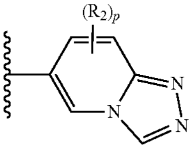

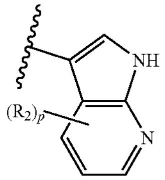

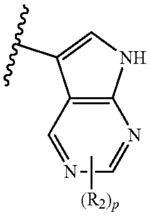

or

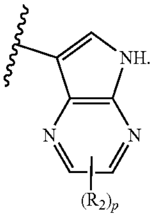

Included in this embodiment are compounds in which each $R_2$ is independently Cl, —$CH_3$, —$CH_2CH_3$, —$CH_2OH$, —$CH_2CH_2OH$, —$CH_2CN$, —$OCH_3$, —$CH_2OCH_3$, or —$CH_2CH_2S(O)_2CH_3$.

In one embodiment, a compound of Formula (I) or stereoisomers, tautomer, solvates or salts thereof is provided wherein G is:

(i) phenyl substituted with 1 to 2 substituents independently selected from —$OCH_3$, —$S(O)_2CH_3$, —$S(O)_2N(CH_3)_2$, and —$S(O)(NH)N(CH_3)_2$;

(ii)

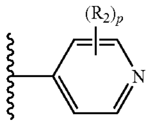

or

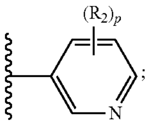

;

(iii)

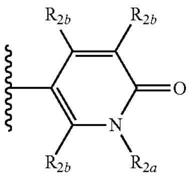

or

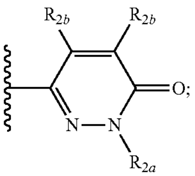

or

-continued (iv)

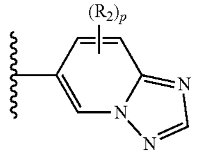

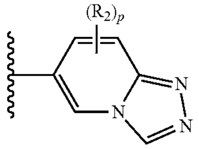

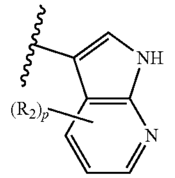

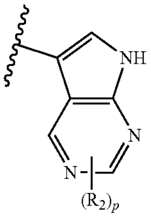

or

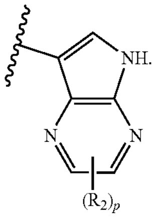

Included in this embodiment are compounds in which each $R_2$ is independently Cl, —$CH_3$, —$CH_2CH_3$, —$CH_2OH$, —$CH_2CH_2OH$, —$CH_2CN$, —$OCH_3$, —$CH_2OCH_3$, or —$CH_2CH_2S(O)_2CH_3$.

In one embodiment, a compound of Formula (I) or stereoisomers, tautomer, solvates or salts thereof is provided wherein p is zero, 1, 2, or 3. Included in this embodiment are compounds in which p is 1 or 2.

In one embodiment, a compound of Formula (I) or stereoisomers, tautomer, solvates or salts thereof is provided wherein A is piperidinyl, phenyl, pyridinyl, pyrimidinyl, 6-azabicyclo[3.2.1]octanyl, or azabicyclo[3.2.1]octanyl, each substituted with -L-$R_4$ and zero to 2 $R_{4b}$.

In one embodiment, a compound of Formula (I) or stereoisomers, tautomer, solvates or salts thereof is provided wherein A is piperidinyl, phenyl, pyridinyl, pyrimidinyl, 6-azabicyclo[3.2.1]octanyl, or azabicyclo[3.2.1]octanyl, each substituted with -L-$R_4$ and zero to 1 $R_{4b}$.

In one embodiment, a compound of Formula (I) or stereoisomers, tautomer, solvates or salts thereof is provided wherein A is piperidinyl, phenyl, or pyridinyl, each substituted with -L-$R_4$ and zero to 2 $R_{4b}$. Included in this embodiment are compounds in which A is piperidinyl or phenyl, each substituted with -L-$R_4$ and zero to 1 $R_{4b}$. Also, included in this embodiment are compounds in which A is phenyl or pyridinyl, each substituted with -L-$R_4$ and zero to 1 $R_{4b}$.

In one embodiment, a compound of Formula (I) or stereoisomers, tautomer, solvates or salts thereof is provided wherein A is piperidinyl, phenyl, or pyridinyl, each substituted with -L-$R_4$ and zero to 1 $R_{4b}$. Included in this embodiment are compounds in which A is piperidinyl or phenyl, each substituted with -L-$R_4$ and zero to 1 $R_{4b}$. Also, included in this embodiment are compounds in which A is phenyl or pyridinyl, each substituted with -L-$R_4$ and zero to 1 $R_{4b}$.

In one embodiment, a compound of Formula (I) or stereoisomers, tautomer, solvates or salts thereof is provided wherein A is piperidinyl, phenyl, pyridinyl, or pyrimidinyl, each substituted with -L-$R_4$ and zero to 2 $R_{4b}$; and L is a bond. Included in this embodiment are compounds in which A is piperidinyl, phenyl, or pyridinyl, each substituted with -L-$R_4$ and zero to 1 $R_{4b}$; and L is a bond.

In one embodiment, a compound of Formula (I) or stereoisomers, tautomer, solvates or salts thereof is provided wherein A is piperidinyl, phenyl, pyridinyl, or pyrimidinyl, each substituted with -L-$R_4$ and zero to 1 $R_{4b}$; and L is a bond. Included in this embodiment are compounds in which A is piperidinyl, phenyl, or pyridinyl, each substituted with -L-$R_4$ and zero to 1 $R_{4b}$; and L is a bond.

In one embodiment, a compound of Formula (I) or stereoisomers, tautomer, solvates or salts thereof is provided wherein L is a bond.

In one embodiment, a compound of Formula (I) or stereoisomers, tautomer, solvates or salts thereof is provided wherein L is —$CR_xR_x$—. Included in this embodiment are compounds in which L is —$CH_2$—.

In one embodiment, a compound of Formula (I) or stereoisomers, tautomer, solvates or salts thereof is provided wherein L is —$C(O)(CR_xR_x)_{0-2}$—. Included in this embodiment are compounds in which L is —$C(O)(CH_2)_{0-2}$—. Also included in this embodiment are compounds in which L is —$C(O)(CH_2)_{0-1}$—. Additionally, included in this embodiment are compounds in which L is —C(O)—.

In one embodiment, a compound of Formula (I) or stereoisomers, tautomer, solvates or salts thereof is provided wherein L is —$CR_xR_x$— or —$C(O)(CR_xR_x)_{0-2}$—. Included in this embodiment are compounds in which L is —$CR_xR_x$— or —$C(O)(CR_xR_x)_{0-1}$—. Also included in this embodiment are compounds in which L is —$CR_xR_x$— or —C(O)—. Additionally, included in this embodiment are compounds in which each $R_x$ is hydrogen.

In one embodiment, a compound of Formula (I) or stereoisomers, tautomer, solvates or salts thereof is provided wherein L is a bond, —$CH_2$— or —$C(O)(CH_2)_{0-2}$—. Included in this embodiment are compounds in which L is a bond or —C(O)—.

In one embodiment, a compound of Formula (I) or stereoisomers, tautomer, solvates or salts thereof is provided wherein $R_4$ is —$N(CH_3)_2$.

In one embodiment, a compound of Formula (I) or stereoisomers, tautomer, solvates or salts thereof is provided wherein $R_4$ is morpholinyl, pyrrolidinyl, piperidinyl, piperazinyl, pyridinyl, dioxothiomorpholinyl, azaspiro[3.3]heptanyl, azabicyclo[3.2.1]octanyl, diazabicyclo[2.2.2]octanyl, or diazabicyclo[3.2.1]octanyl, each substituted with zero to 4 $R_{4a}$.

In one embodiment, a compound of Formula (I) or stereoisomers, tautomer, solvates or salts thereof is provided wherein $R_4$ is morpholinyl, pyrrolidinyl, piperidinyl, piperazinyl, pyridinyl, dioxothiomorpholinyl, azabicyclo[3.2.1]octanyl, diazabicyclo[2.2.2]octanyl, or diazabicyclo[3.2.1]octanyl, each substituted with zero to 4 $R_{4a}$.

In one embodiment, a compound of Formula (I) or stereoisomers, tautomer, solvates or salts thereof is provided wherein $R_4$ is pyrrolidinyl, piperidinyl, piperazinyl, or pyridinyl, each substituted with zero to 4 $R_{4a}$.

In one embodiment, a compound of Formula (I) or stereoisomers, tautomer, solvates or salts thereof is provided wherein $R_4$ is pyrrolidinyl, piperidinyl, piperazinyl, pyridinyl, azaspiro[3.3]heptanyl, or azabicyclo[3.2.1]octanyl, each substituted with zero to 2 $R_{4a}$.

In one embodiment, a compound of Formula (I) or stereoisomers, tautomer, solvates or salts thereof is provided wherein $R_4$ is pyrrolidinyl, piperidinyl, piperazinyl, or pyridinyl, each substituted with zero to 2 $R_{4a}$. Included in this embodiment are compounds in which $R_4$ is piperidinyl, piperazinyl, or pyridinyl. Also included in this embodiment are compounds in which $R_4$ is piperidinyl or piperazinyl.

In one embodiment, a compound of Formula (I) or stereoisomers, tautomer, solvates or salts thereof is provided wherein $R_4$ is

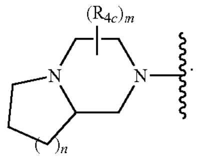

Included in this embodiment are compounds in which n is 1 or 2. Also included in this embodiment are compounds in which n is 1. Additionally, included in this embodiment are compounds in which n is 2.

In one embodiment, a compound of Formula (I) or stereoisomers, tautomer, solvates or salts thereof is provided wherein $R_4$ is pyrrolidinyl, piperidinyl, piperazinyl, or pyridinyl, each substituted with zero to 2 $R_{4a}$; or

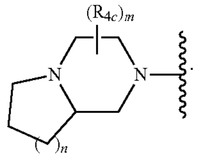

In one embodiment, a compound of Formula (I) or stereoisomers, tautomer, solvates or salts thereof is provided wherein $R_4$ is pyrrolidinyl, piperidinyl, piperazinyl, or pyridinyl, each substituted with zero to 2 $R_{4a}$; or

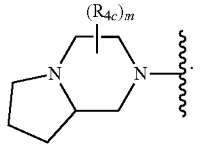

Included in this embodiment are compounds in which $R_4$ is pyrrolidinyl, piperidinyl, piperazinyl, or pyridinyl, each substituted with zero to 2 $R_{4a}$; or

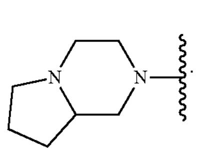 [SMILES: *N1CCN2CCCC2C1]

In one embodiment, a compound of Formula (I) or stereoisomers, tautomer, solvates or salts thereof is provided wherein each $R_{4a}$ is independently —OH, $C_{1-6}$ alkyl, $C_{1-3}$ fluoroalkyl, $C_{3-6}$ cycloalkyl, —$CH_2$($C_{3-6}$ cycloalkyl), —C(O)($C_{1-4}$ alkyl), —C(O)($C_{3-6}$ cycloalkyl), —C(O)(phenyl), —C(O)$CH_2$($C_{3-6}$ cycloalkyl), —C(O)$CH_2$(phenyl), or —C(O)O($C_{1-4}$ alkyl).

In one embodiment, a compound of Formula (I) or stereoisomers, tautomer, solvates or salts thereof is provided wherein each $R_{4a}$ is independently —OH, $C_{1-6}$ alkyl, $C_{1-3}$ fluoroalkyl, —$CH_2$($C_{3-6}$ cycloalkyl), —C(O)($C_{1-4}$ alkyl), —C(O)(phenyl), —C(O)$CH_2$(phenyl), —C(O)$OCH_2CH_3$, or $C_{3-6}$ cycloalkyl.

In one embodiment, a compound of Formula (I) or stereoisomers, tautomer, solvates or salts thereof is provided wherein each $R_{4a}$ is independently —OH, —$CH_3$, —$CHCH_3$, —$CH(CH_3)_2$, —$CH_2CH(CH_3)_2$, —$C(CH_3)_3$, —$CH_2C(CH_3)_3$, —$CH_2CH_2C(CH_3)_3$, —$CF_3$, —$CH_2CH_2OH$, —$CH_2CH_2CH_2OH$, —$CH_2C(CH_3)_2OH$, —$CH_2CH_2C(CH_3)_2OH$, —$CH_2CH_2OCH_3$, —$CH_2$(cyclopropyl), —C(O)$CH_3$, —C(O)$CH(CH_3)_2$, —C(O)$CH_2CH_3$, —C(O)(phenyl), —C(O)$CH_2$(phenyl), —C(O)$OCH_2CH_3$, —C(O)O(phenyl), cyclopropyl, cyclobutyl, oxetanyl, tetrahydrofuranyl, tetrahydropyranyl, —$(CH_2)_{1-2}$(bromophenyl), or —$(CH_2)_{1-2}$(iodophenyl).

In one embodiment, a compound of Formula (I) or stereoisomers, tautomer, solvates or salts thereof is provided wherein each $R_{4a}$ is independently —OH, —$CH_3$, —$CHCH_3$, —$CH(CH_3)_2$, —$CH_2CH(CH_3)_2$, —$C(CH_3)_3$, —$CF_3$, —$CH_2CH_2OH$, —$CH_2CH_2CH_2OH$, —$CH_2C(CH_3)_2OH$, —$CH_2CH_2C(CH_3)_2OH$, —$CH_2CH_2OCH_3$, —$CH_2$(cyclopropyl), —C(O)$CH_3$, —C(O)(phenyl), —C(O)$OCH_2CH_3$, cyclopropyl, cyclobutyl, oxetanyl, tetrahydrofuranyl, tetrahydropyranyl, —$(CH_2)_{1-2}$(bromophenyl), or —$(CH_2)_{1-2}$(iodophenyl).

In one embodiment, a compound of Formula (I) or stereoisomers, tautomer, solvates or salts thereof is provided wherein each $R_{4b}$ is independently F or —$CH_3$. Included in this embodiment are compounds in which each $R_{4b}$ is —$CH_3$.

In one embodiment, a compound of Formula (I) or stereoisomers, tautomer, solvates or salts thereof is provided wherein $R_{4b}$ is F or Cl. Included in this embodiment are compounds in which $R_{4b}$ is F.

In one embodiment, a compound of Formula (I) or stereoisomers, tautomer, solvates or salts thereof is provided wherein A is phenyl substituted with -L-$R_4$ and zero to 2 $R_{4b}$. Included in this embodiment are compounds in which each $R_{4b}$ is F.

In one embodiment, a compound of Formula (I) or stereoisomers, tautomer, solvates or salts thereof is provided wherein each $R_{4c}$ is independently $C_{1-4}$ alkyl, $C_{1-2}$ fluoroalkyl, —$CH_2$($C_{3-6}$ cycloalkyl), —C(O)($C_{1-3}$ alkyl), —C(O)(phenyl), —C(O)$CH_2$(phenyl), —C(O)$OCH_2CH_3$, or $C_{3-6}$ cycloalkyl. Included in this embodiment are compounds in which each $R_{4c}$ is independently $C_{1-3}$ alkyl, $C_{1-2}$ fluoroalkyl, —$CH_2$($C_{3-4}$ cycloalkyl), —C(O)($C_{1-2}$ alkyl), —C(O)(phenyl), —C(O)$CH_2$(phenyl), —C(O)$OCH_2CH_3$, or $C_{3-4}$ cycloalkyl.

In one embodiment, a compound of Formula (I) or stereoisomers, tautomer, solvates or salts thereof is provided wherein $R_1$ is hydrogen, $C_{1-2}$ alkyl, —$CH_2F$, —$CHF_2$, —$CF_3$, or $C_{3-4}$ cycloalkyl. Included in this embodiment are compounds in which $R_1$ is hydrogen, —$CH_3$, —$CF_3$, or cyclopropyl. Also included in this embodiment are compounds in which $R_1$ is hydrogen or —$CH_3$.

In one embodiment, a compound of Formula (I) or stereoisomers, tautomer, solvates or salts thereof is provided wherein $R_1$ is hydrogen, $C_{1-2}$ alkyl, —$CH_2F$, —$CHF_2$, —$CF_3$, or cyclopropyl. Included in this embodiment are compounds in which $R_1$ is hydrogen, —$CH_3$, —$CHF_2$, or cyclopropyl. Also included in this embodiment are compounds in which $R_1$ is hydrogen. Also included in this embodiment are compounds in which $R_1$ is —$CH_3$, —$CHF_2$, or cyclopropyl.

In one embodiment, a compound of Formula (I) or stereoisomers, tautomer, solvates or salts thereof is provided wherein each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, —$(CH_2)_{0-2}O(C_{1-3}$ alkyl), $C_{3-6}$ cycloalkyl, —$NR_xR_x$, —$(CH_2)_{0-2}C(O)NR_xR_x$, —$CH_2(C_{3-6}$ cycloalkyl), —$CH_2$(phenyl), or phenyl. Included in this embodiment are compounds in which each $R_2$ is independently Cl, —$CH_3$, —$CH_2CH_3$, —$CH_2OH$, —$CH_2CH_2OH$, —$CH_2CN$, —$OCH_3$, —$CH_2OCH_3$, or —$CH_2CH_2S(O)_2CH_3$. Also, included in this embodiment are compounds in which each $R_2$ is independently Cl, —$CH_3$, —$CH_2OH$, or —$OCH_3$.

In one embodiment, a compound of Formula (I) or stereoisomers, tautomer, solvates or salts thereof is provided wherein $R_{2a}$ is $C_{1-4}$ alkyl, $C_{1-2}$ fluoroalkyl, $C_{1-4}$ hydroxyalkyl, —$(CH_2)_{1-3}OCH_3$, $C_{3-6}$ cycloalkyl, —$CH_2C(O)NR_xR_x$, —$CH_2(C_{3-6}$ cycloalkyl), —$CH_2$(phenyl), tetrahydrofuranyl, or phenyl; and each $R_{2b}$ is independently H, F, Cl, —CN, —$NR_xR_x$, $C_{1-6}$ alkyl, $C_{1-2}$ fluoroalkyl, $C_{1-3}$ hydroxyalkyl, —$(CH_2)_{0-2}O(C_{1-2}$ alkyl), —$(CH_2)_{0-2}C(O)NR_xR_x$, —$(CH_2)_{1-3}$ (cyclopropyl), —$C(O)O(C_{1-2}$ alkyl), —$C(O)NR_x(C_{1-3}$ alkyl), —$CR_x$═$CH_2$, or —CH═CH($C_{3-6}$ cycloalkyl). Also included in this embodiment are compounds in which $R_{2a}$ is —$CH_3$; and each $R_{2b}$ is independently H, Cl, or —$CH_3$.

In one embodiment, a compound of Formula (I) or stereoisomers, tautomer, solvates or salts thereof is provided wherein $R_3$ is hydrogen, F, $C_{1-3}$ alkyl, or $C_{3-4}$ cycloalkyl. Included in this embodiment are compounds in which $R_3$ is hydrogen, F, $C_{1-2}$ alkyl, or cyclopropyl. Also included in this embodiment are compounds in which $R_3$ is hydrogen, F, —$CH_3$, or cyclopropyl.

In one embodiment, a compound of Formula (I) or stereoisomers, tautomer, solvates or salts thereof is provided wherein $R_3$ is hydrogen, $C_{1-2}$ alkyl, or $C_{3-4}$ cycloalkyl. Included in this embodiment are compounds in which $R_3$ is hydrogen, $C_{1-2}$ alkyl, or cyclopropyl. Also included in this embodiment are compounds in which $R_3$ is hydrogen or —$CH_3$.

In one embodiment, a compound of Formula (I) or stereoisomers, tautomer, solvates or salts thereof is provided wherein each $R_5$ is independently hydrogen, F, Cl, $C_{1-3}$ alkyl, $C_{1-3}$ hydroxyalkyl, $C_{1-2}$ alkoxy, cyclopropyl, or morpholinyl. Included in this embodiment are compounds in which each $R_5$ is independently hydrogen, —$CH_3$, —$C(CH_3)_2OH$, —$OCH_3$, or morpholinyl.

In one embodiment, a compound of Formula (I) or stereoisomers, tautomer, solvates or salts thereof is provided wherein each $R_5$ is independently hydrogen, F, Cl, —$CH_3$, or cyclopropyl. Included in this embodiment are compounds in which each $R_5$ is independently hydrogen, —$CH_3$, or cyclopropyl. Also included are compounds in which each $R_5$ is hydrogen or —$CH_3$.

In one embodiment, a compound of Formula (I) or stereoisomers, tautomer, solvates or salts thereof is provided wherein: G is phenyl substituted with 1 to 2 substituents independently selected from —$OCH_3$, —$S(O)_2CH_3$, —$S(O)_2N(CH_3)_2$, and —$S(O)_2$(cyclopropyl); A is piperidinyl, phenyl, or pyridinyl, each substituted with -L-$R_4$ and zero to 2 $R_{4b}$; L is a bond, —$CH_2$—, —C(O)—, —C(O)$CH_2$—, or —$C(O)CH_2CH_2$—; $R_1$ is hydrogen, —$CH_3$, —$CHF_2$, or cyclopropyl; $R_3$ is hydrogen, F, —$CH_3$, or cyclopropyl; $R_4$ is: (i) —$N(CH_3)_2$; or (ii) pyrrolidinyl, piperidinyl, piperazinyl, or pyridinyl, each substituted with zero to 4 $R_{4a}$; each $R_{4a}$ is independently $C_{1-6}$ alkyl, $C_{1-3}$ fluoroalkyl, —$CH_2(C_{3-6}$ cycloalkyl), —$C(O)(C_{1-4}$ alkyl), —C(O)(phenyl), —$C(O)CH_2$(phenyl), —$C(O)OCH_2CH_3$, or $C_{3-6}$ cycloalkyl; each $R_{4b}$ is independently F, Cl, or —$CH_3$; each $R_{4c}$ is independently $C_{1-6}$ alkyl, $C_{1-3}$ fluoroalkyl, —$CH_2(C_{3-6}$ cycloalkyl), —$C(O)(C_{1-4}$ alkyl), —C(O)(phenyl), —$C(O)CH_2$(phenyl), —$C(O)OCH_2CH_3$, or $C_{3-6}$ cycloalkyl; each $R_5$ is independently hydrogen, F, Cl, $C_{1-3}$ alkyl, $C_{1-3}$ hydroxyalkyl, $C_{1-2}$ alkoxy, cyclopropyl, or morpholinyl; m is zero, 1, or 2; and n is zero, 1, or 2.

In one embodiment, a compound of Formula (I) or stereoisomers, tautomer, solvates or salts thereof is provided wherein: G is phenyl substituted with 1 to 2 substituents independently selected from —$OCH_3$, —$S(O)_2CH_3$, —$S(O)_2N(CH_3)_2$, and —$S(O)_2$(cyclopropyl); A is piperidinyl, phenyl, or pyridinyl, each substituted with -L-$R_4$ and zero to 2 $R_{4b}$; L is a bond, —$CH_2$—, —C(O)—, —C(O)$CH_2$—, or —$C(O)CH_2CH_2$—; $R_1$ is hydrogen or —$CH_3$; $R_3$ is hydrogen, F, —$CH_3$, or cyclopropyl; $R_4$ is: (i) —$N(CH_3)_2$; or (ii) pyrrolidinyl, piperidinyl, piperazinyl, or pyridinyl, each substituted with zero to 4 $R_{4a}$; each $R_{4a}$ is independently —OH, —$CH_3$, —$CHCH_3$, —$CH(CH_3)_2$, —$CH_2CH(CH_3)_2$, —$C(CH_3)_3$, —$CH_2C(CH_3)_3$, —$CH_2CH_2C(CH_3)_3$, —$CF_3$, —$CH_2CH_2OH$, —$CH_2CH_2CH_2OH$, —$CH_2C(CH_3)_2OH$, —$CH_2CH_2C(CH_3)_2OH$, —$CH_2CH_2OCH_3$, —$CH_2$(cyclopropyl), —$C(O)CH_3$, —$C(O)CH(CH_3)_2$, —$C(O)CH_2CH_3$, —C(O)(phenyl), —$C(O)CH_2$(phenyl), —$C(O)OCH_2CH_3$, —C(O)O(phenyl), cyclopropyl, cyclobutyl, oxetanyl, tetrahydrofuranyl, tetrahydropyranyl, —$(CH_2)_{1-2}$(bromophenyl), or —$(CH_2)_{1-2}$(iodophenyl); each $R_{4b}$ is F; and each $R_5$ is independently hydrogen, —$CH_3$, —$C(CH_3)_2OH$, —$OCH_3$, or morpholinyl.

In one embodiment, a compound of Formula (I) or stereoisomers, tautomer, solvates or salts thereof is provided wherein:

G is:

(i) phenyl substituted with 1 to 2 substituents independently selected from —$OCH_3$, —$S(O)_2CH_3$, —$S(O)_2N(CH_3)_2$, and —$S(O)(NH)N(CH_3)_2$;

(ii)

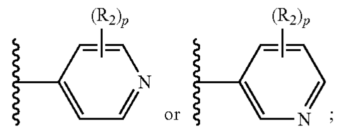

or ;

(iii)

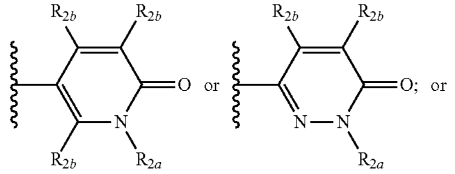

or ; or (iv)

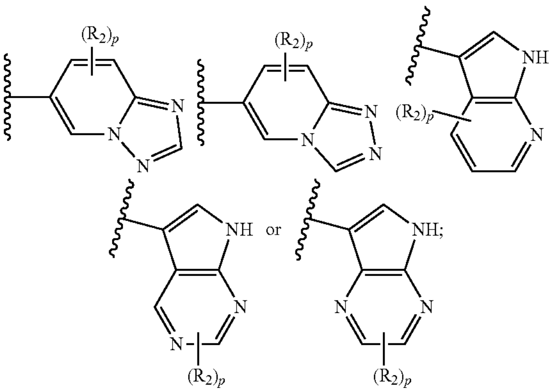

or ;

A is piperidinyl, phenyl, pyridinyl, or pyrimidinyl, each substituted with -L-$R_4$ and zero to 1 $R_{4b}$;

L is a bond, $—CR_xR_x—$ or $—C(O)(CR_xR_x)_{0-2}—$;

$R_1$ is hydrogen, $C_{1-3}$ alkyl, $C_{1-2}$ fluoroalkyl, or $C_{3-4}$ cycloalkyl;

each $R_2$ is independently F, Cl, —CN, —OH, $C_{1-3}$ alkyl, $C_{1-2}$ fluoroalkyl, $C_{1-2}$ cyanoalkyl, $C_{1-3}$ hydroxyalkyl, $C_{1-2}$ aminoalkyl, $—(CH_2)_{0-2}O(C_{1-3}$ alkyl), $C_{3-6}$ cycloalkyl, $—NR_xR_x$, $—(CH_2)_{0-2}C(O)NR_xR_x$, $—CH_2(C_{3-6}$ cycloalkyl), $—CH_2$(phenyl), or phenyl;

$R_{2a}$ is $C_{1-4}$ alkyl, $C_{1-2}$ fluoroalkyl, $C_{1-4}$ hydroxyalkyl, $—(CH_2)_{1-3}OCH_3$, $C_{3-6}$ cycloalkyl, $—CH_2C(O)NR_xR_x$, $—CH_2(C_{3-6}$ cycloalkyl), $—CH_2$(phenyl), tetrahydrofuranyl, or phenyl;

each $R_{2b}$ is independently H, F, Cl, —CN, $—NR_xR_x$, $C_{1-6}$ alkyl, $C_{1-2}$ fluoroalkyl, $C_{1-3}$ hydroxyalkyl, $—(CH_2)_{0-2}O(C_{1-2}$ alkyl), $—(CH_2)_{0-2}C(O)NR_xR_x$, $—(CH_2)_{1-3}$(cyclopropyl), $—C(O)O(C_{1-2}$ alkyl), $—C(O)NR_x(C_{1-3}$ alkyl), $—CR_x{=}CH_2$, or $—CH{=}CH(C_{3-6}$ cycloalkyl);

$R_3$ is hydrogen, $C_{1-3}$ alkyl, or $C_{3-4}$ cycloalkyl;

$R_4$ is:

(i) $—N(CH_3)_2$;

(ii) pyrrolidinyl, piperidinyl, piperazinyl, or pyridinyl, each substituted with zero to 2 $R_{4a}$; or

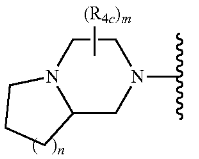

(iii)

each $R_{4a}$ is independently $C_{1-6}$ alkyl, $C_{1-3}$ fluoroalkyl, $C_{3-6}$ cycloalkyl, $—CH_2(C_{3-6}$ cycloalkyl), $—C(O)(C_{1-4}$ alkyl), $—C(O)(C_{3-6}$ cycloalkyl), —C(O)(phenyl), $—C(O)CH_2(C_{3-6}$ cycloalkyl), $—C(O)CH_2$(phenyl), or $—C(O)O(C_{1-4}$ alkyl);

$R_{4b}$ is F, Cl, or $—CH_3$;

each $R_{4c}$ is independently $C_{1-6}$ alkyl, $C_{1-3}$ fluoroalkyl, $—CH_2(C_{3-6}$ cycloalkyl), $—C(O)(C_{1-4}$ alkyl), —C(O)(phenyl), $—C(O)CH_2$(phenyl), $—C(O)OCH_2CH_3$, or $C_{3-6}$ cycloalkyl;

each $R_5$ is independently hydrogen, F, Cl, $C_{1-2}$ alkyl, or cyclopropyl;

each $R_x$ is independently H or $—CH_3$;

each $R_y$ is independently H or $C_{1-6}$ alkyl;

m is zero, 1, or 2;

n is zero, 1, or 2; and p is zero, 1, 2, 3, or 4.

In one embodiment, a compound of Formula (I) or stereoisomers, tautomer, solvates or salts thereof is provided wherein: G is phenyl substituted with 1 to 2 substituents independently selected from $—OCH_3$ and $—S(O)_2CH_3$; A is piperidinyl, phenyl, or pyridinyl, each substituted with $-L-R_4$ and zero to 1 $R_{4b}$; L is a bond, $—CH_2—$, —C(O)—, $—C(O)CH_2—$, or $—C(O)CH_2CH_2—$; $R_1$ is hydrogen or $—CH_3$; $R_3$ is hydrogen or $—CH_3$; $R_4$ is: (i) $—N(CH_3)_2$; or (ii) pyrrolidinyl, piperidinyl, piperazinyl, or pyridinyl, each substituted with zero to 2 $R_{4a}$; $R_{4a}$ is independently $C_{1-6}$ alkyl, $C_{1-3}$ fluoroalkyl, $—CH_2(C_{3-6}$ cycloalkyl), $—C(O)(C_{1-4}$ alkyl), —C(O)(phenyl), $—C(O)CH_2$(phenyl), $—C(O)OCH_2CH_3$, or $C_{3-6}$ cycloalkyl; $R_{4b}$ is F, Cl, or $—CH_3$; $R_{4c}$ is $C_{1-6}$ alkyl, $C_{1-3}$ fluoroalkyl, $—CH_2(C_{3-6}$ cycloalkyl), $—C(O)(C_{1-4}$ alkyl), —C(O)(phenyl), $—C(O)CH_2$(phenyl), $—C(O)OCH_2CH_3$, or $C_{3-6}$ cycloalkyl; each $R_5$ is independently hydrogen, F, Cl, or $C_{1-2}$ alkyl; m is zero, 1, or 2; and n is zero, 1, or 2.

In one embodiment, a compound of Formula (I) or stereoisomers, tautomer, solvates or salts thereof is provided wherein: G is phenyl substituted with 1 to 2 substituents independently selected from $—OCH_3$ and $—S(O)_2CH_3$; A is piperidinyl, phenyl, or pyridinyl, each substituted with $-L-R_4$ and zero to 1 $R_{4b}$; L is a bond, $—CH_2—$, —C(O)—, $—C(O)CH_2—$, or $—C(O)CH_2CH_2—$; $R_1$ is hydrogen or $—CH_3$; $R_3$ is hydrogen or $—CH_3$; $R_4$ is: (i) $—N(CH_3)_2$; or (ii) pyrrolidinyl, piperidinyl, piperazinyl, or pyridinyl, each substituted with zero to 2 $R_{4a}$; $R_{4a}$ is independently $—CH_3$, $—CH(CH_3)_2$, $—CH_2CH(CH_3)_2$, $—CH_2C(CH_3)_3$, $—CH_2CH_2C(CH_3)_3$, $—CF_3$, $—CH_2$(cyclopropyl), $—C(O)CH_3$, $—C(O)CH(CH_3)_2$, $—C(O)CH_2CH_3$, —C(O)(phenyl), $—C(O)CH_2$(phenyl), $—C(O)OCH_2CH_3$, cyclopropyl, or cyclobutyl; $R_{4b}$ is F; and each $R_5$ is independently hydrogen or $—CH_3$.

In one embodiment, a compound of Formula (I) or stereoisomers, tautomer, solvates or salts thereof is provided wherein: X is C-A; Y is N; $Q_1$ is G; $Q_2$ is $R_3$; G is phenyl substituted with 2 substituents selected from $—OCH_3$; A is piperidinyl or phenyl, each substituted with $-L-R_4$; $R_1$ is hydrogen or $—CH_3$; $R_3$ is $—CH_3$; L is a bond, —C(O)—, $—C(O)CH_2—$, or $—C(O)CH_2CH_2—$; $R_4$ is: (i) $—N(CH_3)_2$; or (ii) pyrrolidinyl, piperidinyl, piperazinyl, or pyridinyl, each substituted with zero to 2 $R_{4a}$; $R_{4a}$ is independently $—CH_3$, $—CH(CH_3)_2$, $—CH_2CH(CH_3)_2$, $—CH_2C(CH_3)_3$, $—C(O)CH(CH_3)_2$, —C(O)(phenyl), $—C(O)CH_2$(phenyl), or cyclopropyl; and each $R_5$ is hydrogen.

In one embodiment, a compound of Formula (I) or stereoisomers, tautomer, solvates or salts thereof is provided wherein: X is C-A; Y is N; $Q_1$ is $R_3$; $Q_2$ is G; G is phenyl substituted with 2 substituents selected from $—OCH_3$; A is piperidinyl or phenyl, each substituted with $-L-R_4$; L is a bond; $R_1$ is $—CH_3$; $R_3$ is $—CH_3$; $R_4$ is piperidinyl or piperazinyl, each substituted with $R_{4a}$; $R_{4a}$ is independently $—CH(CH_3)_2$ or $—CH_2CH(CH_3)_2$; and each $R_5$ is hydrogen.

In one embodiment, a compound of Formula (I) or stereoisomers, tautomer, solvates or salts thereof is provided wherein: X is N; Y is C-A; $Q_1$ is $R_3$; $Q_2$ is G; G is phenyl substituted with 1 to 2 substituents independently selected from $—OCH_3$ and $—S(O)_2CH_3$; A is piperidinyl or phenyl, each substituted with $-L-R_4$ and zero to 1 $R_{4b}$; L is a bond, $—CH_2—$, or $—C(O)CH_2—$; $R_1$ is $—CH_3$; $R_3$ is hydrogen; $R_4$ is: piperidinyl, piperazinyl, or pyridinyl, each substituted with zero to 2 $R_{4a}$; $R_{4a}$ is independently $—CH_3$, $—CH(CH_3)_2$, $—CH_2CH(CH_3)_2$, $—CF_3$, $—CH_2$(cyclopropyl), $—C(O)CH_3$, —C(O)(phenyl), $—C(O)OCH_2CH_3$, or cyclobutyl; $R_{4b}$ is F; and each $R_5$ is independently hydrogen or $—CH_3$.

One embodiment provides a compound of Formula (I) or stereoisomers, tautomer, solvates or salts thereof, wherein said compound is: 2-(3,4-dimethoxyphenyl)-5-(4-(4-isopropylpiperazin-1-yl)phenyl)-3-methyl-1H-pyrrolo[2,3-c]pyridine (1); or 2-(3,4-dimethoxyphenyl)-5-(1'-isobutyl-[1,4'-bipiperidin]-4-yl)-1,3-dimethyl-1H-pyrrolo[2,3-c]pyridine (13).

One embodiment provides a compound of Formula (I) or a salt thereof, wherein said compound is: 2-(3,4-dimethoxyphenyl)-5-(4-(4-isopropylpiperazin-1-yl)phenyl)-3-methyl-1H-pyrrolo[2,3-c]pyridine (2); 1-(4-(4-(3-(3,4-dimethoxyphenyl)-1,2-dimethyl-1H-pyrrolo[2,3-c]pyridin-5-yl)phenyl)piperazin-1-yl)-2-methylpropan-2-ol (3); benzyl 4-(3-(3,4-dimethoxyphenyl)-2-methyl-1H-pyrrolo[2,3-c]pyridin-5-yl)-[1,4'-bipiperidine]-1'-carboxylate (4); (1-cyclopropylpiperidin-4-yl)(4-(3-(3,4-dimethoxyphenyl)-2-methyl-1H-pyrrolo[2,3-c]pyridin-5-yl)piperidin-1-yl)methanone (5); 3-(3,4-dimethoxyphenyl)-5-(1-(2,6-dimethylpyridin-4-yl)piperidin-4-yl)-2-methyl-1H-pyrrolo

[2,3-c]pyridine (6); (4-(3-(3,4-dimethoxyphenyl)-2-methyl-1H-pyrrolo[2,3-c]pyridin-5-yl)-[1,4'-bipiperidin]-1'-yl)(phenyl)methanone (14); 1-(4-(3-(3,4-dimethoxyphenyl)-2-methyl-1H-pyrrolo[2,3-c]pyridin-5-yl)-[1,4'-bipiperidin]-1'-yl)-2-methylpropan-1-one (15); 1-(4-(3-(3,4-dimethoxyphenyl)-2-methyl-1H-pyrrolo[2,3-c]pyridin-5-yl)piperidin-1-yl)-2-(piperidin-1-yl)ethan-1-one (16); 3-(3,4-dimethoxyphenyl)-5-(1'-isobutyl-[1,4'-bipiperidin]-4-yl)-1,2-dimethyl-1H-pyrrolo[2,3-c]pyridine (17); 1-(4-(3-(3,4-dimethoxyphenyl)-1,2-dimethyl-1H-pyrrolo[2,3-c]pyridin-5-yl)-[1,4'-bipiperidin]-1'-yl)-2-methylpropan-1-one (18); (4-(3-(3,4-dimethoxyphenyl)-1,2-dimethyl-1H-pyrrolo[2,3-c]pyridin-5-yl)-[1,4'-bipiperidin]-1'-yl)(phenyl)methanone (19); ethyl 4-(3-(3,4-dimethoxyphenyl)-1,2-dimethyl-1H-pyrrolo[2,3-c]pyridin-5-yl)-[1,4'-bipiperidine]-1'-carboxylate (20); 1-(4-(3-(3,4-dimethoxyphenyl)-2-methyl-1H-pyrrolo[2,3-c]pyridin-5-yl)piperidin-1-yl)-2-(pyrrolidin-1-yl)ethan-1-one (21); 1-(4-(3-(3,4-dimethoxyphenyl)-2-methyl-1H-pyrrolo[2,3-c]pyridin-5-yl)piperidin-1-yl)-2-(dimethylamino)ethan-1-one (22); 1-(4-(3-(3,4-dimethoxyphenyl)-2-methyl-1H-pyrrolo[2,3-c]pyridin-5-yl)piperidin-1-yl)-3-(pyrrolidin-1-yl)propan-1-one (23); 3-(3,4-dimethoxyphenyl)-5-(4-(4-isopropylpiperazin-1-yl)phenyl)-1,2-dimethyl-1H-pyrrolo[2,3-c]pyridine (32); or 4-(4-(4-(3-(3,4-dimethoxyphenyl)-1,2-dimethyl-1H-pyrrolo[2,3-c]pyridin-5-yl)phenyl)piperazin-1-yl)-2-methylbutan-2-ol (33).

One embodiment provides a compound of Formula (I) or stereoisomers, tautomer, solvates or salts thereof, wherein said compound is: ethyl 4-(2-(3,4-dimethoxyphenyl)-1-methyl-1H-pyrrolo[3,2-c]pyridin-6-yl)-[1,4'-bipiperidine]-1'-carboxylate (7); 2-(3,4-dimethoxyphenyl)-1-methyl-6-(1-((6-methylpyridin-3-yl)methyl)piperidin-4-yl)-1H-pyrrolo[3,2-c]pyridine (8); 6-(4-(4-(cyclopropylmethyl)piperazin-1-yl)phenyl)-2-(3,4-dimethoxyphenyl)-1-methyl-1H-pyrrolo[3,2-c]pyridine (9); 6-(4-(4-cyclobutylpiperazin-1-yl)phenyl)-2-(3,4-dimethoxyphenyl)-1-methyl-1H-pyrrolo[3,2-c]pyridine (10); 6-(4-(4-isopropylpiperazin-1-yl)phenyl)-1,4-dimethyl-2-(4-(methylsulfonyl)phenyl)-1H-pyrrolo[3,2-c]pyridine (11); 6-(3-fluoro-4-(4-isopropylpiperazin-1-yl)phenyl)-1,4-dimethyl-2-(4-(methylsulfonyl) phenyl)-1H-pyrrolo[3,2-c]pyridine (12); 2-(3,4-dimethoxyphenyl)-6-(4-(4-isopropylpiperazin-1-yl)phenyl)-1-methyl-1H-pyrrolo[3,2-c]pyridine (24); 1-(4-(2-(3,4-dimethoxyphenyl)-1-methyl-1H-pyrrolo[3,2-c]pyridin-6-yl)piperidin-1-yl)-2-(piperidin-1-yl)ethan-1-one (25); (4-(2-(3,4-dimethoxyphenyl)-1-methyl-1H-pyrrolo[3,2-c]pyridin-6-yl)-[1,4'-bipiperidin]-1'-yl)(phenyl)methanone (26); 2-(3,4-dimethoxyphenyl)-1-methyl-6-(4-(4-methylpiperazin-1-yl)phenyl)-1H-pyrrolo[3,2-c]pyridine (27); 2-(3,4-dimethoxyphenyl)-1-methyl-6-(1-((6-(trifluoromethyl)pyridin-3-yl)methyl)piperidin-4-yl)-1H-pyrrolo[3,2-c]pyridine (28); (4-(4-(2-(3,4-dimethoxyphenyl)-1-methyl-1H-pyrrolo[3,2-c]pyridin-6-yl)phenyl)piperazin-1-yl)(phenyl)methanone (29); 1-(4-(4-(2-(3,4-dimethoxyphenyl)-1-methyl-1H-pyrrolo[3,2-c]pyridin-6-yl)phenyl)piperazin-1-yl) ethan-1-one (30); 2-(3,4-dimethoxyphenyl)-6-(6-(4-isopropylpiperazin-1-yl)pyridin-3-yl)-1-methyl-1H-pyrrolo[3,2-c]pyridine (31); 6-(4-(4-isobutylpiperazin-1-yl)phenyl)-1,4-dimethyl-2-(4-(methylsulfonyl)phenyl)-1H-pyrrolo[3,2-c]pyridine (34); 1,4-dimethyl-2-(4-(methylsulfonyl)phenyl)-6-(4-(4-(tetrahydro-2H-pyran-4-yl)piperazin-1-yl)phenyl)-1H-pyrrolo[3,2-c]pyridine (35); 3-(4-(4-(1,4-dimethyl-2-(4-(methylsulfonyl)phenyl)-1H-pyrrolo[3,2-c]pyridin-6-yl)phenyl) piperazin-1-yl)propan-1-ol (36); 1,4-dimethyl-2-(4-(methylsulfonyl)phenyl)-6-(4-(4-(tetrahydrofuran-3-yl) piperazin-1-yl)phenyl)-1H-pyrrolo[3,2-c]pyridine (37); 6-(4-(4-(2-methoxyethyl)piperazin-1-yl)phenyl)-1,4-dimethyl-2-(4-(methylsulfonyl)phenyl)-1H-pyrrolo[3,2-c]pyridine (38); 6-(4-(4-isopropylpiperazin-1-yl)phenyl)-1,4-dimethyl-2-(3-(methylsulfonyl)phenyl)-1H-pyrrolo[3,2-c] pyridine (39); 6-(4-(4-isobutylpiperazin-1-yl)phenyl)-1,4-dimethyl-2-(3-(methylsulfonyl)phenyl)-1H-pyrrolo[3,2-c] pyridine (40); 3-(4-(4-(1,4-dimethyl-2-(4-(methylsulfonyl) phenyl)-1H-pyrrolo[3,2-c]pyridin-6-yl)phenyl)piperidin-1-yl)propan-1-ol (41); 2-(4-(cyclopropylsulfonyl)phenyl)-6-(4-(4-isopropylpiperazin-1-yl)phenyl)-1,4-dimethyl-1H-pyrrolo[3,2-c]pyridine (42); 6-(2,5-difluoro-4-(piperazin-1-yl)phenyl)-1,4-dimethyl-2-(4-(methylsulfonyl)phenyl)-1H-pyrrolo[3,2-c]pyridine (43); 1-(4-(4-(1,4-dimethyl-2-(4-(methylsulfonyl)phenyl)-1H-pyrrolo[3,2-c]pyridin-6-yl) benzyl)piperazin-1-yl)-2-methylpropan-2-ol (44); 3-((1R,4R)-5-(4-(1,4-dimethyl-2-(4-(methylsulfonyl) phenyl)-1H-pyrrolo[3,2-c]pyridin-6-yl)benzyl)-2,5-diazabicyclo[2.2.2]octan-2-yl)-2,2-dimethylpropan-1-ol (45); 2-(4-(cyclopropylsulfonyl)phenyl)-6-(4-(4-isobutylpiperazin-1-yl)phenyl)-1,4-dimethyl-1H-pyrrolo[3,2-c]pyridine (46); 3-(4-(4-(2-(4-(cyclopropylsulfonyl)phenyl)-1,4-dimethyl-1H-pyrrolo[3,2-c]pyridin-6-yl)phenyl) piperazin-1-yl)propan-1-ol (47); 2-(4-(cyclopropylsulfonyl)phenyl)-6-(4-(4-(2-methoxyethyl)piperazin-1-yl)phenyl)-1,4-dimethyl-1H-pyrrolo[3,2-c]pyridine (48); 4-(6-(4-(4-isopropylpiperazin-1-yl)phenyl)-1,4-dimethyl-1H-pyrrolo[3,2-c]pyridin-2-yl)-N,N-dimethylbenzenesulfonamide (49); 4-(1,4-dimethyl-6-(4-(4-(oxetan-3-yl)piperazin-1-yl) phenyl)-1H-pyrrolo[3,2-c]pyridin-2-yl)-N,N-dimethylbenzenesulfonamide (50); 4-(6-(4-(4-(2-methoxyethyl)piperazin-1-yl)phenyl)-1,4-dimethyl-1H-pyrrolo[3,2-c]pyridin-2-yl)-N,N-dimethylbenzenesulfonamide (51); 4-(1,4-dimethyl-6-(4-(4-(tetrahydrofuran-3-yl) piperazin-1-yl)phenyl)-1H-pyrrolo[3,2-c]pyridin-2-yl)-N,N-dimethylbenzenesulfonamide (52); 6-(4-(4-isobutylpiperazin-1-yl)phenyl)-1-methyl-2-(4-(methylsulfonyl)phenyl)-1H-pyrrolo[3,2-c]pyridine (53); 6-(4-(4-isopropylpiperazin-1-yl)phenyl)-1-methyl-2-(4-(methylsulfonyl)phenyl)-1H-pyrrolo[3,2-c]pyridine (54); 3-(4-(4-(1,4-dimethyl-2-(4-(methylsulfonyl)phenyl)-1H-pyrrolo[3,2-c]pyridin-6-yl)-2,3-difluorophenyl)piperazin-1-yl)propan-1-ol (55); 3-(4-(4-(1,4-dimethyl-2-(4-(methylsulfonyl)phenyl)-1H-pyrrolo[3,2-c]pyridin-6-yl)-2,5-difluorophenyl)piperazin-1-yl)propan-1-ol (56); 6-(4-((4-isobutylpiperazin-1-yl)methyl)phenyl)-1,4-dimethyl-2-(4-(methylsulfonyl)phenyl)-1H-pyrrolo[3,2-c]pyridine (57); 3-(4-(4-(1,4-dimethyl-2-(4-(methylsulfonyl)phenyl)-1H-pyrrolo[3,2-c]pyridin-6-yl)benzyl)piperazin-1-yl)propan-1-ol (58); 1-(4-(1,4-dimethyl-2-(4-(methylsulfonyl)phenyl)-1H-pyrrolo[3,2-c]pyridin-6-yl)benzyl)-4-methylpiperidin-4-ol (59); 4-(4-(4-(1,4-dimethyl-2-(4-(methylsulfonyl) phenyl)-1H-pyrrolo[3,2-c]pyridin-6-yl)benzyl)piperazin-1-yl)-2-methylbutan-2-ol (60); 4-((1S,4S)-5-(4-(1,4-dimethyl-2-(4-(methylsulfonyl)phenyl)-1H-pyrrolo[3,2-c]pyridin-6-yl)benzyl)-2,5-diazabicyclo[2.2.2]octan-2-yl)-2-methylbutan-2-ol (61); 6-(4-(4-cyclopropylpiperazin-1-yl) phenyl)-1,4-dimethyl-2-(4-(methylsulfonyl)phenyl)-1H-pyrrolo[3,2-c]pyridine (62); 6-(4-(hexahydropyrrolo[1,2-a] pyrazin-2(1H)-yl)phenyl)-1,4-dimethyl-2-(4-(methylsulfonyl)phenyl)-1H-pyrrolo[3,2-c]pyridine (63); 6-(4-(8-isopropyl-3,8-diazabicyclo[3.2.1]octan-3-yl)phenyl)-1,4-dimethyl-2-(4-(methylsulfonyl)phenyl)-1H-pyrrolo[3,2-c]pyridine (64); 6-(3-fluoro-4-(hexahydropyrrolo[1,2-a]pyrazin-2(1H)-yl) phenyl)-1,4-dimethyl-2-(4-(methylsulfonyl)phenyl)-1H-pyrrolo[3,2-c]pyridine (65); 6-(3-fluoro-4-(4-(2-methoxyethyl)piperazin-1-yl)phenyl)-1,4-dimethyl-2-(4-(methylsulfonyl) phenyl)-1H-pyrrolo[3,2- c]pyridine (66); 6-(3-(4-isopropylpiperazin-1-yl)phenyl)-1,4-dimethyl-2-(4-(methylsulfonyl)phenyl)-1H-pyrrolo[3,2-c]pyridine (67); 6-(3-(4-cyclopropylpiperazin-1-yl)phenyl)-1,4-dimethyl-2-(4-(methylsulfonyl)phenyl)-1H-pyrrolo[3,2-c]pyridine (68); 2-(4-(4-(1,4-dimethyl-2-(4-(methylsulfonyl)phenyl)-1H-pyrrolo[3,2-c]pyridin-6-yl)-2-fluorophenyl)piperazin-1-yl)ethan-1-ol (69); 6-(3-fluoro-4-(4-(tetrahydrofuran-3-yl)piperazin-1-yl)phenyl)-1,4-dimethyl-2-(4-(methylsulfonyl) phenyl)-1H-pyrrolo[3,2-c]pyridine (70); 6-(3-fluoro-4-(4-(tetrahydro-2H-pyran-4-yl) piperazin-1-yl)phenyl)-1,4-dimethyl-2-(4-(methylsulfonyl) phenyl)-1H-pyrrolo[3,2-c]pyridine (71); 6-(3-fluoro-4-(4-isobutylpiperazin-1-yl)phenyl)-1,4-dimethyl-2-(4-(methylsulfonyl)phenyl)-1H-pyrrolo[3,2-c]pyridine (72); 6-(4-(8-isobutyl-3,8-diazabicyclo[3.2.1]octan-3-yl)phenyl)-1,4-dimethyl-2-(4-(methylsulfonyl)phenyl)-1H-pyrrolo[3,2-c] pyridine (73); 6-(4-(8-(2-methoxyethyl)-3,8-diazabicyclo [3.2.1]octan-3-yl) phenyl)-1,4-dimethyl-2-(4-(methylsulfonyl)phenyl)-1H-pyrrolo[3,2-c]pyridine (74); 6-(3-fluoro-4-(8-(2-methoxyethyl)-3,8-diazabicyclo[3.2.1] octan-3-yl)phenyl)-1,4-dimethyl-2-(4-(methylsulfonyl)phenyl)-1H-pyrrolo[3,2-c]pyridine (75); 3-(3-(4-(1,4-dimethyl-2-(4-(methylsulfonyl)phenyl)-1H-pyrrolo[3,2-c]pyridin-6-yl)phenyl)-3,8-diazabicyclo[3.2.1]octan-8-yl)propan-1-ol (76); 3-(3-(4-(1,4-dimethyl-2-(4-(methylsulfonyl)phenyl)-1H-pyrrolo[3,2-c]pyridin-6-yl)-2-fluorophenyl)-3,8-diazabicyclo[3.2.1]octan-8-yl)propan-1-ol (77); 6-(2,5-difluoro-4-(8-(2-methoxyethyl)-3,8-diazabicyclo[3.2.1]octan-3-yl) phenyl)-1,4-dimethyl-2-(4-(methylsulfonyl)phenyl)-1H-pyrrolo[3,2-c]pyridine (78); 3-(3-(4-(1,4-dimethyl-2-(4-(methylsulfonyl)phenyl)-1H-pyrrolo[3,2-c]pyridin-6-yl)-2,5-difluorophenyl)-3,8-diazabicyclo[3.2.1]octan-8-yl) propan-1-ol (79-80); 6-(2,5-difluoro-4-(4-(tetrahydro-2H-pyran-4-yl)piperazin-1-yl) phenyl)-1,4-dimethyl-2-(4-(methylsulfonyl)phenyl)-1H-pyrrolo[3,2-c]pyridine (81); 6-(2,3-difluoro-4-(4-isobutylpiperazin-1-yl)phenyl)-1,4-dimethyl-2-(4-(methylsulfonyl) phenyl)-1H-pyrrolo[3,2-c] pyridine (82); 6-(2,3-difluoro-4-(4-(tetrahydro-2H-pyran-4-yl) piperazin-1-yl)phenyl)-1,4-dimethyl-2-(4-(methylsulfonyl)phenyl)-1H-pyrrolo[3,2-c]pyridine (83); 6-(3,5-difluoro-4-(4-isobutylpiperazin-1-yl)phenyl)-1,4-dimethyl-2-(4-(methylsulfonyl)phenyl)-1H-pyrrolo[3,2-c] pyridine (84); 4-(4-(1,4-dimethyl-2-(4-(methylsulfonyl)phenyl)-1H-pyrrolo[3,2-c]pyridin-6-yl)phenyl)thiomorpholine 1,1-dioxide (85); 4-(4-(1,4-dimethyl-2-(4-(methylsulfonyl) phenyl)-1H-pyrrolo[3,2-c]pyridin-6-yl)phenyl)morpholine (86); 1-cyclopropyl-4-(4-(1,4-dimethyl-2-(4-(methylsulfonyl) phenyl)-1H-pyrrolo[3,2-c]pyridin-6-yl)phenyl)piperidin-4-ol (87); 4-(4-(1,4-dimethyl-2-(4-(methylsulfonyl)phenyl)-1H-pyrrolo[3,2-c]pyridin-6-yl)phenyl)-1-isopropylpiperidin-4-ol (88); 6-(3,5-difluoro-4-(4-(tetrahydro-2H-pyran-4-yl)piperazin-1-yl)phenyl)-1,4-dimethyl-2-(4-(methylsulfonyl)phenyl)-1H-pyrrolo[3,2-c] pyridine (89); 4-(4-(1,4-dimethyl-2-(4-(methylsulfonyl) phenyl)-1H-pyrrolo[3,2-c]pyridin-6-yl)-2-fluorophenyl)-1-isobutylpiperidin-4-ol (90); (1R,3r,5S)-3-(4-(1,4-dimethyl-2-(4-(methylsulfonyl) phenyl)-1H-pyrrolo[3,2-c]pyridin-6-yl)-2-fluorophenyl)-8-isobutyl-8-azabicyclo[3.2.1]octan-3-ol (91); 4-(4-(1,4-dimethyl-2-(4-(methylsulfonyl)phenyl)-1H-pyrrolo[3,2-c]pyridin-6-yl)-2-fluorophenyl)-1-(2-methoxyethyl)piperidin-4-ol (92); 1-cyclopropyl-4-(4-(1,4-dimethyl-2-(4-(methylsulfonyl)phenyl)-1H-pyrrolo[3,2-c] pyridin-6-yl)-2-fluorophenyl)piperidin-4-ol (93); 4-(4-(1,4-dimethyl-2-(4-(methylsulfonyl) phenyl)-1H-pyrrolo[3,2-c] pyridin-6-yl)-2,5-difluorophenyl)-1-isobutylpiperidin-4-ol (94); 4-(4-(1,4-dimethyl-2-(4-(methylsulfonyl)phenyl)-1H-pyrrolo[3,2-c]pyridin-6-yl)-2,5-difluorophenyl)-1-(2-methoxyethyl)piperidin-4-ol (95); 1-cyclopropyl-4-(4-(1,4-dimethyl-2-(4-(methylsulfonyl)phenyl)-1H-pyrrolo[3,2-c] pyridin-6-yl)-2,5-difluorophenyl)piperidin-4-ol (96); 6-(2,5-difluoro-4-(hexahydropyrrolo[1,2-a]pyrazin-2(1H)-yl) phenyl)-1,4-dimethyl-2-(4-(methylsulfonyl)phenyl)-1H-pyrrolo[3,2-c]pyridine (97); 6-(3,5-difluoro-4-(hexahydropyrrolo[1,2-a]pyrazin-2(1H)-yl)phenyl)-1,4-dimethyl-2-(4-(methylsulfonyl)phenyl)-1H-pyrrolo[3,2-c] pyridine (98); 6-(2,3-difluoro-4-(hexahydropyrrolo[1,2-a] pyrazin-2(1H)-yl)phenyl)-1,4-dimethyl-2-(4-(methylsulfonyl) phenyl)-1H-pyrrolo[3,2-c]pyridine (99); (1R,3r,5S)-3-(4-(1,4-dimethyl-2-(4-(methylsulfonyl)phenyl)-1H-pyrrolo[3,2-c]pyridin-6-yl)-2-fluorophenyl)-8-isopropyl-8-azabicyclo[3.2.1]octan-3-ol (100); (1R,3r,5S)-3-(4-(1,4-dimethyl-2-(4-(methylsulfonyl) phenyl)-1H-pyrrolo [3,2-c]pyridin-6-yl)-2-fluorophenyl)-8-ethyl-8-azabicyclo [3.2.1]octan-3-ol (101); (1R,3r,5S)-3-(4-(1,4-dimethyl-2-(4-(methylsulfonyl) phenyl)-1H-pyrrolo[3,2-c]pyridin-6-yl)-2-fluorophenyl)-8-methyl-8-azabicyclo[3.2.1]octan-3-ol (102); (1R,3r,5S)-3-(4-(1,4-dimethyl-2-(4-(methylsulfonyl) phenyl)-1H-pyrrolo[3,2-c]pyridin-6-yl)-3-fluorophenyl)-8-isopropyl-8-azabicyclo[3.2.1]octan-3-ol (103); 1-(tert-butyl)-4-(4-(1,4-dimethyl-2-(4-(methylsulfonyl) phenyl)-1H-pyrrolo[3,2-c]pyridin-6-yl)-2-fluorophenyl)piperidin-4-ol (104); (R)-4-(4-(1,4-dimethyl-2-(4-(methylsulfonyl) phenyl)-1H-pyrrolo[3,2-c]pyridin-6-yl)-2-fluorophenyl)-1-isopropyl-2,2-dimethylpiperidin-4-ol (105); (S)-4-(4-(1,4-dimethyl-2-(4-(methylsulfonyl)phenyl)-1H-pyrrolo[3,2-c] pyridin-6-yl)-2-fluorophenyl)-1-isopropyl-2,2-dimethylpiperidin-4-ol (106); 4-(4-(1,4-dimethyl-2-(4-(methylsulfonyl)phenyl)-1H-pyrrolo[3,2-c]pyridin-6-yl)-2-fluorophenyl)-1-isopropylpiperidin-4-ol (107); 1-(tert-butyl)-4-(4-(1,4-dimethyl-2-(4-(methylsulfonyl)phenyl)-1H-pyrrolo[3,2-c]pyridin-6-yl)-3-fluorophenyl)piperidin-4-ol (108); 4-(4-(1,4-dimethyl-2-(4-(methylsulfonyl)phenyl)-1H-pyrrolo[3,2-c]pyridin-6-yl)-3-fluorophenyl)-1-isopropylpiperidin-4-ol (109); 6-(4-(4-(4-iodophenethyl) piperazin-1-yl)phenyl)-1,4-dimethyl-2-(4-(methylsulfonyl) phenyl)-1H-pyrrolo[3,2-c]pyridine (110); 6-(4-(4-(4-bromophenethyl)piperazin-1-yl)phenyl)-1,4-dimethyl-2-(4-(methylsulfonyl)phenyl)-1H-pyrrolo[3,2-c]pyridine (111); 6-(4-(4-(4-iodobenzyl)piperazin-1-yl)phenyl)-1,4-dimethyl-2-(4-(methylsulfonyl)phenyl)-1H-pyrrolo[3,2-c]pyridine (112); 6-(4-(4-(4-bromobenzyl)piperazin-1-yl)phenyl)-1,4-dimethyl-2-(4-(methylsulfonyl)phenyl)-1H-pyrrolo[3,2-c] pyridine (113); 6-(1-(8-isobutyl-8-azabicyclo[3.2.1]octan-3-yl)piperidin-4-yl)-1,4-dimethyl-2-(4-(methylsulfonyl) phenyl)-1H-pyrrolo[3,2-c]pyridine (114); 4-(4-(4-(3-fluoro-1,4-dimethyl-2-(4-(methylsulfonyl)phenyl)-1H-pyrrolo[3,2-c]pyridin-6-yl)benzyl)piperazin-1-yl)-2-methylbutan-2-ol (115); 4-[4-[[4-[1-cyclopropyl-4-methyl-2-(4-methylsulfonylphenyl)pyrrolo[3,2-c]pyridin-6-yl]phenyl]methyl]piperazin-1-yl]-2-methyl-butan-2-ol (116); 4-[4-[[4-[1-(difluoromethyl)-4-methyl-2-(4-methylsulfonylphenyl)pyrrolo[3,2-c]pyridin-6-yl]phenyl]methyl]piperazin-1-yl]-2-methyl-butan-2-ol (117); 2-[6-[4-(4-isopropylpiperazin-1-yl) phenyl]-1-methyl-2-(4-methylsulfonylphenyl)pyrrolo[3,2-c]pyridin-4-yl]propan-2-ol (118); 6-[4-(4-isopropylpiperazin-1-yl)phenyl]-4-methoxy-1-methyl-2-(4-methylsulfonylphenyl) pyrrolo[3,2-c]pyridine (119); 4-[6-[4-(4-isopropylpiperazin-1-yl)phenyl]-1-methyl-2-(4-methylsulfonylphenyl)pyrrolo[3,2-c]pyridin-4-yl] morpholine (120); 1-[3-[[4-[1-cyclopropyl-2-(4-methylsulfonylphenyl)pyrrolo[3,2-c]pyridin-6-yl]phenyl] methyl]-3,8-diazabicyclo[3.2.1]octan-8-yl]-2-methyl-propan-2-ol (121); 1-(4-(4-(3-fluoro-1,4-dimethyl-2-(4-(methylsulfonyl)phenyl)-1H-pyrrolo[3,2-c]pyridin-6-yl)

benzyl)piperazin-1-yl)-2-methylpropan-2-ol (122); 1-(4-(4-(1-cyclopropyl-4-methyl-2-(4-(methylsulfonyl) phenyl)-1H-pyrrolo[3,2-c]pyridin-6-yl)benzyl)piperazin-1-yl)-2-methylpropan-2-ol (123); 1-(4-(4-(1-(difluoromethyl)-4-methyl-2-(4-(methylsulfonyl)phenyl)-1H-pyrrolo[3,2-c]pyridin-6-yl)benzyl)piperazin-1-yl)-2-methylpropan-2-ol (124); 2-(6-(4-((4-isopropylpiperazin-1-yl)methyl)phenyl)-1-methyl-2-(4-(methylsulfonyl)phenyl)-1H-pyrrolo[3,2-c]pyridin-4-yl)propan-2-ol (125); 6-(4-((4-isopropylpiperazin-1-yl)methyl) phenyl)-4-methoxy-1-methyl-2-(4-(methylsulfonyl)phenyl)-1H-pyrrolo[3,2-c]pyridine (126); 4-(6-(4-((4-isopropylpiperazin-1-yl)methyl)phenyl)-1-methyl-2-(4-(methylsulfonyl)phenyl)-1H-pyrrolo[3,2-c]pyridin-4-yl)morpholine (127); 1-(4-(4-(1-cyclopropyl-2-(4-(methylsulfonyl)phenyl)-1H-pyrrolo[3,2-c]pyridin-6-yl) benzyl) piperazin-1-yl)-2-methylpropan-2-ol (128); 4-(4-(4-(1-cyclopropyl-2-(4-(methylsulfonyl) phenyl)-1H-pyrrolo[3,2-c]pyridin-6-yl)benzyl)piperazin-1-yl)-2-methylbutan-2-ol (129); or 1-(8-(4-(1-cyclopropyl-2-(4-(methylsulfonyl) phenyl)-1H-pyrrolo[3,2-c]pyridin-6-yl) benzyl)-3,8-diazabicyclo[3.2.1]octan-3-yl)-2-methylpropan-2-ol (130).

One embodiment provides compounds of the Formula (I) having TLR9 $IC_{50}$ values of ≤0.6 μM.

One embodiment provides compounds of the Formula (I) having TLR9 $IC_{50}$ values of ≤0.1 μM.

One embodiment provides compounds of the Formula (I) having TLR9 $IC_{50}$ values of ≤0.05 μM.

One embodiment provides compounds of the Formula (I) having TLR9 $IC_{50}$ values of ≤0.025 μM.

One embodiment provides compounds of the Formula (I) having TLR9 $IC_{50}$ values of ≤0.015 μM.

One embodiment provides compounds of the Formula (I) having TLR9 $IC_{50}$ values of ≤0.01 μM.

In another embodiment, the present invention provides a composition comprising at least one of the compounds of the present invention, or a stereoisomer, a tautomer, or a pharmaceutically acceptable salt or a solvate thereof.

In another embodiment, the present invention provides a pharmaceutical composition comprising a pharmaceutically acceptable carrier and at least one of the compounds of the present invention or a stereoisomer, a tautomer, or a pharmaceutically acceptable salt or a solvate thereof.

In another embodiment, the present invention provides a pharmaceutical composition, comprising a pharmaceutically acceptable carrier and a therapeutically effective amount of at least one of the compounds of the present invention or a stereoisomer, a tautomer, or a pharmaceutically acceptable salt or a solvate thereof.

In another embodiment, the present invention provides a process for making a compound of the present invention.

In another embodiment, the present invention provides an intermediate for making a compound of the present invention.

In another embodiment, the present invention provides a pharmaceutical composition as defined above further comprising one or more additional therapeutic agents.

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

As used herein, the phase "compounds" refers to at least one compound. For example, a compound of Formula (I) includes a compound of Formula (I) and two or more compounds of Formula (I).

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "cyano" refers to the group —CN.

The term "amino" refers to the group $—NH_2$.

The term "oxo" refers to the group =O.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_{1-6}$ alkyl" denotes straight and branched chain alkyl groups with one to six carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, $—CF_3$ and $—CH_2CF_3$.

The term "hydroxyalkyl" includes both branched and straight-chain saturated alkyl groups substituted with one or more hydroxyl groups. For example, "hydroxyalkyl" includes $—CH_2OH$, $—CH_2CH_2OH$, and $C_{1-4}$ hydroxyalkyl.

The term "aminoalkyl" includes both branched and straight-chain saturated alkyl groups substituted with one or more amine groups. For example, "aminoalkyl" includes $—CH_2NH_2$, $—CH_2CH_2NH_2$, and $C_{1-4}$ aminoalkyl.

The term "cyanoalkyl" includes both branched and straight-chain saturated alkyl groups substituted with one or more cyano groups. For example, "aminoalkyl" includes $—CH_2CN$, $—CH_2CH_2CN$, and $C_{1-4}$ cyanoalkyl.

The term "alkoxy," as used herein, refers to an alkyl group attached to the parent molecular moiety through an oxygen atom, for example, methoxy group ($—OCH_3$). For example, "$C_{1-3}$ alkoxy" denotes alkoxy groups with one to three carbon atoms.

The terms "fluoroalkoxy" and "—O(fluoroalkyl)" represent a fluoroalkyl group as defined above attached through an oxygen linkage (—O—). For example, "$C_{1-4}$ fluoroalkoxy" is intended to include $C_1$, $C_2$, $C_3$, and $C_4$ fluoroalkoxy groups.

The term "alkoxyalkyl," as used herein, refers to an alkoxy group attached through its oxygen atom to an alkyl group, which is attached to the parent molecular moiety through a carbon atom, for example, methoxymethyl group ($—CH_2OCH_3$). For example, "$C_{2-4}$ alkoxyalkyl" denotes alkoxyalkyl groups with two to four carbon atoms, such as $—CH_2OCH_3$, $—CH_2CH_2OCH_3$, $—CH_2OCH_2CH_3$, and $—CH_2CH_2OCH_2CH_3$.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_{3-6}$ cycloalkyl" denotes cycloalkyl groups with three to six carbon atoms.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The compounds of Formula (I) can be provided as amorphous solids or crystalline solids. Lyophilization can be employed to provide the compounds of Formula (I) as amorphous solids.

It should further be understood that solvates (e.g., hydrates) of the compounds of Formula (I) are also within the scope of the present invention. The term "solvate" means a physical association of a compound of Formula (I) with one or more solvent molecules, whether organic or inorganic. This physical association includes hydrogen bonding. In certain instances the solvate will be capable of isolation, for example when one or more solvent molecules are incorporated in the crystal lattice of the crystalline solid. "Solvate" encompasses both solution-phase and isolable solvates. Exemplary solvates include hydrates, ethanolates, methanolates, isopropanolates, acetonitrile solvates, and ethyl acetate solvates. Methods of solvation are known in the art.

Various forms of prodrugs are well known in the art and are described in Rautio, J. et al., *Nature Review Drug Discovery,* 17, 559-587 (2018).

In addition, compounds of Formula (I), subsequent to their preparation, can be isolated and purified to obtain a composition containing an amount by weight equal to or greater than 99% of a compound of Formula (I), respectively ("substantially pure"), which is then used or formulated as described herein. Such "substantially pure" compounds of Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an inhibitor of TLR9, or effective to treat or prevent disorders associated with a fibrotic disease or disorder, dysregulation of bile acids, such as pathological fibrosis.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting its development; and/or (c) relieving the disease-state, i.e., causing regression of the disease state.

The compounds of the present invention are intended to include all isotopes of atoms occurring in the present compounds. Isotopes include those atoms having the same atomic number but different mass numbers. By way of general example and without limitation, isotopes of hydrogen include deuterium (D) and tritium (T). Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. For example, methyl ($—CH_3$) also includes deuterated methyl groups such as $—CD_3$.

Utility

The compounds of the invention are useful for inhibiting the TLR9 receptor.

One embodiment provides a method for the treatment of a disease, disorder, or condition associated with dysregulation of bile acids in a patient in need of such treatment, and the method comprises administering a therapeutically effective amount of a compound of the present invention, or a stereoisomer, a tautomer, or a pharmaceutically acceptable salt or solvate thereof, to the patient.

One embodiment provides a method for the treatment of a disease, disorder, or condition associated with activity of the TLR9 receptor in a patient in need of such treatment comprising administering a therapeutically effective amount of a compound of the present invention, or a stereoisomer, a tautomer, or a pharmaceutically acceptable salt or solvate thereof, to the patient.

One embodiment provides a method for the treatment of the disease, disorder, or condition comprising administering to a patient in need of such treatment a therapeutically effective amount of at least one of the compounds of the present invention, alone, or, optionally, in combination with another compound of the present invention and/or at least one other type of therapeutic agent.

One embodiment provides a method for eliciting an TLR9 receptor agonizing effect in a patient comprising administering a therapeutically effective amount of a compound of the present invention, or a stereoisomer, a tautomer, or a pharmaceutically acceptable salt or solvate thereof, to the patient.

In some embodiments, the disease, disorder, or condition is associated with TLR9 dysfunction include pathological fibrosis, cancer, inflammatory disorders, metabolic, or cholestatic disorders.

In some embodiments, the disease, disorder, or condition is associated with fibrosis, including liver, biliary, renal, cardiac, dermal, ocular, and pancreatic fibrosis.

In other embodiments, the disease, disorder, or condition is associated with cell-proliferative disorders, such as cancer. In some embodiments, the cancer includes solid tumor growth or neoplasia. In other embodiments, the cancer includes tumor metastasis. In some embodiments, the cancer is of the liver, gall bladder, small intestine, large intestine, kidney, prostate, bladder, blood, bone, brain, breast, central nervous system, cervix, colon, endometrium, esophagus, genitalia, genitourinary tract, head, larynx, lung, muscle tissue, neck, oral or nasal mucosa, ovary, pancreas, skin, spleen, stomach, testicle, or thyroid. In other embodiments, the cancer is a carcinoma, sarcoma, lymphoma, leukemia, melanoma, mesothelioma, multiple myeloma, or seminoma.

Examples of diseases, disorders, or conditions associated with the activity of FXR that can be prevented, modulated, or treated according to the present invention include, but are not limited to, transplant injection, fibrotic disorders (e.g., liver fibrosis, kidney fibrosis), inflammatory disorders (e.g., acute hepatitis, chronic hepatitis, non-alcoholic steatohepatitis (NASH), irritable bowel syndrome (IBS), inflammatory bowel disease (IBD)), as well as cell-proliferative disorders (e.g., cancer, myeloma, fibroma, hepatocellular carcinoma, colorectal cancer, prostate cancer, leukemia, Kaposi's sarcoma, solid tumors).

The fibrotic disorders, inflammatory disorders, as well as cell-proliferative disorders that are suitable to be prevented or treated by the compounds of the present invention include, but are not limited to, non-alcoholic fatty liver disease (NAFLD), alcoholic or non-alcoholic steatohepatitis (NASH), acute hepatitis, chronic hepatitis, liver cirrhosis, primary biliary cirrhosis, primary sclerosing cholangitis, drug-induced hepatitis, biliary cirrhosis, portal hypertension, regenerative failure, liver hypofunction, hepatic blood flow disorder, nephropathy, irritable bowel syndrome (IBS), inflammatory bowel disease (IBD), abnormal pancreatic secretion, benign prostatic hyperplasia, neuropathic bladder disease, diabetic nephropathy, focal segmental glomerulosclerosis, IgA nephropathy, nephropathy induced by drugs or transplantation, autoimmune nephropathy, lupus nephritis, liver fibrosis, kidney fibrosis, chronic kidney disease (CKD), diabetic kidney disease (DKD), skin fibrosis, keloids, systemic sclerosis, scleroderma, virally-induced fibrosis, idiopathic pulmonary fibrosis (IPF), interstitial lung disease, non-specific interstitial pneumonia (NSIP), usual interstitial pneumonia (UIP), radiation-induced fibrosis, familial pulmonary fibrosis, airway fibrosis, chronic obstructive pulmonary disease (COPD), spinal cord tumor, hernia of intervertebral disk, spinal canal stenosis, heart failure, cardiac fibrosis, vascular fibrosis, perivascular fibrosis, foot-and-mouth disease, cancer, myeloma, fibroma, hepatocellular carcinoma, colorectal cancer, prostate cancer, leukemia, chronic lymphocytic leukemia, Kaposi's sarcoma, solid tumors, cerebral infarction, cerebral hemorrhage, neuropathic pain, peripheral neuropathy, age-related macular degeneration (AMD), glaucoma, ocular fibrosis, corneal scarring, diabetic retinopathy, proliferative vitreoretinopathy (PVR), cicatricial pemphigoid glaucoma filtration surgery scarring, Crohn's disease or systemic lupus erythematosus; keloid formation resulting from abnormal wound healing; fibrosis occurring after organ transplantation, myelofibrosis, and fibroids. In one embodiment, the present invention provides a method for the treatment of a fibrotic disorder, an inflammatory disorder, or a cell-proliferative disorder, comprising administering to a patient in need of such treatment a therapeutically effective amount of at least one of the compounds of the present invention, alone, or, optionally, in combination with another compound of the present invention and/or at least one other type of therapeutic agent.

In another embodiment, the present invention provides a compound of the present invention for use in therapy.

In another embodiment, the present invention provides a compound of the present invention for use in therapy for the treatment of a fibrotic disorder, an inflammatory disorder, or a cell-proliferative disorder thereof.

In another embodiment, the present invention also provides the use of a compound of the present invention for the manufacture of a medicament for the treatment of a fibrotic disorder, an inflammatory disorder, or a cell-proliferative disorder thereof.

In another embodiment, the present invention provides a method for the treatment of a fibrotic disorder, an inflammatory disorder, or a cell-proliferative disorder, comprising administering to a patient in need thereof a therapeutically effective amount of a first and second therapeutic agent, wherein the first therapeutic agent is a compound of the present invention.

In another embodiment, the present invention provides a combined preparation of a compound of the present invention and additional therapeutic agent(s) for simultaneous, separate or sequential use in therapy.

In another embodiment, the present invention provides a combined preparation of a compound of the present invention and additional therapeutic agent(s) for simultaneous, separate or sequential use in the treatment of a fibrotic disorder, an inflammatory disorder, or a cell-proliferative disorder.

The compounds of the present invention may be employed in combination with additional therapeutic agent(s), such as one or more anti-fibrotic and/or anti-inflammatory therapeutic agents.

In one embodiment, additional therapeutic agent(s) used in combined pharmaceutical compositions or combined methods or combined uses, are selected from one or more, preferably one to three, of the following therapeutic agents: TGFβ receptor inhibitors (for example, galunisertib), inhibitors of TGFβ synthesis (for example, pirfenidone), inhibitors of vascular endothelial growth factor (VEGF), platelet-derived growth factor (PDGF) and fibroblast growth factor (FGF) receptor kinases (for example, nintedanib), humanized anti-αvβ6 integrin monoclonal antibody (for example, 3G9), human recombinant pentraxin-2, recombinant human Serum Amyloid P, recombinant human antibody against TGFβ-1, -2, and -3, endothelin receptor antagonists (for example, macitentan), interferon gamma, c-Jun amino-terminal kinase (INK) inhibitor (for example, 4-[[9-[(3S)-tetrahydro-3-furanyl]-8-[(2,4,6-trifluorophenyl)amino]-9H-purin-2-yl]amino]-trans-cyclohexanol, 3-pentylbenzeneacetic acid (PBI-4050), tetra-substituted porphyrin derivative containing manganese (III), monoclonal antibody targeting eotaxin-2, interleukin-13 (IL-13) antibody (for example, lebrikizumab, tralokinumab), bispecific antibody targeting interleukin 4 (IL-4) and interleukin 13 (IL-13), NK1 tachykinin receptor agonist (for example, $Sar^9$, $Met(O_2)^{11}$-Substance P), Cintredekin Besudotox, human recombinant DNA-derived, IgG1 kappa monoclonal antibody to connective growth factor, and fully human IgG1 kappa antibody, selective for CC-chemokine ligand 2 (for example, carlumab, CCX140), antioxidants (for example, N-acetylcysteine), phosphodiesterase 5 (PDE5) inhibitors (for example, sildenafil), agents for treatment of obstructive airway diseases such as muscarinic antagonists (for example, tiotropium, ipatropium bromide), adrenergic β2 agonists (for example, salbutamol, salmeterol), corticosteroids (for example, triamcinolone, dexamethasone, fluticasone), immunosuppressive agents (for example, tacrolimus, rapamycin, pimecrolimus), and therapeutic agents useful for the treatment of fibrotic conditions, such as liver, biliary, and kidney fibrosis, Non-Alcoholic Fatty Liver Disease (NALFD), Non-Alcoholic SteatoHepatitis (NASH), cardiac fibrosis, Idiopathic Pulmonary Fibrosis (IPF), and systemic sclerosis. The therapeutic agents useful for the treatment of such fibrotic conditions include, but are not limited to, FXR agonists (for example OCA, GS-9674, and LJN452), LOXL2 inhibitors (for example simtuzumab), LPA1 antagonists (for example, BMS-986020 and SAR 100842), PPAR modulators (for example, elafibrinor, pioglitazone, and saroglitazar, IVA337), SSAO/VAP-1 inhibitors (for example, PXS-4728A and SZE5302), ASK-1 inhibitors (for example GS-4997 or selonsertib), ACC inhibitors (for example, CP-640186 and NDI-010976 or GS-0976), FGF21 mimetics (for example, LY2405319 and BMS-986036), caspase inhibitors (for example, emricasan), NOX4 inhibitors (for example, GKT137831), MGAT2 inhibitor (for example, BMS-963272), αV integrin inhibitors (for example, abituzumab) and bile acid/fatty acid conjugates (for example aramchol). The FXR agonists of various embodiments of the present invention may also be used in combination with one or more therapeutic agents such as CCR2/5 inhibitors (for example, cenicriviroc), Galectin-3 inhibitors (for example, TD-139, GR-MD-02), leukotriene receptor antagonists (for example, tipelukast, montelukast), SGLT2 inhibitors (for example, dapagliflozin, remogliflozin), GLP-1 receptor agonists (for example, liraglutide and semaglutide), FAK inhibitors (for example, GSK-2256098), CB1 inverse agonists (for example, JD-5037), CB2 agonists (for example, APD-371 and JBT-101), autotaxin inhibitors (for example, GLPG1690), prolyl t-RNA synthetase inhibitors (for example, halofugenone), FPR2 agonists (for example, ZK-994), and THR agonists (for example, MGL: 3196). In another embodiment, additional therapeutic agent(s) used in combined pharmaceutical compositions or combined methods or combined uses, are selected from one or more, preferably one to three, of immunoncology agents, such as Alemtuzumab, Atezolizumab, Ipilimumab, Nivolumab, Ofatumumab, Pembrolizumab, and Rituximab.

When the terms “TLR9-associated condition” or “TLR9-associated disease or disorder” are used herein, each is intended to encompass all of the conditions identified above as if repeated at length, as well as any other condition that is affected by inhibition of TLR9.

The above other therapeutic agents, when employed in combination with the compounds of the present invention, may be used, for example, in those amounts indicated in the *Physicians' Desk Reference* (PDR) or as otherwise determined by one of ordinary skill in the art. In the methods of the present invention, such other therapeutic agent(s) may be administered prior to, simultaneously with, or following the administration of the inventive compounds. The present invention also provides pharmaceutical compositions capable of treating TLR9-associated conditions.

The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

Accordingly, the present invention further includes compositions comprising one or more compounds of Formula (I) and a pharmaceutically acceptable carrier.

A “pharmaceutically acceptable carrier” refers to media generally accepted in the art for the delivery of biologically active agents to animals, in particular, mammals. Pharmaceutically acceptable carriers are formulated according to a number of factors well within the purview of those of ordinary skill in the art. These include without limitation the type and nature of the active agent being formulated; the subject to which the agent-containing composition is to be administered; the intended route of administration of the composition; and, the therapeutic indication being targeted. Pharmaceutically acceptable carriers include both aqueous and non-aqueous liquid media, as well as a variety of solid and semi-solid dosage forms. Such carriers can include a number of different ingredients and additives in addition to the active agent, such additional ingredients being included in the formulation for a variety of reasons, e.g., stabilization of the active agent, binders, etc., well known to those of ordinary skill in the art. Descriptions of suitable pharmaceutically acceptable carriers, and factors involved in their selection, are found in a variety of readily available sources such as, for example, *Remington: The Science and Practice of Pharmacy,* $22^{nd}$ Edition (2013).

Compounds in accordance with Formula (I) can be administered by any means suitable for the condition to be treated, which can depend on the need for site-specific treatment or quantity of Formula (I) compound to be delivered.

The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly, and intrasternally in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g. magnesium stearate and a disintegrating agent such as crospovidone. The carrier mixture may be filled into a gelatin capsule or compressed as a tablet. The pharmaceutical composition may be administered as an oral dosage form or an infusion, for example.

For oral administration, the pharmaceutical composition may be in the form of, for example, a tablet, capsule, liquid capsule, suspension, or liquid. The pharmaceutical composition is preferably made in the form of a dosage unit containing a particular amount of the active ingredient. For example, the pharmaceutical composition may be provided as a tablet or capsule comprising an amount of active ingredient in the range of from about 0.1 to 1000 mg, preferably from about 0.25 to 250 mg, and more preferably from about 0.5 to 100 mg. A suitable daily dose for a human or other mammal may vary widely depending on the condition of the patient and other factors, but, can be determined using routine methods.

Any pharmaceutical composition contemplated herein can, for example, be delivered orally via any acceptable and suitable oral preparations. Exemplary oral preparations, include, but are not limited to, for example, tablets, troches, lozenges, aqueous and oily suspensions, dispersible powders or granules, emulsions, hard and soft capsules, liquid capsules, syrups, and elixirs. Pharmaceutical compositions intended for oral administration can be prepared according to any methods known in the art for manufacturing pharmaceutical compositions intended for oral administration. In order to provide pharmaceutically palatable preparations, a pharmaceutical composition in accordance with the invention can contain at least one agent selected from sweetening agents, flavoring agents, coloring agents, demulcents, antioxidants, and preserving agents.

A tablet can, for example, be prepared by admixing at least one compound of Formula (I) with at least one non-toxic pharmaceutically acceptable excipient suitable for the manufacture of tablets. Exemplary excipients include, but are not limited to, for example, inert diluents, such as, for example, calcium carbonate, sodium carbonate, lactose, calcium phosphate, and sodium phosphate; granulating and disintegrating agents, such as, for example, microcrystalline cellulose, sodium crosscarmellose, corn starch, and alginic acid; binding agents, such as, for example, starch, gelatin, polyvinyl-pyrrolidone, and acacia; and lubricating agents, such as, for example, magnesium stearate, stearic acid, and talc. Additionally, a tablet can either be uncoated, or coated by known techniques to either mask the bad taste of an unpleasant tasting drug, or delay disintegration and absorption of the active ingredient in the gastrointestinal tract thereby sustaining the effects of the active ingredient for a longer period. Exemplary water soluble taste masking materials, include, but are not limited to, hydroxypropyl-methylcellulose and hydroxypropyl-cellulose. Exemplary time delay materials, include, but are not limited to, ethyl cellulose and cellulose acetate butyrate.

Hard gelatin capsules can, for example, be prepared by mixing at least one compound of Formula (I) with at least one inert solid diluent, such as, for example, calcium carbonate; calcium phosphate; and kaolin.

Soft gelatin capsules can, for example, be prepared by mixing at least one compound of Formula (I) with at least one water soluble carrier, such as, for example, polyethylene glycol; and at least one oil medium, such as, for example, peanut oil, liquid paraffin, and olive oil.

An aqueous suspension can be prepared, for example, by admixing at least one compound of Formula (I) with at least one excipient suitable for the manufacture of an aqueous suspension. Exemplary excipients suitable for the manufacture of an aqueous suspension, include, but are not limited to, for example, suspending agents, such as, for example, sodium carboxymethylcellulose, methylcellulose, hydroxypropylmethyl-cellulose, sodium alginate, alginic acid, polyvinyl-pyrrolidone, gum tragacanth, and gum acacia; dispersing or wetting agents, such as, for example, a naturally-occurring phosphatide, e.g., lecithin; condensation products of alkylene oxide with fatty acids, such as, for example, polyoxyethylene stearate; condensation products of ethylene oxide with long chain aliphatic alcohols, such as, for example heptadecaethylene-oxycetanol; condensation products of ethylene oxide with partial esters derived from fatty acids and hexitol, such as, for example, polyoxyethylene sorbitol monooleate; and condensation products of ethylene oxide with partial esters derived from fatty acids and hexitol anhydrides, such as, for example, polyethylene sorbitan monooleate. An aqueous suspension can also contain at least one preservative, such as, for example, ethyl and n-propyl p-hydroxybenzoate; at least one coloring agent; at least one flavoring agent; and/or at least one sweetening agent, including but not limited to, for example, sucrose, saccharin, and aspartame.

Oily suspensions can, for example, be prepared by suspending at least one compound of Formula (I) in either a vegetable oil, such as, for example, arachis oil; olive oil; sesame oil; and coconut oil; or in mineral oil, such as, for example, liquid paraffin. An oily suspension can also contain at least one thickening agent, such as, for example, beeswax; hard paraffin; and cetyl alcohol. In order to provide a palatable oily suspension, at least one of the sweetening agents already described hereinabove, and/or at least one flavoring agent can be added to the oily suspension. An oily suspension can further contain at least one preservative, including, but not limited to, for example, an antioxidant, such as, for example, butylated hydroxyanisol, and alpha-tocopherol.

Dispersible powders and granules can, for example, be prepared by admixing at least one compound of Formula (I) with at least one dispersing and/or wetting agent; at least one suspending agent; and/or at least one preservative. Suitable dispersing agents, wetting agents, and suspending agents are as already described above. Exemplary preservatives include, but are not limited to, for example, anti-oxidants, e.g., ascorbic acid. In addition, dispersible powders and granules can also contain at least one excipient, including, but not limited to, for example, sweetening agents; flavoring agents; and coloring agents.

An emulsion of at least one compound of Formula (I) thereof can, for example, be prepared as an oil-in-water emulsion. The oily phase of the emulsions comprising compounds of Formula (I) may be constituted from known ingredients in a known manner. The oil phase can be provided by, but is not limited to, for example, a vegetable oil, such as, for example, olive oil and arachis oil; a mineral oil, such as, for example, liquid paraffin; and mixtures thereof. While the phase may comprise merely an emulsifier, it may comprise a mixture of at least one emulsifier with a fat or an oil or with both a fat and an oil. Suitable emulsifying agents include, but are not limited to, for example, naturally-occurring phosphatides, e.g., soy bean lecithin; esters or partial esters derived from fatty acids and hexitol anhydrides, such as, for example, sorbitan monooleate; and condensation products of partial esters with ethylene oxide, such as, for example, polyoxyethylene sorbitan monooleate. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. An emulsion can also contain a sweetening agent, a flavoring agent, a preservative, and/or an antioxidant. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The compounds of Formula (I) can, for example, also be delivered intravenously, subcutaneously, and/or intramuscularly via any pharmaceutically acceptable and suitable injectable form. Exemplary injectable forms include, but are not limited to, for example, sterile aqueous solutions comprising acceptable vehicles and solvents, such as, for example, water, Ringer's solution, and isotonic sodium chloride solution; sterile oil-in-water microemulsions; and aqueous or oleaginous suspensions.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

A sterile injectable oil-in-water microemulsion can, for example, be prepared by 1) dissolving at least one compound of Formula (I) in an oily phase, such as, for example, a mixture of soybean oil and lecithin; 2) combining the Formula (I) containing oil phase with a water and glycerol mixture; and 3) processing the combination to form a microemulsion.

A sterile aqueous or oleaginous suspension can be prepared in accordance with methods already known in the art. For example, a sterile aqueous solution or suspension can be prepared with a non-toxic parenterally-acceptable diluent or solvent, such as, for example, 1,3-butane diol; and a sterile oleaginous suspension can be prepared with a sterile non-toxic acceptable solvent or suspending medium, such as, for example, sterile fixed oils, e.g., synthetic mono- or diglycerides; and fatty acids, such as, for example, oleic acid.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens, polyethoxylated castor oil such as CREMOPHOR surfactant (BASF), or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

The pharmaceutically active compounds of this invention can be processed in accordance with conventional methods of pharmacy to produce medicinal agents for administration to patients, including humans and other mammals. The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.001 to 100 mg/kg body weight, preferably between about 0.0025 and about 50 mg/kg body weight and most preferably between about 0.005 to 10 mg/kg body weight, may be appropriate. The daily dose can be administered in one to four doses per day. Other dosing schedules include one dose per week and one dose per two day cycle.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

Pharmaceutical compositions of this invention comprise at least one compound of Formula (I) and optionally an additional agent selected from any pharmaceutically acceptable carrier, adjuvant, and vehicle. Alternate compositions of this invention comprise a compound of the Formula (I) described herein, or a prodrug thereof, and a pharmaceutically acceptable carrier, adjuvant, or vehicle.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a cardiovascular disorder, diuresis, and/or natriuresis. In another embodiment, the package insert states that the pharmaceutical composition can be used in combination (as defined previously) with a second therapeutic agent to treat cardiovascular disorder, diuresis, and/or natriuresis. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, or other written sheet that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic) on which the desired information has been formed (e.g., printed or applied).

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below.

The reactions and techniques described in this section are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene et al. (*Protective Groups in Organic Synthesis*, Third Edition, Wiley and Sons (1999)).

SCHEME 1

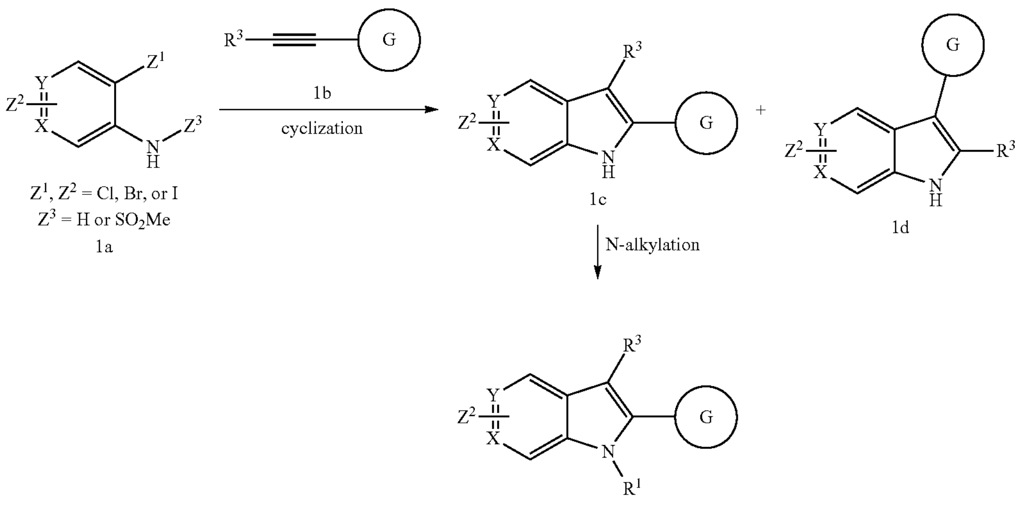

1a 1c 1d 1e

-continued

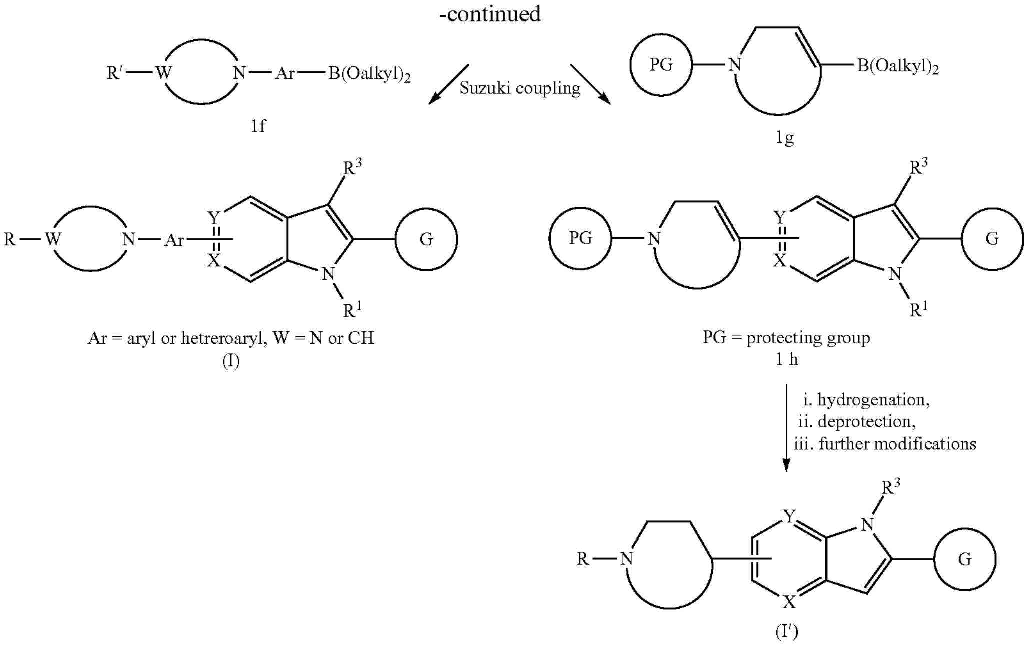

Scheme 1 describes the synthesis of compounds of Formula (I) and (I'). Cyclization of 1a and alkyne 1b in the presence of a palladium catalyst such as bis(triphenylphosphine)palladium(II) chloride together with copper(I) iodide can supply 1c and 1d. N-alkylation of 1c can provide 1e. Suzuki coupling of 1e with boronate ester if can afford the compounds of Formula (I) or the precursor to (I). Likewise, Suzuki coupling of 1e with boronate ester 1g can yield 1h, which can be converted to the compounds of Formula (I') by hydrogenation, deprotection, and further modifications.

SCHEME 2

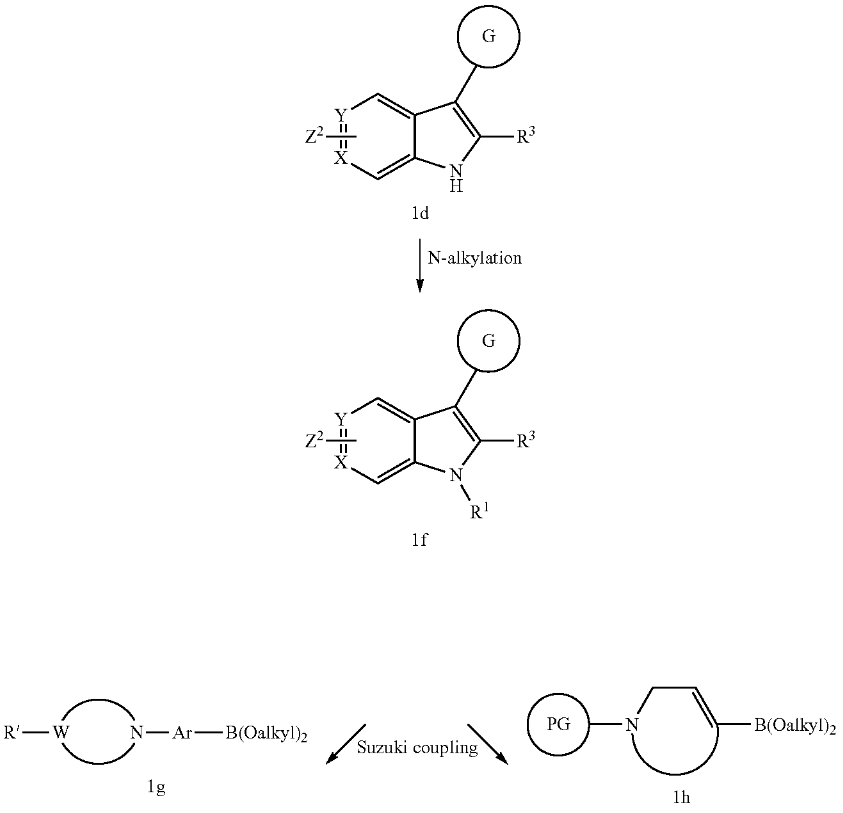

-continued

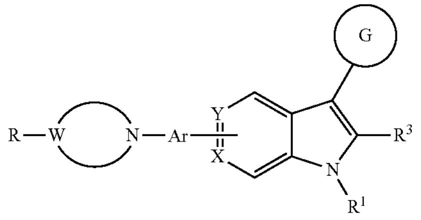

Ar = aryl or hetreroaryl, W = N or CH
(II)

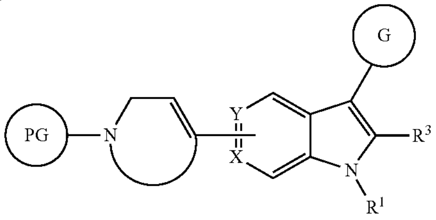

PG = protecting group
1i

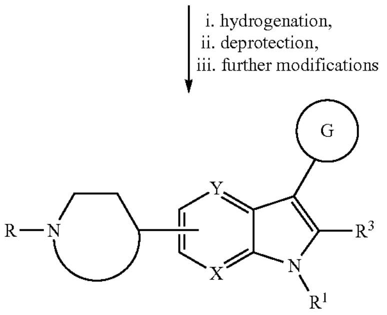

(II')

Scheme 2 describes the synthesis of compounds of Formula (II) and (II'). N-alkylation of 1d, obtained from the cyclization of 1a and alkyne 1b in Scheme, can provide 1f. Suzuki coupling of 1f with boronate ester 1g can afford the compounds of Formula (II) or the precursor to (II). Likewise, Suzuki coupling of 1f with boronate ester 1h can yield i, which can be converted to the compounds of Formula (II') by hydrogenation, deprotection, and further modifications.

EXAMPLES

Compounds of the current invention and intermediates used in the preparation of compounds of the current invention can be prepared using procedures shown in the following examples and related procedures. The methods and conditions used in these examples, and the actual compounds prepared in these examples, are not meant to be limiting, but are meant to demonstrate how the compounds of the current invention can be prepared. Starting materials and reagents used in these examples, when not prepared by a procedure described herein, are generally either commercially available, or are reported in the chemical literature, or may be prepared by using procedures described in the chemical literature. The invention is further defined in the following Examples. It should be understood that the Examples are given by way of illustration only. From the above discussion and the Examples, one skilled in the art can ascertain the essential characteristics of the invention, and without departing from the spirit and scope thereof, can make various changes and modifications to adapt the invention to various uses and conditions. As a result, the invention is not limited by the illustrative examples set forth herein below, but rather defined by the claims appended hereto.

In the examples given, the phrase "dried and concentrated" generally refers to drying of a solution in an organic solvent over either sodium sulfate or magnesium sulfate, followed by filtration and removal of the solvent from the filtrate (generally under reduced pressure and at a temperature suitable to the stability of the material being dried and concentrated).

Chemical names were determined using ChemDraw Ultra, version 16.0.1.4 (CambridgeSoft). The following abbreviations are used:

aq. aqueous
BINAP 2,2'-bis(diphenylphosphino)-1,1'-binaphthyl
BOP benzotriazol-1-yloxytris-(dimethylamino)-phosphonium hexafluorophosphate
n-BuLi n-butyl lithium
brine saturated aqueous sodium chloride
Chloramine-T sodium chloro(4-methylbenzene-1-sulfonyl)azanide
$Cu(OAc)_2$ copper(II) acetate
DCE dichloroethane
DCM dichloromethane
DIEA diisopropylethylamine
DMF N,N-dimethylformamide
DMSO dimethyl sulfoxide
dppf 1,1'-bis(diphenylphosphino)ferrocene
EtOAc ethyl acetate
EtOH ethanol
g gram(s)
h hour(s)
HPLC High Performance Liquid Chromatography
KOAc potassium acetate
LCMS Liquid Chromatography-Mass Spectroscopy
MeI methyl iodide
MeOH methanol
$NaBH(OAc)_3$ sodium triacetoxyborohydride
NaOtBu sodium tertiary-butoxide
$NH_4OAc$ ammonium acetate
$Pd_2(dba)_3$ tris-(dibenzylideneacetone)dipalladium
$PdCl_2(dppf)$ [1,1'-bis(diphenylphosphino)ferrocene]dichloropalladium(II)
$Pd(PPh_3)_4$ tetrakis(triphenylphosphine)palladium
pet ether petroleum ether
t-BuOH tert-butanol
t-BuOK potassium tertiary-butoxide
TEA triethylamine
TFA trifluoroacetic acid
THF tetrahydrofuran XPhos-Pd-G3 (2-dicyclohexylphosphino-2',4',6'-triisopropyl-1,1'-biphenyl)[2-(2'-amino-1,1'-biphenyl)] palladium(II) methanesulfonate Preparation All reagents purchased from commercial sources were used without further purification unless otherwise noted. All reactions involving air or moisture sensitive reagents were performed under an inert atmosphere. Proton magnetic resonance spectra were recorded either on a Bruker 400 or a JEOL Eclipse 500 spectrometer. LCMS analyses were performed on Waters Acquity UPLC system coupled with Waters TUV and SQ mass detector (Column: BEH C18 2.1×50 mm; Mobile Phase A: water with 0.05% TFA; Mobile Phase B: acetonitrile with 0.05% TFA; Gradient: 2-98% B over 1.6 minutes; Flow: 0.8 mL/min); HPLC analyses were performed on Shimadzu LC10-AT HPLC system coupled with SPD-10AV UV detector (Column YMC S5 Combiscreen ODS 4.6×50 mm; Mobile Phase A: 5:95 acetonitrile:water with 0.1% TFA; Mobile Phase B: 95:5 acetonitrile:water with 0.1% TFA; Gradient: 0-100% B over 40 minutes, then a 1-minute hold at 100% B; Flow: 1 mL/min); Preparative HPLC purifications were conducted on Shimadzu LC-8 preparative HPLC system coupled with SPD 20 UV detector. Detailed conditions are described in experimental procedures.

Example 1

2-(3,4-Dimethoxyphenyl)-5-(4-(4-isopropylpiperazin-1-yl)phenyl)-3-methyl-1H-pyrrolo[2,3-c]pyridine (1)

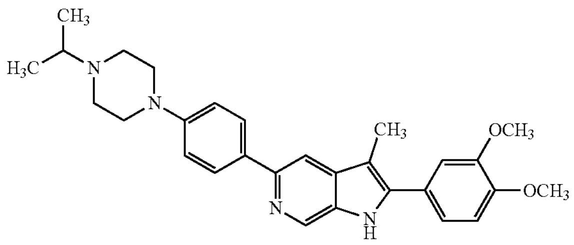

Step 1. 1,2-Dimethoxy-4-(prop-1-yn-1-yl)benzene

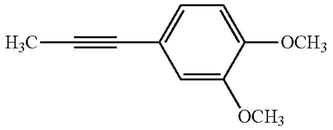

To a solution of 4-ethynyl-1,2-dimethoxybenzene (2.0 g, 12.33 mmol) in THF (70 mL) at −10° C. was added n-BuLi in hexane (1.6 M, 15.41 mL, 24.66 mmol) over 15 min. The mixture was stirred at −10° C. for 45 min before MeI (1.735 mL, 27.7 mmol) was added over 3 min. The mixture was then stirred at room temperature for 1 h. The reaction was quenched with saturated ammonium chloride solution (70 mL). The reaction mixture was concentrated under vacuum to a volume of approximately 100 mL, and extracted with dichloromethane (3×60 mL). The combined extract was dried over anhydrous $Na_2SO_4$ and concentrated under vacuum. The residue was subjected to ISCO chromatography (200 g silica gel, 0-10% ethyl acetate/hexane) to provide 1,2-dimethoxy-4-(prop-1-yn-1-yl)benzene (1.65 g, 9.36 mmol, 76% yield) as a white solid. LCMS $(M+H)^+=177.0$.

Step 2. 6-Chloro-4-iodopyridin-3-amine

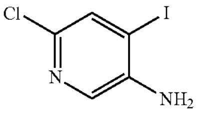

To a solution of tert-butyl (6-chloro-4-iodopyridin-3-yl) carbamate (1.939 g, 5.47 mmol) in dichloromethane (30 mL) at 0° C. was added TFA (30 mL) over 3 min. The resulting solution was stirred at 0° C. for 30 min and then at room temperature for 1.5 h. The mixture was concentrated to near dryness. To the residue was added 1 N $K_2HPO_4$ (30 mL), and the resulting mixture was extracted with dichloromethane (4×40 mL). The combined extract was dried over anhydrous $MgSO_4$. Removal of the solvent under vacuum provided 6-chloro-4-iodopyridin-3-amine (1.356 g, 5.33 mmol, 97% yield) as a pale yellow solid. LCMS $(M+H)^+$ =254.8.

Step 3. 5-Chloro-2-(3,4-dimethoxyphenyl)-3-methyl-1H-pyrrolo[2,3-c]pyridine and 5-chloro-3-(3,4-dimethoxyphenyl)-2-methyl-1H-pyrrolo[2,3-c]pyridine

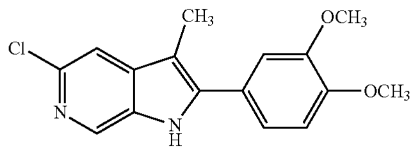

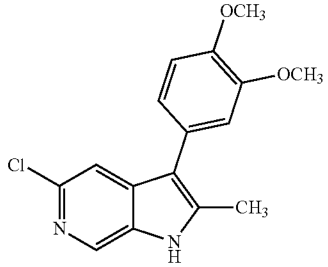

A mixture of 6-chloro-4-iodopyridin-3-amine (1.90 g, 7.47 mmol), 1,2-dimethoxy-4-(prop-1-yn-1-yl)benzene (1.513 g, 8.59 mmol), lithium chloride (0.317 g, 7.47 mmol), sodium carbonate (3.96 g, 37.3 mmol) and $PdCl_2(dppf)-CH_2Cl_2$-adduct (0.366 g, 0.448 mmol) in DMF (25 mL) was degassed and heated in a sealed vial at 100° C. for 16 h. Upon cooling to room temperature, the mixture was diluted with ethyl acetate (100 mL) and filtered through Celite. The filtrate was further diluted with ethyl acetate (200 mL), washed with water (3×50 mL) and brine (50 mL), and dried over anhydrous $MgSO_4$. After the solvent was removed under vacuum, the residue was subjected to ISCO chromatography (220 g silica gel, solid loading, 0-4% methanol/dichloromethane) to provide a mixture (1.62 g) of the two isomers. The isomeric mixture was then subjected to SFC separation (Instrument: Berger MG II (CTR-L409-PSFC1. Column: Chiralpak AD-H, 21×250 mm, 5 micron. Mobile Phase: 30% methanol/70% $CO_2$. Flow Conditions: 45 mL/min, 150 Bar, 40° C.) to afford 5-chloro-2-(3,4-dimethoxyphenyl)-3-methyl-1H-pyrrolo[2,3-c]pyridine (0.866 g, 2.86 mmol, 38.3% yield) and 5-chloro-3-(3,4-dimethoxyphenyl)-2-methyl-1H-pyrrolo[2,3-c]pyridine (0.408 g, 1.348 mmol, 18.05% yield). Both isomers were isolated as beige solids.

5-chloro-2-(3,4-dimethoxyphenyl)-3-methyl-1H-pyrrolo[2,3-c]pyridine: LCMS $(M+H)^+$=303.2. $^1$H NMR (500 MHz, DMSO-$d_6$) δ 11.76 (br s, 1H), 8.46 (s, 1H), 7.58 (s, 1H), 7.32-7.26 (m, 2H), 7.14 (d, J=8.0 Hz, 1H), 3.87 (s, 3H), 3.84 (s, 3H), 2.39 (s, 3H).

5-chloro-3-(3,4-dimethoxyphenyl)-2-methyl-1H-pyrrolo[2,3-c]pyridine: LCMS $(M+H)^+$=303.2. $^1$H NMR (500 MHz, DMSO-$d_6$) δ 11.84 (br s, 1H), 8.46 (s, 1H), 7.44 (s, 1H), 7.07 (d, J=8.0 Hz, 1H), 7.03-6.95 (m, 2H), 3.82 (s, 3H), 3.81 (s, 3H), 2.52 (br s, 3H).

Step 4. Example 1

A mixture of 5-chloro-2-(3,4-dimethoxyphenyl)-3-methyl-1H-pyrrolo[2,3-c]pyridine (20 mg, 0.066 mmol), 1-isopropyl-4-(4-(4,4,5,5-tetramethyl-1,3,2-dioxaborolan-2-yl)phenyl)piperazine (26.2 mg, 0.079 mmol), (2-dicyclohexylphosphino-2',4',6'-triisopropyl-1,1'-biphenyl)[2-(2'-amino-1,1'-biphenyl)]palladium(II) methanesulfonate, XPhos-Pd-G3 (5.59 mg, 6.61 μmol), and potassium phosphate tribasic (0.116 mL, 0.231 mmol) in 1,4-dioxane (0.8 mL) was degassed and heated in a closed vial at 80° C. for 12 h. Upon cooling to room temperature, the reaction mixture was diluted with methanol, filtered through an acrodisc, and injected to preparative HPLC (Column: Phenomenex Luna AXIA 5 u C18 21.2×100. Solvent A: 90% $H_2O$-10% methanol-0.1% TFA; Solvent B: 10% methanol-90% $H_2O$ 0.1% TFA. Flow rate: 20 mL/min. Gradient Time: 15 minutes. Start % B: 10; Final % B: 100). The correct fractions were concentrated under vacuum, basified with 1 N NaOH solution, and extracted with dichloromethane (4×40 mL). The combined extract was dried over anhydrous $Na_2SO_4$. Removal of the solvent under vacuum provided 2-(3,4-dimethoxyphenyl)-5-(4-(4-isopropylpiperazin-1-yl)phenyl)-3-methyl-1H-pyrrolo[2,3-c]pyridine (14.6 mg, 0.030 mmol, 46.0% yield) as a pale solid. LCMS $(M+H)^+$=471.5. $^1$H NMR (500 MHz, DMSO-$d_6$) δ 11.48 (s, 1H), 8.70 (d, J=1.1 Hz, 1H), 8.00 (d, J=9.1 Hz, 2H), 7.93 (s, 1H), 7.31 (d, J=1.9 Hz, 1H), 7.30-7.27 (m, 1H), 7.14 (d, J=8.5 Hz, 1H), 7.00 (d, J=9.1 Hz, 2H), 3.88 (s, 3H), 3.84 (s, 3H), 3.21-3.17 (m, 4H), 2.70 (dt, J=13.1, 6.4 Hz, 1H), 2.63-2.59 (m, 4H), 2.46 (s, 3H), 1.03 (d, J=6.6 Hz, 6H).

Example 2

2-(3,4-Dimethoxyphenyl)-5-(4-(4-isopropylpiperazin-1-yl)phenyl)-3-methyl-1H-pyrrolo[2,3-c]pyridine (2)

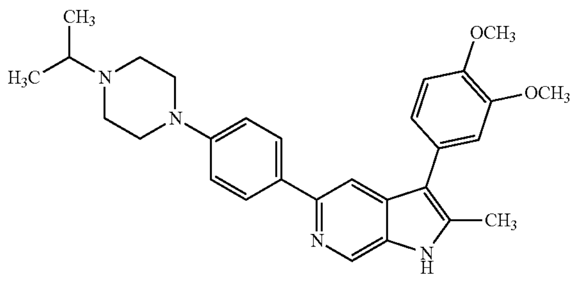

A mixture of 5-chloro-3-(3,4-dimethoxyphenyl)-2-methyl-1H-pyrrolo[2,3-c]pyridine (20 mg, 0.066 mmol), 1-isopropyl-4-(4-(4,4,5,5-tetramethyl-1,3,2-dioxaborolan-2-yl)phenyl)piperazine (26.2 mg, 0.079 mmol), (2-dicyclohexylphosphino-2',4',6'-triisopropyl-1,1'-biphenyl)[2-(2'-amino-1,1'-biphenyl)]palladium(II) methanesulfonate, XPhos-Pd-G3 (5.59 mg, 6.61 μmol), and potassium phosphate tribasic (0.116 mL, 0.231 mmol) in 1,4-dioxane (0.8 mL) was degassed and heated in a closed vial at 80° C. for 12 h. Additional 1-isopropyl-4-(4-(4,4,5,5-tetramethyl-1,3,2-dioxaborolan-2-yl)phenyl) piperazine (26.2 mg, 0.079 mmol) and (2-dicyclohexylphosphino-2',4',6'-triisopropyl-1,1'-biphenyl)[2-(2'-amino-1,1'-biphenyl)]palladium(II) methanesulfonate, XPhos-Pd-G3 (5.59 mg, 6.61 μmol) were added. The mixture was degassed and heated at 105° C. for additional 3 h. Upon cooling to room temperature, the reaction mixture was diluted with methanol, filtered through an acrodisc, and injected to preparative HPLC (Column: Phenomenex Luna AXIA 5 u C18 21.2×100. Solvent A: 90% $H_2O$-10% methanol-0.1% TFA; Solvent B: 10% methanol-90% $H_2O$ 0.1% TFA. Flow rate: 20 mL/min. Gradient Time: 15 minutes. Start % B: 8; Final % B: 100). The correct fractions were concentrated under vacuum, basified with 1 N NaOH solution, and extracted with dichloromethane (4×40 mL). The combined extract was dried over anhydrous $Na_2SO_4$. Removal of the solvent under vacuum provided 3-(3,4-dimethoxyphenyl)-5-(4-(4-isopropylpiperazin-1-yl)phenyl)-2-methyl-1H-pyrrolo[2,3-c]pyridine (11 mg, 0.023 mmol, 34.7% yield) as a pale solid. LCMS $(M+H)^+$=471.5. $^1$H NMR (500 MHz, methanol-$d_4$) δ 8.61 (d, J=0.8 Hz, 1H), 7.80 (d, J=0.8 Hz, 1H), 7.76 (d, J=8.8 Hz, 2H), 7.14-7.11 (m, 1H), 7.10 (d, J=1.9 Hz, 1H), 7.09-7.05 (m, 3H), 3.92 (s, 3H), 3.91 (s, 3H), 3.30-3.27 (m, 4H), 2.80-2.72 (m, 5H), 2.57 (s, 3H), 1.16 (d, J=6.6 Hz, 6H).

Example 3

1-(4-(4-(3-(3,4-Dimethoxyphenyl)-1,2-dimethyl-1H-pyrrolo[2,3-c]pyridin-5-yl)phenyl) piperazin-1-yl)-2-methylpropan-2-ol (3)

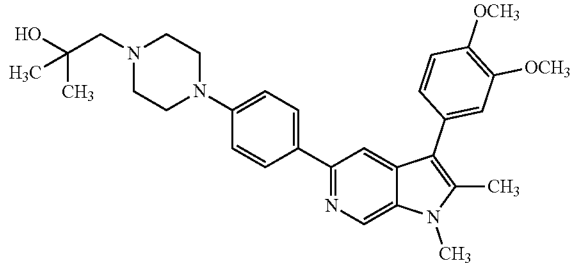

Step 1. 5-Chloro-3-(3,4-dimethoxyphenyl)-1,2-dimethyl-1H-pyrrolo[2,3-c]pyridine

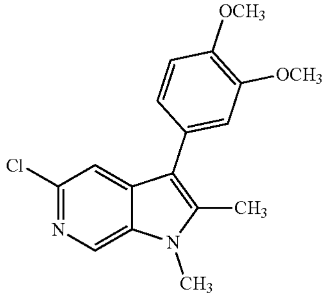 [SMILES: COc1ccc(-c2c(C)n(C)c3cnc(Cl)cc23)cc1OC]

To a solution of 5-chloro-3-(3,4-dimethoxyphenyl)-2-methyl-1H-pyrrolo[2,3-c]pyridine (400 mg, 1.321 mmol) and iodomethane (375 mg, 2.64 mmol) in DMF (6 mL) at 0° C. was added sodium hydride (60% oil dispersion) (159 mg, 3.96 mmol) in one portion. The mixture was stirred at room temperature for 1 h, then quenched with acetic acid (0.378 mL, 6.61 mmol), and concentrated under vacuum to dryness. The residue was diluted with ethyl acetate (150 mL), washed with 1 N $K_2HPO_4$ solution (25 mL), water (25 mL) and brine (25 mL) successively. The organic solution was dried over anhydrous $MgSO_4$. The product, 5-chloro-3-(3,4-dimethoxyphenyl)-1,2-dimethyl-1H-pyrrolo[2,3-c]pyridine (357 mg, 1.127 mmol, 85% yield), was isolated as a white solid by ISCO chromatography (40 g silica gel, solid loading, 35-100% ethyl acetate/hexane). LCMS $(M+H)^+$=317.1. $^1H$ NMR (500 MHz, DMSO-$d_6$) δ 8.67 (s, 1H), 7.42 (s, 1H), 7.09 (d, J=8.3 Hz, 1H), 6.99-6.92 (m, 2H), 3.85 (s, 3H), 3.82 (s, 3H), 3.81 (s, 3H), 2.52 (br s, 3H).

Step 2. 2-Methyl-1-(4-(4-(4,4,5,5-tetramethyl-1,3,2-dioxaborolan-2-yl)phenyl)piperazin-1-yl)propan-2-ol

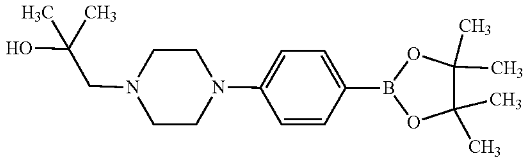 [SMILES: CC(C)(O)CN1CCN(c2ccc(B3OC(C)(C)C(C)(C)O3)cc2)CC1]

To a mixture of 1-(4-(4,4,5,5-tetramethyl-1,3,2-dioxaborolan-2-yl)phenyl) piperazine (150 mg, 0.520 mmol) and potassium carbonate (108 mg, 0.781 mmol) in MeOH (2 mL) at 0° C. was added 2,2-dimethyloxirane (56.3 mg, 0.781 mmol) in DMF (0.2 mL) in one portion. The mixture was stirred at room temperature for 28 h, diluted with ethyl acetate (10 mL), and filtered through Celite. The filtrate was diluted with ethyl acetate (60 mL), washed with water (2×20 mL) and brine (20 mL) successively, and dried over anhydrous $MgSO_4$. The product, 2-methyl-1-(4-(4-(4,4,5,5-tetramethyl-1,3,2-dioxaborolan-2-yl)phenyl)piperazin-1-yl) propan-2-ol (113 mg, 0.314 mmol, 60.3% yield), was isolated as a white solid by ISCO chromatography (24 g silica gel, solid loading, 1-10% ethyl acetate/hexane). LCMS $(M+H)^+$=361.3. $^1H$ NMR (500 MHz, chloroform-d) δ 7.73 (d, J=8.8 Hz, 2H), 6.91 (d, J=8.5 Hz, 2H), 3.35-3.25 (m, 4H), 2.88-2.76 (m, 4H), 2.41 (s, 2H), 1.35 (s, 12H), 1.22 (s, 6H).

Step 3. Example 3

A mixture of 5-chloro-3-(3,4-dimethoxyphenyl)-1,2-dimethyl-1H-pyrrolo[2,3-c]pyridine (30 mg, 0.095 mmol), 1-isopropyl-4-(4-(4,4,5,5-tetramethyl-1,3,2-dioxaborolan-2-yl)phenyl)piperazine (42.2 mg, 0.128 mmol), (2-dicyclohexylphosphino-2',4',6'-triisopropyl-1,1'-biphenyl)[2-(2'-amino-1,1'-biphenyl)]palladium(II) methanesulfonate, XPhos-Pd-G3 (8.02 mg, 9.47 μmol), and potassium phosphate tribasic (0.166 mL, 0.331 mmol) in 1,4-dioxane (1 mL) was degassed and heated in a closed vial at 85° C. for 15 h. Upon cooling to room temperature, the reaction mixture was diluted with methanol, filtered through an acrodisc, and injected to preparative HPLC (Column: Phenomenex Luna AXIA 5 u C18 21.2×100. Solvent A: 90% $H_2O$-10% methanol-0.1% TFA; Solvent B: 10% methanol-90% $H_2O$ 0.1% TFA. Flow rate: 20 mL/min. Gradient Time: 15 minutes. Start % B: 15; Final % B: 100). The correct fractions were concentrated under vacuum, basified with 1 N NaOH solution, and extracted with dichloromethane (4×40 mL). The combined extract was dried over anhydrous $Na_2SO_4$. Removal of the solvent under vacuum provided 3-(3,4-dimethoxyphenyl)-5-(4-(4-isopropylpiperazin-1-yl) phenyl)-1,2-dimethyl-1H-pyrrolo[2,3-c]pyridine (21.8 mg, 0.045 mmol, 47.0% yield) as a white solid. LCMS $(M+H)^+$=485.1. $^1H$ NMR (500 MHz, chloroform-d) δ 8.77 (s, 1H), 7.93 (d, J=8.5 Hz, 2H), 7.87 (s, 1H), 7.05-7.00 (m, 5H), 3.99 (s, 3H), 3.95 (s, 3H), 3.87 (s, 3H), 3.33-3.26 (m, 4H), 2.79-2.69 (m, 6H), 2.54 (s, 3H), 1.13 (s, 3H), 1.12 (s, 3H).

Example 4

Benzyl 4-(3-(3,4-dimethoxyphenyl)-2-methyl-1H-pyrrolo[2,3-c]pyridin-5-yl)-[1,4'-bipiperidine]-1'-carboxylate (4)

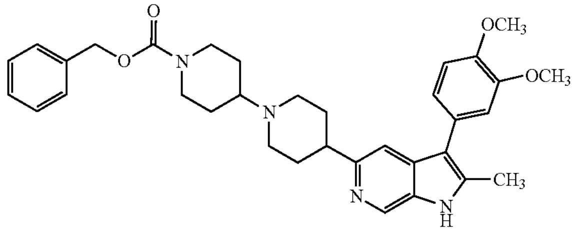

Step 1. Benzyl 4-(3-(3,4-dimethoxyphenyl)-2-methyl-1H-pyrrolo[2,3-c]pyridin-5-yl)-3,6-dihydropyridine-1(2H)-carboxylate

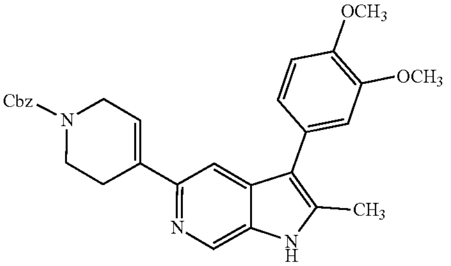 [SMILES: COc1ccc(-c2c(C)[nH]c3cnc(C4=CCN(C(=O)OCc5ccccc5)CC4)cc23)cc1OC]

A mixture of 5-chloro-3-(3,4-dimethoxyphenyl)-2-methyl-1H-pyrrolo[2,3-c] pyridine (408 mg, 1.348 mmol), benzyl 4-(4,4,5,5-tetramethyl-1,3,2-dioxaborolan-2-yl)-3,6-dihydropyridine-1(2H)-carboxylate (555 mg, 1.617 mmol), (2-dicyclohexylphosphino-2',4',6'-triisopropyl-1,1'-biphenyl)[2-(2'-amino-1,1'-biphenyl)]palladium(II) methanesulfonate, XPhos-Pd-G3 (114 mg, 0.135 mmol), and potassium phosphate tribasic (2.358 mL, 4.72 mmol) in 1,4-dioxane (14 mL) was degassed and heated in a closed vial at 80° C. for 16 h. Upon cooling to room temperature, the mixture was diluted with ethyl acetate (20 mL) and filtered through Celite. The filtrate was further diluted with ethyl acetate (120 mL), washed with water (2×30 mL) and brine (30 mL) successively, and dried over anhydrous $MgSO_4$. The product, benzyl 4-(3-(3,4-dimethoxyphenyl)-2-methyl-1H-pyrrolo[2,3-c]pyridin-5-yl)-3,6-dihydropyridine-1(2H)-carboxylate (414 mg, 0.856 mmol, 63.5% yield), was isolated as a beige solid by ISCO chromatography (80 g silica gel, solid loading, 3-12% methanol/dichloromethane). LCMS $(M+H)^+$=484.4. $^1H$ NMR (500 MHz, DMSO-$d_6$) δ 11.60 (s, 1H), 8.63 (d, J=0.8 Hz, 1H), 7.55 (s, 1H), 7.42-7.30 (m, 5H), 7.08 (d, J=8.3 Hz, 1H), 7.04-6.98 (m, 2H), 6.60 (br s, 1H), 5.13 (s, 2H), 4.18-4.06 (m, 2H), 3.82 (s, 6H), 3.69-3.60 (m, 2H), 2.63 (br d, J=1.4 Hz, 2H), 2.50 (s, 3H).

Step 2. 3-(3,4-Dimethoxyphenyl)-2-methyl-5-(piperidin-4-yl)-1H-pyrrolo[2,3-c]pyridine

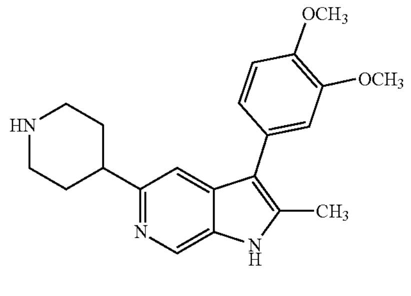 [SMILES: COc1ccc(-c2c(C)[nH]c3cnc(C4CCNCC4)cc23)cc1OC]

A mixture of benzyl 4-(3-(3,4-dimethoxyphenyl)-2-methyl-1H-pyrrolo[2,3-c]pyridin-5-yl)-3,6-dihydropyridine-1(2H)-carboxylate (260 mg, 0.538 mmol) and 10% Pd/C (114 mg, 0.108 mmol) in MeOH (30 mL) and THF (10 mL) was stirred under $H_2$, provided from a hydrogen balloon, at room temperature for 5 h. The mixture was diluted with dichloromethane (10 mL) and filtered through Celite. The filtrate was concentrated under vacuum to dryness to yield 3-(3,4-dimethoxyphenyl)-2-methyl-5-(piperidin-4-yl)-1H-pyrrolo[2,3-c]pyridine (187 mg, 0.532 mmol, 99% yield) as slightly yellow solid. LCMS $(M+H)^+$=352.4.

Step 3. Example 4

To a solution of 3-(3,4-dimethoxyphenyl)-2-methyl-5-(piperidin-4-yl)-1H-pyrrolo[2,3-c]pyridine (20 mg, 0.057 mmol), benzyl 4-oxopiperidine-1-carboxylate (53.1 mg, 0.228 mmol), magnesium sulfate (137 mg, 1.138 mmol), and acetic acid (0.049 mL, 0.854 mmol) in DMF (1.2 mL) at room temperature was added sodium triacetoxyborohydride (60.3 mg, 0.285 mmol) in one portion. The mixture was stirred at room temperature for 2.5 days (weekend). The heterogeneous mixture was diluted with ethyl acetate (10 mL) and filtered through Celite. The filtrate was concentrated under vacuum. The residue was diluted with methanol and injected to preparative HPLC (Column: Phenomenex Luna AXIA 5 u C18 21.2×100. Solvent A: 90% $H_2O$-10% methanol-0.1% TFA; Solvent B: 10% methanol-90% $H_2O$ 0.1% TFA. Flow rate: 20 mL/min. Gradient Time: 15 minutes. Start % B: 16; Final % B: 100). The correct fractions were concentrated under vacuum, basified with 2 N NaOH solution, and extracted with dichloromethane (4×30 mL). The combined extract was dried over anhydrous $Na_2SO_4$. Removal of the solvent under vacuum provided benzyl 4-(3-(3,4-dimethoxyphenyl)-2-methyl-1H-pyrrolo[2,3-c]pyridin-5-yl)-[1,4'-bipiperidine]-1'-carboxylate (11.5 mg, 0.020 mmol, 35.2% yield) as a white solid. LCMS $(M+H)^+$=569.4. $^1H$ NMR (500 MHz, chloroform-d) δ 8.67 (s, 1H), 8.20 (br s, 1H), 7.43 (s, 1H), 7.40-7.37 (m, 4H), 7.34 (dq, J=8.6, 4.2 Hz, 1H), 7.03-6.99 (m, 3H), 5.15 (s, 2H), 4.27 (br s, 2H), 3.98 (s, 3H), 3.95 (s, 3H), 3.07 (br d, J=11.3 Hz, 2H), 2.88-2.76 (m, 3H), 2.57 (s, 3H), 2.54-2.47 (m, 1H), 2.36 (br t, J=11.1 Hz, 2H), 2.06 (br d, J=10.7 Hz, 2H), 1.92-1.80 (m, 4H), 1.57-1.49 (m, 2H).

Example 5

(1-Cyclopropylpiperidin-4-yl)(4-(3-(3,4-dimethoxyphenyl)-2-methyl-1H-pyrrolo[2,3-c] pyridin-5-yl) piperidin-1-yl)methanone (5)

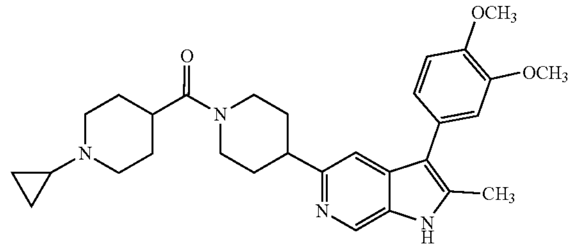

A mixture of 3-(3,4-dimethoxyphenyl)-2-methyl-5-(piperidin-4-yl)-1H-pyrrolo[2,3-c]pyridine (20 mg, 0.057 mmol), 1-cyclopropylpiperidine-4-carboxylic acid (11.56 mg, 0.068 mmol), (benzotriazol-1-yloxy)tris(dimethylamino)phosphonium hexafluorophosphate (BOP) (37.8 mg, 0.085 mmol), and N,N-diisopropylethylamine (0.040 mL, 0.228 mmol) in DMF (1.2 mL) was stirred at room temperature for 2 h. The mixture was diluted with MeOH and injected to preparative HPLC (Column: Phenomenex Luna AXIA 5 u C18 21.2×100. Solvent A: 90% $H_2O$-10% methanol-0.1% TFA; Solvent B: 10% methanol-90% $H_2O$ 0.1% TFA. Flow rate: 20 mL/min. Gradient Time: 15 minutes. Start % B: 10; Final % B: 100). The correct fractions were combined, concentrated under vacuum, basified with 2 N NaOH solution, and extracted with dichloromethane (4×30 mL). The combined extract was dried over anhydrous $Na_2SO_4$. Removal of the solvent under vacuum provided (1-cyclopropylpiperidin-4-yl) (4-(3-(3,4-dimethoxyphenyl)-2-methyl-1H-pyrrolo[2,3-c]pyridin-5-yl)piperidin-1-yl) methanone (18 mg, 0.035 mmol, 61.7% yield) as a white solid. LCMS $(M+H)^+$=503.2. $^1$H NMR (500 MHz, chloroform-d) δ 8.68 (d, J=0.8 Hz, 1H), 8.34 (br s, 1H), 7.37 (s, 1H), 7.06-7.01 (m, 2H), 6.99 (d, J=1.4 Hz, 1H), 4.83 (br d, J=12.9 Hz, 1H), 4.11-4.04 (m, 1H), 3.98 (s, 3H), 3.95 (s, 3H), 3.19 (br t, J=12.8 Hz, 1H), 3.13-3.08 (m, 2H), 3.02 (tt, J=12.0, 3.6 Hz, 1H), 2.57 (s, 3H), 2.56-2.50 (m, 1H), 2.23 (td, J=11.8, 2.5 Hz, 2H), 2.13-1.98 (m, 2H), 1.90-1.75 (m, 4H), 1.71 (br d, J=13.2 Hz, 2H), 1.61-1.58 (m, 2H), 0.47-0.42 (m, 4H).

Example 6

3-(3,4-Dimethoxyphenyl)-5-(1-(2,6-dimethylpyridin-4-yl)piperidin-4-yl)-2-methyl-1H-pyrrolo[2,3-c]pyridine (6)

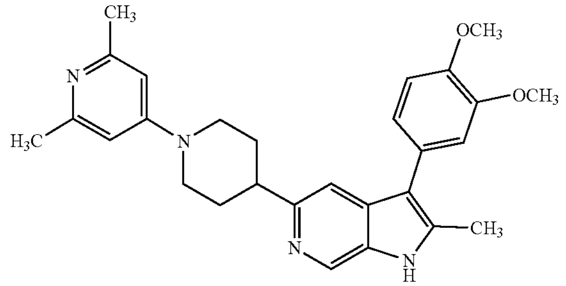

A mixture of 3-(3,4-dimethoxyphenyl)-2-methyl-5-(piperidin-4-yl)-1H-pyrrolo[2,3-c]pyridine (20 mg, 0.057 mmol), 4-chloro-2,6-dimethylpyridine (24.17 mg, 0.171 mmol), and N,N-diisopropylethylamine (0.040 mL, 0.228 mmol) in isopropanol (0.8 mL) was heated at 150° C. in a closed vial for 15 h. The solvent was found to have leaked. The residue was diluted with methanol and injected to preparative HPLC (Column: Phenomenex Luna AXIA 5 u C18 21.2×100. Solvent A: 90% $H_2O$-10% methanol-0.1% TFA; Solvent B: 10% methanol-90% $H_2O$ 0.1% TFA. Flow rate: 20 mL/min. Gradient Time: 15 minutes. Start % B: 13; Final % B: 100). The correct fractions were combined, concentrated under vacuum, basified with 1 N NaOH solution, and extracted with dichloromethane (3×35 mL). The combined extract was dried over anhydrous $Na_2SO_4$. Removal of the solvent under vacuum provided 3-(3,4-dimethoxyphenyl)-5-(1-(2,6-dimethylpyridin-4-yl)piperidin-4-yl)-2-methyl-1H-pyrrolo[2,3-c]pyridine (17 mg, 0.036 mmol, 64.1% yield) as a pale solid. LCMS $(M+H)^+$=457.5. $^1$H NMR (500 MHz, CHLOROFORM-d) δ 8.68 (d, J=0.8 Hz, 1H), 8.37 (br s, 1H), 7.38 (s, 1H), 7.05-6.98 (m, 3H), 6.46 (s, 2H), 4.04 (br d, J=12.9 Hz, 2H), 3.98 (s, 3H), 3.95 (s, 3H), 3.06-2.96 (m, 3H), 2.57 (s, 3H), 2.45 (s, 6H), 2.10 (br d, J=11.6 Hz, 2H), 1.92 (qd, J=12.6, 4.0 Hz, 2H).

Example 7

Ethyl 4-(2-(3,4-dimethoxyphenyl)-1-methyl-1H-pyrrolo[3,2-c]pyridin-6-yl)-[1,4'-bipiperidine]-1'-carboxylate (7)

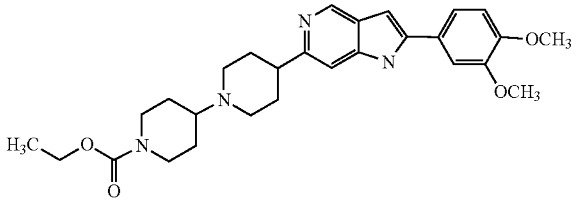

Step 1. N-(2-Chloro-5-iodopyridin-4-yl)-N-(methylsulfonyl)methanesulfonamide

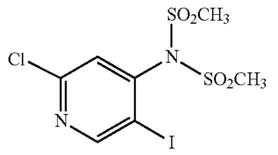 [SMILES: CS(=O)(=O)N(c1cc(Cl)ncc1I)S(C)(=O)=O]

To a solution of 2-chloro-5-iodopyridin-4-amine (2.0 g, 7.86 mmol) and triethylamine (5.48 mL, 39.3 mmol) in dichloromethane (20 mL) at 0° C. was added methanesulfonyl chloride (3.04 mL, 39.3 mmol) in dichloromethane (20 mL) over 30 min. The mixture was stirred at room temperature for 15 h. The mixture was diluted with dichloromethane (80 mL), washed with water (2x30 mL) and brine (30 mL) successively, and dried over anhydrous $MgSO_4$. The product, N-(2-chloro-5-iodopyridin-4-yl)-N-(methylsulfonyl) methanesulfonamide (2.35 g, 5.72 mmol, 72.8% yield), was isolated as a white solid by ISCO chromatography (220 g silica gel, 15-50% ethyl acetate/hexane). LCMS $(M+H)^+$=411.1. $^1$H NMR (500 MHz, chloroform-d) δ 8.91 (s, 1H), 7.39 (s, 1H), 3.59 (s, 6H).

Step 2. N-(2-Chloro-5-iodopyridin-4-yl)methanesulfonamide

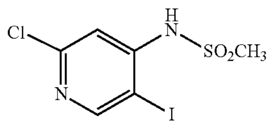 [SMILES: CS(=O)(=O)Nc1cc(Cl)ncc1I]

To a solution of N-(2-chloro-5-iodopyridin-4-yl)-N-(methylsulfonyl) methanesulfonamide (2.34 g, 5.70 mmol) in THF (10 mL) at room temperature was added 10% sodium hydroxide solution (10 ml, 27.5 mmol) over 3 min. The mixture was stirred at room temperature for 14 h, and then concentrated under vacuum to a volume of approximately 10 mL. The residue was diluted with water (5 mL) and neutralized with concentrated hydrochloric acid to pH 6-7. The precipitating product, N-(2-chloro-5-iodopyridin-4-yl)methanesulfonamide (1.66 g, 4.99 mmol, 88% yield), was collected as a white solid by suction filtration and dried at 50° C. under vacuum. LCMS $(M+H)^+$=333.0. $^1$H NMR (500 MHz, chloroform-d) δ 8.62 (s, 1H), 7.58 (s, 1H), 7.09 (br s, 1H), 3.22 (s, 3H).

Step 3. 6-Chloro-2-(3,4-dimethoxyphenyl)-1H-pyrrolo[3,2-c]pyridine

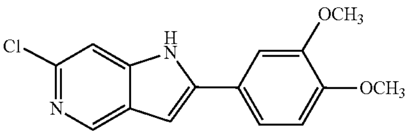 [SMILES: COc1ccc(-c2cc3cnc(Cl)cc3[nH]2)cc1OC]

A mixture of N-(2-chloro-5-iodopyridin-4-yl)methanesulfonamide (120 mg, 0.361 mmol), 4-ethynyl-1,2-dimethoxybenzene (88 mg, 0.541 mmol), bis(triphenylphosphine) palladium(II) chloride (15.20 mg, 0.022 mmol), and copper(I) iodide (4.12 mg, 0.022 mmol) in DMF (1.5 mL) was degassed and heated in a sealed vial at 100° C. for 25 h. Upon cooling to room temperature, the mixture was diluted with ethyl acetate (10 mL) and filtered through Celite. The filtrate was concentrated under vacuum to near dryness. The residue was diluted with methanol and injected to preparative HPLC (Phenomenex Luna AXIA 5 u C18 30.0x100. Solvent A: 90% $H_2O$-10% methanol-0.1% TFA; Solvent B: 10% methanol-90% $H_2O$ 0.1% TFA. Flow rate: 40 mL/min. Gradient Time: 15 minutes. Start % B: 15; Final % B: 100). The correct fractions were combined, concentrated under vacuum, basified with 1 N $K_2HPO_4$ solution, and extracted with dichloromethane (3x40 mL). The combined extract was dried over anhydrous $Na_2SO_4$. Removal of the solvent under vacuum provided 6-chloro-2-(3,4-dimethoxyphenyl)-1H-pyrrolo[3,2-c]pyridine (53 mg, 0.184 mmol, 50.9% yield). LCMS $(M+H)^+$=289.2. $^1$H NMR (500 MHz, CHLOROFORM-d) δ 8.67 (s, 1H), 8.66 (br. s, 1H), 7.35 (s, 1H), 7.24 (dd, J=8.3, 2.2 Hz, 1H), 7.19 (d, J=1.9 Hz, 1H), 6.99 (d, J=8.3 Hz, 1H), 6.78 (dd, J=1.9, 0.8 Hz, 1H), 4.00 (s, 3H), 3.97 (s, 3H).

Step 4. 6-Chloro-2-(3,4-dimethoxyphenyl)-1-methyl-1H-pyrrolo[3,2-c]pyridine

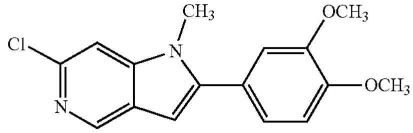 [SMILES: COc1ccc(-c2cc3cnc(Cl)cc3n2C)cc1OC]

To a solution of 6-chloro-2-(3,4-dimethoxyphenyl)-1H-pyrrolo[3,2-c]pyridine (52 mg, 0.180 mmol) and iodomethane (63.9 mg, 0.450 mmol) in DMF (2 mL) at 0° C. was added sodium hydride (60% oil dispersion) (18.01 mg, 0.450 mmol) in one portion. The mixture was stirred at room temperature for 1 h, quenched with acetic acid (0.2 mL), diluted with methanol and injected to preparative HPLC (Phenomenex Luna AXIA 5 u C18 30.0x100. Solvent A: 90% $H_2O$-10% methanol-0.1% TFA; Solvent B: 10% methanol-90% $H_2O$ 0.1% TFA. Flow rate: 40 mL/min. Gradient Time: 15 minutes. Start % B: 18; Final % B: 100). The correct fractions were combined, concentrated under vacuum, basified with saturated $NaHCO_3$ solution, and extracted with dichloromethane (3x35 mL). The combined extract was dried over anhydrous $Na_2SO_4$. Removal of the solvent under vacuum provided 6-chloro-2-(3,4-dimethoxyphenyl)-1-methyl-1H-pyrrolo[3,2-c]pyridine (39 mg, 0.129 mmol, 71.5% yield) as a white solid. LCMS $(M+H)^+$=303.2.

Step 5. Benzyl 4-(2-(3,4-dimethoxyphenyl)-1-methyl-1H-pyrrolo[3,2-c]pyridin-6-yl)-3,6-dihydropyridine-1(2H)-carboxylate

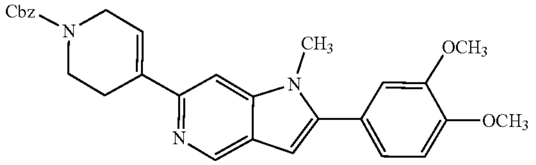 [SMILES: COc1ccc(-c2cc3cnc(C4=CCN(C(=O)OCc5ccccc5)CC4)cc3n2C)cc1OC]

A mixture of 6-chloro-2-(3,4-dimethoxyphenyl)-1-methyl-1H-pyrrolo[3,2-c] pyridine (172 mg, 0.568 mmol), benzyl 4-(4,4,5,5-tetramethyl-1,3,2-dioxaborolan-2-yl)-3,6-dihydropyridine-1(2H)-carboxylate (244 mg, 0.710 mmol), (2-dicyclohexylphosphino-2',4',6'-triisopropyl-1,1'-biphenyl)[2-(2'-amino-1,1'-biphenyl)]palladium(II) methanesulfonate, XPhos-Pd-G3 (48.1 mg, 0.057 mmol), and potassium phosphate tribasic (0.994 mL, 1.988 mmol) in 1,4-dioxane (6 mL) was degassed and heated in a closed vial at 85° C. for 11 h. Upon cooling to room temperature, the mixture was diluted with ethyl acetate (20 mL) and filtered through Celite. The filtrate was further diluted with ethyl acetate (120 mL), washed with water (30 mL) and brine (30 mL) successively, and dried over anhydrous $MgSO_4$. The product, benzyl 4-(2-(3,4-dimethoxyphenyl)-1-methyl-1H-pyrrolo[3,2-c]pyridin-6-yl)-3,6-dihydropyridine-1(2H)-carboxylate (180 mg, 0.365 mmol, 64.2% yield), was isolated as a white solid by ISCO chromatography (40 g silica gel, solid loading, 45-80% ethyl acetate/hexane). LCMS $(M+H)^+$=484.5. $^1$H NMR (500 MHz, CHLOROFORM-d) δ 8.87 (d, J=0.8 Hz, 1H), 7.46-7.31 (m, 6H), 7.10-7.06 (m, 1H), 7.04-7.00 (m, 2H), 6.72 (br s, 1H), 6.60 (s, 1H), 5.23 (s, 2H), 4.29 (q, J=2.6 Hz, 2H), 3.98 (s, 3H), 3.96 (s, 3H), 3.85-3.80 (m, 2H), 3.77 (s, 3H), 2.80 (br d, J=1.4 Hz, 2H).

Step 6. 2-(3,4-Dimethoxyphenyl)-1-methyl-6-(piperidin-4-yl)-1H-pyrrolo[3,2-c]pyridine

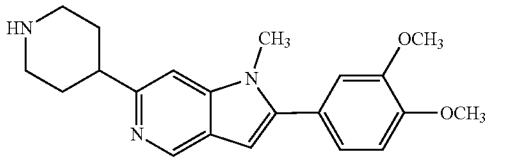 [SMILES: COc1ccc(-c2cc3cnc(C4CCNCC4)cc3n2C)cc1OC]

A mixture of benzyl 4-(2-(3,4-dimethoxyphenyl)-1-methyl-1H-pyrrolo[3,2-c]pyridin-6-yl)-3,6-dihydropyridine-1(2H)-carboxylate (177 mg, 0.366 mmol) and 10% Pd/C (78 mg, 0.073 mmol) in MeOH (21 mL) and THF (7 mL) was stirred at room temperature under $H_2$, provided from a hydrogen balloon, for 13 h. The mixture was diluted with dichloromethane (10 mL) and filtered through Celite. The filtrate was concentrated under vacuum to dryness to yield 2-(3,4-dimethoxyphenyl)-1-methyl-6-(piperidin-4-yl)-1H-pyrrolo[3,2-c]pyridine (97 mg, 0.276 mmol, 75% yield) as slightly yellow solid. LCMS $(M+H)^+$=352.3.

Step 7. Example 7

To a solution of 2-(3,4-dimethoxyphenyl)-1-methyl-6-(piperidin-4-yl)-1H-pyrrolo[3,2-c]pyridine (18 mg, 0.051 mmol), ethyl 4-oxopiperidine-1-carboxylate (35.1 mg, 0.205 mmol), magnesium sulfate (123 mg, 1.024 mmol), and acetic acid (0.044 mL, 0.768 mmol) in DMF (1.2 mL) at room temperature was added sodium triacetoxyborohydride (54.3 mg, 0.256 mmol) in one portion. The mixture was stirred at room temperature for 2.5 days (weekend). The heterogeneous mixture was diluted with ethyl acetate (10 mL) and filtered through Celite. The filtrate was concentrated under vacuum. The residue was diluted with methanol and injected to preparative HPLC (Column: Phenomenex Luna AXIA 5 u C18 21.2×100. Solvent A: 90% $H_2O$-10% methanol-0.1% TFA; Solvent B: 10% methanol-90% $H_2O$ 0.1% TFA. Flow rate: 20 mL/min. Gradient Time: 15 minutes. Start % B: 12; Final % B: 100). The correct fractions were concentrated under vacuum, basified with 1 N NaOH solution, and extracted with dichloromethane (4×30 mL). The combined extract was dried over anhydrous $Na_2SO_4$. Removal of the solvent under vacuum provided ethyl 4-(2-(3,4-dimethoxyphenyl)-1-methyl-1H-pyrrolo[3,2-c]pyridin-6-yl)-[1,4'-bipiperidine]-1'-carboxylate (5.3 mg, 10.25 μmol, 20.02% yield), as a pale yellow solid. LCMS $(M+H)^+$=507.5. $^1$H NMR (500 MHz, chloroform-d) δ 8.83 (s, 1H), 7.16 (s, 1H), 7.08-7.04 (m, 1H), 7.02-6.99 (m, 2H), 6.56 (s, 1H), 4.33-4.20 (m, 2H), 4.16 (q, J=7.2 Hz, 2H), 3.98 (s, 3H), 3.95 (s, 3H), 3.72 (s, 3H), 3.12 (br d, J=10.2 Hz, 2H), 2.94-2.86 (m, 1H), 2.80 (br t, J=11.4 Hz, 2H), 2.55 (br t, J=9.8 Hz, 1H), 2.43 (br t, J=11.0 Hz, 2H), 2.14 (br d, J=12.4 Hz, 2H), 1.91 (br d, J=12.1 Hz, 4H), 1.60-1.51 (m, 2H), 1.29 (t, J=7.0 Hz, 3H).

Example 8

2-(3,4-Dimethoxyphenyl)-1-methyl-6-(1-((6-methylpyridin-3-yl)methyl)piperidin-4-yl)-1H-pyrrolo[3,2-c]pyridine (8)

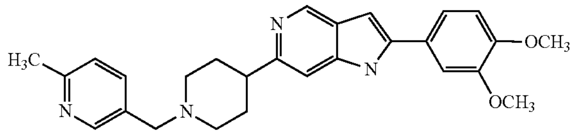

To a solution of 2-(3,4-dimethoxyphenyl)-1-methyl-6-(piperidin-4-yl)-1H-pyrrolo[3,2-c]pyridine (25 mg, 0.057 mmol), 6-methylnicotinaldehyde (24.13 mg, 0.199 mmol), magnesium sulfate (137 mg, 1.138 mmol), and acetic acid (0.049 mL, 0.854 mmol) in DMF (1.2 mL) at room temperature was added sodium triacetoxyborohydride (54.3 mg, 0.256 mmol). The heterogeneous mixture was stirred at room temperature for 23 h, diluted with ethyl acetate (10 mL) and filtered through Celite. The filtrate was concentrated under vacuum. The residue was diluted with methanol and subjected to preparative HPLC (Column: Phenomenex Luna AXIA 5 u C18 21.2×100. Solvent A: 90% $H_2O$-10% methanol-0.1% TFA; Solvent B: 10% methanol-90% $H_2O$ 0.1% TFA. Flow rate: 20 mL/min. Gradient Time: 15 minutes. Start % B: 9; Final % B: 100). The correct fractions were concentrated under vacuum, basified with 2 N NaOH solution, and extracted with dichloromethane (3×35 mL). The combined extract was dried over anhydrous $Na_2SO_4$. Removal of the solvent under vacuum provided 2-(3,4-dimethoxyphenyl)-1-methyl-6-(1-((6-methylpyridin-3-yl)methyl)piperidin-4-yl)-1H-pyrrolo[3,2-c]pyridine (18.8 mg, 0.040 mmol, 70.9% yield) as a white solid. LCMS $(M+H)^+$=457.5. $^1$H NMR (500 MHz, chloroform-d) δ 8.84 (s, 1H), 8.48 (d, J=1.7 Hz, 1H), 7.64 (dd, J=8.0, 2.2 Hz, 1H), 7.19-7.11 (m, 2H), 7.09-7.03 (m, 1H), 7.03-6.99 (m, 2H), 6.56 (s, 1H), 3.98 (s, 3H), 3.95 (s, 3H), 3.73 (s, 3H), 3.56 (s, 2H), 3.06 (br d, J=11.3 Hz, 2H), 2.89 (tt, J=12.1, 3.6 Hz, 1H), 2.58 (s, 3H), 2.24-2.17 (m, 2H), 2.06 (br d, J=11.6 Hz, 2H), 1.99-1.89 (m, 2H).

Example 9

6-(4-(4-(Cyclopropylmethyl)piperazin-1-yl)phenyl)-2-(3,4-dimethoxyphenyl)-1-methyl-1H-pyrrolo[3,2-c]pyridine (9)

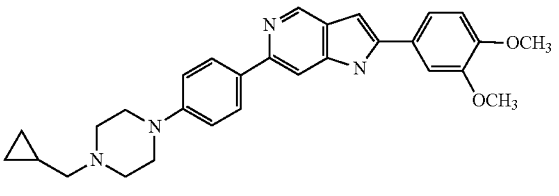

Step 1. 1-(Cyclopropylmethyl)-4-(4-(4,4,5,5-tetramethyl-1,3,2-dioxaborolan-2-yl)phenyl) piperazine

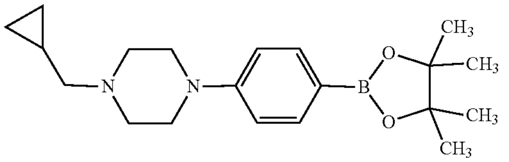

To a mixture of 1-(4-(4,4,5,5-tetramethyl-1,3,2-dioxaborolan-2-yl)phenyl) piperazine (100 mg, 0.347 mmol) and potassium carbonate (71.9 mg, 0.520 mmol) in DMF (1 mL) at 0° C. was added (bromomethyl)cyclopropane (73.2 mg, 0.520 mmol) in DMF (0.2 mL) in one portion. The mixture was stirred at room temperature for 12 h, diluted with ethyl acetate (10 mL), and filtered through Celite. The filtrate was diluted with ethyl acetate (60 mL), washed with water (2×20 mL) and brine (20 mL) successively, and dried over anhydrous $MgSO_4$. The product, 1-(cyclopropylmethyl)-4-(4-(4,4,5,5-tetramethyl-1,3,2-dioxaborolan-2-yl)phenyl)piperazine (72 mg, 0.210 mmol, 60.6% yield), was isolated as a white solid by ISCO chromatography (25 g silica gel, solid loading, 40-80% ethyl acetate/hexane). LCMS $(M+H)^+$=343.3. $^1$H NMR (500 MHz, chloroform-d) δ 7.73 (d, J=8.8 Hz, 2H), 6.92 (d, J=8.8 Hz, 2H), 3.42-3.27 (m, 4H), 2.80-2.59 (m, 4H), 2.33 (d, J=6.6 Hz, 2H), 1.35 (s, 12H), 1.01-0.84 (m, 1H), 0.65-0.49 (m, 2H), 0.16 (d, J=5.5 Hz, 2H).

Step 2. Example 9

A mixture of 6-chloro-2-(3,4-dimethoxyphenyl)-1-methyl-1H-pyrrolo[3,2-c]pyridine (18 mg, 0.059 mmol), 1-(cyclopropylmethyl)-4-(4-(4,4,5,5-tetramethyl-1,3,2-dioxaborolan-2-yl)phenyl)piperazine (25.4 mg, 0.074 mmol), (2-dicyclohexylphosphino-2',4',6'-triisopropyl-1,1'-biphenyl)[2-(2'-amino-1,1'-biphenyl)]palladium(II) methanesulfonate, XPhos-Pd-G3 (5.03 mg, 5.95 μmol), and potassium phosphate tribasic (0.104 mL, 0.208 mmol) in 1,4-dioxane (0.8 mL) was degassed and heated in a closed vial at 80° C. for 15 h. Upon cooling to room temperature, the reaction mixture was diluted with methanol, filtered through an acrodisc, and injected to preparative HPLC (Column: Phenomenex Luna AXIA 5 u C18 21.2×100. Solvent A: 90% $H_2O$-10% methanol-0.1% TFA; Solvent B: 10% methanol- 90% $H_2O$ 0.1% TFA. Flow rate: 20 mL/min. Gradient Time: 15 minutes. Start % B: 15; Final % B: 100). The correct fractions were concentrated under vacuum, basified with 1 N NaOH solution, and extracted with dichloromethane (4×40 mL). The combined extract was dried over anhydrous $Na_2SO_4$. Removal of the solvent under vacuum provided 6-(4-(4-(cyclopropylmethyl)piperazin-1-yl)phenyl)-2-(3,4-dimethoxyphenyl)-1-methyl-1H-pyrrolo[3,2-c]pyridine (9 mg, 0.018 mmol, 31.1% yield) as a white solid. LCMS $(M+H)^+$=483.4. $^1$H NMR (500 MHz, chloroform-d) δ 8.95 (s, 1H), 8.02 (d, J=8.8 Hz, 2H), 7.60 (s, 1H), 7.12-7.04 (m, 4H), 7.04-7.00 (m, 1H), 6.60 (s, 1H), 3.99 (s, 3H), 3.97 (s, 3H), 3.79 (s, 3H), 3.37-3.33 (m, 4H), 2.78-2.74 (m, 4H), 2.37 (d, J=6.6 Hz, 2H), 1.01-0.91 (m, 1H), 0.62-0.55 (m, 2H), 0.21-0.16 (m, 2H).

Example 10

6-(4-(4-Cyclobutylpiperazin-1-yl)phenyl)-2-(3,4-dimethoxyphenyl)-1-methyl-1H-pyrrolo[3,2-c]pyridine (10)

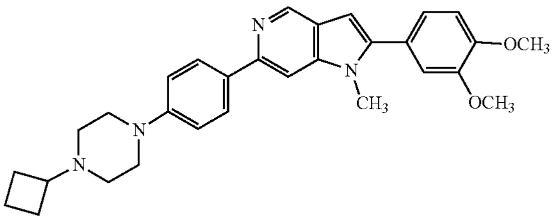

Step 1. 1-Cyclobutyl-4-(4-(4,4,5,5-tetramethyl-1,3,2-dioxaborolan-2-yl)phenyl) piperazine

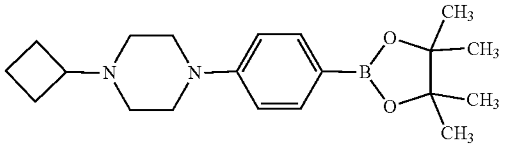 [SMILES: CC1(C)OB(c2ccc(N3CCN(C4CCC4)CC3)cc2)OC1(C)C]

To a solution of 1-(4-(4,4,5,5-tetramethyl-1,3,2-dioxaborolan-2-yl)phenyl) piperazine (150 mg, 0.520 mmol), cyclobutanone (128 mg, 1.822 mmol), magnesium sulfate (1253 mg, 10.41 mmol), and acetic acid (0.298 mL, 5.20 mmol) in DMF (1.2 mL) at room temperature was added sodium triacetoxyborohydride (496 mg, 2.342 mmol) in one portion. The mixture was stirred at room temperature for 12 h. The heterogeneous mixture was diluted with ethyl acetate (20 mL) and filtered through Celite. The filtrate was further diluted with ethyl acetate (80 mL), washed with saturated $NaHCO_3$ solution (25 mL), water (2×25 mL) and brine (25 mL) successively, and dried over anhydrous $MgSO_4$. The product, 1-cyclobutyl-4-(4-(4,4,5,5-tetramethyl-1,3,2-dioxaborolan-2-yl) phenyl)piperazine (108 mg, 0.316 mmol, 60.6% yield), was isolated as a white solid by ISCO chromatography (24 g silica gel, solid loading, 35-80% ethyl acetate/hexane). LCMS $(M+H)^+$=343.2.

Step 2. Example 10

A mixture of 6-chloro-2-(3,4-dimethoxyphenyl)-1-methyl-1H-pyrrolo[3,2-c] pyridine (20 mg, 0.066 mmol), 1-cyclobutyl-4-(4-(4,4,5,5-tetramethyl-1,3,2-dioxaborolan-2-yl)phenyl)piperazine (28.3 mg, 0.083 mmol), (2-dicyclohexylphosphino-2',4',6'-triisopropyl-1,1'-biphenyl)[2-(2'-amino-1,1'-biphenyl)]palladium(II) methanesulfonate, XPhos-Pd-G3 (5.59 mg, 6.61 μmol), and potassium phosphate tribasic (0.116 mL, 0.231 mmol) in 1,4-dioxane (0.8 mL) was degassed and heated in a closed vial at 85° C. for 15 h. Upon cooling to room temperature, the reaction mixture was diluted with methanol, filtered through an acrodisc, and injected to preparative HPLC (Column: Phenomenex Luna AXIA 5 u C18 21.2×100. Solvent A: 90% $H_2O$-10% methanol-0.1% TFA; Solvent B: 10% methanol-90% $H_2O$ 0.1% TFA. Flow rate: 20 mL/min. Gradient Time: 15 minutes. Start % B: 15; Final % B: 100). The correct fractions were concentrated under vacuum, basified with 1 N NaOH, and extracted with dichloromethane (4×40 mL). The combined extract was dried over anhydrous $Na_2SO_4$. Removal of the solvent under vacuum provided 6-(4-(4-cyclobutylpiperazin-1-yl) phenyl)-2-(3,4-dimethoxyphenyl)-1-methyl-1H-pyrrolo[3,2-c]pyridine (14 mg, 0.028 mmol, 43.0% yield) as a pale yellow solid. $^1H$ NMR (500 MHz, chloroform-d) δ 8.95 (s, 1H), 8.02 (d, J=8.8 Hz, 2H), 7.60 (s, 1H), 7.12-7.08 (m, 1H), 7.08-7.04 (m, 3H), 7.04-7.00 (m, 1H), 6.60 (s, 1H), 3.99 (s, 3H), 3.97 (s, 3H), 3.80 (s, 3H), 3.34-3.31 (m, 4H), 2.84 (quin, J=7.9 Hz, 1H), 2.57-2.53 (m, 4H), 2.15-2.08 (m, 2H), 2.02-1.93 (m, 2H), 1.82-1.71 (m, 2H).

Example 11

6-(4-(4-Isopropylpiperazin-1-yl)phenyl)-1,4-dimethyl-2-(4-(methylsulfonyl)phenyl)-1H-pyrrolo[3,2-c]pyridine (11)

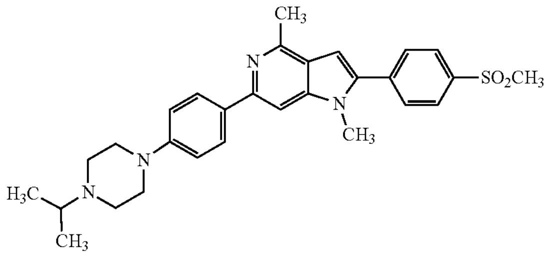

Step 1. 6-Chloro-3-iodo-2-methylpyridin-4-amine

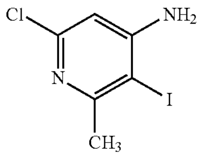

To a solution of 2-chloro-6-methylpyridin-4-amine (1.94 g, 13.61 mmol) in ethanol (55 mL) at room temperature was added silver sulfate (4.24 g, 13.61 mmol), followed by iodine (3.64 g, 13.61 mmol) in one portion. The mixture was stirred at room temperature for 16 h. To the mixture was added ethyl acetate (80 mL) and triethylamine (1.896 mL, 13.61 mmol). The mixture was stirred at room temperature for 10 min and then filtered through Celite. The filtrate was concentrated under vacuum and the residue was subjected to ISCO chromatography (220 g silica gel, solid loading, 20-80% ethyl acetate/hexane) to afford 6-chloro-3-iodo-2-methylpyridin-4-amine (1.03 g, 3.84 mmol, 28.2% yield) and 2-chloro-3-iodo-6-methylpyridin-4-amine (1.05 g, 3.91 mmol, 28.7% yield). Both products were obtained as white solids.

6-chloro-3-iodo-2-methylpyridin-4-amine: LCMS $(M+H)^+$=269.0. $^1H$ NMR (400 MHz, chloroform-d) δ 6.46 (s, 1H), 4.80 (br s, 2H), 2.68 (s, 3H).

2-chloro-3-iodo-6-methylpyridin-4-amine: LCMS $(M+H)^+$=269.0. $^1H$ NMR (400 MHz, chloroform-d) δ 6.35 (s, 1H), 4.79 (br s, 2H), 2.38 (s, 3H).

Step 2. N-(6-Chloro-3-iodo-2-methylpyridin-4-yl)-N-(methylsulfonyl) methanesulfonamide

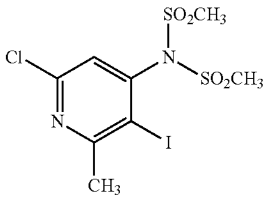 [SMILES: Cc1nc(Cl)cc(N(S(C)(=O)=O)S(C)(=O)=O)c1I]

To a solution of 6-chloro-3-iodo-2-methylpyridin-4-amine (1.56 g, 5.81 mmol) and triethylamine (4.05 mL, 29.1 mmol) in dichloromethane (25 mL) at 0° C. was added methanesulfonyl chloride (2.248 mL, 29.1 mmol) in dichloromethane (25 mL) over 10 min. The mixture was stirred at room temperature for 18 h. The mixture was diluted with dichloromethane (150 mL), washed with water (2×40 mL) and brine (40 mL), and dried over anhydrous $MgSO_4$. N-(6-chloro-3-iodo-2-methylpyridin-4-yl)-N-(methylsulfonyl)methanesulfonamide (1.91 g, 4.50 mmol, 77% yield), was isolated as a white solid by ISCO chromatography (220 g silica gel, 10-50% ethyl acetate/hexane). $^1H$ NMR (400 MHz, chloroform-d) δ 7.17 (s, 1H), 3.60 (s, 6H), 2.89 (s, 3H).

Step 3. N-(6-Chloro-3-iodo-2-methylpyridin-4-yl) methanesulfonamide

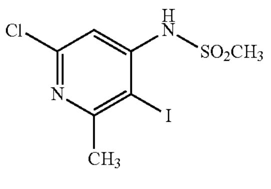

To a solution of N-(6-chloro-3-iodo-2-methylpyridin-4-yl)-N-(methylsulfonyl) methanesulfonamide (1.91 g, 4.50 mmol) in THF (10 mL) at room temperature was added 10% sodium hydroxide (9 mL, 24.75 mmol) over 3 min. The mixture was stirred at room temperature for 15 h, and then concentrated under vacuum to a volume of approximately 10 mL. The residue was diluted with water (5 mL) and neutralized with concentrated hydrochloric acid to pH 6-7. The precipitating product, N-(6-chloro-3-iodo-2-methylpyridin- 4-yl)methanesulfonamide (1.10 g, 3.17 mmol, 70.6% yield), was collected as a white solid by suction filtration and dried at 50° C. under vacuum. LCMS $(M+H)^+=347.0$.

Step 4. 6-Chloro-4-methyl-2-(4-(methylsulfonyl)phenyl)-1H-pyrrolo[3,2-c]pyridine

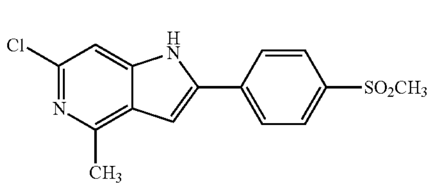 [SMILES: Cc1nc(Cl)cc2[nH]c(-c3ccc(S(C)(=O)=O)cc3)cc12]

A mixture of N-(6-chloro-3-iodo-2-methylpyridin-4-yl)methanesulfonamide (0.500 g, 1.443 mmol), 1-ethynyl-4-(methylsulfonyl)benzene (0.325 g, 1.803 mmol), bis(triphenylphosphine)palladium(II) chloride (0.061 g, 0.087 mmol) and copper(I) iodide (0.016 g, 0.087 mmol) in DMF (6 mL) was degassed and heated in a sealed vial at 100° C. for 15 h. Upon cooling to room temperature, the mixture was diluted with ethyl acetate (50 mL) and filtered through Celite. The filtrate was further diluted with ethyl acetate (150 mL), washed with water (3×40 mL) and brine (40 mL) successively, and dried over anhydrous $MgSO_4$. After the solvent was removed under vacuum, the residue was subjected to ISCO chromatography (80 g silica gel, solid loading, 0-5% methanol/dichloromethane). The product (0.275 g) thus obtained was further purified by preparative HPLC (Phenomenex Luna AXIA 5 u C18 30.0×100. Solvent A: 90% $H_2O$-10% methanol-0.1% TFA; Solvent B: 10% methanol-90% $H_2O$ 0.1% TFA. Flow rate: 40 mL/min. Gradient Time: 12 minutes. Start % B: 11; Final % B: 100). The correct fractions were combined, concentrated under vacuum, basified with saturated $NaHCO_3$ solution to pH 10, and extracted with dichloromethane (3×50 mL). The combined extract was dried over anhydrous $MgSO_4$. Removal of the solvent under vacuum provided 6-chloro-4-methyl-2-(4-(methylsulfonyl)phenyl)-1H-pyrrolo[3,2-c]pyridine (0.210 g, 0.655 mmol, 45.4% yield) as a white solid. LCMS $(M+H)^+=321.2$. $^1H$ NMR (400 MHz, DMSO-$d_6$) δ 12.29 (s, 1H), 8.16 (d, J=8.6 Hz, 2H), 8.04 (d, J=8.6 Hz, 2H), 7.40 (d, J=0.8 Hz, 1H), 7.27 (s, 1H), 3.28 (s, 3H), 2.67 (s, 3H).

Step 5. 6-Chloro-1,4-dimethyl-2-(4-(methylsulfonyl)phenyl)-1H-pyrrolo[3,2-c]pyridine

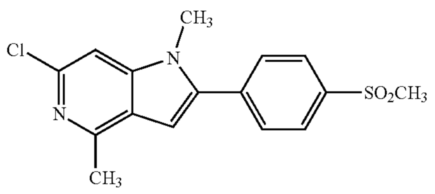 [SMILES: Cc1nc(Cl)cc2c1cc(-c1ccc(S(C)(=O)=O)cc1)n2C]

To a solution of 6-chloro-4-methyl-2-(4-(methylsulfonyl)phenyl)-1H-pyrrolo[3,2-c]pyridine (205 mg, 0.639 mmol) and iodomethane (227 mg, 1.598 mmol) in DMF (6 mL) at 0° C. was added sodium hydride (60% oil dispersion) (63.9 mg, 1.598 mmol) in one portion. The mixture was stirred at room temperature for 1 h. The reaction was quenched with acetic acid (0.183 mL, 3.20 mmol). The resulting mixture was concentrated under vacuum to almost dryness. The residue was diluted with ethyl acetate (120 mL), washed with saturated $NaHCO_3$ solution (2×25 mL), and dried over anhydrous $MgSO_4$. The product, 6-chloro-1,4-dimethyl-2-(4-(methylsulfonyl)phenyl)-1H-pyrrolo[3,2-c]pyridine (172 mg, 0.514 mmol, 80% yield), was isolated as a white solid by ISCO chromatography (40 g silica gel, 0-6% methanol/dichloromethane). LCMS $(M+H)^+=335.2$. $^1H$ NMR (500 MHz, acetonitrile-$d_3$) δ 8.07 (d, J=8.5 Hz, 2H), 7.84 (d, J=8.5 Hz, 2H), 7.36 (s, 1H), 6.86 (d, J=0.6 Hz, 1H), 3.75 (s, 3H), 3.16 (s, 3H), 2.70 (s, 3H).

Step 6. Example 11

A mixture of 6-chloro-1,4-dimethyl-2-(4-(methylsulfonyl)phenyl)-1H-pyrrolo[3,2-c]pyridine (40 mg, 0.119 mmol), 1-isopropyl-4-(4-(4,4,5,5-tetramethyl-1,3,2-dioxaborolan-2-yl)phenyl)piperazine (53.3 mg, 0.161 mmol), (2-dicyclohexylphosphino-2',4',6'-triisopropyl-1,1'-biphenyl)[2-(2'-amino-1,1'-biphenyl)]palladium(II) methanesulfonate, XPhos-Pd-G3 (10.11 mg, 0.012 mmol), and potassium phosphate tribasic (0.209 mL, 0.418 mmol) in 1,4-dioxane (1.5 mL) was degassed and heated in a closed vial at 85° C. for 18 h. Upon cooling to room temperature, the reaction mixture was diluted with methanol, filtered through an acrodisc, and injected to preparative HPLC (Phenomenex Luna AXIA 5 u C18 30.0×100. Solvent A: 90% $H_2O$-10% methanol-0.1% TFA; Solvent B: 10% methanol-90% $H_2O$ 0.1% TFA. Flow rate: 40 mL/min. Gradient Time: 15 minutes. Start % B: 10; Final % B: 100). The correct fractions were concentrated under vacuum, basified with 1 N NaOH, and extracted with dichloromethane (4×40 mL). The combined extract was dried over anhydrous $Na_2SO_4$. Removal of the solvent under vacuum provided 6-(4-(4-isopropylpiperazin-1-yl)phenyl)-1,4-dimethyl-2-(4-(methylsulfonyl)phenyl)-1H-pyrrolo[3,2-c]pyridine (41.6 mg, 0.081 mmol, 67.9% yield) as a pale yellow solid. LCMS $(M+H)^+=503.4$. $^1H$ NMR (500 MHz, chloroform-d) δ 8.09 (d, J=8.2 Hz, 2H), 8.01 (d, J=8.5 Hz, 2H), 7.77 (d, J=8.2 Hz, 2H), 7.47 (s, 1H), 7.06 (d, J=8.8 Hz, 2H), 6.74 (s, 1H), 3.83 (s, 3H), 3.35-3.27 (m, 4H), 3.16 (s, 3H), 2.85 (s, 3H), 2.81-2.71 (m, 5H), 1.13 (d, J=6.3 Hz, 6H).

Example 12

6-(3-Fluoro-4-(4-isopropylpiperazin-1-yl)phenyl)-1,4-dimethyl-2-(4-(methylsulfonyl)phenyl)-1H-pyrrolo[3,2-c]pyridine (12)

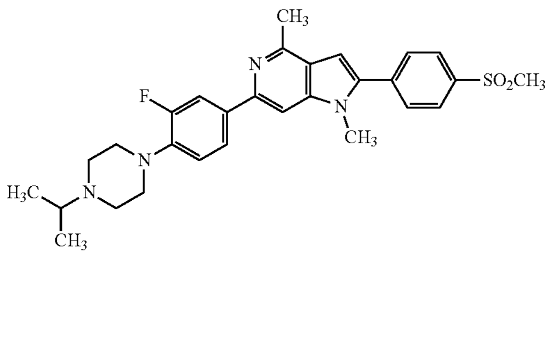

Step 1. 1-(2-Fluoro-4-nitrophenyl)-4-isopropylpiperazine

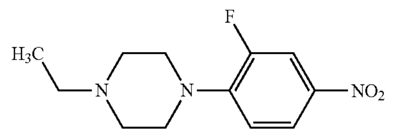 [SMILES: CCN1CCN(c2ccc([N+](=O)[O-])cc2F)CC1]

A mixture of 1,2-difluoro-4-nitrobenzene (0.90 g, 5.66 mmol), 1-isopropylpiperazine (0.834 g, 6.51 mmol), and potassium carbonate (0.938 g, 6.79 mmol) in DMF (35 mL) was stirred at room temperature for 24 h, and then concentrated under vacuum to almost dryness. The residue was diluted with ethyl acetate (160 mL), washed with water (2×25 mL) and brine (25 mL) successively, and dried over anhydrous $MgSO_4$. The product, 1-(2-fluoro-4-nitrophenyl)-4-isopropylpiperazine (1.36 g, 5.09 mmol, 90% yield), was isolated as yellow oil by ISCO chromatography (80 g silica gel, solid loading, 1-5% methanol/dichloromethane). LCMS $(M+H)^+$=268.2. $^1H$ NMR (500 MHz, chloroform-d) δ 8.00 (dd, J=8.7, 2.3 Hz, 1H), 7.92 (dd, J=13.2, 2.8 Hz, 1H), 6.93 (t, J=8.8 Hz, 1H), 3.38-3.32 (m, 4H), 2.77 (dt, J=13.1, 6.5 Hz, 1H), 2.74-2.70 (m, 4H), 1.11 (d, J=6.6 Hz, 6H).

Step 2. 3-Fluoro-4-(4-isopropylpiperazin-1-yl)aniline

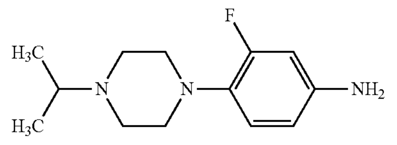 [SMILES: CC(C)N1CCN(c2ccc(N)cc2F)CC1]

A mixture of 1-(2-fluoro-4-nitrophenyl)-4-isopropylpiperazine (1.36 g, 5.09 mmol) and 10% Pd/C (0.35 g, 0.329 mmol) in MeOH (30 mL) and THF (10 mL) was stirred under $H_2$, provided from a $H_2$ balloon, at room temperature for 2 h. The catalyst was removed by suction filtration through Celite. The filtrate was concentrated under vacuum to dryness. The residue was dissolved in ethyl acetate (150 mL) and dried over anhydrous $Na_2SO_4$. Removal of the solvent under vacuum provided 3-fluoro-4-(4-isopropylpiperazin-1-yl)aniline (1.20 g, 5.06 mmol, 99% yield), as a tan solid. LCMS $(M+H)^+$=238.2. $^1H$ NMR (500 MHz, chloroform-d) δ 6.84 (t, J=8.9 Hz, 1H), 6.48-6.39 (m, 2H), 3.55 (br s, 2H), 3.07-3.00 (m, 4H), 2.78-2.69 (m, 5H), 1.11 (d, J=6.6 Hz, 6H).

Step 3. 1-(4-Bromo-2-fluorophenyl)-4-isopropylpiperazine

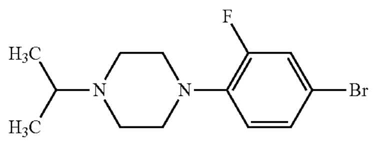

To a mixture of 3-fluoro-4-(4-isopropylpiperazin-1-yl) aniline (0.55 g, 2.318 mmol) and copper(II) bromide (0.621 g, 2.78 mmol) in acetonitrile (15 mL) at 0° C. was added tert-butyl nitrite (0.551 mL, 4.64 mmol) over 5 min. The mixture was stirred at 0° C. for 1.5 h and then at room temperature for 5.5 h. The mixture was diluted with ethyl acetate (15 mL) and filtered through Celite. The filtrate was concentrated under vacuum to dryness. To the residue was added water (10 mL) and the mixture was extracted with dichloromethane (4×40 mL). The combined extract was dried over anhydrous $Na_2SO_4$. The product, 1-(4-bromo-2-fluorophenyl)-4-isopropylpiperazine (94 mg, 0.312 mmol, 13.47% yield) was isolated as a tan solid by ISCO chromatography (40 g silica gel, solid loading, 0-5% methanol/dichloromethane). LCMS $(M+H)^+$=301.1.

Step 4. 1-(2-Fluoro-4-(4,4,5,5-tetramethyl-1,3,2-dioxaborolan-2-yl)phenyl)-4-isopropylpiperazine

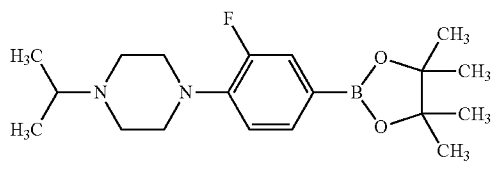 [SMILES: CC(C)N1CCN(c2ccc(B3OC(C)(C)C(C)(C)O3)cc2F)CC1]

A mixture of 1-(4-bromo-2-fluorophenyl)-4-isopropylpiperazine (94 mg, 0.312 mmol), 4,4,4',4',5,5,5',5'-octamethyl-2,2'-bi(1,3,2-dioxaborolane) (119 mg, 0.468 mmol), $PdCl_2(dppf)-CH_2Cl_2$ adduct (15.29 mg, 0.019 mmol), and potassium acetate (92 mg, 0.936 mmol) in 1,4-dioxane (3 ml) in a pressure bottle was heated at 110° C. for 20 h. The mixture was diluted with ethyl acetate (5 mL) and filtered through Celite. The filtrate was concentrated under vacuum, and the residue was subjected to ISCO chromatography (24 g silica gel, solid loading, 0-5% methanol/chloromethane) to provide 1-(2-fluoro-4-(4,4,5,5-tetramethyl-1,3,2-dioxaborolan-2-yl)phenyl)-4-isopropylpiperazine (39 mg, 0.112 mmol, 35.9% yield) as a white solid. LCMS $(M+H)^+$=349.2. $^1H$ NMR (500 MHz, chloroform-d) δ 7.52 (d, J=7.7 Hz, 1H), 7.45 (d, J=13.5 Hz, 1H), 6.94 (t, J=8.3 Hz, 1H), 3.24-3.18 (m, 4H), 2.79-2.71 (m, 5H), 1.35 (s, 12H), 1.12 (d, J=6.6 Hz, 6H).

Step 5. Example 12

A mixture of 6-chloro-1,4-dimethyl-2-(4-(methylsulfonyl)phenyl)-1H-pyrrolo[3,2-c]pyridine (28 mg, 0.084 mmol), 1-(2-fluoro-4-(4,4,5,5-tetramethyl-1,3,2-dioxaborolan-2-yl)phenyl)-4-isopropylpiperazine (37.9 mg, 0.109 mmol), (2-dicyclohexylphosphino-2',4',6'-triisopropyl-1,1'-biphenyl)[2-(2'-amino-1,1'-biphenyl)]palladium(II) methanesulfonate, XPhos-Pd-G3 (7.08 mg, 8.36 μmol), and potassium phosphate tribasic (0.146 mL, 0.293 mmol) in 1,4-dioxane (1.5 mL) was degassed and heated in a closed vial at 85° C. for 18 h. Upon cooling to room temperature, the reaction mixture was diluted with methanol, filtered through an acrodisc, and injected to preparative HPLC (Column: Phenomenex Luna AXIA 5 u C18 21.2×100. Solvent A: 90% $H_2O$-10% methanol-0.1% TFA; Solvent B: 10% methanol-90% $H_2O$ 0.1% TFA. Flow rate: 20 mL/min. Gradient Time: 15 minutes. Start % B: 11; Final % B: 100). The correct fractions were concentrated under vacuum, basified with 1 N NaOH, and extracted with dichloromethane (4×40 mL). The combined extract was dried over anhydrous $Na_2SO_4$ and concentrated under vacuum to provide 6-(3-fluoro-4-(4-isopropylpiperazin-1-yl)phenyl)-1,4-dimethyl-2-(4-(methylsulfonyl)phenyl)-1H-pyrrolo[3,2-c]pyridine (17 mg, 0.032 mmol, 38.7% yield) as a pale solid. LCMS $(M+H)^+$=521.4. $^1H$ NMR (400 MHz, chloroform-d) δ 8.13-8.07 (m, 2H), 7.86-7.79 (m, 2H), 7.78-7.75 (m, 2H), 7.47 (s, 1H), 7.07 (t, J=8.8 Hz, 1H), 6.75 (s, 1H), 3.83 (s, 3H), 3.22 (br s, 4H), 3.16 (s, 3H), 2.85 (s, 3H), 2.81-2.75 (m, 5H), 1.14 (br d, J=6.5 Hz, 6H).
Examples 13-33 in Table 1 were prepared according to the synthetic routes described for the preparation of example 1-12.
TABLE 1
| Ex. No. | Structure |
|---|---|
| 13 | 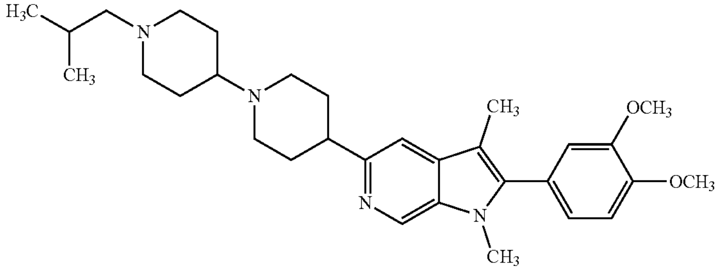 |
| 14 | 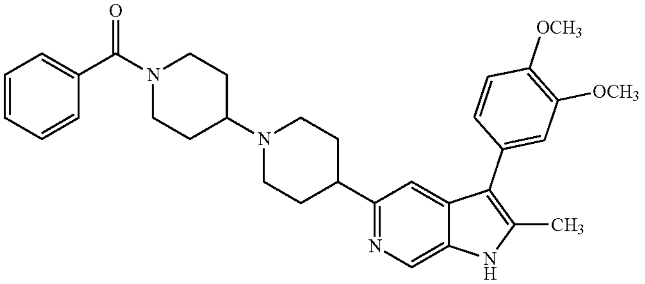 [SMILES: COc1ccc(-c2c(C)[nH]c3cnc(C4CCN(C5CCN(C(=O)c6ccccc6)CC5)CC4)cc23)cc1OC] |
| 15 | 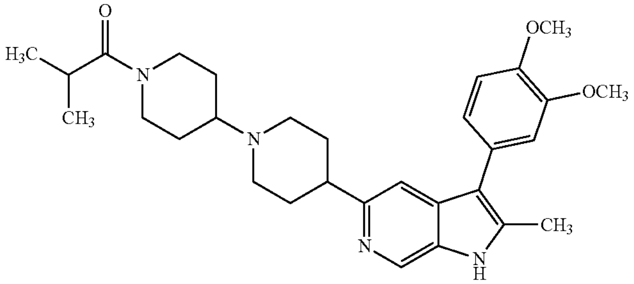 [SMILES: COc1ccc(-c2c(C)[nH]c3cnc(C4CCN(C5CCN(C(=O)C(C)C)CC5)CC4)cc23)cc1OC] |
| 16 | 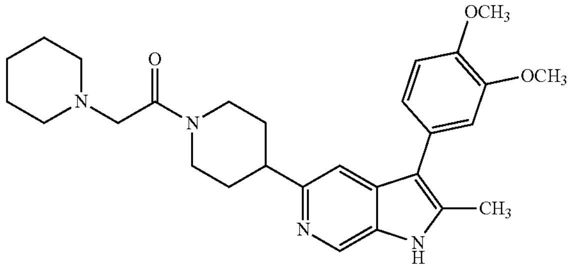 [SMILES: COc1ccc(-c2c(C)[nH]c3cnc(C4CCN(C(=O)CN5CCCCC5)CC4)cc23)cc1OC] |
| 17 | 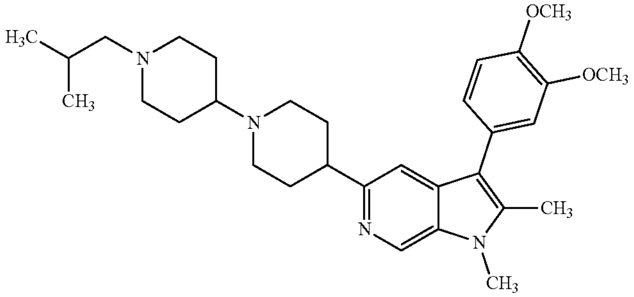 [SMILES: COc1ccc(-c2c(C)n(C)c3cnc(C4CCN(C5CCN(CC(C)C)CC5)CC4)cc23)cc1OC] |

TABLE 1-continued
| Ex. No. | Structure |
| --- | --- |
| 18 | 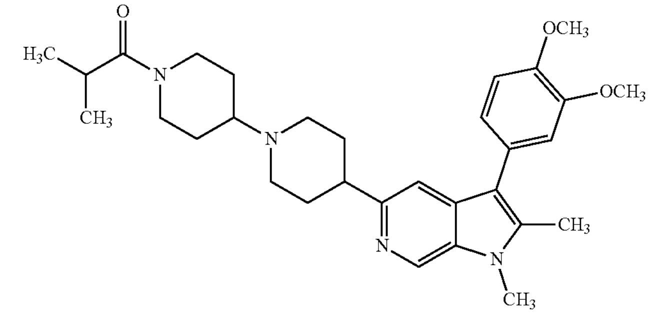 [SMILES: COc1ccc(-c2c(C)n(C)c3cnc(C4CCN(C5CCN(C(=O)C(C)C)CC5)CC4)cc23)cc1OC] |
| 19 | 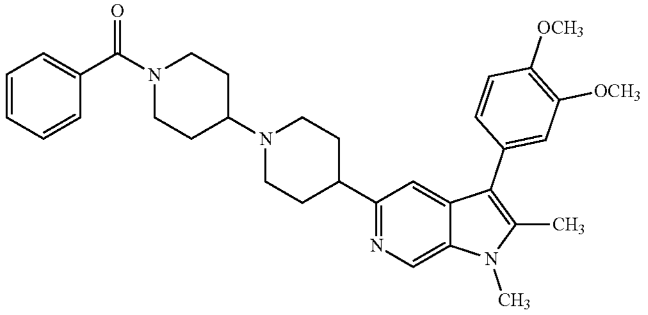 [SMILES: COc1ccc(-c2c(C)n(C)c3cnc(C4CCN(C5CCN(C(=O)c6ccccc6)CC5)CC4)cc23)cc1OC] |
| 20 | 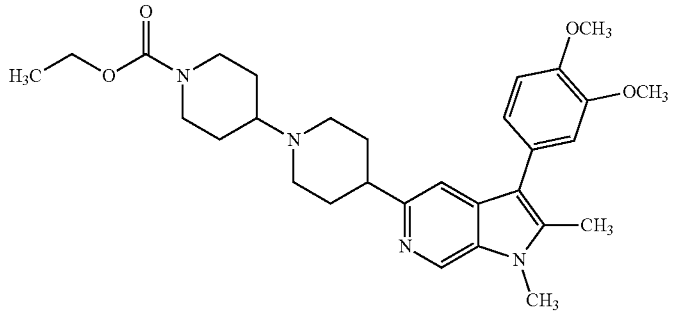 [SMILES: CCOC(=O)N1CCC(N2CCC(c3cc4c(-c5ccc(OC)c(OC)c5)c(C)n(C)c4cn3)CC2)CC1] |
| 21 | 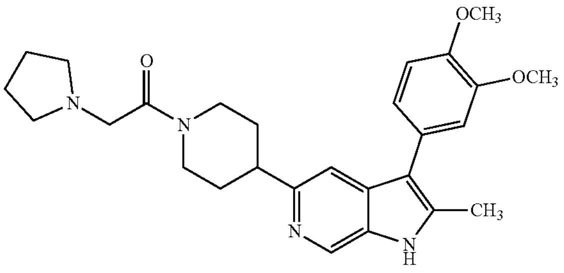 [SMILES: COc1ccc(-c2c(C)[nH]c3cnc(C4CCN(C(=O)CN5CCCC5)CC4)cc23)cc1OC] |
| 22 | 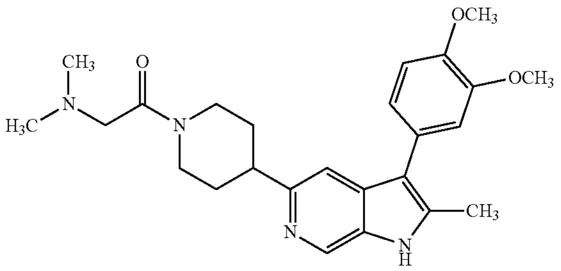 [SMILES: COc1ccc(-c2c(C)[nH]c3cnc(C4CCN(C(=O)CN(C)C)CC4)cc23)cc1OC] |

TABLE 1-continued
| Ex. No. | Structure |
| --- | --- |
| 23 | 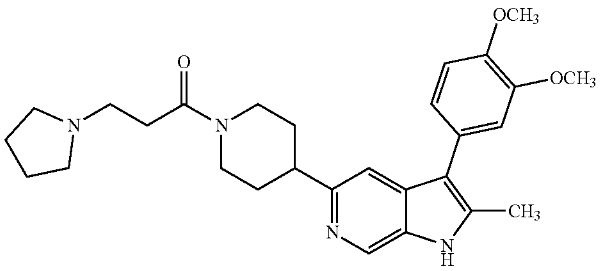 [SMILES: COc1ccc(-c2c(C)[nH]c3cnc(C4CCN(C(=O)CCN5CCCC5)CC4)cc23)cc1OC] |
| 24 | 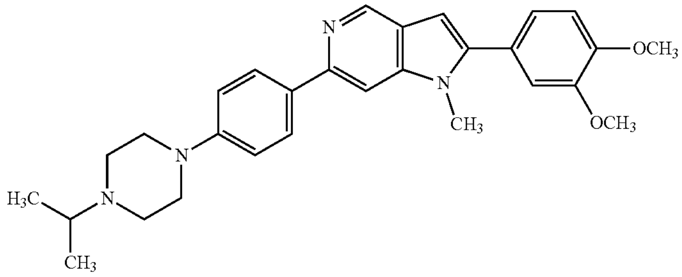 |
| 25 | 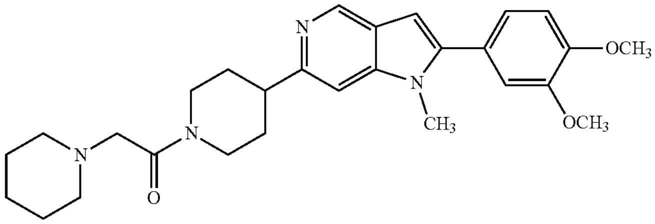 |
| 26 | 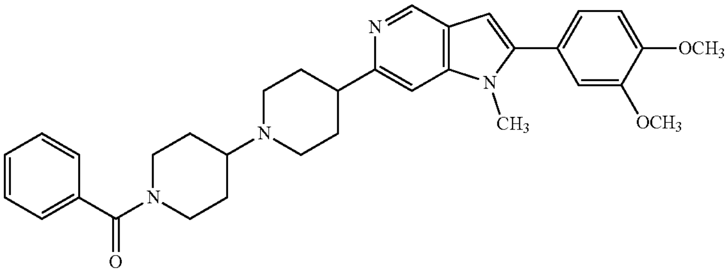 |
| 27 | 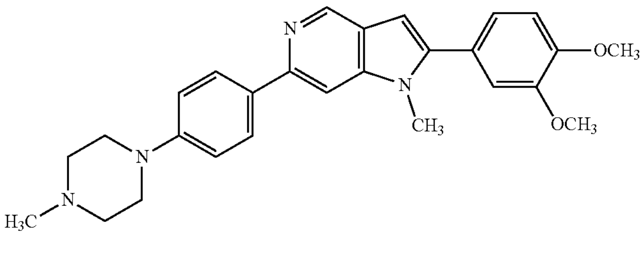 |
| 28 | 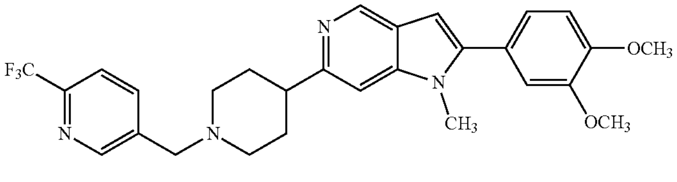 |

TABLE 1-continued
| Ex. No. | Structure |
| --- | --- |
| 29 | 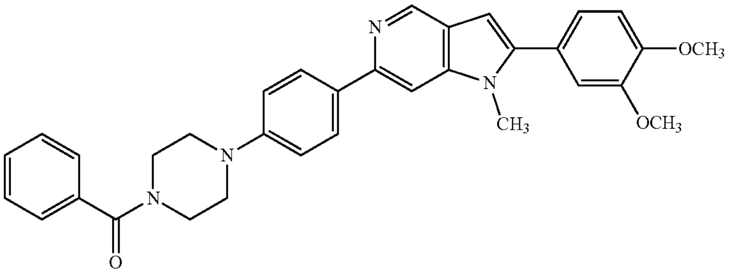 |
| 30 | 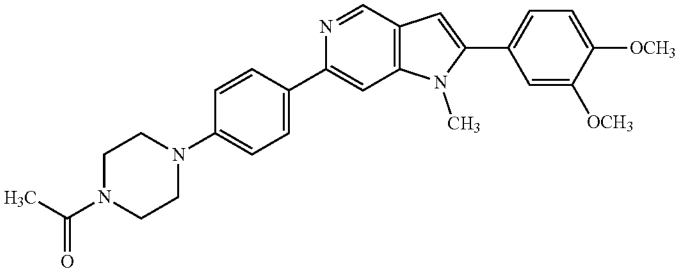 |
| 31 | 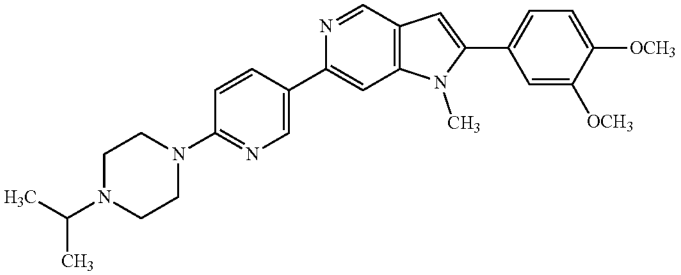 |
| 32 | 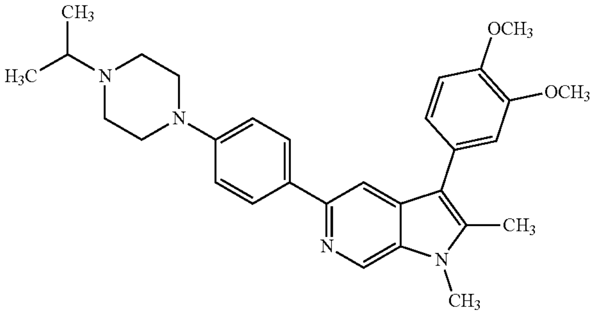 [SMILES: COc1ccc(-c2c(C)n(C)c3cnc(-c4ccc(N5CCN(C(C)C)CC5)cc4)cc23)cc1OC] |
| 33 | 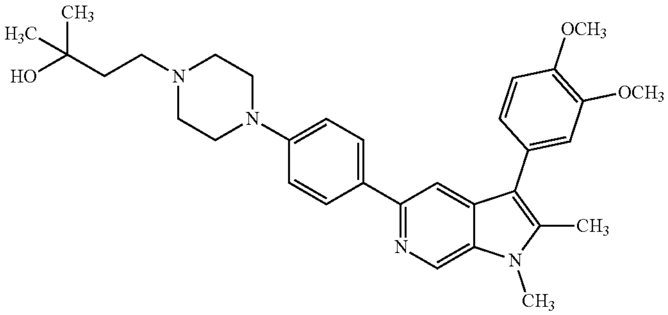 [SMILES: COc1ccc(-c2c(C)n(C)c3cnc(-c4ccc(N5CCN(CCC(C)(C)O)CC5)cc4)cc23)cc1OC]

TABLE 1-continued
| Ex. No. | Structure |
|---|---|
| 34 | 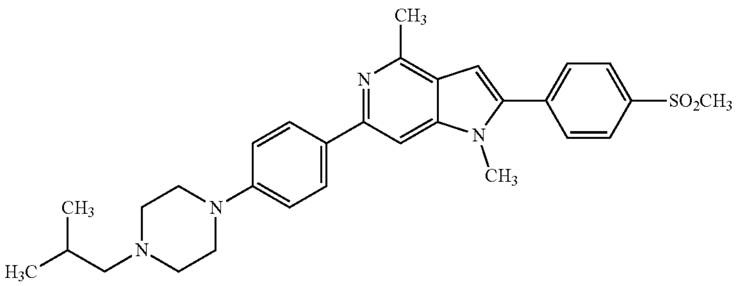 |
| 35 | 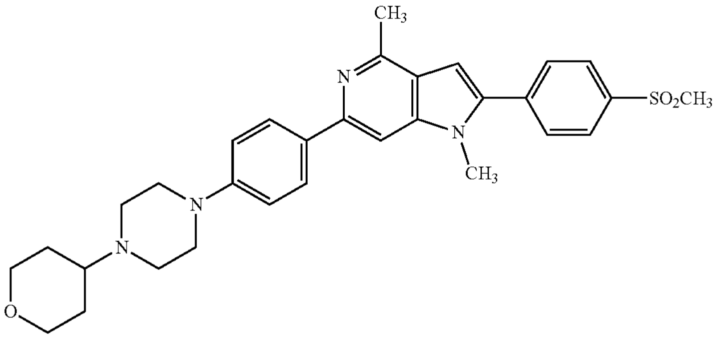 |
| 36 | 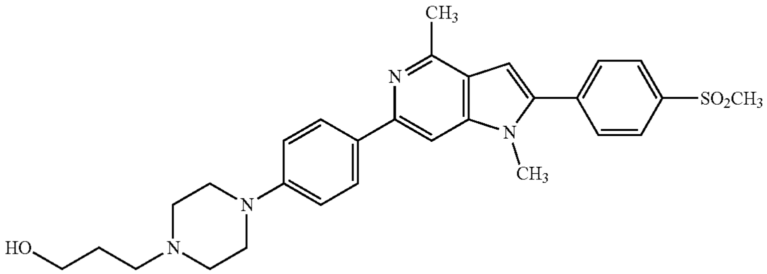 |
| 37 | 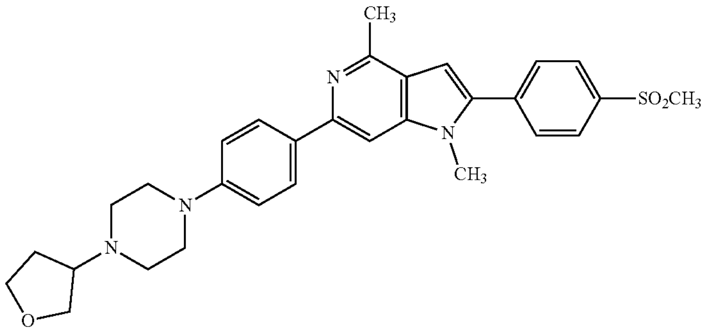 |
| 38 | 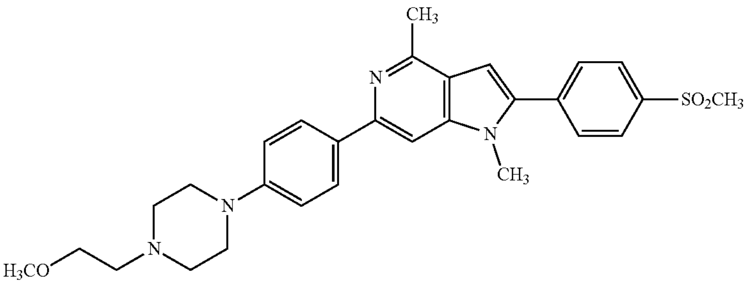 |

TABLE 1-continued

| Ex. No. | Structure |
|---|---|
| 39 | 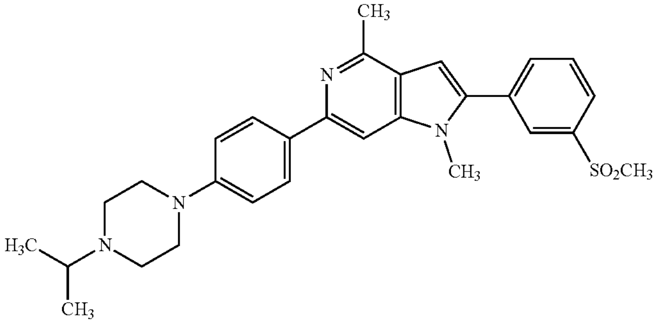 |
| 40 | 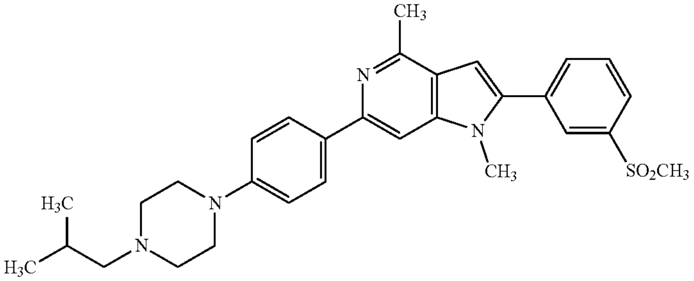 |

| Ex. No. | Analytical data |
|---|---|
| 13 | LCMS $(M + H)^+$ = 505.4. $^1H$ NMR (500 MHz, dichloromethane-$d_2$) δ 8.66 (s, 1H), 7.36 (s, 1H), 7.08-7.03 (m, 1H), 7.01-6.97 (m, 1H), 6.93 (d, J = 1.7 Hz, 1H), 3.95 (s, 3H), 3.90 (s, 3H), 3.69 (s, 3H), 3.11 (br d, J = 10.2 Hz, 2H), 2.95 (br d, J = 11.6 Hz, 2H), 2.86-2.75 (m, 1H), 2.44-2.30 (m, 3H), 2.26 (s, 3H), 2.10-2.01 (m, 4H), 1.94-1.78 (m, 8H), 1.63-1.60 (m, 2H), 0.92 (d, J = 6.6 Hz, 6H) |
| 14 | LCMS $(M + H)^+$ = 539.4. $^1H$ NMR (500 MHz, chloroform-d) δ 8.68 (s, 1H), 7.48-7.38 (m, 6H), 7.03-6.98 (m, 3H), 4.88-4.73 (m, 1H), 3.98 (s, 3H), 3.95 (s, 3H), 3.90-3.77 (m, 1H), 3.10 (br d, J = 11.0 Hz, 2H), 3.07-2.99 (m, 1H), 2.88-2.77 (m, 2H), 2.65-2.58 (m, 1H), 2.57 (s, 3H), 2.38 (br t, J = 11.0 Hz, 2H), 2.12-1.98 (m, 3H), 1.86 (qd, J = 12.3, 3.4 Hz, 4H), 1.59-1.47 (m, 2H) |
| 15 | LCMS $(M + H)^+$ = 505.2. |
| 16 | LCMS $(M + H)^+$ = 477.5. $^1H$ NMR (500 MHz, chloroform-d) δ 8.68 (s, 1H), 8.32 (br s, 1H), 7.37 (s, 1H), 7.05-6.97 (m, 3H), 4.77 (br d, J = 13.2 Hz, 1H), 4.34 (br d, J = 13.2 Hz, 1H), 3.98 (s, 3H), 3.95 (s, 3H), 3.26-3.20 (m, 1H), 3.18-3.10 (m, 2H), 3.03 (tt, J = 12.0, 3.6 Hz, 1H), 2.76-2.69 (m, 1H), 2.57 (s, 3H), 2.46 (br d, J = 3.6 Hz, 4H), 2.06 (br t, J = 11.8 Hz, 2H), 1.88-1.70 (m, 2H), 1.61-1.57 (m, 4H), 1.44 (br d, J = 5.0 Hz, 2H) |
| 17 | LCMS $(M + H)^+$ = 505.3. $^1H$ NMR (500 MHz, chloroform-d) δ 8.65 (s, 1H), 7.42 (s, 1H), 7.04-6.94 (m, 3H), 3.98 (s, 3H), 3.94 (s, 3H), 3.83 (s, 3H), 3.09 (br d, J = 11.0 Hz, 2H), 2.95 (br d, J = 11.6 Hz, 2H), 2.86-2.77 (m, 1H), 2.52 (s, 3H), 2.42-2.29 (m, 3H), 2.07 (br d, J = 7.4 Hz, 4H), 1.94-1.77 (m, 7H), 1.69-1.66 (m, 2H), 0.91 (d, J = 6.3 Hz, 6H) |
| 18 | LCMS $(M + H)^+$ = 519.2. $^1H$ NMR (500 MHz, chloroform-d) δ 8.65 (s, 1H), 7.40 (s, 1H), 7.03-7.00 (m, 1H), 6.99-6.95 (m, 2H), 4.73 (br d, J = 12.9 Hz, 1H), 4.06-3.99 (m, 1H), 3.98 (s, 3H), 3.94 (s, 3H), 3.83 (s, 3H), 3.13-3.00 (m, 3H), 2.88-2.78 (m, 2H), 2.62-2.53 (m, 2H), 2.43-2.30 (m, 2H), 2.11-2.03 (m, 2H), 1.99-1.80 (m, 7H), 1.58-1.42 (m, 2H), 1.15 (br t, J = 7.4 Hz, 6H) |
| 19 | LCMS $(M + H)^+$ = 553.2. $^1H$ NMR (500 MHz, chloroform-d) δ 8.66 (s, 1H), 7.42 (s, 5H), 7.41 (s, 1H), 7.03-7.00 (m, 1H), 6.99-6.95 (m, 2H), 4.89-4.71 (m, 1H), 3.98 (s, 3H), 3.94 (s, 3H), 3.83 (s, 4H), 3.14-2.99 (m, 3H), 2.83 (tt, J = 12.1, 3.6 Hz, 2H), 2.67-2.56 (m, 1H), 2.52 (s, 3H), 2.38 (br t, J = 11.0 Hz, 2H), 2.12-2.00 (m, 3H), 1.95-1.80 (m, 3H), 1.70-1.48 (m, 2H) |
| 20 | LCMS $(M + H)^+$ = 521.5. $^1H$ NMR (500 MHz, chloroform-d) δ 8.65 (s, 1H), 7.41 (s, 1H), 7.03-7.00 (m, 1H), 6.99-6.94 (m, 2H), 4.30-4.18 (m, 2H), 4.15 (q, J = 7.2 Hz, 2H), 3.98 (s, 3H), 3.94 (s, 3H), 3.83 (s, 3H), 3.07 (br d, J = 11.3 Hz, 2H), 2.85-2.73 (m, 3H), 2.52 (s, 3H), 2.51-2.46 (m, 1H), 2.37 (br t, J = 10.9 Hz, 2H), 2.06 (br d, J = 12.9 Hz, 2H), 1.91-1.79 (m, 4H), 1.51 (qd, J = 12.1, 4.1 Hz, 2H), 1.28 (t, J = 7.2 Hz, 3H) |
| 21 | LCMS $(M + H)^+$ = 463.5. $^1H$ NMR (500 MHz, chloroform-d) δ 9.28 (br s, 1H), 8.67 (s, 1H), 7.36 (s, 1H), 7.05-6.96 (m, 3H), 4.77 (br d, J = 13.2 Hz, 1H), 4.22 (br d, J = 13.2 Hz, 1H), 3.97 (s, 3H), 3.94 (s, 3H), 3.42-3.32 (m, |

-continued

| Ex. No. | Analytical data |
|---|---|
| | 2H), 3.15 (br t, J = 12.0 Hz, 1H), 3.02 (tt, J = 12.0, 3.6 Hz, 1H), 2.75-2.70 (m, 1H), 2.62 (br t, J = 5.4 Hz, 4H), 2.57 (s, 3H), 2.04 (br t, J = 11.6 Hz, 2H), 1.94 (br s, 2H), 1.81-1.78 (m, 4H) |
| 22 | LCMS $(M + H)^+$ = 437.5. $^1H$ NMR (500 MHz, chloroform-d) δ 8.68 (s, 1H), 8.42 (br s, 1H), 7.37 (s, 1H), 7.05-6.98 (m, 3H), 4.78 (br d, J = 12.9 Hz, 1H), 4.25 (br d, J = 13.2 Hz, 1H), 3.98 (s, 3H), 3.95 (s, 3H), 3.20-3.12 (m, 3H), 3.02 (tt, J = 11.9, 3.5 Hz, 1H), 2.76-2.70 (m, 1H), 2.57 (s, 3H), 2.32 (s, 6H), 2.09-2.02 (m, 2H), 1.87-1.72 (m, 2H) |
| 23 | LCMS $(M + H)^+$ = 477.5. $^1H$ NMR (500 MHz, chloroform-d) δ 8.91 (br s, 1H), 8.66 (s, 1H), 7.35 (s, 1H), 7.04-6.97 (m, 3H), 4.80 (br d, J = 13.2 Hz, 1H), 4.02 (br d, J = 13.5 Hz, 1H), 3.97 (s, 3H), 3.95 (s, 3H), 3.18 (td, J = 13.1, 2.2 Hz, 1H), 3.01 (tt, J = 11.9, 3.5 Hz, 1H), 2.88-2.82 (m, 2H), 2.66-2.61 (m, 2H), 2.58 (br s, 4H), 2.56 (s, 3H), 2.09-1.98 (m, 2H), 1.88-1.75 (m, 7H) |
| 24 | LCMS $(M + H)^+$ = 471.5. $^1H$ NMR (500 MHz, chloroform-d) δ 8.95 (d, J = 0.8 Hz, 1H), 8.06-7.98 (m, 2H), 7.60 (s, 1H), 7.12-7.08 (m, 1H), 7.08-7.04 (m, 3H), 7.04-7.00 (m, 1H), 6.60 (s, 1H), 3.99 (s, 3H), 3.97 (s, 3H), 3.79 (s, 3H), 3.35-3.30 (m, 4H), 2.79-2.73 (m, 5H), 1.14 (d, J = 6.6 Hz, 6H) |
| 25 | LCMS $(M + H)^+$ = 477.4. $^1H$ NMR (500 MHz, chloroform-d) δ 8.85 (s, 1H), 7.09 (s, 1H), 7.08-7.05 (m, 1H), 7.02-6.99 (m, 2H), 6.58 (s, 1H), 4.81 (br d, J = 13.2 Hz, 1H), 4.37 (br d, J = 13.2 Hz, 1H), 3.98 (s, 3H), 3.95 (s, 3H), 3.74 (s, 3H), 3.28-3.23 (m, 1H), 3.21-3.08 (m, 3H), 2.76 (td, J = 12.8, 2.2 Hz, 1H), 2.48 (br d, J = 4.1 Hz, 4H), 2.20-2.06 (m, 2H), 1.82 (quind, J = 12.4, 4.1 Hz, 2H), 1.62 (quin, J = 5.6 Hz, 4H), 1.46 (br d, J = 4.4 Hz, 2H). |
| 26 | LCMS $(M + H)^+$ = 539.5. $^1H$ NMR (500 MHz, chloroform-d) δ 8.84 (s, 1H), 7.43 (s, 5H), 7.15 (s, 1H), 7.09-7.04 (m, 1H), 7.02-6.99 (m, 2H), 6.57 (s, 1H), 4.82 (br d, J = 1.9 Hz, 1H), 3.98 (s, 3H), 3.95 (s, 3H), 3.92-3.80 (m, 1H), 3.73 (s, 3H), 3.15 (br d, J = 10.7 Hz, 2H), 3.05 (br s, 1H), 2.96-2.77 (m, 2H), 2.69-2.59 (m, 1H), 2.42 (br t, J = 11.1 Hz, 2H), 2.14 (br d, J = 12.7 Hz, 2H), 2.06 (br d, J = 14.9 Hz, 1H), 1.98-1.83 (m, 3H), 1.60-1.51 (m, 2H) |
| 27 | LCMS $(M + H)^+$ = 443.5. $^1H$ NMR (500 MHz, chloroform-d) δ 8.96 (d, J = 0.8 Hz, 1H), 8.02 (d, J = 8.8 Hz, 2H), 7.60 (s, 1H), 7.12-7.04 (m, 4H), 7.03-7.00 (m, 1H), 6.60 (d, J = 0.8 Hz, 1H), 3.99 (s, 3H), 3.97 (s, 3H), 3.80 (s, 3H), 3.35-3.31 (m, 4H), 2.66-2.62 (m, 4H), 2.40 (s, 3H) |
| 28 | LCMS $(M + H)^+$ = 511.5. $^1H$ NMR (500 MHz, chloroform-d) δ 8.85 (s, 1H), 8.74 (s, 1H), 7.96 (br d, J = 8.0 Hz, 1H), 7.68 (d, J = 8.3 Hz, 1H), 7.13 (s, 1H), 7.09-7.04 (m, 1H), 7.03-6.99 (m, 2H), 6.57 (s, 1H), 3.98 (s, 3H), 3.95 (s, 3H), 3.74 (s, 3H), 3.67 (s, 2H), 3.04 (br d, J = 11.3 Hz, 2H), 2.90 (tt, J = 12.0, 3.7 Hz, 1H), 2.31-2.24 (m, 2H), 2.10-2.04 (m, 2H), 2.03-1.92 (m, 2H) |
| 29 | LCMS $(M + H)^+$ = 533.5. $^1H$ NMR (500 MHz, chloroform-d) δ 8.97 (s, 1H), 8.04 (d, J = 8.8 Hz, 2H), 7.62 (s, 1H), 7.51-7.45 (m, 5H), 7.12-7.04 (m, 4H), 7.04-7.01 (m, 1H), 6.62 (s, 1H), 4.07-3.99 (m, 2H), 3.99 (s, 3H), 3.97 (s, 3H), 3.81 (s, 3H), 3.66 (br s, 2H), 3.44-3.21 (m, 4H) |
| 30 | LCMS $(M + H)^+$ = 471.5. $^1H$ NMR (500 MHz, chloroform-d) δ 8.97 (s, 1H), 8.04 (d, J = 8.5 Hz, 2H), 7.61 (s, 1H), 7.12-7.08 (m, 1H), 7.08-7.04 (m, 3H), 7.04-7.00 (m, 1H), 6.61 (s, 1H), 3.99 (s, 3H), 3.97 (s, 3H), 3.86-3.82 (m, 2H), 3.81 (s, 3H), 3.71-3.67 (m, 2H), 3.29 (dt, J = 17.1, 5.1 Hz, 4H), 2.19 (s, 3H) |
| 31 | LCMS $(M + H)^+$ = 472.5. $^1H$ NMR (500 MHz, chloroform-d) δ 8.95 (s, 1H), 8.85 (d, J = 2.5 Hz, 1H), 8.28 (dd, J = 8.8, 2.5 Hz, 1H), 7.57 (s, 1H), 7.12-7.08 (m, 1H), 7.06-7.00 (m, 2H), 6.80 (d, J = 9.1 Hz, 1H), 6.61 (s, 1H), 3.99 (s, 3H), 3.97 (s, 3H), 3.79 (s, 3H), 3.69-3.65 (m, 4H), 2.77 (dt, J = 13.1, 6.4 Hz, 1H), 2.72-2.68 (m, 4H), 1.13 (d, J = 6.3 Hz, 6H) |
| 32 | LCMS $(M + H)^+$ = 485.1. $^1H$ NMR (500 MHz, chloroform-d) δ 8.77 (s, 1H), 7.93 (d, J = 8.5 Hz, 2H), 7.87 (s, 1H), 7.06-7.00 (m, 5H), 3.99 (s, 3H), 3.95 (s, 3H), 3.87 (s, 3H), 3.32-3.27 (m, 4H), 2.78-2.71 (m, 5H), 2.54 (s, 3H), 1.13 (d, J = 6.3 Hz, 6H) |
| 33 | LCMS $(M + H)^+$ = 529.5. $^1H$ NMR (400 MHz, chloroform-d) δ 8.67 (d, J = 1.1 Hz, 1H), 7.86-7.80 (m, 2H), 7.76 (d, J = 0.9 Hz, 1H), 6.95-6.88 (m, 5H), 5.23 (s, 1H), 3.89 (s, 3H), 3.85 (s, 3H), 3.77 (s, 3H), 3.21-3.16 (m, 4H), 2.66-2.61 (m, 6H), 2.44 (s, 3H), 1.63-1.58 (m, 2H), 1.18 (s, 6H) |
| 34 | LCMS $(M + H)^+$ = 517.4. $^1H$ NMR (500 MHz, chloroform-d) δ 8.09 (d, J = 8.2 Hz, 2H), 8.01 (d, J = 8.8 Hz, 2H), 7.77 (d, J = 8.5 Hz, 2H), 7.47 (s, 1H), 7.05 (d, J = 8.5 Hz, 2H), 6.74 (s, 1H), 3.83 (s, 3H), 3.33-3.27 (m, 4H), 3.16 (s, 3H), 2.85 (s, 3H), 2.64-2.58 (m, 4H), 2.18 (d, J = 7.6 Hz, 2H), 1.86 (dt, J = 13.6, 6.8 Hz, 1H), 0.96 (d, J = 6.6 Hz, 6H) |
| 35 | LCMS $(M + H)^+$ = 545.4. $^1H$ NMR (400 MHz, chloroform-d) δ 8.06 (d, J = 8.4 Hz, 2H), 7.99 (d, J = 8.8 Hz, 2H), 7.74 (d, J = 8.2 Hz, 2H), 7.44 (s, 1H), 7.03 (d, J = 8.8 Hz, 2H), 6.71 (s, 1H), 4.06 (br dd, J = 10.9, 3.6 Hz, 2H), 3.80 (s, 3H), 3.47-3.37 (m, 2H), 3.33-3.27 (m, 4H), 3.13 (s, 3H), 2.83 (s, 3H), 2.79-2.73 (m, 4H), 2.50 (br t, J = 11.2 Hz, 1H), 1.88-1.78 (m, 2H), 1.67-1.59 (m, 2H) |
| 36 | LCMS $(M + H)^+$ = 519.0. $^1H$ NMR (400 MHz, chloroform-d) δ 8.09-8.04 (m, 2H), 7.99 (d, J = 8.8 Hz, 2H), 7.77-7.71 (m, 2H), 7.44 (s, 1H), 7.02 (d, J = 8.8 Hz, 2H), 6.72 (s, 1H), 3.87-3.82 (m, 2H), 3.80 (s, 3H), 3.33-3.26 (m, 4H), 3.13 (s, 3H), 2.83 (s, 3H), 2.77-2.68 (m, 6H), 1.83-1.75 (m, 2H) |
| 37 | LCMS $(M + H)^+$ = 545.4. $^1H$ NMR (400 MHz, chloroform-d) δ 8.07 (d, J = 8.4 Hz, 2H), 7.99 (d, J = 8.8 Hz, 2H), 7.77-7.72 (m, 2H), 7.44 (s, 1H), 7.02 (d, |

-continued

| Ex. No. | Analytical data |
|---|---|
| | J = 8.8 Hz, 2H), 6.72 (s, 1H), 3.93-3.84 (m, 2H), 3.80 (s, 3H), 3.79-3.73 (m, 1H), 3.55 (dd, J = 8.5, 6.0 Hz, 1H), 3.27 (t, J = 5.1 Hz, 4H), 3.13 (s, 3H), 2.84 (s, 3H), 2.69-2.58 (m, 4H), 2.46-2.41 (m, 1H), 2.05 (dtd, J = 12.5, 7.6, 5.3 Hz, 1H), 1.72-1.63 (m, 1H) |
| 38 | LCMS $(M + H)^+$ = 519.4. $^1H$ NMR (500 MHz, chloroform-d) δ 8.09 (br d, J = 8.0 Hz, 2H), 8.02 (br d, J = 8.5 Hz, 2H), 7.77 (d, J = 8.0 Hz, 2H), 7.47 (s, 1H), 7.05 (br d, J = 8.5 Hz, 2H), 6.74 (s, 1H), 3.83 (s, 3H), 3.62 (br s, 2H), 3.41 (s, 3H), 3.36 (br s, 4H), 3.16 (s, 3H), 2.87 (s, 3H), 2.82-2.68 (m, 6H) |
| 39 | LCMS $(M + H)^+$ = 503.1. $^1H$ NMR (500 MHz, chloroform-d) δ 8.15 (t, J = 1.7 Hz, 1H), 8.05-7.98 (m, 3H), 7.84 (dt, J = 7.9, 1.3 Hz, 1H), 7.76-7.69 (m, 1H), 7.46 (s, 1H), 7.08-7.02 (m, 2H), 6.72 (d, J = 0.8 Hz, 1H), 3.81 (s, 3H), 3.34-3.28 (m, 4H), 3.15 (s, 3H), 2.84 (s, 3H), 2.81-2.71 (m, 5H), 1.13 (d, J = 6.5 Hz, 6H) |
| 40 | LCMS $(M + H)^+$ = 517.3. $^1H$ NMR (400 MHz, chloroform-d) δ 8.05 (t, J = 1.7 Hz, 1H), 7.96-7.87 (m, 3H), 7.75 (dt, J = 7.8, 1.3 Hz, 1H), 7.68-7.59 (m, 1H), 7.37 (s, 1H), 6.95 (d, J = 8.8 Hz, 2H), 6.63 (d, J = 0.8 Hz, 1H), 3.71 (s, 3H), 3.24-3.16 (m, 4H), 3.06 (s, 3H), 2.75 (s, 3H), 2.54-2.48 (m, 4H), 2.09 (d, J = 7.4 Hz, 2H), 1.76 (dt, J = 13.5, 6.7 Hz, 1H), 0.87 (d, J = 6.7 Hz, 6H) |

Example 41

3-(4-(4-(1,4-Dimethyl-2-(4-(methylsulfonyl)phenyl)-1H-pyrrolo[3,2-c]pyridin-6-yl) phenyl)piperidin-1-yl)propan-1-ol (41)

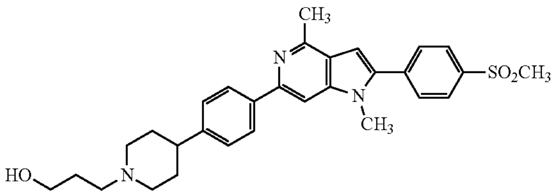

Step 1. tert-butyl 4-(4-(1,4-dimethyl-2-(4-(methyl-sulfonyl)phenyl)-1H-pyrrolo[3,2-c] pyridin-6-yl) phenyl)piperidine-1-carboxylate

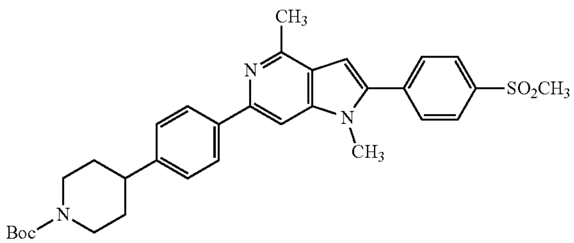 [SMILES: Cc1nc(-c2ccc(C3CCN(C(=O)OC(C)(C)C)CC3)cc2)cc2c1cc(-c1ccc(S(C)(=O)=O)cc1)n2C]

A mixture of 6-chloro-1,4-dimethyl-2-(4-(methylsulfonyl)phenyl)-1H-pyrrolo[3,2-c]pyridine (180 mg, 0.538 mmol), tert-butyl 4-(4-(4,4,5,5-tetramethyl-1,3,2-dioxaborolan-2-yl)phenyl)piperidine-1-carboxylate (Example 11, Step 5) (250 mg, 0.645 mmol), (2-dicyclohexylphosphino-2',4',6'-triisopropyl-1,1'-biphenyl)[2-(2'-amino-1,1'-biphenyl)]palladium(II) methanesulfonate (XPhos-Pd-G3) (45.5 mg, 0.054 mmol), and potassium phosphate tribasic (0.941 mL, 1.882 mmol) in 1,4-dioxane (7 mL) was degassed and heated in a closed vial at 85° C. for 18 h. Upon cooling to room temperature, the reaction mixture was diluted with ethyl acetate (120 mL) and filtered through Celite. The filtrate was washed with brine (25 mL) and dried over anhydrous $MgSO_4$. The title intermediate (196 mg, 0.350 mmol, 65.1% yield) was isolated as a beige solid by ISCO chromatography (40 g silica gel, 40-85% ethyl acetate/hexane). LCMS $(M+H)^+$=560.4. $^1H$ NMR (400 MHz, chloroform-d) δ 8.07 (d, J=8.6 Hz, 2H), 8.00 (d, J=8.4 Hz, 2H), 7.75 (d, J=8.6 Hz, 2H), 7.50 (s, 1H), 7.32 (d, J=8.2 Hz, 2H), 6.73 (d, J=0.8 Hz, 1H), 4.26 (br s, 2H), 3.82 (s, 3H), 3.14 (s, 3H), 2.89-2.65 (m, 3H), 2.84 (s, 3H), 1.87 (br d, J=12.3 Hz, 2H), 1.75-1.61 (m, 2H), 1.50 (s, 9H).

Step 2. 1,4-Dimethyl-2-(4-(methylsulfonyl)phenyl)-6-(4-(piperidin-4-yl)phenyl)-1H-pyrrolo[3,2-c]pyridine

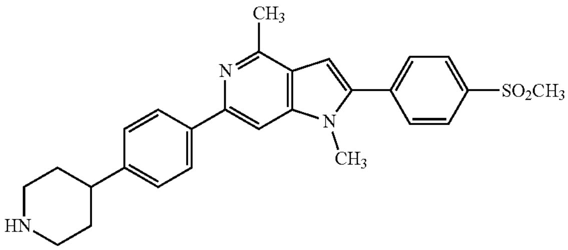 [SMILES: Cc1nc(-c2ccc(C3CCNCC3)cc2)cc2c1cc(-c1ccc(S(C)(=O)=O)cc1)n2C]

To a solution of tert-butyl 4-(4-(1,4-dimethyl-2-(4-(methylsulfonyl)phenyl)-1H-pyrrolo[3,2-c]pyridin-6-yl)phenyl) piperidine-1-carboxylate (194 mg, 0.347 mmol) in dichloromethane (8 mL) at 0° C. was added TFA (8 mL, 104 mmol) over 2 min. The mixture was stirred at 0° C. for 30 min and then concentrated under vacuum to dryness. The residue was neutralized with saturated $NaHCO_3$ solution and extracted with dichloromethane (4 times). The combined extract was dried over anhydrous $Na_2SO_4$. Removal of the solvent under vacuum provided the title intermediate (168 mg, 0.366 mmol, 105% yield) as a beige solid. LCMS $(M+H)^+$=460.4.

Step 3. 3-(4-(4-(1,4-Dimethyl-2-(4-(methylsulfonyl) phenyl)-1H-pyrrolo[3,2-c]pyridin-6-yl)phenyl)piperidin-1-yl)propan-1-ol A mixture of 1,4-dimethyl-2-(4-(methylsulfonyl)phenyl)-6-(4-(piperidin-4-yl) phenyl)-1H-pyrrolo[3,2-c]pyridine (30 mg, 0.065 mmol), 3-bromopropan-1-ol (18.14 mg, 0.131 mmol), and potassium carbonate (18.04 mg, 0.131 mmol) in DMF (0.5 mL) was stirred at room temperature for 36 h. The mixture was diluted with ethyl acetate (5 mL) and filtered through Celite. The filtrate was concentrated under vacuum to dryness. The residue was diluted with MeOH and injected to prep. HPLC. The correct fractions were combined, concentrated under vacuum, basified with saturated $NaHCO_3$ solution, and extracted with dichloromethane (4 times). The combined extract was dried over anhydrous $Na_2SO_4$. Removal of the solvent under vacuum provided the title compound (1.5 mg, 2.81 μmol, 4.31% yield) as a white solid. LCMS $(M+H)^+$=518.5.

Example 42

2-(4-(Cyclopropylsulfonyl)phenyl)-6-(4-(4-isopropylpiperazin-1-yl)phenyl)-1,4-dimethyl-1H-pyrrolo[3,2-c]pyridine (42)

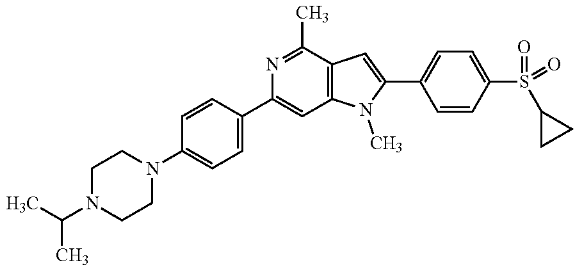

Step 1. ((4-(Cyclopropylsulfonyl)phenyl)ethynyl) trimethylsilane

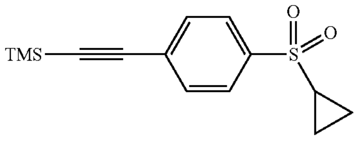 [SMILES: C[Si](C)(C)C#Cc1ccc(S(=O)(=O)C2CC2)cc1]

A mixture of 1-bromo-4-(cyclopropylsulfonyl)benzene (1.0 g, 3.83 mmol), bis(triphenylphosphine)palladium(II) chloride (0.054 g, 0.077 mmol), copper(I) iodide (0.036 g, 0.191 mmol), and triethylamine (2.85 mL, 20.46 mmol) in DMF (3.8 mL) was bubbled with $N_2$ for 5 min before ethynyl trimethylsilane (1.060 mL, 7.66 mmol) was added. The reaction vial was sealed and heated at 90° C. for 18 h. Upon cooling to room temperature, the mixture was diluted with EtOAc (300 mL), washed with water (100 mL), dried over $Mg_2SO_4$, and concentrated under vacuum. The residue was purified by ISCO chromatography (80 g silica gel, 0-60% Hexane/EtOAc) to give the title intermediate (1.06 g, 3.81 mmol, 99% yield) as a light brown solid. $^1$H NMR (400 MHz, chloroform-d) δ 7.63 (d, J=8.4 Hz, 2H), 7.44-7.39 (m, 2H), 2.24 (tt, J=8.0, 4.7 Hz, 1H), 1.18-1.11 (m, 2H), 0.88-0.79 (m, 2H), 0.07 (s, 9H).

Step 2. 1-(cyclopropylsulfonyl)-4-ethynylbenzene

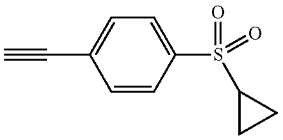

To a mixture of ((4-(cyclopropylsulfonyl)phenyl)ethynyl) trimethylsilane (1.06 g, 3.81 mmol) in MeOH (50 mL) was added potassium carbonate (52.0 mg, 0.376 mmol). The reaction mixture was stirred at room temperature for 1.25 h. The solvent was removed under vacuum. The residue was diluted with dichloromethane (400 ml), washed with water (100 ml), dried over $MgSO_4$. Removal of the solvent under vacuum afforded the title intermediate (0.77 g, 3.73 mmol, 98% yield) as a light brown solid. $^1$H NMR (400 MHz, chloroform-d) δ 7.98-7.82 (m, 2H), 7.76-7.61 (m, 2H), 2.50 (tt, J=8.0, 4.8 Hz, 1H), 1.63 (s, 1H), 1.49-1.34 (m, 2H), 1.18-1.02 (m, 2H).

Step 3. 3-((4-(Cyclopropylsulfonyl)phenyl)ethynyl)-2,6-dimethylpyridin-4-amine

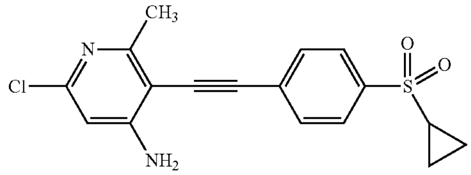 [SMILES: Cc1nc(Cl)cc(N)c1C#Cc1ccc(S(=O)(=O)C2CC2)cc1]

To a stirred solution of 6-chloro-3-iodo-2-methylpyridin-4-amine (Example 11, Step 1) (0.4 g, 1.490 mmol) in DMF (6 mL) was added 1-(cyclopropylsulfonyl)-4-ethynylbenzene (0.369 g, 1.79 mmol), bis(triphenylphosphine)palladium(II) dichloride (0.105 g, 0.149 mmol), copper(I) iodide (0.028 g, 0.149 mmol) and triethylamine (0.623 mL, 4.47 mmol). The resulting mixture was degassed with nitrogen and then heated at 100° C. for 2 h. Upon cooling to room temperature, the mixture was diluted with water (20 mL) and extracted with EtOAc (3×80 mL). The combined extract was dried over $Na_2SO_4$ and concentrated under reduced pressure. The residue was purified by ISCO chromatography (80 g silica gel, 0-5% $MeOH/CH_2Cl_2$) to the title intermediate (267 mg, 0.770 mmol, 51.7% yield) as a light yellow solid. LCMS $(M+H)^+$=347.0.

Step 4. 6-Chloro-2-(4-(cyclopropylsulfonyl)phenyl)-4-methyl-1H-pyrrolo[3,2-c]pyridine

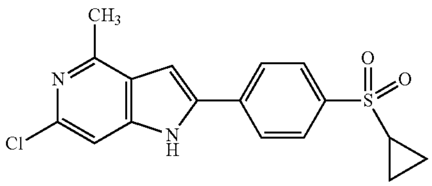 [SMILES: Cc1nc(Cl)cc2[nH]c(-c3ccc(S(=O)(=O)C4CC4)cc3)cc12]

To a stirred solution of 6-chloro-3-((4-(cyclopropylsulfonyl)phenyl)ethynyl)-2-methylpyridin-4-amine (267 mg, 0.770 mmol) in DMF (2.9 mL) at room temperature was added potassium tert-butoxide (259 mg, 2.309 mmol) in one portion. The mixture was stirred at 80° C. for 1 h. Upon cooling to room temperature, the mixture was diluted with water (80 mL) and extracted with EtOAc (3×60 mL). The combined extract was washed with brine, dried over $Na_2SO_4$, and concentrated under reduced pressure. The residue was subjected to a silica gel column with 1:1 EtOAc/petroleum ether as the effluent to afford the title intermediate (187 mg, 0.539 mmol, 70.0% yield) as a yellow solid. LCMS $(M+H)^+$=346.7. $^1H$ NMR (400 MHz, chloroform-d) δ 9.65 (br s, 1H), 7.90-7.83 (m, 2H), 7.81-7.73 (m, 2H), 7.15 (s, 1H), 6.91 (d, J=1.0 Hz, 1H), 2.67 (s, 3H), 2.44 (tt, J=8.0, 4.8 Hz, 1H), 1.39-1.26 (m, 2H), 1.08-0.96 (m, 2H).

Step 5. 6-Chloro-2-(4-(cyclopropylsulfonyl)phenyl)-1,4-dimethyl-1H-pyrrolo[3,2-c] pyridine

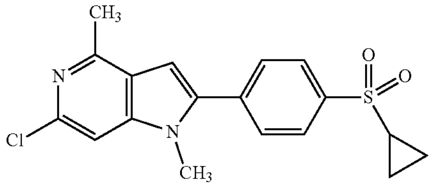 [SMILES: Cc1nc(Cl)cc2c1cc(-c1ccc(S(=O)(=O)C3CC3)cc1)n2C]

To a solution of 6-chloro-2-(4-(cyclopropylsulfonyl)phenyl)-4-methyl-1H-pyrrolo[3,2-c]pyridine (187 mg, 0.539 mmol) and iodomethane (0.084 mL, 1.348 mmol) in DMF (6 mL) at 0° C. was added sodium hydride (60% dispersion in oil) (53.9 mg, 1.348 mmol) in one portion. The mixture was stirred at room temperature for 1 h and then quenched with acetic acid (0.154 mL, 2.70 mmol). The resulting mixture was concentrated under vacuum to almost dryness. The residue was diluted with ethyl acetate (120 mL), washed with saturated $NaHCO_3$ solution (2×25 mL), dried over anhydrous $MgSO_4$, and concentrated under vacuum. The residue was subjected to ISCO chromatography (24 g silica gel, 0-100% Hexane/EtOAc)) to provide the title intermediate (136 mg, 0.378 mmol, 70%) as a beige solid. LCMS $(M+H)^+$=361.0. $^1H$ NMR (400 MHz, chloroform-d) δ 7.95 (d, J=8.2 Hz, 2H), 7.63 (d, J=8.2 Hz, 2H), 7.10 (s, 1H), 6.62 (s, 1H), 3.66 (s, 3H), 2.66 (s, 3H), 2.46 (tt, J=8.0, 4.7 Hz, 1H), 1.39-1.31 (m, 2H), 1.07-0.99 (m, 2H).

Step 6. 2-(4-(Cyclopropylsulfonyl)phenyl)-6-(4-(4-isopropylpiperazin-1-yl)phenyl)-1,4-dimethyl-1H-pyrrolo[3,2-c]pyridine A mixture of 6-chloro-2-(4-(cyclopropylsulfonyl)phenyl)-1,4-dimethyl-1H-pyrrolo[3,2-c]pyridine (25.4 mg, 0.070 mmol), 1-isopropyl-4-(4-(4,4,5,5-tetramethyl-1,3,2-dioxaborolan-2-yl)phenyl)piperazine (48 mg, 0.145 mmol), (2-dicyclohexylphosphino-2',4',6'-triisopropyl-1,1'-biphenyl)[2-(2'-amino-1,1'-biphenyl)]palladium(II) methanesulfonate (XPhos-Pd-G3) (11 mg, 0.013 mmol), and potassium phosphate tribasic (0.123 mL, 0.246 mmol) in 1,4-dioxane (1.5 mL) was degassed and heated in a closed vial at 85° C. for 18 h. Upon cooling to room temperature, the reaction mixture was diluted with methanol, filtered through an Acrodisc, and injected to prep. HPLC. The correct fractions were concentrated under vacuum, basified with 1 N NaOH, and extracted with dichloromethane (3×40 mL). The combined extract was dried over anhydrous $Na_2SO_4$. Removal of the solvent under vacuum provided the title compound (9.01 mg, 0.016 mmol, 22.75% yield) as a beige solid. LCMS $(M+H)^+$=529.1. $^1H$ NMR (400 MHz, chloromethane-d) δ 7.93 (dd, J=12.8, 8.7 Hz, 4H), 7.65 (d, J=8.4 Hz, 2H), 7.37 (s, 1H), 6.96 (d, J=9.0 Hz, 2H), 6.64 (s, 1H), 3.73 (s, 3H), 3.26-3.19 (m, 4H), 2.76 (s, 3H), 2.69-2.63 (m, 5H), 2.51-2.42 (m, 1H), 1.37-1.32 (m, 2H), 1.07-1.01 (m, 8H).

Example 43

6-(2,5-Difluoro-4-(piperazin-1-yl)phenyl)-1,4-dimethyl-2-(4-(methylsulfonyl) phenyl)-1H-pyrrolo[3,2-c]pyridine (43)

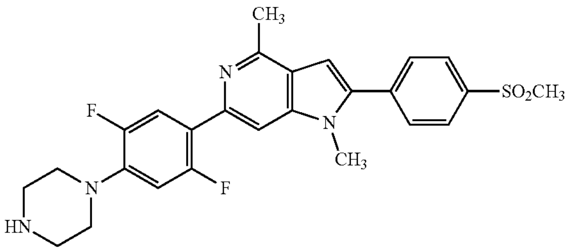

Step 1. tert-Butyl 4-(4-bromo-2,5-difluorophenyl) piperazine-1-carboxylate

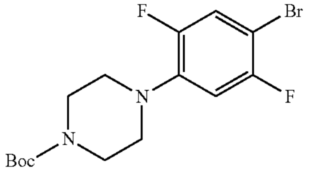 [SMILES: CC(C)(C)OC(=O)N1CCN(c2cc(F)c(Br)cc2F)CC1]

To a solution of tert-butyl piperazine-1-carboxylate (1.0 g, 5.37 mmol) in toluene (10 mL) at room temperature was added 1-bromo-2,5-difluoro-4-iodo-benzene (1.71 g, 5.37 mmol), NaOtBu (1.03 g, 10.74 mmol), BINAP (0.67 g, 1.07 mmol) and $Pd_2(dba)_3$ (0.49 g, 0.54 mmol). The resulting mixture was degassed three times with nitrogen and stirred at 90° C. overnight. The mixture was concentrated under reduced pressure, diluted with EtOAc (200 mL), washed with water (200 mL), and dried over anhydrous sodium sulfate. After the solvent was removed under reduced pressure, the residue was purified by silica gel column chromatography with petroleum ether/EtOAc (20/1) as the eluent to afford the title intermediate (1.6 g, 79% yield) as a yellow solid. LCMS $(M+H)^+$=320.9.

Step 2. tert-Butyl 4-(2,5-difluoro-4-(4,4,5,5-tetramethyl-1,3,2-dioxaborolan-2-yl)phenyl) piperazine-1-carboxylate

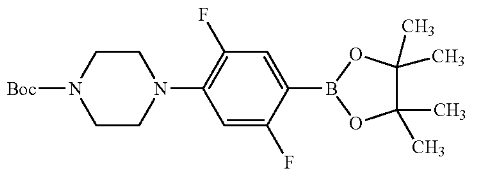 [SMILES: CC(C)(C)OC(=O)N1CCN(c2cc(F)c(B3OC(C)(C)C(C)(C)O3)cc2F)CC1]

To a solution of tert-butyl 4-(4-bromo-2,5-difluoro-phenyl)piperazine-1-carboxylate (1.6 g, 4.24 mmol) in 1,4-dioxane (15 mL) was added bis(pinacolato)diboron (2.15 g, 8.48 mmol), KOAc (1.25 g, 12.72 mmol), and $PdCl_2$(dppf) (0.31 g, 0.42 mmol). The resulting mixture was degassed three times with nitrogen and stirred at 90° C. for 2 h. The mixture was concentrated under vacuum, and the residue was purified by silica gel column chromatography with petroleum ether/EtOAc (10/1) as the eluent to afford the title intermediate (1.522 g, 78% yield) as a brown solid. LCMS $(M+H)^+$=425.4. $^1$H NMR (300 MHz, Chloroform-d) δ 7.50-7.29 (m, 1H), 6.69-6.43 (m, 1H), 3.64-3.55 (m, 4H), 3.15-3.05 (m, 4H), 1.48 (s, 9H), 1.23 (s, 12H).

Step 3. tert-Butyl 4-(4-(1,4-dimethyl-2-(4-(methylsulfonyl)phenyl)-1H-pyrrolo[3,2-c] pyridin-6-yl)-2,5-difluorophenyl)piperazine-1-carboxylate

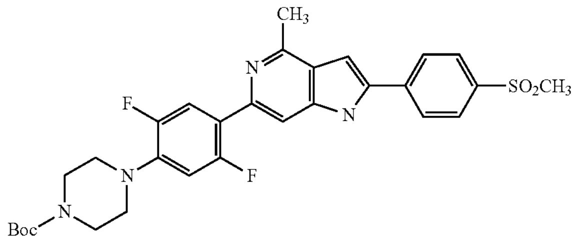

A mixture of 6-chloro-1,4-dimethyl-2-(4-(methylsulfonyl)phenyl)-1H-pyrrolo[3,2-c]pyridine (Example 11, Step 5) (75 mg, 0.224 mmol), tert-butyl 4-(2,5-difluoro-4-(4,4,5,5-tetramethyl-1,3,2-dioxaborolan-2-yl)phenyl)piperazine-1-carboxylate (119 mg, 0.280 mmol), (2-dicyclohexylphosphino-2',4',6'-triisopropyl-1,1'-biphenyl)[2-(2'-amino-1,1'-biphenyl)]palladium(II) methanesulfonate (XPhos-Pd-G3) (18.96 mg, 0.022 mmol), and potassium phosphate tribasic (0.392 mL, 0.784 mmol) in 1,4-dioxane (3 mL) was degassed and heated in a closed vial at 85° C. for 16 h. Upon cooling to room temperature, the reaction mixture was diluted with ethyl acetate (10 mL) and filtered through Celite. The filtrate was diluted with ethyl acetate (50 mL), washed with brine (10 mL), and dried over anhydrous $MgSO_4$. The title intermediate (87 mg, 0.146 mmol, 65.1% yield) was isolated as a yellow solid by ISCO chromatography (40 g silica gel, 30-80% ethyl acetate/hexane). LCMS $(M+H)^+$=597.4.

Step 4. 6-(2,5-Difluoro-4-(piperazin-1-yl)phenyl)-1,4-dimethyl-2-(4-(methylsulfonyl) phenyl)-1H-pyrrolo[3,2-c]pyridine To a solution of tert-butyl 4-(4-(1,4-dimethyl-2-(4-(methylsulfonyl)phenyl)-1H-pyrrolo[3,2-c]pyridin-6-yl)-2,5-difluorophenyl)piperazine-1-carboxylate (87 mg, 0.146 mmol) in dichloromethane (2 mL) at 0° C. was added TFA (2 mL, 26.0 mmol) over 2 min. The mixture was stirred at 0° C. for 40 min and then concentrated under vacuum to dryness. The residue was neutralized with saturated $NaHCO_3$ solution (10 mL) and extracted with dichloromethane (4×30 mL). The combined extract was dried over anhydrous $Na_2SO_4$. Removal of the solvent under vacuum provided the title product (55 mg, 0.107 mmol, 73.7% yield) as a pale yellow solid. LCMS $(M+H)^+$=497.1. $^1$H NMR (400 MHz, DMSO-$d_6$) δ 8.08 (d, J=8.6 Hz, 2H), 7.95 (d, J=8.4 Hz, 2H), 7.88 (dd, J=14.5, 7.4 Hz, 1H), 7.77 (s, 1H), 7.01-6.92 (m, 2H), 3.84 (s, 3H), 3.31 (s, 3H), 3.09 (br dd, J=5.9, 3.5 Hz, 4H), 2.99-2.91 (m, 4H), 2.74 (s, 3H).

Example 44

1-(4-(4-(1,4-Dimethyl-2-(4-(methylsulfonyl)phenyl)-1H-pyrrolo[3,2-c]pyridin-6-yl) benzyl)piperazin-1-yl)-2-methylpropan-2-ol (44)

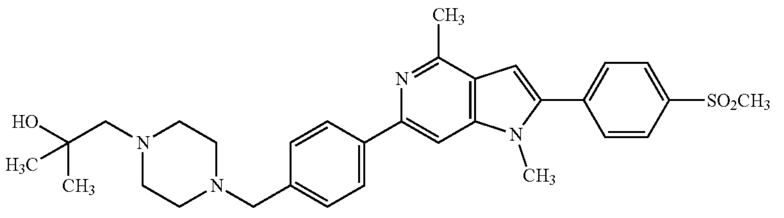

Step 1. 4-(1,4-Dimethyl-2-(4-(methylsulfonyl)phenyl)-1H-pyrrolo[3,2-c]pyridin-6-yl) benzaldehyde

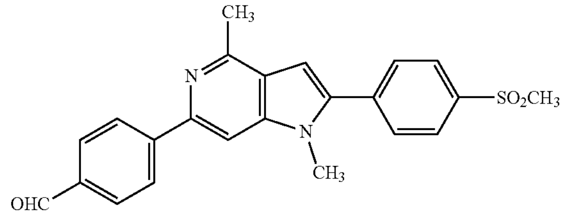 [SMILES: Cc1nc(-c2ccc(C=O)cc2)cc2c1cc(-c1ccc(S(C)(=O)=O)cc1)n2C]

A mixture of 6-chloro-1,4-dimethyl-2-(4-(methylsulfonyl)phenyl)-1H-pyrrolo[3,2-c]pyridine (Example 11, Step 5) (160 mg, 0.478 mmol), 4-(4,4,5,5-tetramethyl-1,3,2-dioxaborolan-2-yl)benzaldehyde (150 mg, 0.645 mmol), (2-dicyclohexylphosphino-2',4',6'-triisopropyl-1,1'-biphenyl)[2-(2'-amino-1,1'-biphenyl)]palladium(II) methanesulfonate, (XPhos-Pd-G3) (40.4 mg, 0.048 mmol), and potassium phosphate tribasic (0.836 mL, 1.673 mmol) in 1,4-dioxane (5 mL) was degassed and heated in a closed vial at 90° C. for 7.5 h. Upon cooling to room temperature, the reaction mixture was diluted with ethyl acetate (120 mL) and filtered through Celite. The filtrate was washed with brine (25 mL) and dried over anhydrous $MgSO_4$. The title intermediate (150 mg, 0.371 mmol, 78% yield) was isolated as a pale yellow solid by ISCO chromatography (40 g silica gel, 45-100% ethyl acetate/hexane). LCMS $(M+H)^+$=405.0. $^1$H NMR (400 MHz, DMSO-$d_6$) δ 10.07 (s, 1H), 8.48 (d, J=8.2 Hz, 2H), 8.23 (s, 1H), 8.09 (d, J=8.4 Hz, 2H), 8.06-7.95 (m, 4H), 7.01 (s, 1H), 3.93 (s, 3H), 3.32 (s, 3H), 2.78 (s, 3H).

Step 2. 1-(4-(4-(1,4-Dimethyl-2-(4-(methylsulfonyl)phenyl)-1H-pyrrolo[3,2-c]pyridin-6-yl)benzyl)piperazin-1-yl)-2-methylpropan-2-ol To a mixture of 4-(1,4-dimethyl-2-(4-(methylsulfonyl)phenyl)-1H-pyrrolo[3,2-c] pyridin-6-yl)benzaldehyde (30 mg, 0.074 mmol), 2-methyl-1-(piperazin-1-yl)propan-2-ol (35.2 mg, 0.223 mmol), magnesium sulfate (179 mg, 1.483 mmol), and acetic acid (0.042 mL, 0.742 mmol) in DMF (1.2 mL) at room temperature was added sodium triacetoxyborohydride (62.9 mg, 0.297 mmol) in one portion. The mixture was stirred at room temperature for 18 h. The heterogeneous mixture was diluted with ethyl acetate (5 mL) and filtered through Celite. The filtrate was concentrated under vacuum to dryness. The residue was dissolved in MeOH and injected to prep. HPLC. The correct fractions were combined, concentrated under vacuum, basified with 1 N NaOH solution, and extracted with dichloromethane (4×35 mL). The combined extract was dried over anhydrous $Na_2SO_4$. Removal of the solvent under vacuum provided the title compound (12.5 mg, 0.022 mmol, 30.2% yield) as a white solid. LCMS $(M+H)^+$=547.3. $^1$H NMR (500 MHz, CHLOROFORM-d) δ 8.10 (d, J=8.5 Hz, 2H), 8.04 (br d, J=7.9 Hz, 2H), 7.80-7.75 (m, 2H), 7.54 (s, 1H), 7.50-7.43 (m, 2H), 6.77 (s, 1H), 3.85 (s, 3H), 3.72-3.56 (m, 2H), 3.16 (s, 3H), 2.87 (s, 3H), 2.81-2.49 (m, 7H), 2.37 (br s, 2H), 1.19 (br s, 6H).

Example 45

3-((1R,4R)-5-(4-(1,4-Dimethyl-2-(4-(methylsulfonyl)phenyl)-1H-pyrrolo[3,2-c]pyridin-6-yl)benzyl)-2,5-diazabicyclo[2.2.2]octan-2-yl)-2,2-dimethylpropan-1-ol (45)

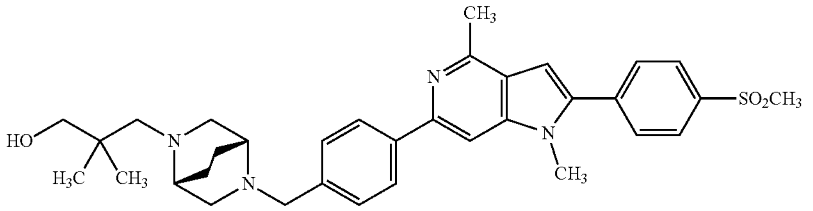

Step 1. tert-Butyl (1R,4R)-5-(4-(1,4-dimethyl-2-(4-(methylsulfonyl)phenyl)-1H-pyrrolo[3,2-c]pyridin-6-yl)benzyl)-2,5-diazabicyclo[2.2.2]octane-2-carboxylate

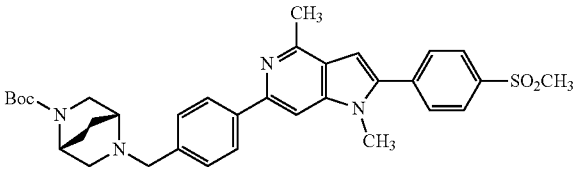

To a mixture of 4-(1,4-dimethyl-2-(4-(methylsulfonyl) phenyl)-1H-pyrrolo[3,2-c] pyridin-6-yl)benzaldehyde (Example 44, Step 1) (40 mg, 0.099 mmol), tert-butyl (1R,4R)-2,5-diazabicyclo[2.2.2]octane-2-carboxylate (50.4 mg, 0.237 mmol), magnesium sulfate (238 mg, 1.978 mmol), and acetic acid (0.057 mL, 0.989 mmol) in DMF (2 mL) at room temperature was added sodium triacetoxyborohydride (84 mg, 0.396 mmol) in one portion. The mixture was stirred at room temperature for 24 h. The heterogeneous mixture was diluted with ethyl acetate (5 mL) and filtered through Celite. The filtrate was concentrated under vacuum to dryness. The residue was dissolved in ethyl acetate (60 mL), washed with saturated $NaHCO_3$ solution (2×15 mL), and dried over anhydrous $MgSO_4$. The title intermediate (36 mg, 0.060 mmol, 60.6% yield) was isolated as a white solid by ISCO chromatography (24 g silica gel, 40-100% ethyl acetate/hexane). LCMS $(M+H)^+$=601.5.

Step 2. (1R,4R)-2-(4-(1,4-Dimethyl-2-(4-(methylsulfonyl)phenyl)-1H-pyrrolo[3,2-c] pyridin-6-yl) benzyl)-2,5-diazabicyclo[2.2.2]octane

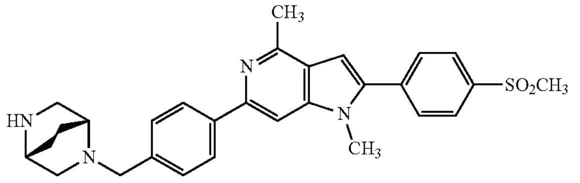

To a solution of tert-butyl (1R,4R)-5-(4-(1,4-dimethyl-2-(4-(methylsulfonyl) phenyl)-1H-pyrrolo[3,2-c]pyridin-6-yl) benzyl)-2,5-diazabicyclo[2.2.2]octane-2-carboxylate (36 mg, 0.060 mmol) in dichloromethane (2 mL) at 0° C. was added TFA (2 mL, 26.0 mmol) over 1 min. The mixture was stirred at 0° C. for 1.5 h and then concentrated under vacuum to dryness. To the residue was added saturated $NaHCO_3$ solution (6 mL), and the mixture was extracted with dichloromethane (4×30 mL). The combined extract was dried over anhydrous $Na_2SO_4$. Removal of the solvent under vacuum provided the title intermediate (30 mg, 0.060 mmol, 100% yield), as a white solid. LCMS $(M+H)^+$=501.2.

Step 3. 3-((1R,4R)-5-(4-(1,4-Dimethyl-2-(4-(methylsulfonyl)phenyl)-1H-pyrrolo[3,2-c] pyridin-6-yl) benzyl)-2,5-diazabicyclo[2.2.2]octan-2-yl)-2,2-dimethylpropan-1-ol To a mixture of (1R,4R)-2-(4-(1,4-dimethyl-2-(4-(methylsulfonyl)phenyl)-1H-pyrrolo[3,2-c]pyridin-6-yl)benzyl)-2,5-diazabicyclo[2.2.2]octane (30 mg, 0.060 mmol), 3-hydroxy-2,2-dimethylpropanal (21.42 mg, 0.210 mmol), magnesium sulfate (144 mg, 1.198 mmol), and acetic acid (0.034 mL, 0.599 mmol) in DMF (1.2 mL) at room temperature was added sodium triacetoxyborohydride (57.1 mg, 0.270 mmol) in one portion. The mixture was stirred at room temperature for 24 h. The heterogeneous mixture was diluted with ethyl acetate (5 mL) and filtered through Celite. The filtrate was concentrated under vacuum to dryness. The residue was dissolved in MeOH and injected to prep. HPLC. The correct fractions were combined, concentrated under vacuum, basified with 1 N NaOH solution, and extracted with dichloromethane (4×35 mL). The combined extract was dried over anhydrous $Na_2SO_4$. Removal of the solvent under vacuum provided the title product (5 mg, 8.35 μmol, 13.94% yield) as a white solid. LCMS $(M+H)^+$=587.2. $^1H$ NMR (400 MHz, chloroform-d) δ 8.08 (d, J=8.4 Hz, 2H), 8.02 (br d, J=7.8 Hz, 2H), 7.78-7.72 (m, 2H), 7.52 (s, 3H), 6.74 (d, J=0.8 Hz, 1H), 3.82 (s, 3H), 3.53 (s, 2H), 3.14 (s, 3H), 3.10-2.91 (m, 2H), 2.86-2.59 (m, 8H), 2.14-1.92 (m, 2H), 1.84-1.50 (m, 5H), 0.96 (s, 3H), 0.94 (s, 3H).

| Ex. No. | Structure |
|---|---|
| 46 | 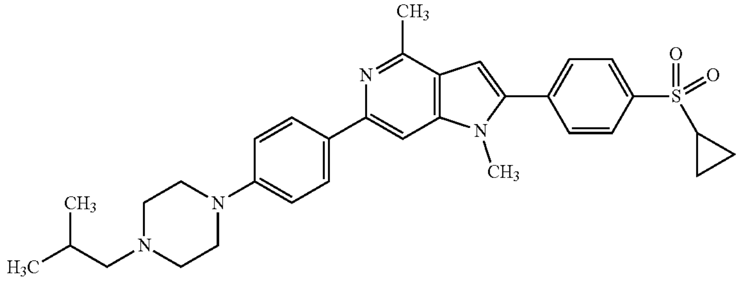 |
| 47 | 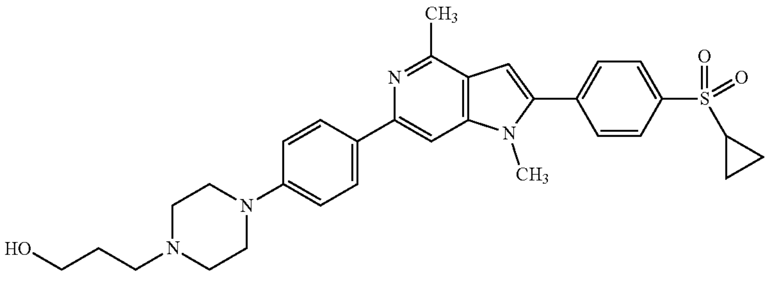 |
| 48 | 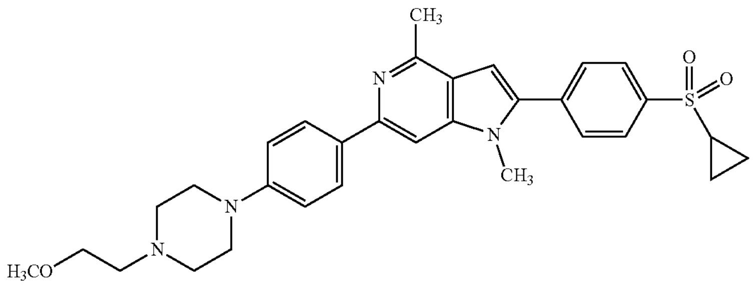 |

-continued
| Ex. No. | Structure |
| --- | --- |
| 49 | 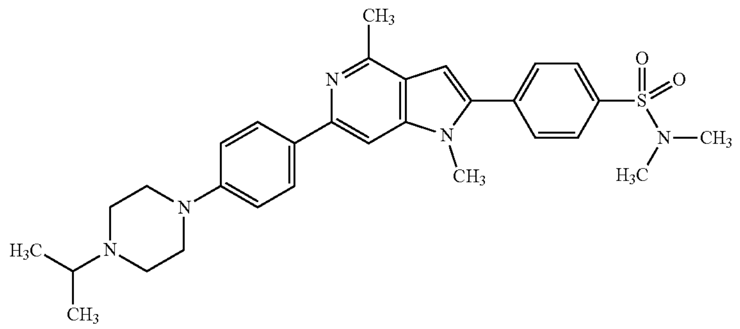 |
| 50 | 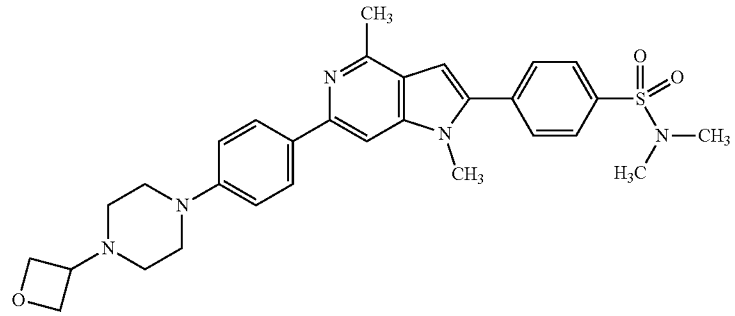 |
| 51 | 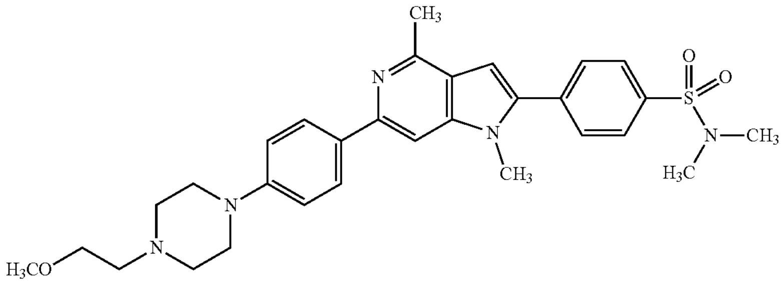 |
| 52 | 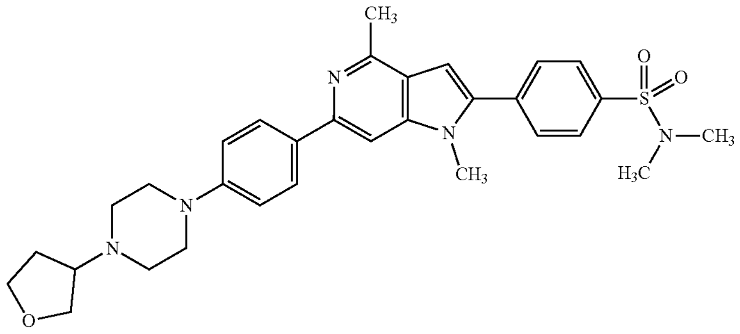 |
| 53 | 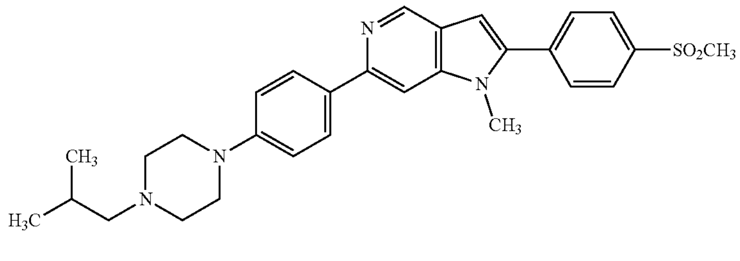

-continued
| Ex. No. | Structure |
|---|---|
| 54 | 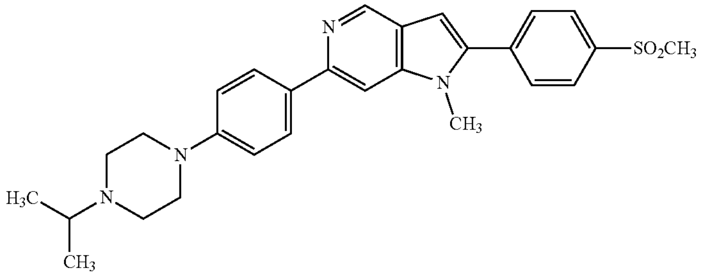 |
| 55 | 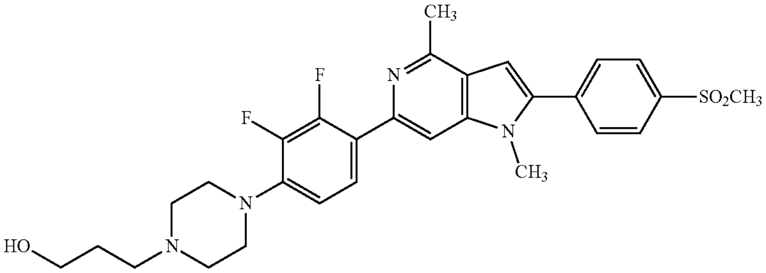 |
| 56 | 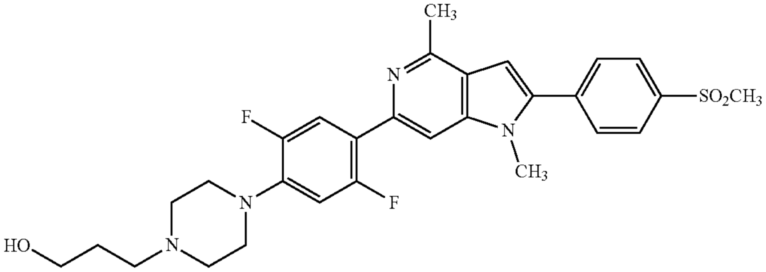 |
| 57 | 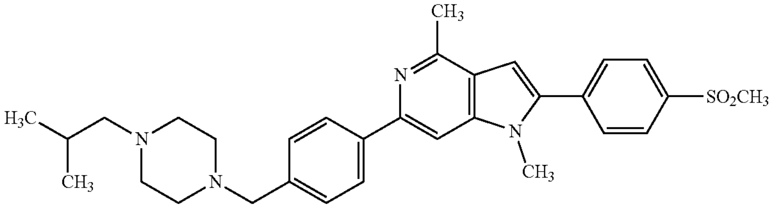 |
| 58 | 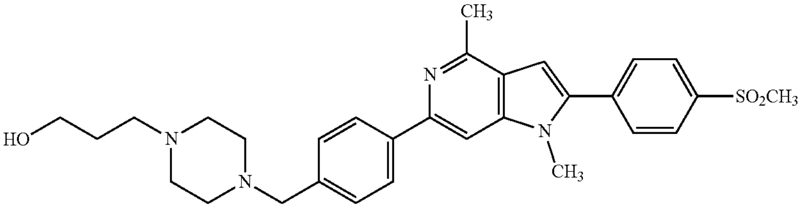 |
| 59 | 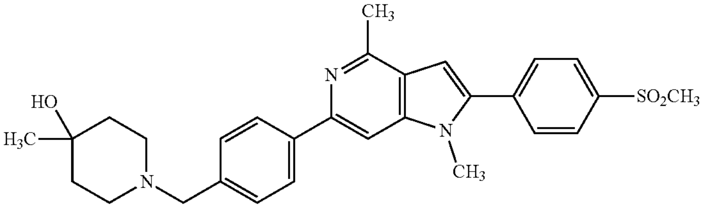 |

-continued
| Ex. No. | Structure |
| --- | --- |
| 60 | 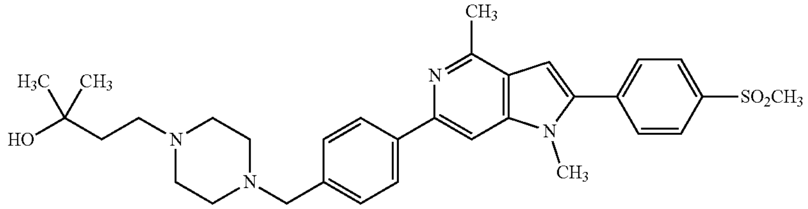 |
| 61 | 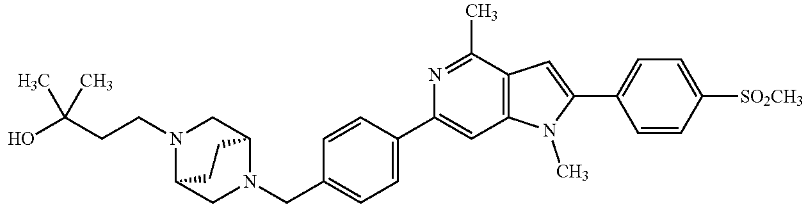 |
| 62 | 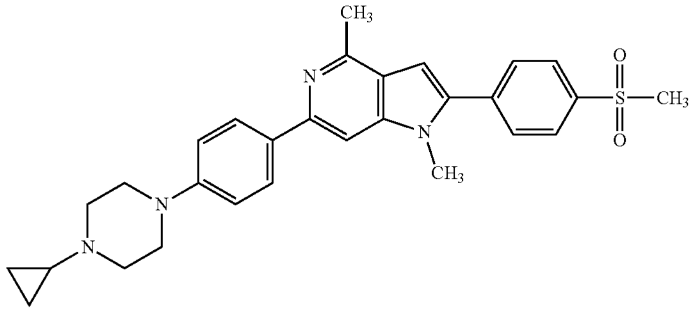 [SMILES: Cc1nc(-c2ccc(N3CCN(C4CC4)CC3)cc2)cc2c1cc(-c1ccc(S(C)(=O)=O)cc1)n2C] |
| 63 | 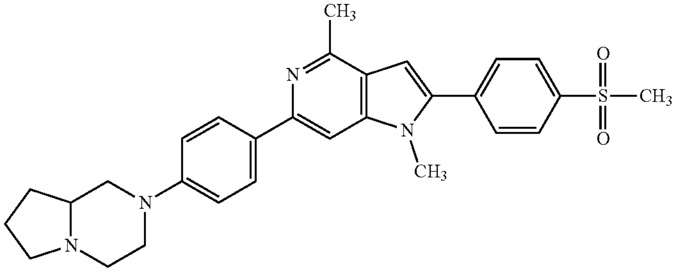 [SMILES: Cc1nc(-c2ccc(N3CCN4CCCC4C3)cc2)cc2c1cc(-c1ccc(S(C)(=O)=O)cc1)n2C] |
| 64 | 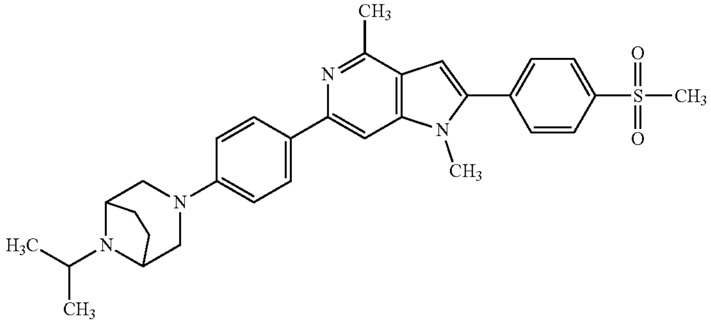 [SMILES: Cc1nc(-c2ccc(N3CC4CCC(C3)N4C(C)C)cc2)cc2c1cc(-c1ccc(S(C)(=O)=O)cc1)n2C] |

-continued
| Ex. No. | Structure |
|---|---|
| 65 | 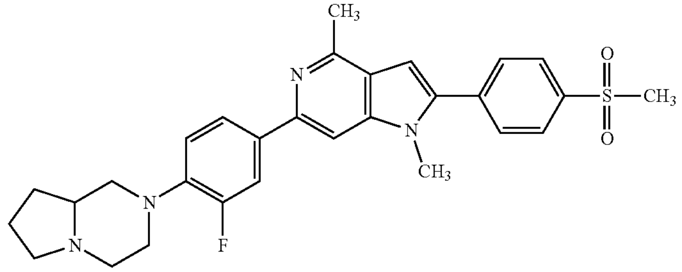 [SMILES: Cc1nc(-c2ccc(N3CCN4CCCC4C3)c(F)c2)cc2c1cc(-c1ccc(S(C)(=O)=O)cc1)n2C] |
| 66 | 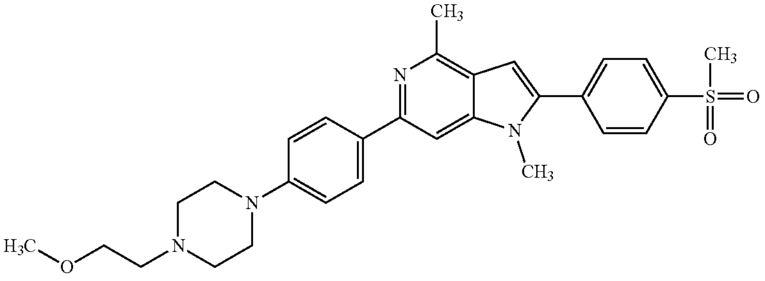 [SMILES: COCCN1CCN(c2ccc(-c3cc4c(cc(-c5ccc(S(C)(=O)=O)cc5)n4C)c(C)n3)cc2)CC1] |
| 67 | 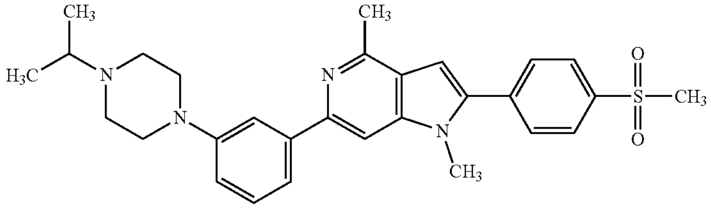 [SMILES: Cc1nc(-c2cccc(N3CCN(C(C)C)CC3)c2)cc2c1cc(-c1ccc(S(C)(=O)=O)cc1)n2C] |
| 68 | 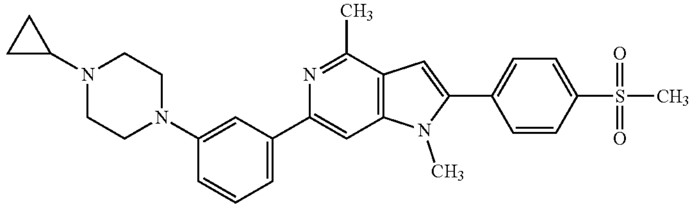 [SMILES: Cc1nc(-c2cccc(N3CCN(C4CC4)CC3)c2)cc2c1cc(-c1ccc(S(C)(=O)=O)cc1)n2C] |
| 69 | 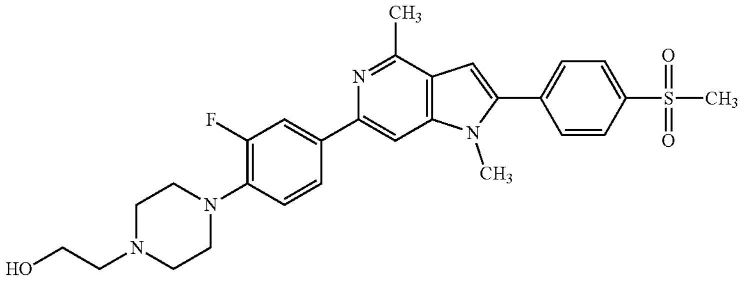 [SMILES: Cc1nc(-c2ccc(N3CCN(CCO)CC3)c(F)c2)cc2c1cc(-c1ccc(S(C)(=O)=O)cc1)n2C] |

-continued
| Ex. No. | Structure |
| --- | --- |
| 70 | 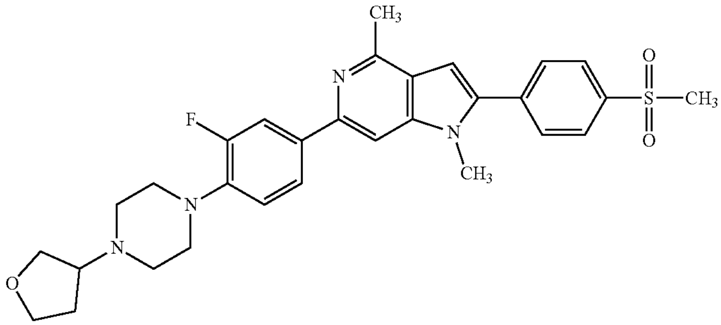 [SMILES: Cc1nc(-c2ccc(N3CCN(C4CCOC4)CC3)c(F)c2)cc2c1cc(-c1ccc(S(C)(=O)=O)cc1)n2C] |
| 71 | 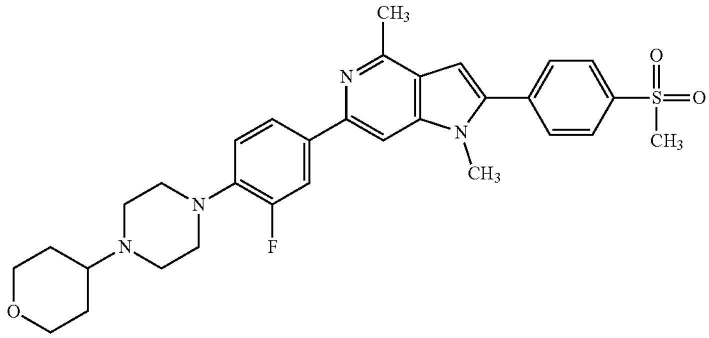 [SMILES: Cc1nc(-c2ccc(N3CCN(C4CCOCC4)CC3)c(F)c2)cc2c1cc(-c1ccc(S(C)(=O)=O)cc1)n2C] |
| 72 | 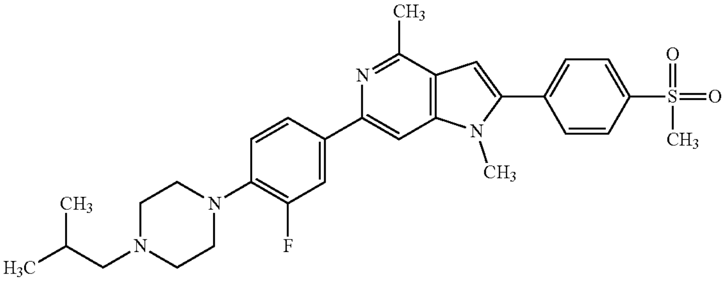 [SMILES: Cc1nc(-c2ccc(N3CCN(CC(C)C)CC3)c(F)c2)cc2c1cc(-c1ccc(S(C)(=O)=O)cc1)n2C] |
| 73 | 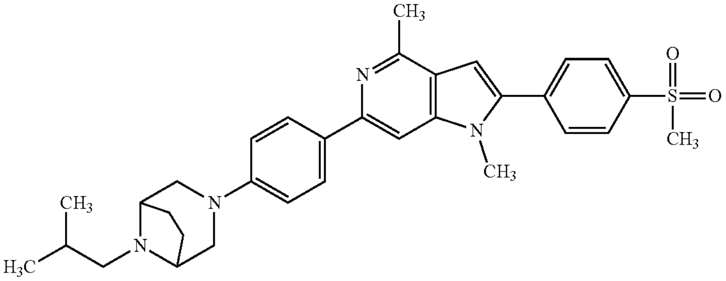 [SMILES: Cc1nc(-c2ccc(N3CC4CCC(C3)N4CC(C)C)cc2)cc2c1cc(-c1ccc(S(C)(=O)=O)cc1)n2C] |
| 74 | 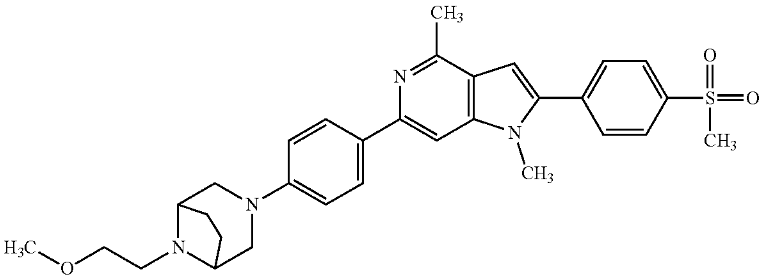 [SMILES: COCCN1C2CCC1CN(c1ccc(-c3cc4c(cc(-c5ccc(S(C)(=O)=O)cc5)n4C)c(C)n3)cc1)C2] |

-continued
| Ex. No. | Structure |
| --- | --- |
| 75 | 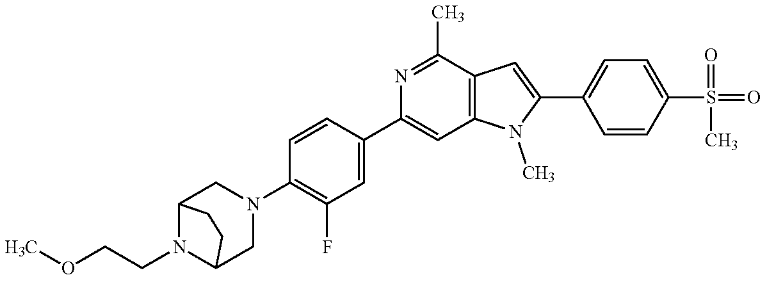 |
| 76 | 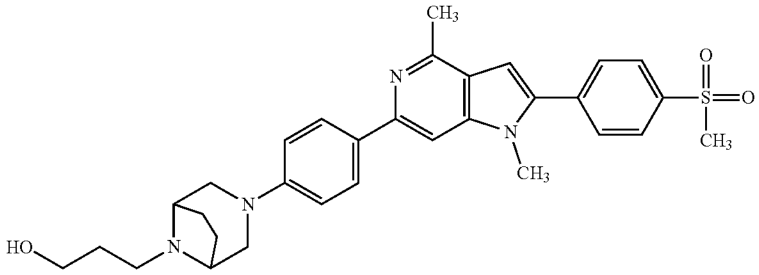 [SMILES: Cc1nc(-c2ccc(N3CC4CCC(C3)N4CCCO)cc2)cc2c1cc(-c1ccc(S(C)(=O)=O)cc1)n2C] |
| 77 | 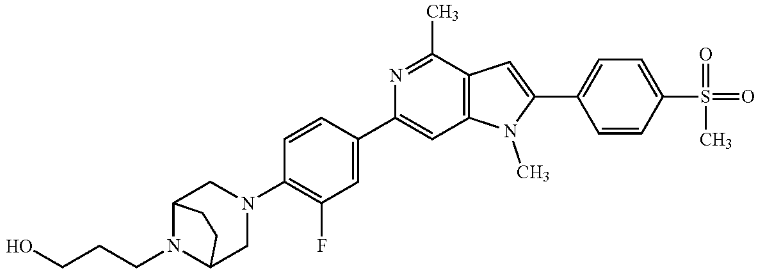 [SMILES: Cc1nc(-c2ccc(N3CC4CCC(C3)N4CCCO)c(F)c2)cc2c1cc(-c1ccc(S(C)(=O)=O)cc1)n2C] |
| 78 | 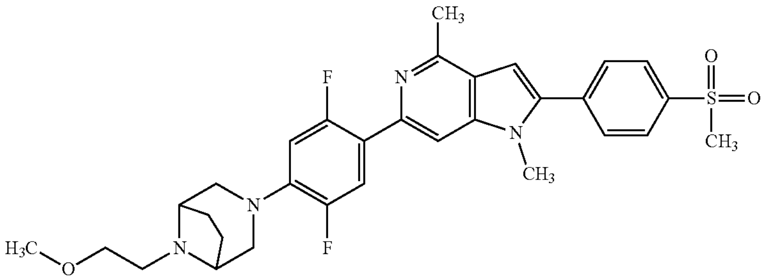 [SMILES: COCCN1C2CCC1CN(c1cc(F)c(-c3cc4c(cc(-c5ccc(S(C)(=O)=O)cc5)n4C)c(C)n3)cc1F)C2] |
| 79 | 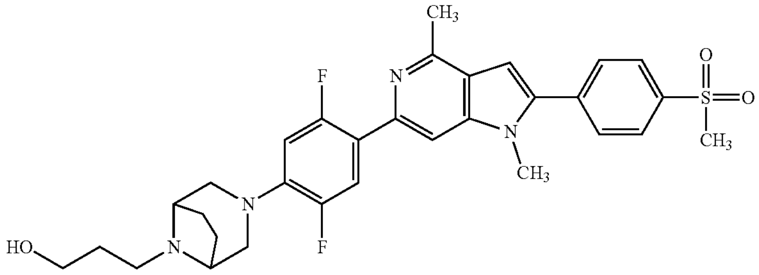 [SMILES: Cc1nc(-c2cc(F)c(N3CC4CCC(C3)N4CCCO)cc2F)cc2c1cc(-c1ccc(S(C)(=O)=O)cc1)n2C] |

-continued
| Ex. No. | Structure |
|---|---|
| 80 | 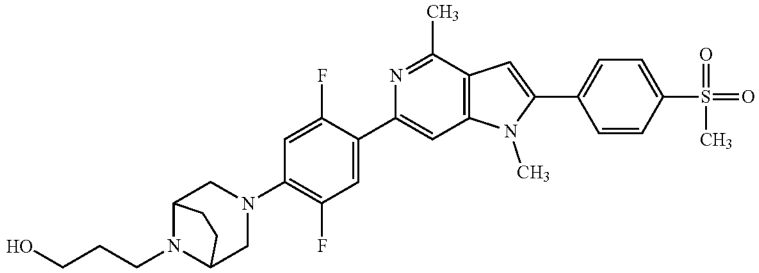 |
| 81 | 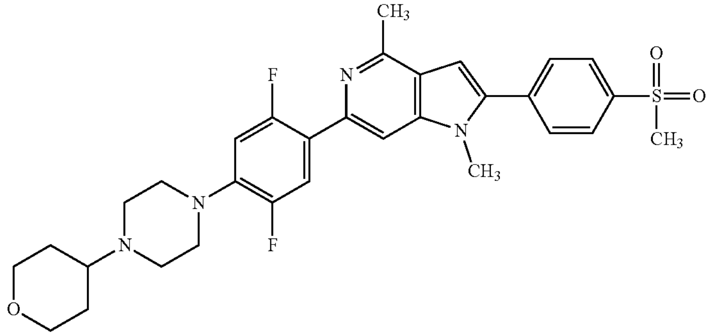 [SMILES: Cc1nc(-c2cc(F)c(N3CCN(C4CCOCC4)CC3)cc2F)cc2c1cc(-c1ccc(S(C)(=O)=O)cc1)n2C] |
| 82 | 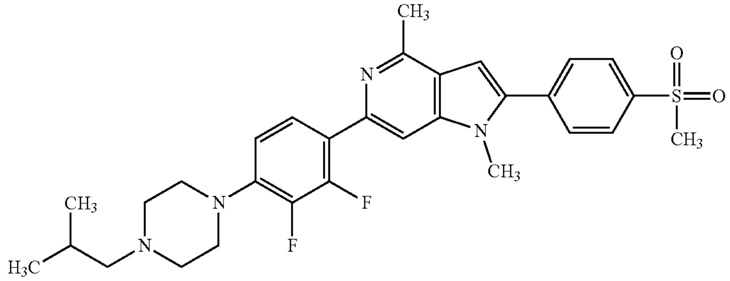 [SMILES: Cc1nc(-c2ccc(N3CCN(CC(C)C)CC3)c(F)c2F)cc2c1cc(-c1ccc(S(C)(=O)=O)cc1)n2C] |
| 83 | 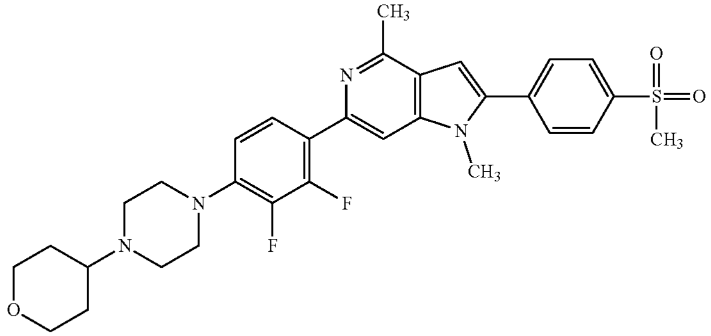 [SMILES: Cc1nc(-c2ccc(N3CCN(C4CCOCC4)CC3)c(F)c2F)cc2c1cc(-c1ccc(S(C)(=O)=O)cc1)n2C] |
| 84 | 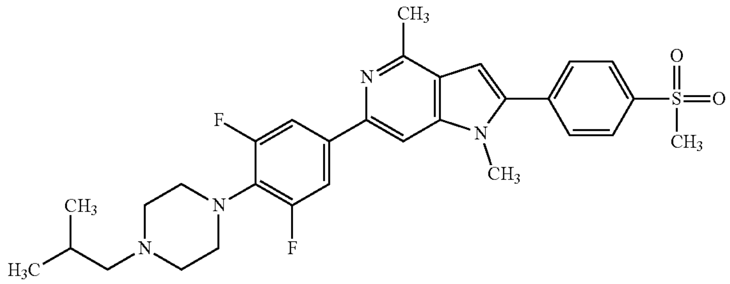 [SMILES: Cc1nc(-c2cc(F)c(N3CCN(CC(C)C)CC3)c(F)c2)cc2c1cc(-c1ccc(S(C)(=O)=O)cc1)n2C] |

-continued
| Ex. No. | Structure |
|---|---|
| 85 | 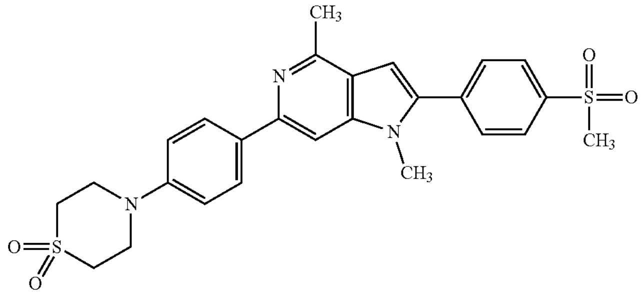 [SMILES: Cc1nc(-c2ccc(N3CCS(=O)(=O)CC3)cc2)cc2c1cc(-c1ccc(S(C)(=O)=O)cc1)n2C] |
| 86 | 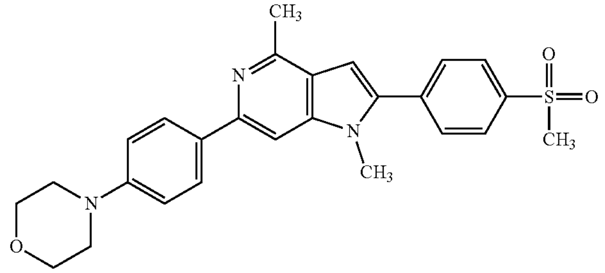 [SMILES: Cc1nc(-c2ccc(N3CCOCC3)cc2)cc2c1cc(-c1ccc(S(C)(=O)=O)cc1)n2C] |
| 87 | 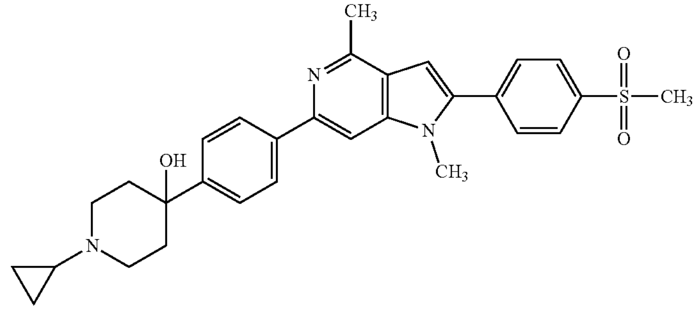 [SMILES: Cc1nc(-c2ccc(C3(O)CCN(C4CC4)CC3)cc2)cc2c1cc(-c1ccc(S(C)(=O)=O)cc1)n2C] |
| 88 | 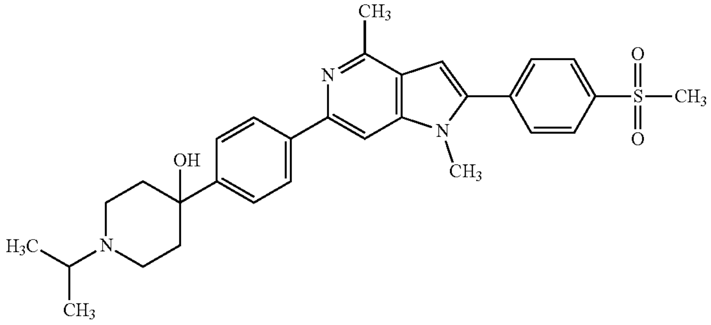 [SMILES: Cc1nc(-c2ccc(C3(O)CCN(C(C)C)CC3)cc2)cc2c1cc(-c1ccc(S(C)(=O)=O)cc1)n2C] |
| 89 | 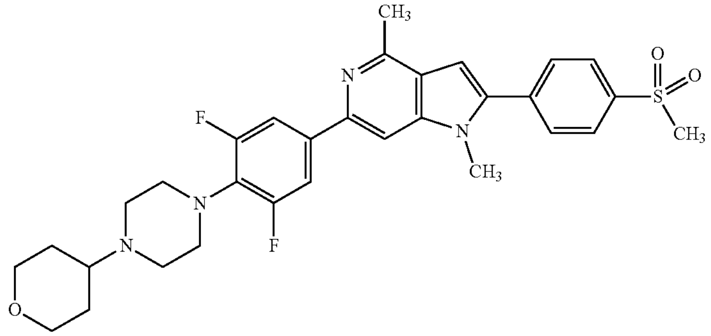 [SMILES: Cc1nc(-c2cc(F)c(N3CCN(C4CCOCC4)CC3)c(F)c2)cc2c1cc(-c1ccc(S(C)(=O)=O)cc1)n2C] |

-continued
| Ex. No. | Structure |
|---|---|
| 90 | 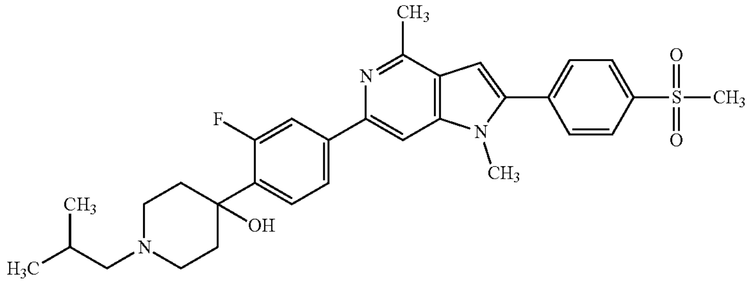 [SMILES: Cc1nc(-c2ccc(C3(O)CCN(CC(C)C)CC3)c(F)c2)cc2c1cc(-c1ccc(S(C)(=O)=O)cc1)n2C] |
| 91 | 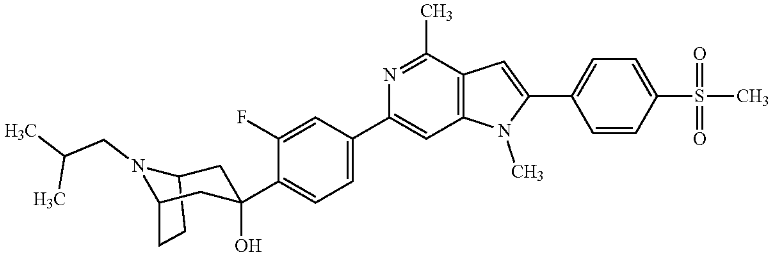 [SMILES: Cc1nc(-c2ccc(C3(O)CC4CCC(C3)N4CC(C)C)c(F)c2)cc2c1cc(-c1ccc(S(C)(=O)=O)cc1)n2C] |
| 92 | 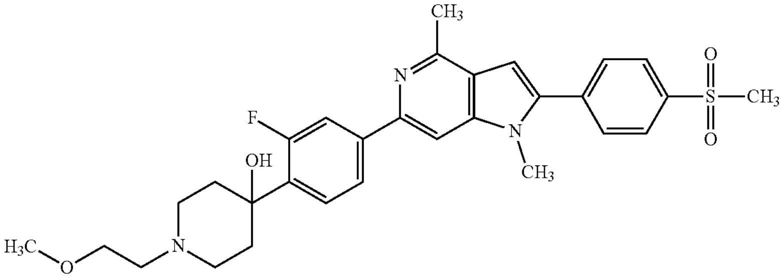 |
| 93 | 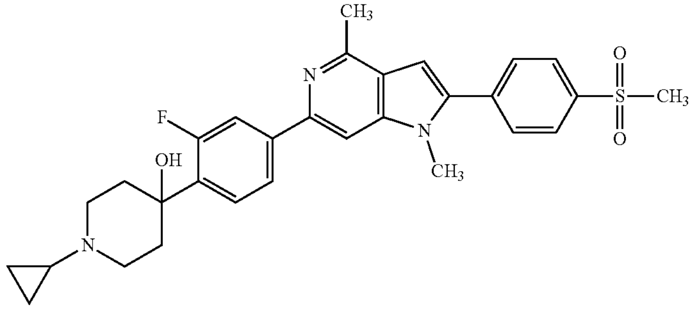 [SMILES: Cc1nc(-c2ccc(C3(O)CCN(C4CC4)CC3)c(F)c2)cc2c1cc(-c1ccc(S(C)(=O)=O)cc1)n2C] |
| 94 | 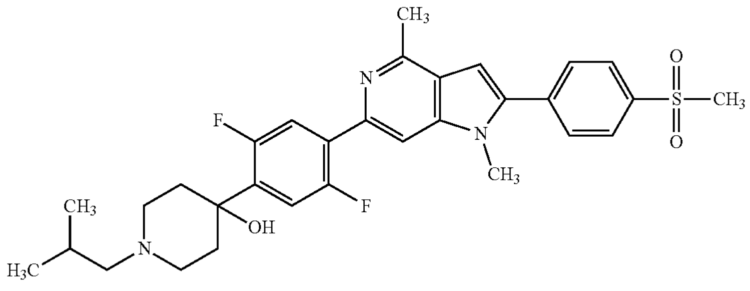 |

-continued
| Ex. No. | Structure |
| --- | --- |
| 95 | 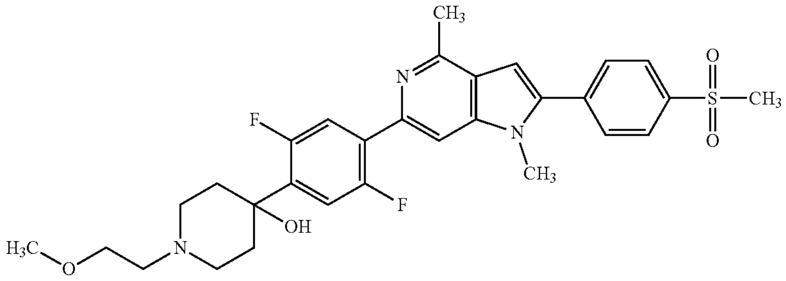 |
| 96 | 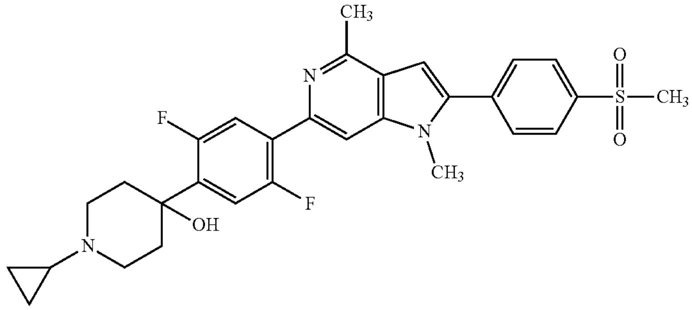 [SMILES: Cc1nc(-c2cc(F)c(C3(O)CCN(C4CC4)CC3)cc2F)cc2c1cc(-c1ccc(S(C)(=O)=O)cc1)n2C] |
| 97 | 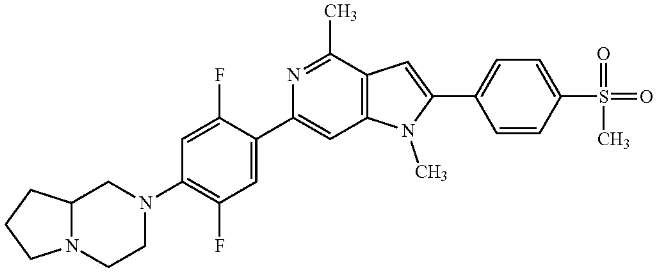 [SMILES: Cc1nc(-c2cc(F)c(N3CCN4CCCC4C3)cc2F)cc2c1cc(-c1ccc(S(C)(=O)=O)cc1)n2C] |
| 98 | 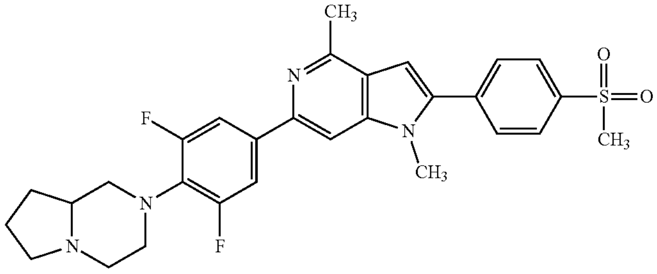 [SMILES: Cc1nc(-c2cc(F)c(N3CCN4CCCC4C3)c(F)c2)cc2c1cc(-c1ccc(S(C)(=O)=O)cc1)n2C] |
| 99 | 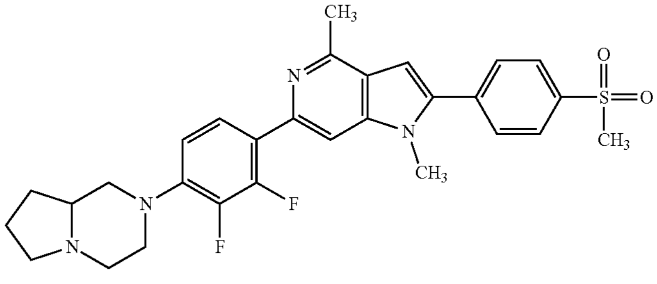 [SMILES: Cc1nc(-c2ccc(N3CCN4CCCC4C3)c(F)c2F)cc2c1cc(-c1ccc(S(C)(=O)=O)cc1)n2C] |

-continued
| Ex. No. | Structure |
| --- | --- |
| 100 | 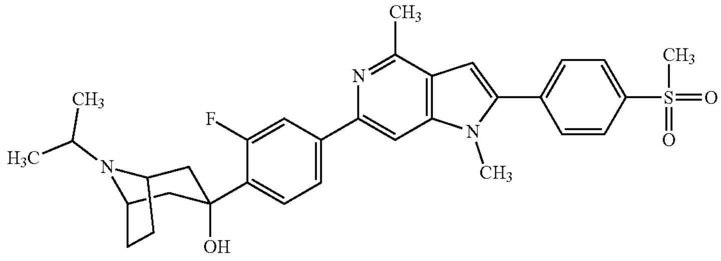 [SMILES: Cc1nc(-c2ccc(C3(O)CC4CCC(C3)N4C(C)C)c(F)c2)cc2c1cc(-c1ccc(S(C)(=O)=O)cc1)n2C] |
| 101 | 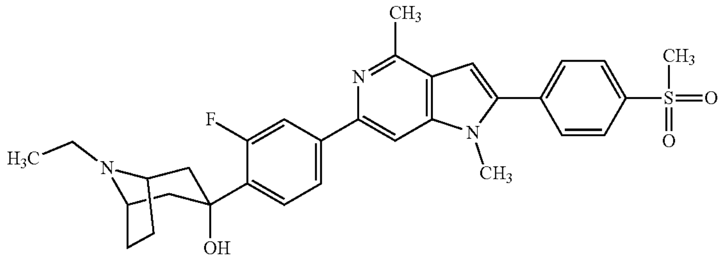 [SMILES: CCN1C2CCC1CC(O)(c1ccc(-c3cc4c(cc(-c5ccc(S(C)(=O)=O)cc5)n4C)c(C)n3)cc1F)C2] |
| 102 | 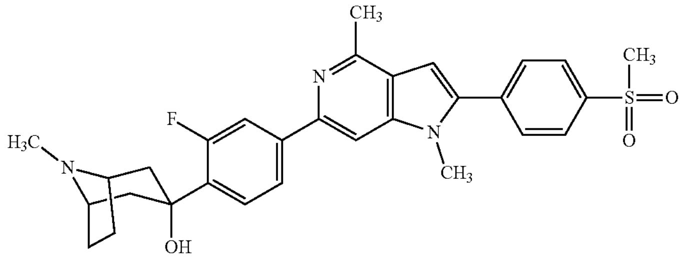 [SMILES: Cc1nc(-c2ccc(C3(O)CC4CCC(C3)N4C)c(F)c2)cc2c1cc(-c1ccc(S(C)(=O)=O)cc1)n2C] |
| 103 | 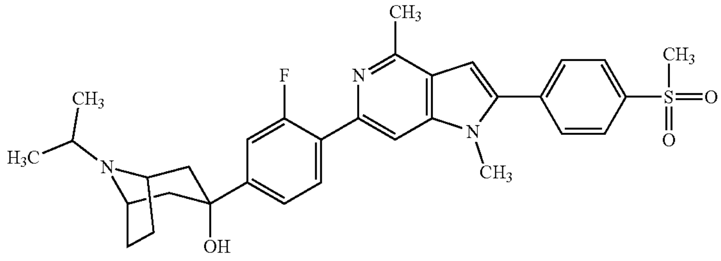 [SMILES: Cc1nc(-c2ccc(C3(O)CC4CCC(C3)N4C(C)C)cc2F)cc2c1cc(-c1ccc(S(C)(=O)=O)cc1)n2C] |
| 104 | 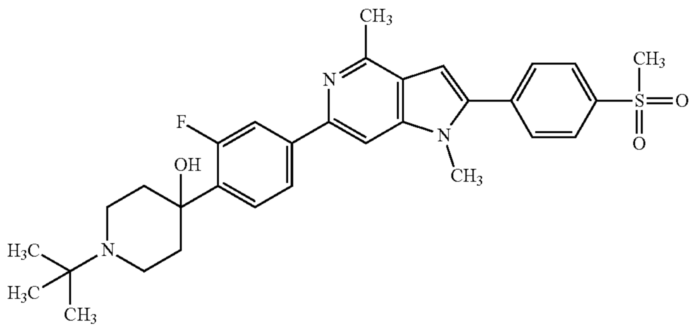 [SMILES: Cc1nc(-c2ccc(C3(O)CCN(C(C)(C)C)CC3)c(F)c2)cc2c1cc(-c1ccc(S(C)(=O)=O)cc1)n2C] |

-continued
| Ex. No. | Structure |
| --- | --- |
| 105 | 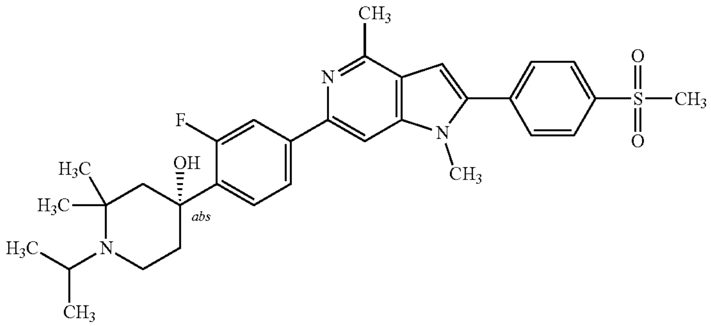 [SMILES: Cc1nc(-c2ccc([C@@]3(O)CCN(C(C)C)C(C)(C)C3)c(F)c2)cc2c1cc(-c1ccc(S(C)(=O)=O)cc1)n2C] |
| 106 | 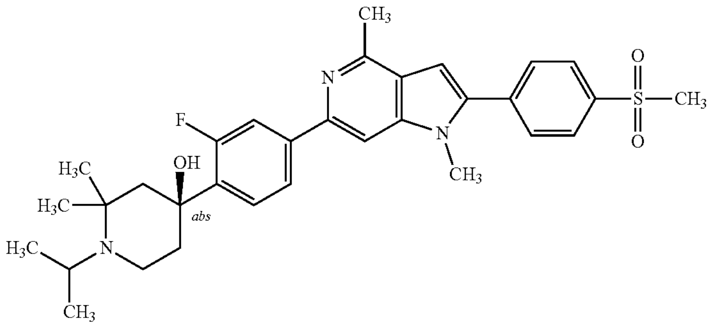 [SMILES: Cc1nc(-c2ccc([C@]3(O)CCN(C(C)C)C(C)(C)C3)c(F)c2)cc2c1cc(-c1ccc(S(C)(=O)=O)cc1)n2C] |
| 107 | 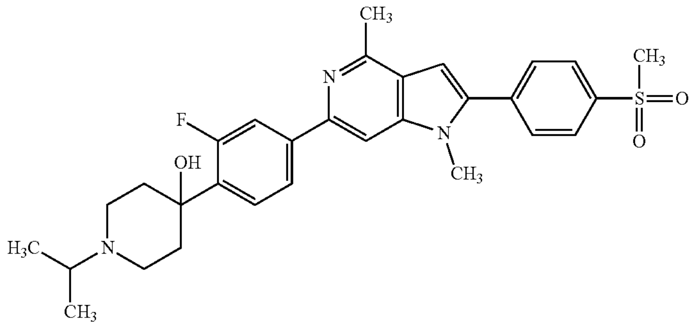 [SMILES: Cc1nc(-c2ccc(C3(O)CCN(C(C)C)CC3)c(F)c2)cc2c1cc(-c1ccc(S(C)(=O)=O)cc1)n2C] |
| 108 | 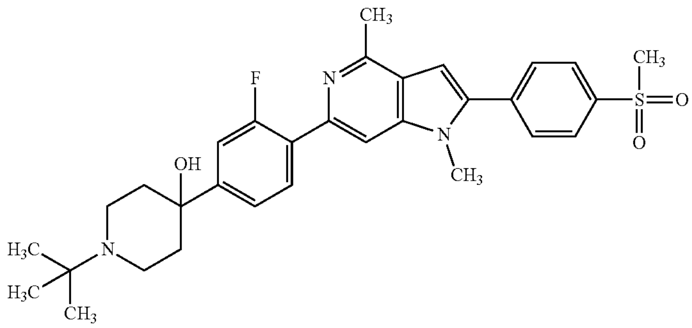 [SMILES: Cc1nc(-c2ccc(C3(O)CCN(C(C)(C)C)CC3)cc2F)cc2c1cc(-c1ccc(S(C)(=O)=O)cc1)n2C] |

-continued
| Ex. No. | Structure |
|---|---|
| 109 | 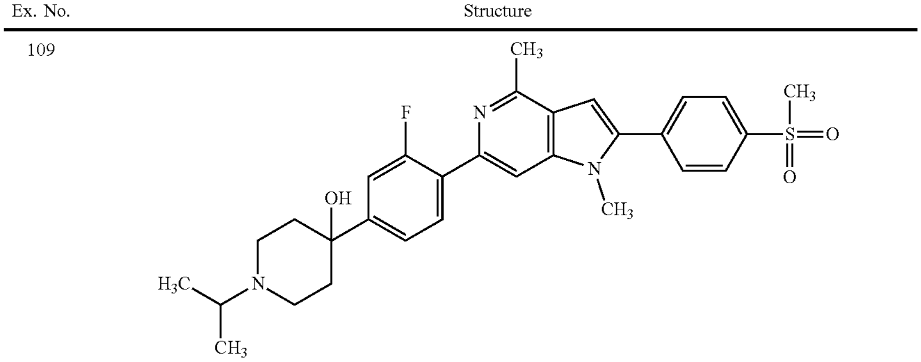 |
| 110 | 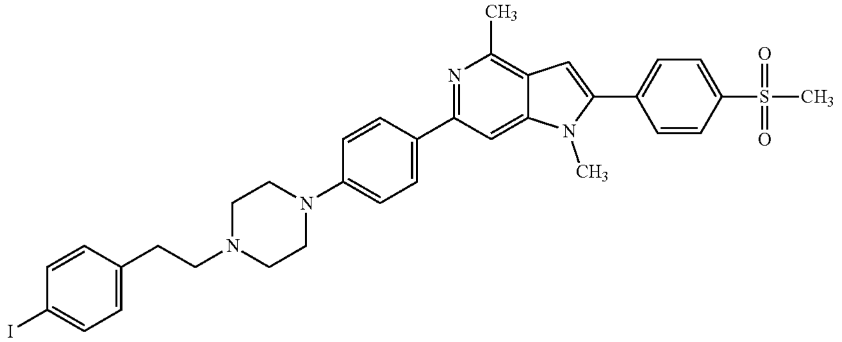 [SMILES: Cc1nc(-c2ccc(N3CCN(CCc4ccc(I)cc4)CC3)cc2)cc2c1cc(-c1ccc(S(C)(=O)=O)cc1)n2C] |
| 111 | 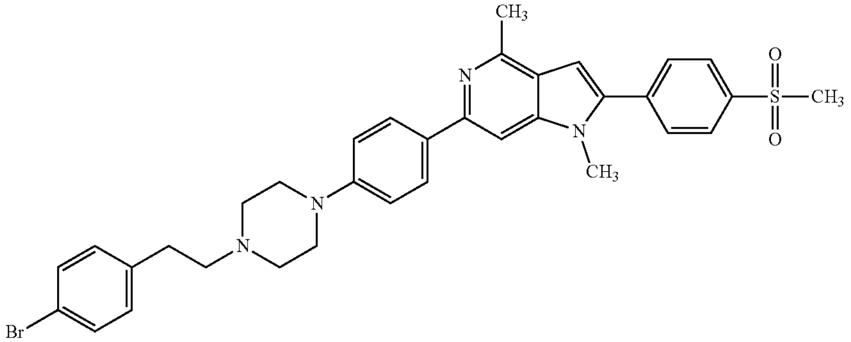 [SMILES: Cc1nc(-c2ccc(N3CCN(CCc4ccc(Br)cc4)CC3)cc2)cc2c1cc(-c1ccc(S(C)(=O)=O)cc1)n2C] |
| 112 | 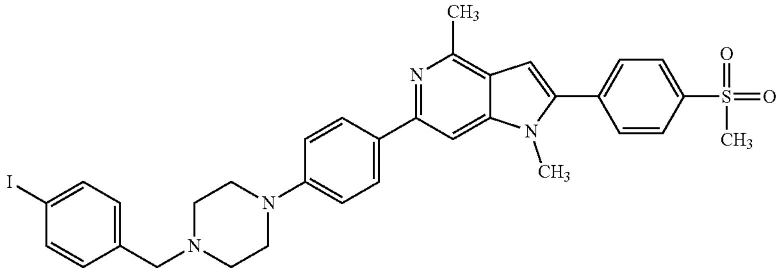 [SMILES: Cc1nc(-c2ccc(N3CCN(Cc4ccc(I)cc4)CC3)cc2)cc2c1cc(-c1ccc(S(C)(=O)=O)cc1)n2C] |
| 113 | 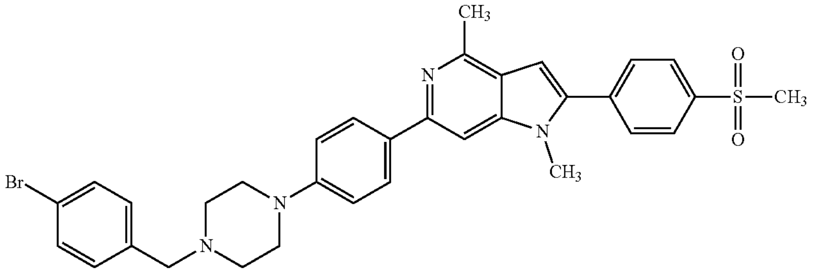 [SMILES: Cc1nc(-c2ccc(N3CCN(Cc4ccc(Br)cc4)CC3)cc2)cc2c1cc(-c1ccc(S(C)(=O)=O)cc1)n2C] |

-continued

| Ex. No. | Structure |
|---|---|
| 114 | 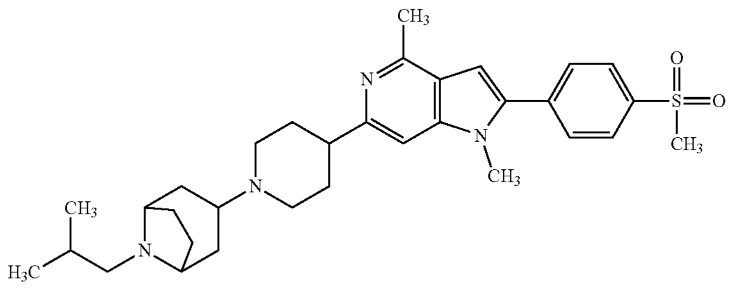 [SMILES: Cc1nc(C2CCN(C3CC4CCC(C3)N4CC(C)C)CC2)cc2c1cc(-c1ccc(S(C)(=O)=O)cc1)n2C] |

| Ex. No. | Analytical data |
|---|---|
| 46 | LCMS $(M + H)^+$ = 529.1. $^1$H NMR (400 MHz, chloroform-d) δ 7.93 (dd, J = 12.8, 8.7 Hz, 4H), 7.65 (d, J = 8.4 Hz, 2H), 7.37 (s, 1H), 6.96 (d, J = 9.0 Hz, 2H), 6.64 (s, 1H), 3.73 (s, 3H), 3.25-3.19 (m, 4H), 2.76 (s, 3H), 2.72-2.60 (m, 5H), 2.47 (tt, J = 8.0, 4.8 Hz, 1H), 1.39-1.32 (m, 2H), 1.17-1.14 (m, 1H), 1.07-1.01 (m, 8H) |
| 47 | LCMS $(M + H)^+$ = 545.4. $^1$H NMR (500 MHz, chloroform-d) δ 8.03 (dd, J = 11.5, 8.3 Hz, 4H), 7.75 (d, J = 7.9 Hz, 2H), 7.47 (s, 1H), 7.04 (br d, J = 8.3 Hz, 2H), 6.74 (s, 1H), 3.87 (br t, J = 5.1 Hz, 2H), 3.83 (s, 3H), 3.33 (br s, 4H), 2.86 (s, 3H), 2.76 (br d, J = 12.8 Hz, 6H), 2.60-2.52 (m, 1H), 1.87-1.78 (m, 2H), 1.47-1.42 (m, 2H), 1.16-1.10 (m, 2H) |
| 48 | LCMS $(M + H)^+$ = 545.4. $^1$H NMR (500 MHz, chloroform-d) δ 8.04 (br dd, J = 11.6, 8.5 Hz, 4H), 7.75 (d, J = 8.2 Hz, 2H), 7.47 (s, 1H), 7.05 (br d, J = 8.5 Hz, 2H), 6.76 (s, 1H), 3.84 (s, 3H), 3.67 (br s, 2H), 3.41 (s, 6H), 2.98-2.72 (m, 8H), 2.62-2.52 (m, 1H), 1.76-1.54 (m, 2H), 1.45 (br d, J = 4.9 Hz, 2H), 1.13 (br d, J = 6.4 Hz, 2H) |
| 49 | LCMS $(M + H)^+$ = 532.2. $^1$H NMR (400 MHz, chloroform-d) δ 7.91 (d, J = 8.8 Hz, 2H), 7.83 (d, J = 8.4 Hz, 2H), 7.64 (d, J = 8.4 Hz, 2H), 7.37 (s, 1H), 6.96 (d, J = 9.0 Hz, 2H), 6.63 (s, 1H), 3.73 (s, 3H), 3.25-3.19 (m, 4H), 2.75 (s, 3H), 2.73 (s, 6H), 2.69-2.60 (m, 5H), 1.04 (d, J = 6.5 Hz, 6H) |
| 50 | LCMS $(M + H)^+$ = 546.1. $^1$H NMR (400 MHz, chloroform-d) δ 7.93 (d, J = 8.8 Hz, 2H), 7.83 (d, J = 8.2 Hz, 2H), 7.64 (d, J = 8.4 Hz, 2H), 7.38 (s, 1H), 6.96 (d, J = 8.8 Hz, 2H), 6.65 (s, 1H), 4.68-4.58 (m, 4H), 3.74 (s, 3H), 3.51 (quin, J = 6.5 Hz, 1H), 3.28-3.22 (m, 4H), 2.79 (br s, 3H), 2.73 (s, 6H), 2.50-2.43 (m, 4H) |
| 51 | LCMS $(M + H)^+$ = 548.1. $^1$H NMR (400 MHz, chloroform-d) δ 7.91 (d, J = 8.8 Hz, 2H), 7.83 (d, J = 8.6 Hz, 2H), 7.64 (d, J = 8.4 Hz, 2H), 7.37 (s, 1H), 6.95 (d, J = 8.8 Hz, 2H), 6.63 (s, 1H), 3.73 (s, 3H), 3.50 (t, J = 5.6 Hz, 2H), 3.32 (s, 3H), 3.27-3.21 (m, 4H), 2.75 (s, 3H), 2.73 (s, 6H), 2.61 (dt, J = 15.4, 5.3 Hz, 6H) |
| 52 | LCMS $(M + H)^+$ = 560.2. $^1$H NMR (400 MHz, chloroform-d) δ 7.92 (d, J = 8.8 Hz, 2H), 7.83 (d, J = 8.4 Hz, 2H), 7.64 (d, J = 8.2 Hz, 2H), 7.37 (s, 1H), 6.95 (d, J = 9.0 Hz, 2H), 6.64 (s, 1H), 3.95-3.84 (m, 2H), 3.80-3.69 (m, 4H), 3.64 (dd, J = 8.5, 6.9 Hz, 1H), 3.22 (t, J = 5.0 Hz, 4H), 3.03-2.93 (m, 1H), 2.76 (s, 3H), 2.73 (s, 6H), 2.70-2.62 (m, 2H), 2.59-2.50 (m, 2H), 2.08-1.97 (m, 1H), 1.91-1.81 (m, 1H) |
| 53 | LCMS $(M + H)^+$ = 503.3. $^1$H NMR (500 MHz, chloroform-d) δ 9.01 (d, J = 1.0 Hz, 1H), 8.14-8.06 (m, 2H), 8.05-7.99 (m, 2H), 7.81-7.72 (m, 2H), 7.63 (s, 1H), 7.06 (d, J = 8.9 Hz, 2H), 6.76 (d, J = 0.7 Hz, 1H), 3.84 (s, 3H), 3.37-3.29 (m, 4H), 3.16 (s, 3H), 2.62 (br s, 4H), 2.20 (br d, J = 7.2 Hz, 2H), 1.87 (dt, J = 13.5, 6.7 Hz, 1H), 0.97 (d, J = 6.5 Hz, 6H) |
| 54 | LCMS $(M + H)^+$ = 489.2. $^1$H NMR (500 MHz, CHLOROFORM-d) δ 9.00 (d, J = 1.0 Hz, 1H), 8.13-8.07 (m, 2H), 8.02 (d, J = 9.0 Hz, 2H), 7.80-7.73 (m, 2H), 7.63 (s, 1H), 7.09-7.04 (m, 2H), 6.76 (d, J = 0.8 Hz, 1H), 3.84 (s, 3H), 3.35 (br s, 4H), 3.16 (s, 3H), 2.76 (br s, 5H), 1.15(br d, J = 6.2 Hz, 6H) |
| 55 | LCMS $(M + H)^+$ = 555.2. $^1$H NMR (400 MHz, DMSO-$d_6$) δ 8.11-8.05 (m, 2H), 7.99-7.93 (m, 2H), 7.81-7.72 (m, 2H), 6.99-6.94 (m, 2H), 3.84 (s, 3H), 3.48 (t, J = 6.3 Hz, 2H), 3.32 (s, 3H), 3.17-3.10 (m, 4H), 2.74 (s, 3H), 2.57 (br s, 4H), 2.42 (br t, J = 7.0 Hz, 2H), 1.63 (quin, J = 6.7 Hz, 2H) |
| 56 | LCMS $(M + H)^+$ = 555.3. $^1$H NMR (400 MHz, DMSO-$d_6$) δ 8.11-8.06 (m, 2H), 7.98-7.92 (m, 2H), 7.88 (dd, J = 14.4, 7.5 Hz, 1H), 7.77 (s, 1H), 7.00-6.91 (m, 2H), 3.84 (s, 3H), 3.47 (t, J = 6.3 Hz, 2H), 3.30 (s, 3H), 3.13 (br s, 4H), 2.74 (s, 3H), 2.59-2.53 (m, 4H), 2.42 (br t, J = 6.7 Hz, 2H), 1.63 (quin, J = 6.7 Hz, 2H) |

-continued

| Ex. No. | Analytical data |
|---|---|
| 57 | LCMS $(M + H)^+$ = 531.5. $^1$H NMR (400 MHz, CHLOROFORM-d) δ 8.08 (d, J = 8.4 Hz, 2H), 8.01 (d, J = 8.0 Hz, 2H), 7.75 (d, J = 8.4 Hz, 2H), 7.51 (s, 1H), 7.43 (d, J = 8.0 Hz, 2H), 6.74 (s, 1H), 3.82 (s, 3H), 3.59 (s, 2H), 3.14 (s, 3H), 2.84 (s, 3H), 2.65-2.31 (m, 8H), 2.11 (br d, J = 3.7 Hz, 2H), 1.86-1.72 (m, 1H), 0.90 (d, J = 6.7 Hz, 6H) |
| 58 | LCMS $(M + H)^+$ = 534.4. $^1$H NMR (400 MHz, chloroform-d) δ 8.08 (d, J = 8.4 Hz, 2H), 8.01 (d, J = 8.0 Hz, 2H), 7.75 (d, J = 8.6 Hz, 2H), 7.51 (s, 1H), 7.42 (d, J = 8.0 Hz, 2H), 6.74 (s, 1H), 3.85-3.78 (m, 5H), 3.59 (s, 2H), 3.14 (s, 3H), 2.85 (s, 3H), 2.79-2.48 (m, 8H), 1.76 (br s, 4H) |
| 59 | LCMS $(M + H)^+$ = 504.4. $^1$H NMR (400 MHz, chloroform-d) δ 8.08 (d, J = 8.2 Hz, 2H), 8.01 (d, J = 8.0 Hz, 2H), 7.75 (d, J = 8.4 Hz, 2H), 7.52 (s, 1H), 7.43 (br d, J = 7.8 Hz, 2H), 6.74 (s, 1H), 3.82 (s, 3H), 3.59 (br s, 2H), 3.14 (s, 3H), 2.85 (s, 3H), 2.59 (br s, 2H), 2.41 (br t, J = 9.8 Hz, 2H), 1.73-1.56 (m, 5H), 1.25 (s, 3H) |
| 60 | LCMS $(M + H)^+$ = 561.4. $^1$H NMR (400 MHz, CHLOROFORM-d) δ 8.08 (d, J = 8.4 Hz, 2H), 8.00 (d, J = 8.2 Hz, 2H), 7.78-7.72 (m, 2H), 7.51 (s, 1H), 7.41 (d, J = 8.2 Hz, 2H), 6.74 (s, 1H), 3.82 (s, 3H), 3.57 (s, 2H), 3.14 (s, 3H), 2.85 (s, 3H), 2.79-2.43 (m, 8H), 1.64 (br s, 4H), 1.22 (s, 6H) |
| 61 | LCMS $(M + H)^+$ = 587.3. $^1$H NMR (500 MHz, CHLOROFORM-d) δ 8.13-8.07 (m, 2H), 8.03 (br d, J = 7.9 Hz, 2H), 7.80-7.74 (m, 2H), 7.54 (s, 1H), 7.49 (br d, J = 5.1 Hz, 2H), 6.76 (d, J = 0.7 Hz, 1H), 3.95-3.70 (m, 5H), 3.16 (s, 3H), 3.09-1.51 (m, 12 H), 2.87 (s, 3H), 1.36-1.10 (m, 8H) |
| 62 | LCMS $(M + H)^+$ = 501.1. $^1$H NMR (300 MHz, DMSO-$d_6$) δ 8.13-8.02 (m, 4H), 7.94 (d, J = 8.4 Hz, 2H), 7.85 (s, 1H), 7.02 (d, J = 9.0 Hz, 2H), 6.92 (s, 1H), 3.88 (s, 3H), 3.32 (s, 3H), 3.19-3.13 (m, 4H), 2.79-2.61 (m, 7H), 1.74-1.63 (m, 1H), 0.58-0.33 (m, 4H) |
| 63 | LCMS $(M + H)^+$ = 501.1. $^1$H NMR (300 MHz, Chloroform-d) δ 8.09 (d, J = 8.1 Hz, 2H), 8.02 (d, J = 8.7 Hz, 2H), 7.77 (d, J = 8.4 Hz, 2H), 7.47 (s, 1H), 7.07 (d, J = 8.8 Hz, 2H), 6.74 (s, 1H), 3.90-3.69 (m, 5H), 3.30-3.10 (m, 5H), 3.08-2.97 (m, 1H), 2.86 (s, 3H), 2.75-2.60 (m, 1H), 2.60-2.40 (m, 1H), 2.38-2.15 (m, 2H), 2.05-1.79 (m, 4H) |
| 64 | LCMS $(M + H)^+$ = 529.1. $^1$H NMR (300 MHz, Chloroform-d) δ 8.07 (d, J = 8.4 Hz, 2H), 7.99 (d, J = 8.1 Hz, 2H), 7.75 (d, J = 8.4 Hz, 2H), 7.44 (s, 1H), 6.90 (d, J = 8.7 Hz, 2H), 6.72 (s, 1H), 3.80 (s, 3H), 3.68 (s, 2H), 3.40 (d, J = 10.9 Hz, 2H), 3.25-3.11 (m, 5H), 2.83 (s, 3H), 2.80-2.70 (m, 1H), 2.05-1.95 (m, 2H), 1.83-1.77 (m, 2H), 1.18 (d, J = 6.1 Hz, 6H) |
| 65 | LCMS $(M + H)^+$ = 519.1. $^1$H NMR (300 MHz, Chloroform-d): δ 8.08 (d, J = 8.4 Hz, 2H), 7.88-7.66 (m, 4H), 7.46 (s, 1H), 7.07 (t, J = 8.8 Hz, 1H), 6.73 (s, 1H), 3.82 (s, 3H), 3.63 (d, J = 11.0 Hz, 1H), 3.51 (d, J = 11.5 Hz, 1H), 3.21-3.10 (m, 5H), 3.01 (t, J = 11.2 Hz, 1H), 2.83 (s, 3H), 2.67 (t, J = 10.4 Hz, 1H), 2.54 (t, J = 10.8 Hz, 1H), 2.42-2.12 (m, 2H), 2.00-1.68 (m, 4H) |
| 66 | LCMS $(M + H)^+$ = 537.2. $^1$H NMR (400 MHz, Chloroform-d) δ 8.09 (d, J = 8.4 Hz, 2H), 7.87-7.65 (m, 4H), 7.47 (s, 1H), 7.06 (t, J = 8.6 Hz, 1H), 6.75 (s, 1H), 3.83 (s, 3H), 3.65-3.57 (m, 2H), 3.41 (s, 3H), 3.34-3.18 (m, 4H), 3.16 (s, 3H), 2.85 (s, 3H), 2.81-2.64 (m, 6H) |
| 67 | LCMS $(M + H)^+$ = 503.1. $^1$H NMR (300 MHz, Methanol-$d_4$) δ 8.07 (d, J = 8.7 Hz, 2H), 7.80-7.66 (m, 3H), 7.53-7.45 (m, 2H), 7.35 (t, J = 7.9 Hz, 1H), 7.00-6.91 (m, 1H), 6.73 (s, 1H), 3.81 (s, 3H), 3.39-3.25 (m, 4H), 3.13 (s, 3H), 2.90-2.67 (m, 8H), 1.14 (d, J = 6.6 Hz, 6H) |
| 68 | LCMS $(M + H)^+$ = 501.1. $^1$H NMR (400 MHz, Chloroform-d) δ 8.10 (d, J = 8.4 Hz, 2H), 7.77 (d, J = 8.4 Hz, 2H), 7.71 (s, 1H), 7.55-7.47 (m, 2H), 7.42-7.35 (m, 1H), 7.02-6.95 (m, 1H), 6.78 (s, 1H), 3.85 (s, 3H), 3.37 (s, 4H), 3.16 (s, 3H), 3.00-2.80 (m, 7H), 1.80-1.60 (m, 1H), 0.70-0.47 (m, 4H) |
| 69 | LCMS $(M + H)^+$ = 523.1. $^1$H NMR (400 MHz, Chloroform-d) δ 8.08 (d, J = 8.3 Hz, 2H), 7.88-7.70 (m, 4H), 7.46 (s, 1H), 7.05 (t, J = 8.8 Hz, 1H), 6.74 (s, 1H), 3.82 (s, 3H), 3.69 (t, J = 5.4 Hz, 2H), 3.36-3.04 (m, 7H), 2.89-2.69 (m, 7H), 2.66 (t, J = 5.4 Hz, 2H) |
| 70 | LCMS $(M + H)^+$ = 549.1. $^1$H NMR (300 MHz, Chloroform-d) δ 8.07 (d, J = 8.1 Hz, 2H), 7.90-7.70 (m, 4H), 7.45 (s, 1H), 7.03 (t, J = 8.8 Hz, 1H), 6.72 (s, 1H), 4.05-3.87 (m, 2H), 3.87-3.64 (m, 5H), 3.25-3.15 (m, 4H), 3.15-3.00 (m, 4H), 2.85-2.71 (m, 5H), 2.70-2.55 (m, 2H), 2.21-2.01 (m, 1H), 2.00-1.85 (m, 1H) |
| 71 | LCMS $(M + H)^+$ = 563.2. $^1$H NMR (300 MHz, Chloroform-d) δ 8.08 (d, J = 8.4 Hz, 2H), 7.86-7.71 (m, 4H), 7.46 (s, 1H), 7.05 (t, J = 8.7, 9.0 Hz, 1H), 6.73 (s, 1H), 4.07 (dd, J = 11.1 Hz, 3.3 Hz, 2H), 3.82 (s, 3H), 3.43 (t, J = 11.7, 10.8 Hz, 2H), 3.30-3.15 (m, 7H), 2.89-2.70 (m, 7H), 2.59-2.46 (m, 1H), 1.85 (d, J = 12.7 Hz, 2H), 1.70-1.62 (m, 2H) |
| 72 | LCMS $(M + H)^+$ = 535.3. $^1$H NMR (300 MHz, Chloroform-d) δ 8.09 (d, J = 8.4 Hz, 2H), 7.86-7.71 (m, 4H), 7.46 (s, 1H), 7.05 (t, J = 8.7, 9.0 Hz, 1H), 6.73 (s, 1H), 3.82 (s, 3H), 3.28-3.16 (m, 4H), 3.15 (s, 3H), 2.84 (s, 3H), 2.75-2.53 (m, 4H), 2.21 (s, 2H), 1.93-1.77 (m, 1H), 0.96 (d, J = 6.6 Hz, 6H) |
| 73 | LCMS $(M + H)^+$ = 543.2. $^1$H NMR (300 MHz, Methanol-$d_4$) δ 8.14-8.11 (m, 2H), 7.92-7.89 (m, 2H), 7.84 (d, J = 8.7 Hz, 2H), 7.59 (s, 1H), 6.95 (d, J = 9.0 Hz, 2H), 6.89 (s, 1H), 3.87 (s, 3H), 3.51 (d, J = 11.3 Hz, 2H), 3.40 |

-continued

| Ex. No. | Analytical data |
|---|---|
| | (s, 2H), 3.22 (s, 3H), 3.07 (t, J = 8.2 Hz, 2H), 2.80 (s, 3H), 2.30 (d, J = 7.1 Hz, 2H), 2.09-1.98 (m, 2H), 1.89-1.74 (m, 3H), 1.01 (d, J = 6.6 Hz, 6H) |
| 74 | LCMS $(M + H)^+$ = 545.2. $^1$H NMR (400 MHz, Methanol-$d_4$) δ 8.10-8.08 (m, 2H), 7.89-7.87 (m, 2H), 7.86-7.81 (m, 2H), 7.56 (s, 1H), 6.93 (d, J = 9.2 Hz, 2H), 6.86 (s, 1H), 3.84 (s, 3H), 3.60 (d, J = 5.6 Hz, 2H), 3.51 (d, J = 10.4 Hz, 4H), 3.37 (s, 3H), 3.19 (s, 3H), 3.06 (d, J = 10.3 Hz, 2H), 2.77 (s, 3H), 2.69 (t, J = 5.6 Hz, 2H), 2.11-1.99 (m, 2H), 1.88-1.76 (m, 2H) |
| 75 | LCMS $(M + H)^+$ = 563.2. $^1$H NMR (400 MHz, DMSO-$d_6$) δ 8.07 (d, J = 8.8 Hz, 2H), 8.00-7.90 (m, 5H), 7.10-6.98 (m, 1H), 6.95 (s, 1H), 3.88 (s, 3H), 3.55-3.45 (m, 2H), 3.45-3.38 (m, 4H), 3.32 (s, 3H), 3.28 (s, 3H), 3.18 (d, J = 9.2 Hz, 2H), 2.97 (d, J = 10.4 Hz, 2H), 2.72 (s, 3H), 2.00-1.75 (m, 4H) |
| 76 | LCMS $(M + H)^+$ = 545.1. $^1$H NMR (300 MHz, DMSO-$d_6$) δ 8.07-8.05 (m, 4H), 7.94 (d, J = 8.7 Hz, 2H), 7.82 (s, 1H), 6.91-6.86 (m, 3H), 4.56 (s, 1H), 3.86 (s, 3H), 3.58-3.40 (m, 4H), 3.36-3.34 (m, 2H), 3.31 (s, 3H), 2.87 (d, J = 9.6 Hz, 2H), 2.71 (s, 3H), 2.49-2.44 (m, 2H), 1.98-1.82 (m, 2H), 1.67-1.61 (m, 4H) |
| 77 | LCMS $(M + H)^+$ = 563.3. $^1$H NMR (400 MHz, Methanol-$d_4$) δ 8.11 (d, J = 8.4 Hz, 2H), 7.90 (d, J = 8.4 Hz, 2H), 7.75-7.60 (m, 3H), 7.10-7.00 (m, 1H), 6.90 (s, 1H), 3.87 (s, 3H), 3.73 (d, J = 6.0 Hz, 2H), 3.45 (s, 2H), 3.40-3.30 (m, 2H), 3.22 (s, 3H), 3.07 (d, J = 10.8 Hz, 2H), 2.80 (s, 3H), 2.62 (t, J = 14.4 Hz, 2H), 2.09-1.96 (m, 4H), 1.85-1.75 (m, 2H) |
| 78 | LCMS $(M + H)^+$ = 581.2. $^1$H NMR (400 MHz, DMSO-$d_6$) δ 8.08 (d, J = 8.4 Hz, 2H), 7.94 (d, J = 8.4 Hz, 2H), 7.90-7.80(m, 1H), 7.75 (s, 1H), 6.97 (s, 1H), 6.90-6.80 (m, 1H), 3.83 (s, 3H), 3.55-3.45 (m, 2H), 3.42-3.32 (m, 4H), 3.30 (s, 3H), 3.27 (s, 3H), 3.27-3.20 (m, 2H), 2.96 (d, J = 10.0 Hz, 2H), 2.73 (s, 3H), 1.98-1.85 (m, 2H), 1.80-1.70 (m, 2H) |
| 79 | LCMS $(M + H)^+$ = 581.2. $^1$H NMR (400 MHz, Methanol-$d_4$) δ 8.08 (d, J = 8.4 Hz, 2H), 7.94 (d, J = 8.4 Hz, 2H), 7.90-7.80 (m, 1H), 7.75 (s, 1H), 6.95 (s, 1H), 6.90-6.75 (m, 1H), 4.63-4.50 (m, 1H), 3.87 (s, 3H), 3.55-3.45 (m, 2H), 3.35 (s, 3H), 3.30-3.20 (m, 4H), 2.94 (d, J = 10.0 Hz, 2H), 2.72 (s, 3H), 2.45-2.35 (m, 2H), 1.95-1.85 (m, 2H), 1.77 (d, J = 5.2 Hz, 2H), 1.65-1.55 (m, 2H) |
| 80 | LCMS $(M + H)^+$ = 553.2. $^1$H NMR (400 MHz, Chloroform-d) δ 8.07 (d, J = 8.0 Hz, 2H), 7.91 (dd, J = 14.0, 7.5 Hz, 1H), 7.74 (d, J = 8.0 Hz, 2H), 7.65 (s, 1H), 6.75-6.67 (m, 2H), 3.80 (s, 3H), 3.22-3.15 (m, 4H), 3.14 (s, 3H), 2.82 (s, 3H), 2.66-2.53 (m, 4H), 2.17 (d, J = 7.3 Hz, 2H), 1.89-1.77 (m, 1H), 0.94 (d, J = 6.4 Hz, 6H) |
| 81 | LCMS $(M + H)^+$ = 581.2. $^1$H NMR (400 MHz, Chloroform-d) δ 8.07 (d, J = 8.4 Hz, 2H), 7.97-7.87 (m, 1H), 7.74 (d, J = 8.8 Hz, 2H), 7.65 (s, 1H), 6.76-6.67 (m, 2H), 4.12-4.00 (m, 2H), 3.80 (s, 3H), 3.41 (t, J = 10.4, 11.6, 2H), 3.30-3.14 (m, 7H), 2.90-2.72 (m, 7H), 2.56-2.44 (m, 1H), 1.85-1.78 (m, 2H), 1.66-1.61 (m, 2H) |
| 82 | LCMS $(M + H)^+$ = 553.2. $^1$H NMR (300 MHz, Chloroform-d) δ 8.10 (d, J = 8.3 Hz, 2H), 7.87-7.70 (m, 3H), 7.62 (s, 1H), 6.85 (t, J = 7.8, 7.2 Hz, 1H), 6.74 (s, 1H), 3.80 (s, 3H), 3.30-3.10 (m, 7H), 2.84 (s, 3H), 2.72-2.41 (m, 4H), 2.24-2.18 (m, 2H), 1.94-1.79 (m, 1H), 0.96 (d, J = 6.6 Hz, 6H) |
| 83 | LCMS $(M + H)^+$ = 581.2. $^1$H NMR (300 MHz, Chloroform-d) δ 8.11 (d, J = 8.1 Hz, 2H), 7.92-7.70 (m, 3H), 7.62 (s, 1H), 6.84 (t, J = 7.8, 8.7 Hz, 1H), 6.74 (s, 1H), 4.15-4.03 (m, 2H), 3.81 (s, 3H), 3.44 (t, J = 11.4, 11.1 Hz, 2H), 3.31-3.16 (m, 7H), 2.89-2.70 (m, 7H), 2.62-2.45 (m, 1H), 1.91-1.78 (m, 2H), 1.78-1.60 (m, 2H) |
| 84 | LCMS $(M + H)^+$ = 553.2. $^1$H NMR (300 MHz, Chloroform-d) δ 8.11 (d, J = 9.6 Hz, 2H), 7.77 (d, J = 8.4 Hz, 2H), 7.69-7.56 (m, 2H), 7.46 (s, 1H), 6.73 (s, 1H), 3.82 (s, 3H), 3.39-3.20 (m, 4H), 3.14 (s, 3H), 2.82 (s, 3H), 2.70-2.55 (m, 4H), 2.26-2.10 (m, 2H), 1.95-1.79 (m, 1H), 0.97 (d, J = 6.3 Hz, 6H) |
| 85 | LCMS $(M + H)^+$ = 510.1. $^1$H-NMR (400 MHz, Chloroform-d) δ 8.14-8.00 (m, 4H), 7.77 (d, J = 8.4 Hz, 2H), 7.48 (s, 1H), 7.05 (d, J = 8.4 Hz, 2H), 6.78 (s, 1H), 4.00-3.93 (m, 4H), 3.85 (s, 3H), 3.16 (s, 7H), 2.89 (s, 3H) |
| 86 | LCMS $(M + H)^+$ = 462.1. $^1$H NMR (400 MHz, Chloroform-d): δ 8.07 (d, J = 8.4 Hz, 2H), 8.01 (d, J = 8.8 Hz, 2H), 7.74 (d, J = 8.4 Hz, 2H), 7.45 (s, 1H), 7.02 (d, J = 8.8 Hz, 2H), 6.72 (s, 1H), 3.91-3.88 (m, 4H), 3.80 (s, 3H), 3.25-3.22 (m, 4H), 3.13 (s, 3H), 2.84 (s, 3H) |
| 87 | LCMS $(M + H)^+$ = 516.1. $^1$H NMR (300 MHz, Methanol-$d_4$) δ 8.11 (d, J = 8.7 Hz, 2H), 8.00-7.86 (m, 4H), 7.70 (s, 1H), 7.61 (d, J = 8.4 Hz, 2H), 6.91 (s, 1H), 3.88 (s, 3H), 3.21 (s, 3H), 3.01-2.92 (m, 2H), 2.89-2.75 (m, 5H), 2.22-2.08 (m, 2H), 1.86-1.76 (m, 3H), 1.36-1.25 (m, 1H), 0.61-0.44 (m, 4H) |
| 88 | LCMS $(M + H)^+$ = 518.3. $^1$H NMR (300 MHz, Methanol-$d_4$) δ 8.12 (d, J = 8.1 Hz, 2H), 8.02-7.88 (m, 4H), 7.74-7.61 (m, 3H), 6.91 (s, 1H), 3.89 (s, 3H), 3.21 (s, 3H), 3.07-2.93 (m, 5H), 2.82 (s, 3H), 2.33-2.17 (m, 2H), 1.96-1.86 (m, 3H), 1.24 (d, J = 6.6 Hz, 6H) |

-continued

| Ex. No. | Analytical data |
|---|---|
| 89 | LCMS $(M + H)^+$ = 581.2. $^1$H NMR (300 MHz, Chloroform-d) δ 8.11 (d, J = 8.4 Hz, 2H), 7.74 (d, J = 8.4 Hz, 2H), 7.61 (d, J = 10.6 Hz, 2H), 7.44 (s, 1H), 6.73 (s, 1H), 4.19-4.01 (m, 2H), 3.82 (s, 3H), 3.50-3.29 (m, 6H), 3.14 (s, 3H), 2.88-2.70 (m, 7H), 2.65-2.45 (m, 1H), 1.99-1.80 (m, 2H), 1.78-1.65 (m, 2H) |
| 90 | LCMS $(M + H)^+$ = 550.2. $^1$H NMR (400 MHz, DMSO-$d_6$) δ 8.15-8.00 (m, 4H), 7.99-7.88 (m, 3H), 7.72 (t, J = 8.5 Hz, 1H), 6.96 (s, 1H), 5.03 (s, 1H), 3.90 (s, 3H), 3.31 (s, 3H), 2.74 (s, 3H), 2.63 (d, J = 10.2 Hz, 2H), 2.37 (t, J = 11.4 Hz, 2H), 2.25 (t, J = 12.7, 2H), 2.08 (d, J = 7.3 Hz, 2H), 1.86-1.72 (m, 1H), 1.61 (d, J = 12.4 Hz, 2H), 0.89 (d, J = 6.5 Hz, 6H) |
| 91 | LCMS $(M + H)^+$ = 576.2. $^1$H NMR (400 MHz, DMSO-$d_6$) δ 8.11-8.03 (m, 3H), 8.03-7.87 (m, 4H), 7.68 (t, J = 8.6 Hz, 1H), 6.96 (s, 1H), 4.92 (s, 1H), 3.90 (s, 3H), 3.34 (s, 3H), 3.17 (s, 2H), 2.74 (s, 3H), 2.44-2.32 (m, 2H), 2.25-2.13 (m, 4H), 1.90-1.75 (m, 2H), 1.75-1.58 (m, 3H), 0.95 (d, J = 6.4 Hz, 6H) |
| 92 | LCMS $(M + H)^+$ = 552.1. $^1$H NMR (400 MHz, Methanol-$d_4$) δ 8.13 (d, J = 8.8 Hz, 2H), 7.93 (d, J = 2.0 Hz, 2H), 7.82 (d, J = 2.0 Hz, 1H), 7.80-7.70 (m, 3H), 6.93 (s, 1H), 3.90 (s, 3H), 3.63 (t, J = 5.6 Hz, 2H), 3.39 (s, 3H), 3.22 (s, 3H), 2.90 (d, J = 11.3 Hz, 2H), 2.83 (s, 3H), 2.78-2.62 (m, 4H), 2.60-2.40 (m, 2H), 1.80 (d, J = 13.6 Hz, 2H) |
| 93 | LCMS $(M + H)^+$ = 534.1. $^1$H NMR (300 MHz, DMSO-$d_6$) δ 8.18-7.84 (m, 7H), 7.82-7.62 (m, 1H), 6.96 (s, 1H), 5.08 (s, 1H), 3.90 (s, 3H), 3.31 (s, 3H), 2.75 (s, 7H), 2.31-2.11 (m, 2H), 1.75-1.52 (m, 3H), 0.51-0.26 (m, 4H) |
| 94 | LCMS $(M + H)^+$ = 568.3. $^1$H NMR (400 MHz, DMSO-$d_6$) δ 8.08 (d, J = 8.0 Hz, 2H), 7.95 (d, J = 8.0 Hz, 2H), 7.88-7.72 (m, 2H), 7.49 (dd, J = 12.7, 6.5 Hz, 1H), 6.99 (s, 1H), 5.22 (s, 1H), 3.85 (s, 3H), 3.31 (s, 3H), 2.75 (s, 3H), 2.67 (s, 2H), 2.40-2.20 (m, 4H), 2.09 (d, J = 13.2 Hz, 2H), 1.89-1.71 (m, 1H), 1.60 (d, J = 12.4 Hz, 2H), 0.89 (d, J = 6.4 Hz, 6H) |
| 95 | LCMS $(M + H)^+$ = 570.1. $^1$H NMR (400 MHz, Methanol-$d_4$) δ 8.13 (d, J = 8.4 Hz, 2H), 7.92 (d, J = 8.4 Hz, 2H), 7.73 (s, 1H), 7.70-7.60 (m, 1H), 7.55-7.45 (m, 1H), 6.95 (s, 1H), 3.87 (s, 3H), 3.62 (d, J = 5.6 Hz, 2H), 3.39 (s, 3H), 3.22 (s, 3H), 2.89 (d, J = 11.8 Hz, 2H), 2.82 (s, 3H), 2.73-2.62 (m, 4H), 2.60-2.45 (m, 2H), 1.75 (d, J = 12.4 Hz, 2H) |
| 96 | LCMS $(M + H)^+$ = 552.1. $^1$H NMR (300 MHz, DMSO-$d_6$) δ 8.08 (d, J = 8.7 Hz, 2H), 7.95 (d, J = 7.5 Hz, 2H), 7.87-7.75 (m, 2H), 7.56-7.43 (m, 1H), 7.00 (s, 1H), 5.26 (s, 1H), 3.85 (s, 3H), 3.31 (s, 3H), 2.85-2.60 (m, 7H), 2.24-2.05 (m, 2H), 1.71-1.51 (m, 3H), 0.47-0.26 (m, 4H) |
| 97 | LCMS $(M + H)^+$ = 537.1. $^1$H NMR (400 MHz, Methanol-$d_4$) δ 8.14 (d, J = 8.4 Hz, 2H), 7.93 (d, J = 8.4 Hz, 2H), 7.73 (s, 1H), 7.70-7.60 (m, 1H), 7.10-6.95 (m, 2H), 3.88 (s, 3H), 3.75-3.70 (m, 1H), 3.65-3.55 (m, 1H), 3.50 (s, 1H), 3.22 (s, 3H), 3.20-3.10 (m, 1H), 3.00-2.80 (m, 5H), 2.80-2.70 (m, 1H), 2.05 (s, 4H), 1.80-1.70 (m, 1H), 1.31 (s, 1H) |
| 98 | LCMS $(M + H)^+$ = 537.2. $^1$H NMR (300 MHz, DMSO-$d_6$) δ 8.11-8.06 (m, 3H), 7.98-7.88 (m, 4H), 6.97 (s, 1H), 3.89 (s, 3H), 3.30 (s, 4H), 3.24 (d, J = 11.1 Hz, 2H), 3.19-2.91 (m, 3H), 2.74 (s, 3H), 2.33(d, J = 11.1 Hz, 3H), 1.80-1.69 (m, 3H), 162-1.42 (m, 1H) |
| 99 | LCMS $(M + H)^+$ = 537.1. $^1$H NMR (400 MHz, Methanol-$d_4$) δ 8.13 (d, J = 6.8 Hz, 2H), 7.93 (d, J = 6.8 Hz, 2H), 7.62 (s, 1H), 7.60-7.50 (m, 1H), 7.05-6.90 (m, 2H), 3.87 (s, 3H), 3.66 (d, J = 11.4 Hz, 1H), 3.60-3.50 (m, 1H), 3.25-3.10 (m, 5H), 3.10-2.95 (m, 1H), 2.81 (s, 3H), 2.76-2.67 (m, 1H), 2.60-2.45 (m, 1H), 2.35-2.20 (m, 2H), 2.05-1.80 (m, 3H), 1.65-1.50 (m, 1H) |
| 100 | LCMS $(M + H)^+$ = 562.2. $^1$H NMR (300 MHz, DMSO-$d_6$) δ 8.13-7.87 (m, 7H), 7.71 (t, J = 8.6 Hz, 1H), 6.98 (s, 1H), 4.99 (s, 1H), 3.91 (s, 3H), 3.60-3.41 (m, 2H), 3.33 (s, 3H), 2.93-2.70 (m, 4H), 2.43-2.17 (m, 4H), 1.87-1.52 (m, 4H), 1.06 (s, 6H) |
| 101 | LCMS $(M + H)^+$ = 548.1. $^1$H NMR (400 MHz, DMSO-$d_6$) δ 8.13-8.05 (m, 3H), 8.05-7.87 (m, 4H), 7.69 (t, J = 8.6 Hz, 1H), 6.97 (s, 1H), 4.98 (s, 1H), 3.90 (s, 3H), 3.32 (s, 3H), 3.30-3.24 (m, 2H), 2.75 (s, 3H), 2.51-2.40 (m, 2H), 2.40-2.31 (m, 2H), 2.45-2.15 (m, 2H), 1.86-1.79 (m, 2H), 1.74-1.64 (m, 2H), 1.05 (t, J = 7.1 Hz, 3H) |
| 102 | LCMS $(M + H)^+$ = 534.2. $^1$H NMR (300 MHz, DMSO-$d_6$) δ 8.13-7.87 (m, 7H), 7.70 (t, J = 8.6 Hz, 1H), 6.97 (s, 1H), 4.96 (s, 1H), 3.90 (s, 3H), 3.34 (s, 3H), 3.12 (s, 2H), 2.75 (s, 3H), 2.45-2.32 (m, 2H), 2.30-2.15 (m, 5H), 1.99-1.81 (m, 2H), 1.67 (d, J = 13.3 Hz, 2H) |
| 103 | LCMS $(M + H)^+$ = 562.2. $^1$H NMR (300 MHz, Chloroform-d) δ 8.08 (d, J = 8.1 Hz, 2H), 7.99-7.71 (m, 4H), 7.69-7.40 (m, 2H), 6.74 (s, 1H), 3.82 (s, 3H), 3.63 (s, 2H), 3.14 (s, 3H), 3.04-2.72 (m, 4H), 2.56 (d, J = 14.4 Hz, 1H), 2.28 (d, J = 7.7 Hz, 2H), 2.10-1.90 (m, 3H), 1.84-1.73 (m, 2H), 1.16 (d, J = 6.1 Hz, 6H) |
| 104 | LCMS $(M + H)^+$ = 550.1. $^1$H NMR (400 MHz, Methanol-$d_4$) δ 8.13 (d, J = 8.1 Hz, 2H), 7.91 (d, J = 8.1 Hz, 2H), 7.84 (dd, J = 8.2, 1.7 Hz, 1H), 7.80-7.65 (m, 3H), 6.92 (s, 1H), 3.89 (s, 3H), 3.22 (s, 3H), 3.09 (d, J = 11.2 Hz, 2H), 2.93 (t, J = 11.8 Hz, 2H), 2.82 (s, 3H), 2.50 (td, J = 13.3, 4.2 Hz, 2H), 1.91 (d, J = 13.3 Hz, 2H), 1.26 (s, 9H) |

-continued

| Ex. No. | Analytical data |
|---|---|
| 105 | LCMS (M + H)$^+$ = 564.2. $^1$H NMR (300 MHz, DMSO-$d_6$) δ 8.20-7.83 (m, 7H), 7.70 (t, J = 8.6 Hz, 1H), 6.96 (s, 1H), 4.93 (s, 1H), 3.90 (s, 3H), 3.31 (s, 3H), 2.97-2.71 (m, 4H), 2.50-2.49 (m, 2H), 2.32-2.10 (m, 1H), 2.00 (d, J = 13.3 Hz, 1H), 1.67 (d, J = 12.5 Hz, 1H), 1.50 (d, J = 13.7 Hz, 1H), 1.25 (s, 3H), 1.10 (d, J = 3.8 Hz, 3H), 1.01 (t, J = 5.9 Hz, 6H) |
| 106 | LCMS (M + H)$^+$ = 564.2. $^1$H NMR (300 MHz, DMSO-$d_6$) δ 8.20-7.82 (m, 7H), 7.70 (t, J = 8.6 Hz, 1H), 6.96 (s, 1H), 4.93 (s, 1H), 3.90 (s, 3H), 3.31 (s, 3H), 2.95-2.71 (m, 4H), 2.50-2.49 (m, 2H), 2.30-2.10 (m, 1H), 2.00 (d, J = 13.4 Hz, 1H), 1.67 (d, J = 12.6 Hz, 1H), 1.50 (d, J = 13.8 Hz, 1H), 1.25 (s, 3H), 1.10 (d, J = 3.9 Hz, 3H), 1.01 (t, J = 5.9 Hz, 6H) |
| 107 | LCMS (M + H)$^+$ = 536.2. $^1$H NMR (400 MHz, Methanol-$d_4$) δ 8.13 (d, J = 8.0 Hz, 2H), 7.91 (d, J = 8.0 Hz, 2H), 7.86-7.67 (m, 4H), 6.92 (s, 1H), 3.89 (s, 3H), 3.22 (s, 3H), 3.05-2.64 (m, 8H), 2.57-2.39 (m, 2H), 1.85 (d, J = 13.3 Hz, 2H), 1.18 (d, J = 6.5 Hz, 6H) |
| 108 | LCMS (M + H)$^+$ = 550.2. $^1$H NMR (400 MHz, Methanol-$d_4$) δ 8.10 (d, J = 7.6 Hz, 2H), 7.89 (d, J = 7.6 Hz, 2H), 7.81 (d, J = 8.4 Hz, 1H), 7.75-7.71 (m, 3H), 6.90 (s, 1H), 3.87 (s, 3H), 3.20 (s, 3H), 2.95 (s, 2H), 2.80 (s, 5H), 2.47-2.42 (m, 2H), 1.86 (d, J = 12.8 Hz, 2H), 1.19 (s, 9H) |
| 109 | LCMS (M + H)$^+$ = 536.2. $^1$H NMR (400 MHz, DMSO-$d_6$) δ 8.20-7.82 (m, 7H), 7.77-7.67 (m, 1H), 6.97 (s, 1H), 5.00 (s, 1H), 3.90 (s, 3H), 3.28 (s, 3H), 2.86-2.69 (m, 4H), 2.65-2.55 (m, 4H), 2.29-2.11 (m, 2H), 1.62 (d, J = 12.7 Hz, 2H), 1.02 (d, J = 6.5 Hz, 6H) |
| 110 | LCMS (M + H)$^+$ = 691.1. $^1$H NMR (400 MHz, DMSO-$d_6$) δ 8.09-8.05 (m, 4H), 7.95-7.93 (m, 2H), 7.85 (s, 1H), 7.68-7.63 (m, 2H), 7.10 (d, J = 8.0 Hz, 2H), 7.02 (d, J = 9.2 Hz, 2H), 6.91 (s, 1H), 3.86 (s, 3H), 3.31 (s, 3H), 3.30-3.21 (m, 4H), 2.88-2.71 (m, 5H), 2.67-2.59 (m, 6H) |
| 111 | LCMS (M + H)$^+$ = 643.1. $^1$H NMR (400 MHz, DMSO-$d_6$) δ 8.09-8.05 (m, 4H), 7.94 (d, J = 8.4 Hz, 2H), 7.84 (s, 1H), 7.47 (d, J = 8.4 Hz, 2H), 7.24 (d, J = 8.4 Hz, 2H), 7.02 (d, J = 8.8 Hz, 2H), 6.91 (s, 1H), 3.86 (s, 3H), 3.30 (s, 3H), 3.28-3.21 (m, 4H), 2.85-2.71 (m, 5H), 2.62-2.52 (m, 6H) |
| 112 | LCMS (M + H)$^+$ = 677.1. $^1$H NMR (400 MHz, DMSO-$d_6$) δ 8.08-8.05 (m, 4H), 7.94 (d, J = 8.4 Hz, 2H), 7.85 (s, 1H), 7.71 (d, J = 8.0 Hz, 2H), 7.18 (d, J = 8.0 Hz, 2H), 7.01 (d, J = 9.0 Hz, 2H), 6.91 (s, 1H), 3.86 (s, 3H), 3.50 (s, 2H), 3.31 (s, 3H), 3.22 (t, J = 5.0 Hz, 4H), 2.71 (s, 3H), 2.54-2.50 (m, 4H) |
| 113 | LCMS (M + H)$^+$ = 629.1. $^1$H NMR (400 MHz, DMSO-$d_6$) δ 8.08-8.05 (m, 4H), 7.94 (d, J = 8.4 Hz, 2H), 7.85 (s, 1H), 7.54 (d, J = 8.4 Hz, 2H), 7.32 (d, J = 8.0 Hz, 2H), 7.01 (d, J = 8.8 Hz, 2H), 6.91 (s, 1H), 3.86 (s, 3H), 3.52 (s, 2H), 3.31 (s, 3H), 3.22 (t, J = 5.0 Hz, 4H), 2.71 (s, 3H), 2.55-2.52 (m, 4H) |
| 114 | LCMS (M + H)$^+$ = 549.3. $^1$H NMR (400 MHz, Chloroform-d) δ 8.08 (d, J = 8.8 Hz, 2H), 7.73 (d, J = 8.4 Hz, 2H), 7.07 (s, 1H), 6.71 (d, J = 0.8 Hz, 1H), 3.76 (s, 3H), 3.61-3.30 (m, 4H), 3.15 (s, 3H), 3.10-2.91 (m, 2H), 2.77 (s, 3H), 2.65-2.43 (m, 2H), 2.40-2.33 (m, 2H), 2.22-2.05 (m, 8H), 1.81-1.66 (m, 5H), 0.97 (d, J = 6.8 Hz, 6H) |

Example 115

4-(4-(4-(3-fluoro-1,4-dimethyl-2-(4-(methylsulfonyl)phenyl)-1H-pyrrolo[3,2-c]pyridin-6-yl)benzyl)piperazin-1-yl)-2-methylbutan-2-ol (115)

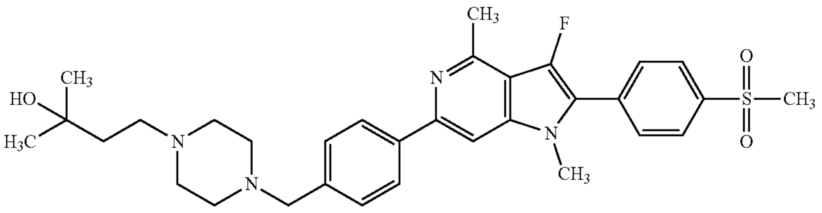

Step 1. 6-chloro-3-fluoro-1,4-dimethyl-2-(4-methylsulfonylphenyl)pyrrolo[3,2-c]pyridine

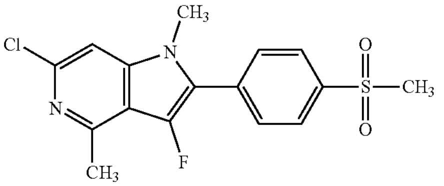

To a stirred solution of 6-chloro-1,4-dimethyl-2-(4-methylsulfonylphenyl)-pyrrolo[3,2-c]pyridine (500 mg, 1.49 mmol) in DMF (6 mL) was added Selectfluor (158 mg, 0.45 mmol). The reaction mixture was degassed three times with nitrogen and stirred at room temperature overnight. The crude mixture was purified by Flash-HPLC (Column: C18; Mobile Phase A: water (0.05% TFA), Mobile Phase B: ACN; Flow rate: 40 mL/min; Gradient: 5% B to 50% B in 30 min; Wave Length: 254/210 nm) to afford the title compound (120 mg, 23% yield) as a light orange solid. $^1$H NMR (400 MHz, DMSO-$d_6$) δ 8.14-8.09 (m, 2H), 7.90 (d, J=8.2 Hz, 2H), 7.67 (d, J=2.5 Hz, 1H), 3.71 (s, 3H), 3.32 (s, 3H), 2.72 (s, 3H). LCMS $(M+H)^+$=601.5.

Step 2. 4-[3-fluoro-1,4-dimethyl-2-(4-methylsulfonylphenyl)pyrrolo[3,2-c]pyridin-6-yl] benzaldehyde

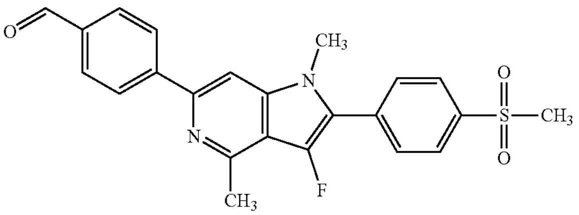

To a stirred solution of 6-chloro-3-fluoro-1,4-dimethyl-2-(4-methylsulfonylphenyl)pyrrolo[3,2-c]pyridine (120 mg, 0.34 mmol) in 1,4-dioxane (3 mL) and water (0.5 mL) were added 4-(4,4,5,5-tetramethyl-1,3,2-dioxaborolan-2-yl) benzaldehyde (158 mg, 0.68 mmol), $K_2CO_3$ (141 mg, 1.02 mmol) and $Pd(PPh_3)_4$ (39 mg, 0.03 mmol). The resulting solution was stirred at 90° C. overnight under a nitrogen atmosphere. The reaction was monitored by LCMS. The reaction mixture was concentrated under reduced pressure and purified by column chromatography (DCM/methanol=20/1) to afford the title compound (110 mg, 62.2% yield) as a yellow solid. $^1$H NMR (400 MHz, DMSO-$d_6$) δ 10.07 (d, J=7.0 Hz, 1H), 8.48 (d, J=8.1 Hz, 2H), 8.16-8.11 (m, 2H), 8.03 (d, J=8.2 Hz, 2H), 7.95 (d, J=8.2 Hz, 2H), 7.92-7.87 (m, 1H), 3.85 (s, 3H), 3.33 (s, 3H), 2.85 (s, 3H). LCMS $(M+H)^+$=423.2.

Step 3. Example 115

To a solution of 4-[3-fluoro-1,4-dimethyl-2-(4-methylsulfonylphenyl)pyrrolo[3,2-c]pyridin-6-yl]benzaldehyde (50 mg, 0.12 mmol) in DCM (5 mL) were added 2-methyl-4-piperazin-1-yl-butan-2-ol (61 mg, 0.36 mmol) and acetic acid (0.01 mL). After stirring at room temperature for 1 hour, to the mixture was added $NaBH(OAc)_3$ (75 mg, 0.36 mmol). After stirring 2 h, the mixture was diluted with water (50 mL) and extracted with DCM (3×50 mL). The combined organic layers were dried over $Na_2SO_4$ and concentrated under reduced pressure. The crude product was purified by Prep-HPLC (Column: XBridge Prep C18 OBD Column, 19*150 mm, 5 μm; Mobile Phase A: water (10 mmol/L $NH_4HCO_3$), Mobile Phase B: ACN; Flow rate: 20 mL/min; Gradient: 40% B to 50% B in 4.5 min, 50% B; Wave Length: 254/210 nm; RT1 (min): 4.35) to afford the title compound (15.8 mg, 22.6% yield) as a white solid. $^1$H NMR (400 MHz, DMSO-$d_6$) δ 8.14 (dd, J=14.7, 8.0 Hz, 4H), 8.02 (s, 1H), 7.93 (d, J=8.0 Hz, 2H), 7.39 (d, J=7.9 Hz, 2H), 4.67 (s, 1H), 3.81 (s, 3H), 3.51 (s, 2H), 2.82 (s, 3H), 2.50 (d, J=1.8 Hz, 2H), 2.60-2.41 (m, 8H), 1.51 (t, J=7.3 Hz, 2H), 1.09 (s, 6H). LCMS $(M+H)^+$=579.2.

Example 116

4-[4-[[4-[1-cyclopropyl-4-methyl-2-(4-methylsulfonylphenyl)pyrrolo[3,2-c]pyridin-6-yl] phenyl] methyl]piperazin-1-yl]-2-methyl-butan-2-ol (116)

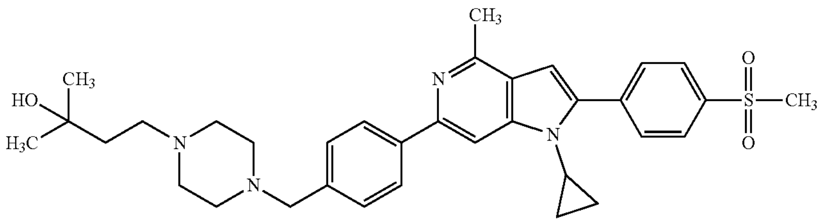

Step 1. 6-chloro-1-cyclopropyl-4-methyl-2-(4-methylsulfonylphenyl)pyrrolo[3,2-c] pyridine

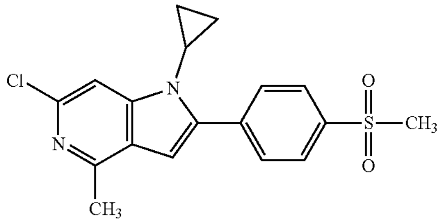

To a solution of 6-chloro-4-methyl-2-(4-methylsulfonylphenyl)-1H-pyrrolo[3,2-c] pyridine (200 mg, 0.62 mmol) in DCE (8 mL) were added $Na_2CO_3$ (198 mg, 1.87 mmol), cyclopropylboronic acid (161 mg, 1.87 mmol), $Cu(OAc)_2$ (148 mg, 0.94 mmol) and 2,2'-bipyridine (146 mg, 0.94 mmol). The resulting solution was stirred at 60° C. After 36 h, the mixture was diluted with water (50 mL) and extracted with EtOAc (3×50 mL). The combined organic layers were dried over $Na_2SO_4$, concentrated under reduced pressure and purified by column chromatography (Petroleum ether/EtOAc=2:1) to afford the title compound (140 mg, 56.6% yield) as an off-white solid. $^1H$ NMR (400 MHz, DMSO-$d_6$) δ 8.05 (s, 4H), 7.47 (s, 1H), 6.99 (s, 1H), 3.76 (tt, J=7.2, 3.9 Hz, 1H), 3.32 (s, 3H), 2.65 (s, 3H), 1.06 (dt, J=7.2, 3.6 Hz, 2H), 0.56 (p, J=5.2, 4.8 Hz, 2H). LCMS $(M+H)^+$=361.

Step 2. 4-[1-cyclopropyl-4-methyl-2-(4-methylsulfonylphenyl)pyrrolo[3,2-c]pyridin-6-yl]benzaldehyde

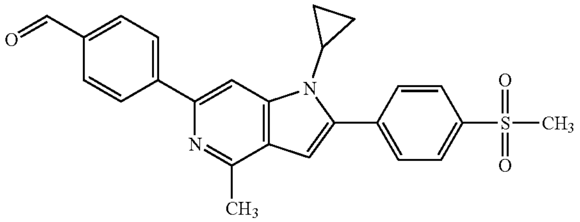

To a solution of 6-chloro-1-cyclopropyl-4-methyl-2-(4-methylsulfonylphenyl) pyrrolo[3,2-c]pyridine (130 mg, 0.36 mmol) in 1,4-dioxane (4 mL) and water (0.8 mL) were added 4-(4,4,5,5-tetramethyl-1,3,2-dioxaborolan-2-yl)benzaldehyde (167 mg, 0.72 mmol), $K_3PO_4$ (229 mg, 1.08 mmol) and Xphos-Pd-G3 (30 mg, 0.04 mmol). The resulting solution was degassed three times with nitrogen and stirred at 90° C. After 3 h, the mixture was diluted with water (50 mL) and extracted with EtOAc (3×50 mL). The combined organic layers were dried over $Na_2SO_4$, concentrated under reduced pressure and purified by column chromatography (petroleum ether/EtOAc=1:1). The crude product was purified by Flash-HPLC (Column: C18 Column; Mobile Phase A: water (0.05% TFA), Mobile Phase B: ACN; Flow rate: 50 mL/min; Gradient: 5% B to 27% B in 12 min; Wave Length: 254/210 nm) to afford the title compound (110 mg, 69.1% yield) as a light yellow solid. LCMS $(M+H)^+$=431.2.

Step 3. Example 116

To a solution of 4-[1-cyclopropyl-4-methyl-2-(4-methylsulfonylphenyl) pyrrolo[3,2-c]pyridin-6-yl]benzaldehyde (50 mg, 0.12 mmol) in DCM (4 mL) were added 2-methyl-4-piperazin-1-yl-butan-2-ol (100 mg, 0.58 mmol) and acetic acid (0.01 mL). After stirring at room temperature for 2 hours, to the mixture was added $NaBH(OAc)_3$ (123 mg, 0.58 mmol). After stirring for 1 h, the mixture was diluted with water (50 mL) and extracted with DCM (3×50 mL). The combined organic layers were dried over $Na_2SO_4$ and concentrated under reduced pressure. The crude product was purified by Prep-HPLC (Column: XBridge Prep C18 OBD Column, 19*150 mm, 5 μm; Mobile Phase A: water (10 mmol/L $NH_4HCO_3$), Mobile Phase B: ACN; Flow rate: 20 mL/min; Gradient: 40% B to 65% B in 4.5 min, 65% B; Wave Length: 254/210 nm) to afford the title compound (16 mg, 22.9% yield) as a white solid. $^1H$ NMR (300 MHz, Methanol-$d_4$) δ 8.07 (q, J=8.6 Hz, 4H), 7.97-7.83 (m, 2H), 7.79 (s, 1H), 7.55-7.36 (m, 2H), 6.91 (s, 1H), 3.78-3.68 (m, 1H), 3.63 (s, 2H), 3.22 (s, 3H), 2.95-2.18 (m, 13H), 1.69 (t, J=7.4 Hz, 2H), 1.22 (s, 6H), 1.13 (dd, J=7.4, 5.6 Hz, 2H), 0.72-0.58 (m, 2H). LCMS $(M+H)^+$=587.2.

Example 117

4-[4-[[4-[1-(difluoromethyl)-4-methyl-2-(4-methylsulfonylphenyl)pyrrolo[3,2-c]pyridin-6-yl]phenyl]methyl]piperazin-1-yl]-2-methyl-butan-2-ol (117)

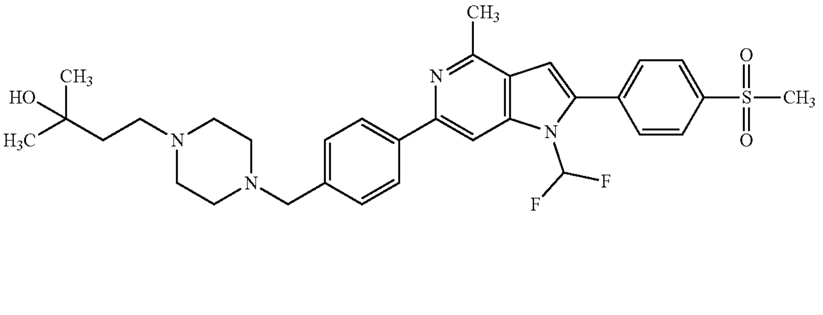

Step 1. 6-chloro-1-(difluoromethyl)-4-methyl-2-(4-methylsulfonylphenyl)pyrrolo[3,2-c] pyridine

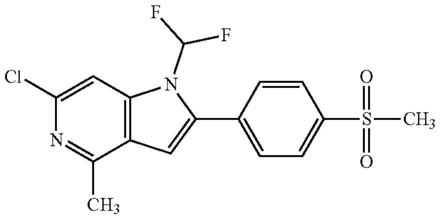

To a stirred solution of 6-chloro-4-methyl-2-(4-methylsulfonylphenyl)-1H-pyrrolo[3,2-c]pyridine (200 mg, 0.62 mmol) in DMF (5 mL) was added NaH (30 mg, 1.25 mmol) at 0° C. After stirring at room temperature for 10 minutes, a solution of 2-chloro-2,2-difluoro-acetate sodium (190 mg, 1.25 mmol) in DMF (2 mL) was added to the mixture. The resulting solution was stirred at room temperature for 10 minutes and then stirred at 80° C. After 1 h, the mixture was diluted with water (50 mL) and extracted with EtOAc (3×50 mL). The combined organic layers were washed with brine, dried over $Na_2SO_4$ and concentrated under reduced pressure. The crude product was purified by flash column chromatography on silica gel (petroleum ether/EtOAc 3:2) to afford the title compound (120 mg, 51.9% yield) as a light yellow solid. $^1$H NMR (400 MHz, DMSO-$d_6$) δ 8.15-8.08 (m, 2H), 8.08-7.75 (m, 3H), 7.69 (s, 1H), 7.21 (s, 1H), 3.32 (s, 3H), 2.70 (s, 3H). LCMS $(M+H)^+$=371.1.

Step 2. 4-[1-(difluoromethyl)-4-methyl-2-(4-methylsulfonylphenyl)pyrrolo[3,2-c] pyridin-6-yl]benzaldehyde

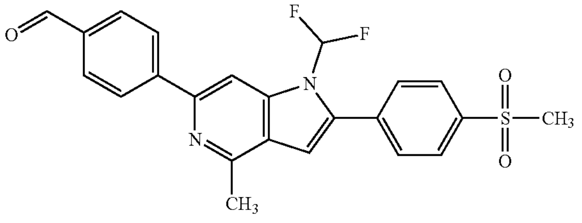

To a stirred solution of 6-chloro-1-(difluoromethyl)-4-methyl-2-(4-methylsulfonylphenyl)pyrrolo[3,2-c]pyridine (120 mg, 0.32 mmol) in 1,4-dioxane (2 mL) and water (0.5 mL) were added $K_2CO_3$ (134 mg, 0.97 mmol), 4-(4,4,5,5-tetramethyl-1,3,2-dioxaborolan-2-yl)benzaldehyde (150 mg, 0.65 mmol) and $Pd(PPh_3)_4$ (37 mg, 0.03 mmol). The resulting solution was degassed three times with nitrogen and stirred at 90° C. under a nitrogen atmosphere. After 2 h, the reaction was concentrated under reduced pressure and purified by column chromatography (petroleum ether/EtOAc 3:2) to afford the title compound (110 mg, 72.8% yield) as a light yellow solid. $^1$H NMR (400 MHz, DMSO-$d_6$) δ 10.09 (s, 1H), 8.44-8.39 (m, 2H), 8.30 (s, 1H), 8.22-8.02 (m, 5H), 7.94-7.89 (m, 2H), 7.24 (s, 1H), 3.33 (s, 3H), 2.82 (s, 3H). LCMS $(M+H)^+$=441.1.

Step 3. Example 117

To a solution of 4-[1-(difluoromethyl)-4-methyl-2-(4-methylsulfonylphenyl) pyrrolo[3,2-c]pyridin-6-yl]benzaldehyde (50 mg, 0.11 mmol) in DCM (4 mL) were added 2-methyl-4-piperazin-1-yl-butan-2-ol (98 mg, 0.57 mmol) and acetic acid (0.01 mL). After stirring at room temperature for 1 hour, to the mixture was added $NaBH(OAc)_3$ (120 mg, 0.57 mmol). After stirring 18 h, the mixture was diluted with water (50 mL) and extracted with DCM (3×50 mL). The combined organic layers were dried over $Na_2SO_4$ and concentrated under reduced pressure. The crude product was purified by Prep-HPLC (Column: XBridge Prep C18 OBD Column, 19*150 mm, 5 μm; Mobile Phase A: water (10 mmol/L $NH_4HCO_3$), Mobile Phase B: ACN; Flow rate: 20 mL/min; Gradient: 55% B to 80% B in 4.5 min, 80% B; Wave Length: 254/210 nm) to afford the title compound (20.5 mg, 30.1% yield) as a white solid. $^1$H NMR (400 MHz, DMSO-$d_6$) δ 8.25-8.05 (m, 2H), 8.00-7.51 (m, 6H), 7.49 (d, J=7.7 Hz, 2H), 7.06 (s, 1H), 3.63 (s, 2H), 3.22 (s, 3H), 3.10-2.05 (m, 13H), 1.69 (t, J=7.4 Hz, 2H), 1.22 (s, 6H). LCMS $(M+H)^+$=597.2.

Example 118

2-[6-[4-(4-isopropylpiperazin-1-yl)phenyl]-1-methyl-2-(4-methylsulfonylphenyl) pyrrolo[3,2-c] pyridin-4-yl]propan-2-ol (118)

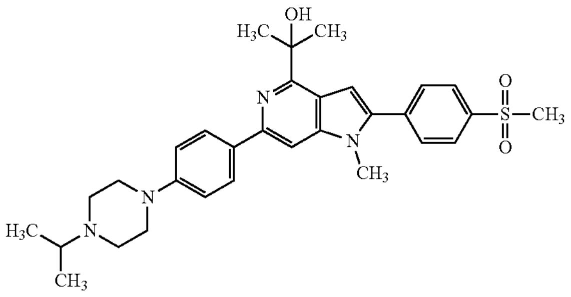

Step 1. 2,6-dichloro-3-iodo-pyridin-4-amine

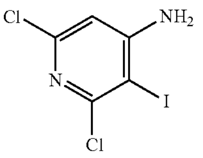

To a solution of 2,6-dichloropyridin-4-amine (1 g, 6.13 mmol) in acetic acid (10 mL) were added KOAc (602 mg, 6.13 mmol) and ICl (1.99 g, 12.27 mmol). The resulting solution was stirred at room temperature. After 4 days, to the mixture was added water (15 mL), the slurry was filtered and dried under reduced pressure to afford the title compound (1.6 g, 86% yield) as a light orange solid. $^1$H NMR (300 MHz, Methanol-$d_4$) δ 6.59 (s, 1H). LCMS $(M+H)^+$=288.9.

Step 2. 2,6-dichloro-3-[2-(4-methylsulfonylphenyl) ethynyl]pyridin-4-amine

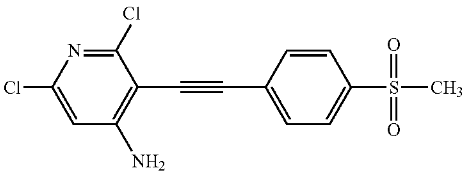 [SMILES: CS(=O)(=O)c1ccc(C#Cc2c(N)cc(Cl)nc2Cl)cc1]

To a solution of 2,6-dichloro-3-iodo-pyridin-4-amine (600 mg, 2.08 mmol) in DMF (5 mL) were added 1-ethynyl-4-methylsulfonyl-benzene (450 mg, 2.49 mmol), $Pd(PPh_3)_2Cl_2$ (145 mg, 0.21 mmol), CuI (40 mg, 0.21 mmol) and TEA (630 mg, 6.23 mmol). The resulting solution was degassed three times with nitrogen and stirred at 90° C. After 4 h, the mixture was diluted with ammonium chloride solution (60 mL) and extracted with EtOAc (3×60 mL). The combined organic layers were dried over $Na_2SO_4$ and concentrated under reduced pressure. LCMS $(M+H)^+$=341.1.

Step 3. 4,6-dichloro-2-(4-methylsulfonylphenyl)-1H-pyrrolo[3,2-c]pyridine

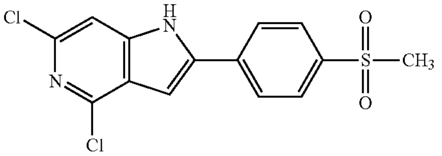 [SMILES: CS(=O)(=O)c1ccc(-c2cc3c(Cl)nc(Cl)cc3[nH]2)cc1]

To a stirred solution of 2,6-dichloro-3-[2-(4-methylsulfonylphenyl)ethynyl] pyridin-4-amine (708 mg, 2.07 mmol) in DMF (5 mL) was added t-BuOK (466 mg, 4.15 mmol) at 0° C. The resulting solution was stirred at 80° C. After 1 h, the mixture was diluted with water (60 mL) and extracted with EtOAc (3×60 mL). The combined organic layers were washed with brine, dried over $Na_2SO_4$ and concentrated under reduced pressure. The crude product was applied on a silica gel column with petroleum ether/EtOAc (1:1) as eluent to afford the title compound (335 mg, 47.3% yield) as a yellow solid. $^1H$ NMR (400 MHz, DMSO-$d_6$) δ 12.78 (s, 1H), 8.26-8.19 (m, 2H), 8.09-8.03 (m, 2H), 7.51 (d, J=0.9 Hz, 1H), 7.35 (s, 1H), 3.29 (s, 3H). LCMS $(M+H)^+$=340.9.

Step 4. 4,6-dichloro-1-methyl-2-(4-methylsulfonylphenyl)pyrrolo[3,2-c]pyridine

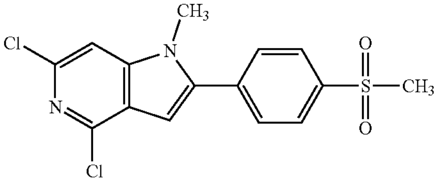 [SMILES: Cn1c(-c2ccc(S(C)(=O)=O)cc2)cc2c(Cl)nc(Cl)cc21]

To a stirred solution of 4,6-dichloro-2-(4-methylsulfonylphenyl)-1H-pyrrolo[3,2-c]pyridine (335 mg, 0.98 mmol) in DMF (4 mL) were added $Cs_2CO_3$ (640 mg, 1.96 mmol) and iodomethane (153 mg, 1.08 mmol). The resulting solution was stirred at room temperature. After 1 h, the solid was filtered, the filtrate was concentrated under reduced pressure and the crude residue was purified by Flash-HPLC (Column: C18; Mobile Phase A: water (0.05% TFA), Mobile Phase B: ACN; Flow rate: 40 mL/min; Gradient: 10% B to 60% B in 20 min; Wave Length: 254/210 nm) to afford the title compound (310 mg, 88.9% yield) as a yellow solid. $^1H$ NMR (400 MHz, DMSO-$d_6$) δ 8.13-8.06 (m, 2H), 7.97 (d, J=8.3 Hz, 2H), 7.89 (s, 1H), 6.90 (s, 1H), 3.83 (s, 3H), 3.33 (s, 3H). LCMS $(M+H)^+$=355.

Step 5. 6-chloro-1-methyl-2-(4-methylsulfonylphenyl)-4-vinyl-pyrrolo[3,2-c]pyridine

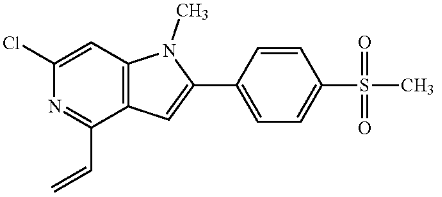 [SMILES: C=Cc1nc(Cl)cc2c1cc(-c1ccc(S(C)(=O)=O)cc1)n2C]

To a solution of 4,6-dichloro-1-methyl-2-(4-methylsulfonylphenyl)pyrrolo[3,2-c] pyridine (310 mg, 0.87 mmol) in 1,4-dioxane (3 mL) and water (0.5 mL) were added 4,4,5,5-tetramethyl-2-vinyl-1,3,2-dioxaborolane (161 mg, 1.05 mmol), $K_2CO_3$ (361 mg, 2.62 mmol) and $PdCl_2$(dppf) (71 mg, 0.09 mmol). The resulting solution was degassed three times with nitrogen and stirred at 90° C. After 2 h, the mixture was concentrated under reduced pressure and the crude product was purified by Flash-HPLC (Column: C18; Mobile Phase A: water (0.05% TFA), Mobile Phase B: ACN; Flow rate: 40 mL/min; Gradient: 5% B to 58% B in 30 min; Wave Length: 254/210 nm) to afford the title compound (190 mg, 62.8% yield) as a light yellow solid. $^1H$ NMR (400 MHz, DMSO-$d_6$) δ 8.09 (d, J=8.1 Hz, 2H), 7.95 (d, J=8.1 Hz, 2H), 7.68 (s, 1H), 7.29-7.22 (m, 1H), 7.19 (d, J=3.7 Hz, 1H), 6.43 (d, J=17.2 Hz, 1H), 5.65 (d, J=10.8 Hz, 1H), 3.81 (s, 3H), 3.32 (s, 3H). LCMS $(M+H)^+$=347.

Step 6. 6-chloro-1-methyl-2-(4-methylsulfonylphenyl)pyrrolo[3,2-c]pyridine-4-carboxylic Acid

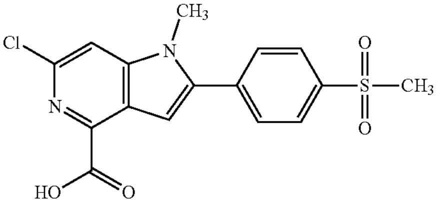 [SMILES: Cn1c(-c2ccc(S(C)(=O)=O)cc2)cc2c(C(=O)O)nc(Cl)cc21]

To a stirred solution of 6-chloro-1-methyl-2-(4-methylsulfonylphenyl)-4-vinyl-pyrrolo[3,2-c]pyridine (185 mg, 0.53 mmol) in acetone (8 mL) was added dropwise a solution of $KMnO_4$ (168 mg, 1.07 mmol) in water (2 mL) at 0° C. The resulting solution was stirred at 0° C. After 2 h, the mixture was concentrated under reduced pressure and purified by Flash-HPLC (Column: p C18; Mobile Phase A: water (0.05% TFA), Mobile Phase B: ACN; Flow rate: 50 mL/min; Gradient: 5% B to 40% B in 15 min; Wave Length:

254/210 nm) to afford the title compound (110 mg, 55.2% yield) as a light yellow solid. $^1$H NMR (400 MHz, DMSO-$d_6$) δ 13.35 (s, 1H), 8.09 (d, J=8.0 Hz, 2H), 8.05 (s, 1H), 7.98 (d, J=8.0 Hz, 2H), 7.22 (s, 1H), 3.85 (s, 3H), 3.32 (s, 3H). LCMS $(M+H)^+$=365.

Step 7. methyl 6-chloro-1-methyl-2-(4-(methylsulfonyl)phenyl)-1H-pyrrolo[3,2-c] pyridine-4-carboxylate

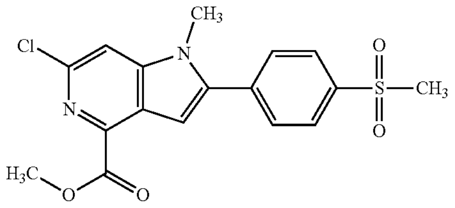 [SMILES: COC(=O)c1nc(Cl)cc2c1cc(-c1ccc(S(C)(=O)=O)cc1)n2C]

To a solution of 6-chloro-1-methyl-2-(4-methylsulfonylphenyl)pyrrolo[3,2-c] pyridine-4-carboxylic acid (105 mg, 0.29 mmol) in methanol (5 mL) was added 20 drops of $H_2SO_4$. The resulting solution was stirred at 65° C. for 5 hours. The mixture was then concentrated under reduced pressure. The residue was partitioned into saturated sodium bicarbonate solution and extracted with DCM (3×50 mL). The combined organic layers were dried over $Na_2SO_4$ and concentrated under reduced pressure to afford the title compound (110 mg crude) as a red solid. LCMS $(M+H)^+$=379.

Step 8. 2-[6-chloro-1-methyl-2-(4-methylsulfonylphenyl)pyrrolo[3,2-c]pyridin-4-yl] propan-2-ol

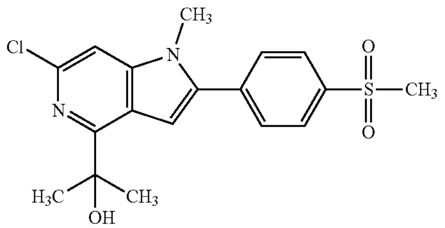 [SMILES: Cn1c(-c2ccc(S(C)(=O)=O)cc2)cc2c(C(C)(C)O)nc(Cl)cc21]

A solution of methyl 6-chloro-1-methyl-2-(4-methylsulfonylphenyl)pyrrolo[3,2-c] pyridine-4-carboxylate (50 mg, 0.13 mmol) in THF (1.5 mL) was degassed three times with nitrogen. Bromo(methyl)magnesium (3 M solution in diethylether) (1.5 mL, 0.4 mmol) was added to the solution at 0° C. The resulting solution was stirred at 0° C. for 2 h, after which time the reaction was quenched by ammonium chloride solution. The reaction mixture was diluted with water (30 mL) and extracted with DCM (3×30 mL). The combined organic layers were dried over $Na_2SO_4$, concentrated under reduced pressure and applied on a silica gel column with petroleum ether/EtOAc (1:1) as eluent to afford the title compound (25 mg, 47.6% yield) as a light yellow solid. $^1$H NMR (300 MHz, Chloroform-d) δ 8.09 (d, J=8.3 Hz, 2H), 7.78-7.70 (m, 2H), 7.27 (s, 1H), 6.81 (d, J=4.8 Hz, 1H), 3.76 (s, 3H), 3.14 (s, 3H), 1.70 (s, 6H). LCMS $(M+H)^+$=379.1.

Step 9. Example 118

To a solution of 2-[6-chloro-1-methyl-2-(4-methylsulfonylphenyl)pyrrolo[3,2-c] pyridin-4-yl]propan-2-ol (25 mg, 0.07 mmol) in 1,4-dioxane (1.5 mL) and water (0.3 mL) were added 1-isopropyl-4-[4-(4,4,5,5-tetramethyl-1,3,2-dioxaborolan-2-yl)phenyl] piperazine (43 mg, 0.13 mmol), $K_3PO_4$ (42 mg, 0.2 mmol) and Xphos-Pd-G3 (6 mg, 0.01 mmol). The resulting solution was degassed three times with nitrogen and stirred at 90° C. After 18 h, the mixture was concentrated under reduced pressure and the crude product was purified by Prep-HPLC (Column: XBridge Prep OBD C18 Column, 30*150 mm, 5 μm; Mobile Phase A: water (10 mmol/L $NH_4HCO_3$), Mobile Phase B: ACN; Flow rate: 25 mL/min; Gradient: 45% B to 75% B in 5.2 min, 75% B; Wave Length: 210 nm) to afford the title compound (13.6 mg, 37.3% yield) as a light yellow solid. $^1$H NMR (400 MHz, Chloroform-d) δ 8.20-7.90 (m, 4H), 7.75 (d, J=8.4 Hz, 2H), 7.55 (s, 1H), 7.04 (d, J=9.2 Hz, 2H), 6.88-6.56 (m, 2H), 3.83 (s, 3H), 3.50-3.30 (m, 4H), 3.14 (s, 3H), 2.90-2.67 (m, 5H), 1.74 (s, 6H), 1.14 (d, J=6.4 Hz, 6H). LCMS $(M+H)^+$=547.2.

Example 119

6-[4-(4-isopropylpiperazin-1-yl)phenyl]-4-methoxy-1-methyl-2-(4-methylsulfonylphenyl) pyrrolo[3,2-c] pyridine (119)

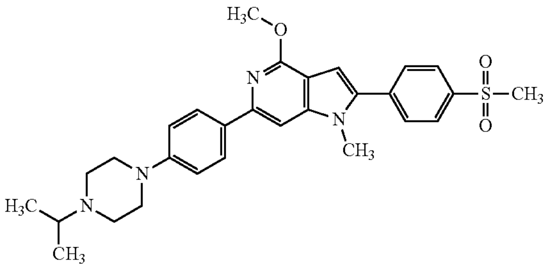

Step 1. 6-chloro-3-iodo-2-methoxy-pyridin-4-amine

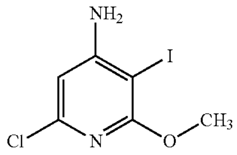

To a stirred solution of 2-chloro-6-methoxy-pyridin-4-amine (500 mg, 3.15 mmol) in acetic acid (5 mL) were added Chloramine-T (1.07 g, 4.73 mmol) and NaI (709 mg, 4.73 mmol). The reaction mixture was stirred at room temperature for 18 h, then 2 M sodium hydroxide solution (60 mL) and ethyl acetate were added to the reaction solution, the layers were partitioned, and the aqueous phase was extracted with ethyl acetate (3×60 mL). The combined organic phase was dried over $Na_2SO_4$ and concentrated under reduced pressure. The obtained residue was purified by Flash-HPLC (Column: C18; Mobile Phase A: water (10 mmol/L $NH_4HCO_3$), Mobile Phase B: ACN; Flow rate: 40 mL/min; Gradient: 5% B to 76% B in 23 min; Wave Length: 254/210 nm) to afford the title compound (470 mg, 51.6% yield) as a white solid. $^1H$ NMR (300 MHz, DMSO-$d_6$) δ 6.44 (s, 2H), 6.36 (s, 1H), 3.79 (s, 3H). LCMS $(M+H)^+$=285.

Step 2. 6-chloro-2-methoxy-3-[2-(4-methylsulfonylphenyl)ethynyl]pyridin-4-amine

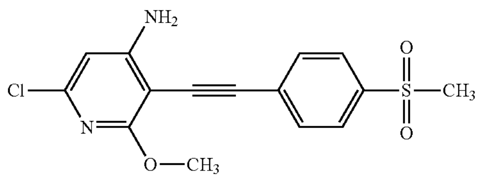

To a stirred solution of 6-chloro-3-iodo-2-methoxy-pyridin-4-amine (400 mg, 1.41 mmol) in DMF (5 mL) were added 1-ethynyl-4-methylsulfonyl-benzene (304 mg, 1.69 mmol), $Pd(PPh_3)_2Cl_2$ (98 mg, 0.14 mmol), CuI (27 mg, 0.14 mmol) and TEA (427 mg, 4.22 mmol). The resulting solution was degassed three times with nitrogen and stirred at 100° C. After 3 h, the mixture was diluted with ammonium chloride solution (60 mL) and extracted with EtOAc (3×60 mL). The combined organic layers were dried over $Na_2SO_4$ and concentrated under reduced pressure. LCMS $(M+H)^+$=337.1.

Step 3. 6-chloro-4-methoxy-2-(4-methylsulfonylphenyl)-1H-pyrrolo[3,2-c]pyridine

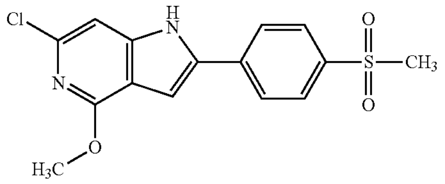 [SMILES: COc1nc(Cl)cc2[nH]c(-c3ccc(S(C)(=O)=O)cc3)cc12]

To a stirred solution of 6-chloro-2-methoxy-3-[2-(4-methylsulfonylphenyl) ethynyl]pyridin-4-amine (crude) in DMF (5 mL) was added t-BuOK (315 mg, 2.81 mmol) at 0° C. The resulting solution was stirred at 80° C. After 1 h, the mixture was diluted with water (60 mL) and extracted with EtOAc (3×60 mL). The combined organic layers were washed with brine, dried over $Na_2SO_4$ and concentrated under reduced pressure. The crude product was applied on a silica gel column with petroleum ether/EtOAc (3:2) as eluent to afford the title compound (160 mg, 32.3% yield) as a light yellow solid. $^1H$ NMR (300 MHz, DMSO-$d_6$) δ 12.35 (s, 1H), 8.13 (d, J=8.3 Hz, 2H), 8.00 (d, J=8.3 Hz, 2H), 7.25 (d, J=1.9 Hz, 1H), 7.10 (s, 1H), 4.00 (s, 3H), 3.26 (s, 3H). LCMS $(M+H)^+$=337.

Step 4. 6-chloro-4-methoxy-1-methyl-2-(4-methylsulfonylphenyl)pyrrolo[3,2-c]pyridine

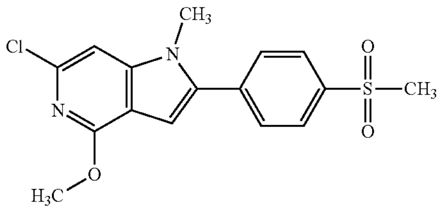 [SMILES: COc1nc(Cl)cc2c1cc(-c1ccc(S(C)(=O)=O)cc1)n2C]

To a stirred solution of 6-chloro-4-methoxy-2-(4-methylsulfonylphenyl)-1H-pyrrolo[3,2-c]pyridine (160 mg, 0.48 mmol) in DMF (3 mL) were added $Cs_2CO_3$ (310 mg, 0.95 mmol) and iodomethane (74 mg, 0.52 mmol). The resulting solution was stirred at room temperature for 1 hour, then mixture was diluted with water (50 mL) and extracted with EtOAc (3×50 mL). The combined organic layers were washed with brine, dried over $Na_2SO_4$ and concentrated under reduced pressure. The crude product was applied on a silica gel column with petroleum ether/EtOAc (2:1) as eluent to afford the title compound (160 mg, 96% yield) as a light orange solid. $^1H$ NMR (400 MHz, DMSO-$d_6$) δ 8.08-8.02 (m, 2H), 7.94-7.89 (m, 2H), 7.43 (d, J=0.9 Hz, 1H), 6.82 (d, J=0.9 Hz, 1H), 4.00 (s, 3H), 3.79 (s, 3H), 3.30 (s, 3H). LCMS $(M+H)^+$=351.1.

Step 5. Example 119

To a stirred solution of 6-chloro-4-methoxy-1-methyl-2-(4-methylsulfonylphenyl) pyrrolo[3,2-c]pyridine (50 mg, 0.14 mmol) in 1,4-dioxane (2 mL) and water (0.4 mL) were added $K_3PO_4$ (90 mg, 0.43 mmol), 1-isopropyl-4-[4-(4,4,5,5-tetramethyl-1,3,2-dioxaborolan-2-yl)phenyl]piperazine (94 mg, 0.29 mmol) and Xphos-Pd-G3 (12 mg, 0.01 mmol). The resulting solution was degassed three times with nitrogen and stirred at 90° C. After 3 days, the mixture was concentrated under reduced pressure and the crude product was purified by Prep-HPLC (Column: XBridge Prep C18 OBD Column, 19*150 mm, 5 μm; Mobile Phase A: water (10 mmol/L $NH_4HCO_3$), Mobile Phase B: ACN; Flow rate: 20 mL/min; Gradient: 50% B to 70% B in 4.5 min, 70% B; Wave Length: 254/210 nm) to afford the title compound (10 mg, 13.2% yield) as a light yellow solid. $^1H$ NMR (300 MHz, Chloroform-d) δ 8.07 (dd, J=8.7, 3.2 Hz, 4H), 7.73 (d, J=8.0 Hz, 2H), 7.31 (s, 1H), 7.05 (d, J=8.5 Hz, 2H), 6.76 (s, 1H), 4.21 (s, 3H), 3.82 (s, 3H), 3.45-3.26 (m, 4H), 3.15 (s, 3H), 2.91-2.69 (m, 5H), 1.17 (d, J=6.5 Hz, 6H). LCMS $(M+H)^+$=519.2.

Example 120

4-[6-[4-(4-isopropylpiperazin-1-yl)phenyl]-1-methyl-2-(4-methylsulfonylphenyl) pyrrolo[3,2-c] pyridin-4-yl]morpholine (120)

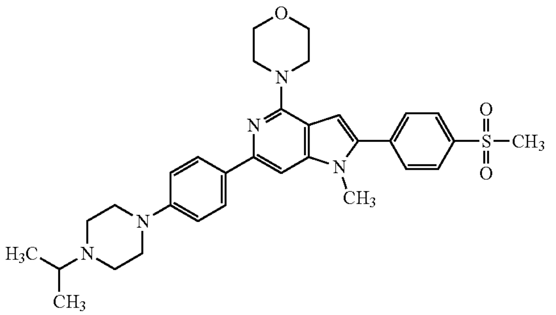

Step 1. 2-chloro-6-morpholino-pyridin-4-amine

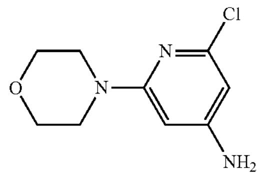 [SMILES: Nc1cc(Cl)nc(N2CCOCC2)c1]

To a solution of 2,6-dichloropyridin-4-amine (1 g, 6.13 mmol) and morpholine (0.53 g, 6.13 mmol) in DMSO (10 mL) was added DIEA (3.21 mL, 18.4 mmol). The resulting mixture was stirred at 90° C. After 2 h, the mixture was cooled to room temperature, diluted with water (200 mL) and extracted with EtOAc (200 mL). The combined organic layers were washed with brine (200 mL), dried over anhydrous sodium sulfate and concentrated under vacuum. The crude product was purified by reverse flash chromatography with the following conditions: column, C18 silica gel; mobile phase, ACN and water (0.05% $NH_4HCO_3$), 10% ACN to 70% ACN gradient in 20 min; detector, UV 254 nm to afford the title compound (0.81 g, 60.3% yield) as a white solid. $^1$H NMR (300 MHz, Methanol-$d_6$) δ 6.05 (s, 2H), 5.97 (s, 1H), 5.76 (s, 1H), 3.66 (t, J=4.8 Hz, 4H), 3.27 (t, J=4.9 Hz, 4H). LCMS $(M+H)^+$=213.9.

Step 2. 6-chloro-3-iodo-2-morpholino-pyridin-4-amine

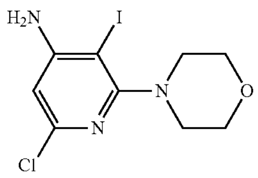 [SMILES: Nc1cc(Cl)nc(N2CCOCC2)c1I]

To a stirred solution of 2-chloro-6-morpholino-pyridin-4-amine (810 mg, 3.79 mmol) in ethanol (10 mL) were added $Ag_2SO_4$ (1.17 g, 3.79 mmol) and 12 (1.06 g, 4.17 mmol) at 0° C. The resulting solution was stirred for 18 h, after which time the mixture was diluted with water (200 mL) and extracted with EtOAc (3×200 mL). The combined organic layers were washed with brine, dried over $Na_2SO_4$ and concentrated under reduced pressure. The crude product was applied on a silica gel column with petroleum ether/EtOAc (2:1) as eluent to afford the title compound (900 mg, 69.9% yield) as a yellow solid. $^1$H NMR (300 MHz, Methanol-$d_6$) δ 6.12 (s, 2H), 5.94 (s, 1H), 3.65 (t, J=4.8 Hz, 4H), 3.26 (t, J=4.9 Hz, 4H). LCMS $(M+H)^+$=339.9.

Step 3. 6-chloro-3-[2-(4-methylsulfonylphenyl)ethynyl]-2-morpholino-pyridin-4-amine

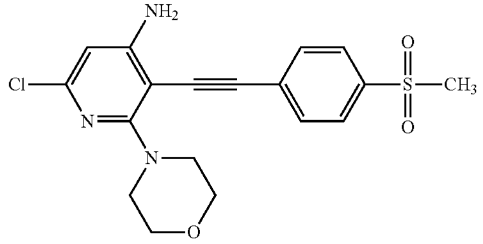 [SMILES: CS(=O)(=O)c1ccc(C#Cc2c(N)cc(Cl)nc2N2CCOCC2)cc1]

To a stirred solution of 6-chloro-3-iodo-2-morpholino-pyridin-4-amine (500 mg, 1.47 mmol) in DMF (5 mL) were added 1-ethynyl-4-methylsulfonyl-benzene (291.9 mg, 1.62 mmol), $Pd(PPh_3)_2Cl_2$ (170.1 mg, 0.15 mmol), CuI (27.9 mg, 0.15 mmol) and TEA (0.77 mL, 4.42 mmol). The resulting mixture was degassed three times with nitrogen and then stirred at 100° C. under a nitrogen atmosphere. After 2 h, the mixture was diluted with water (100 mL) and extracted with EtOAc (3×100 mL). The combined organic layers were washed with brine, dried over $Na_2SO_4$ and concentrated under reduced pressure to afford the title compound (600 mg crude) as a brown solid. LCMS $(M+H)^+$=392.1.

Step 4. 4-[6-chloro-2-(4-methylsulfonylphenyl)-1H-pyrrolo[3,2-c]pyridin-4-yl] morpholine

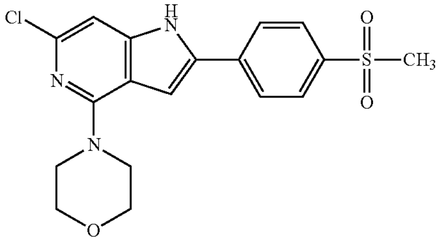 [SMILES: CS(=O)(=O)c1ccc(-c2cc3c(N4CCOCC4)nc(Cl)cc3[nH]2)cc1]

To a stirred solution of 6-chloro-3-[2-(4-methylsulfonylphenyl)ethynyl]-2-morpholino-pyridin-4-amine (500 mg, 1.28 mmol) in DMF (5 mL) was added t-BuOK (436.3 mg, 3.83 mmol). The resulting mixture was degassed three times with nitrogen and then stirred at 80° C. under nitrogen. After 2 h, the mixture was diluted with water (100 mL) and extracted with EtOAc (3×100 mL). The combined organic layers were washed with brine, dried over $Na_2SO_4$ and concentrated under reduced pressure. The crude product was applied on a silica gel column with petroleum ether/EtOAc (1:1) as eluent to afford the title compound (80 mg, 16% yield) as a yellow solid. LCMS $(M+H)^+$=392.1.

Step 5. 4-[6-chloro-1-methyl-2-(4-methylsulfonylphenyl)pyrrolo[3,2-c]pyridin-4-yl] morpholine

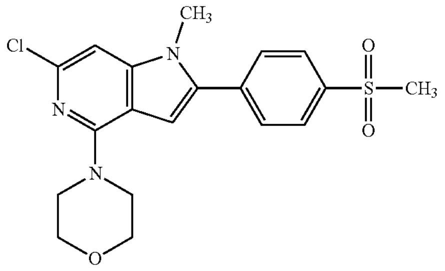 [SMILES: Cn1c(-c2ccc(S(C)(=O)=O)cc2)cc2c(N3CCOCC3)nc(Cl)cc21]

To a stirred solution of 4-[6-chloro-2-(4-methylsulfonylphenyl)-1H-pyrrolo[3,2-c] pyridin-4-yl]morpholine (140 mg, 0.36 mmol) in DMF (2 mL) were added MeI (101.4 mg, 0.71 mmol) and $Cs_2CO_3$ (232.2 mg, 0.71 mmol). The resulting solution was stirred at room temperature for 1 h, after which time the mixture was diluted with water (50 mL) and extracted with EtOAc (3×50 mL). The combined organic layers were washed with brine, dried over $Na_2SO_4$ and concentrated under reduced pressure to afford the title compound (100 mg crude) as a yellow solid. LCMS $(M+H)^+$=406.1.

Step 6. Example 120

To a solution of 4-[6-chloro-1-methyl-2-(4-methylsulfonylphenyl)pyrrolo[3,2-c]pyridin-4-yl]morpholine (70 mg, 0.17 mmol) and 1-isopropyl-4-[4-(4,4,5,5-tetramethyl-1,3,2-dioxaborolan-2-yl)phenyl]piperazine (113.9 mg, 0.34 mmol) in 1,4-dioxane (2 mL) and water (0.5 mL) were added Xphos-Pd-G3 (14.5 mg, 0.02 mmol) and $K_2CO_3$ (71.4 mg, 0.52 mmol). The resulting mixture was degassed three times with nitrogen and then stirred at 90° C. under nitrogen. After 2 h, the mixture was cooled to room temperature and purified by reverse flash chromatography with the following conditions: column, C18 silica gel; mobile phase, ACN and water (0.05% TFA), 10% ACN to 70% ACN gradient in 20 min; detector, UV 254 nm. The product was purified by Prep-HPLC (Column: X Bridge Prep C18 OBD Column, 19*150 mm, 5 μm; Mobile Phase A: water (10 mmol/L $NH_4HCO_3$), Mobile Phase B: ACN; Flow rate: 20 mL/min; Gradient: 50% B to 65% B in 4.5 min, 65% B; Wave Length: 254/210 nm) to afford the title compound (35.6 mg, 35.5% yield) as a yellow solid. $^1H$ NMR (400 MHz, Methanol-$d_6$) δ 8.14-7.82 (m, 6H), 7.05 (d, J=8.8 Hz, 2H), 6.97 (s, 1H), 6.75 (s, 1H), 3.88-3.71 (m, 7H), 3.57-3.49 (m, 4H), 3.29 (s, 3H), 3.26-3.16 (m, 4H), 2.78-2.66 (m, 1H), 2.60 (t, J=5.0 Hz, 4H), 1.02 (d, J=6.5 Hz, 6H). LCMS $(M+H)^+$=574.2.

Example 121

1-[3-[[4-[1-cyclopropyl-2-(4-methylsulfonylphenyl) pyrrolo[3,2-c]pyridin-6-yl] phenyl]methyl]-3,8-diazabicyclo[3.2.1]octan-8-yl]-2-methyl-propan-2-ol (121)

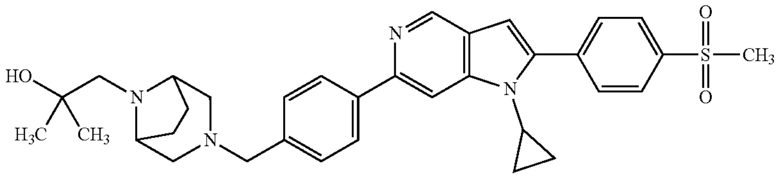

Step 1. tert-butyl 8-(2-hydroxy-2-methyl-propyl)-3,8-diazabicyclo[3.2.1]octane-3-carboxylate

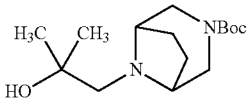

To a solution of tert-butyl 3,8-diazabicyclo[3.2.1]octane-3-carboxylate (1 g, 4.71 mmol) in ethanol (20 mL) were added 1-chloro-2-methyl-propan-2-ol (1.53 g, 14.13 mmol) and DIEA (2.45 g, 18.84 mmol). The resulting solution was stirred at 100° C. for 20 h, after which time the reaction mixture was cooled to room temperature, the solvent was removed under reduced pressure and purified by silica gel column chromatography with petroleum ether/EtOAc (3:1) as eluent to afford the title compound (780 mg, 58.2% yield) as a light yellow oil. $^1$H NMR (400 MHz, DMSO-$d_6$) δ 3.99 (s, 1H), 3.57 (d, J=12.2 Hz, 1H), 3.50 (d, J=12.2 Hz, 1H), 3.13 (d, J=13.2 Hz, 2H), 3.00 (d, J=12.2 Hz, 1H), 2.87 (d, J=12.2 Hz, 1H), 2.11 (s, 2H), 1.80-1.72 (m, 2H), 1.44 (t, J=7.1 Hz, 2H), 1.39 (s, 9H), 1.08 (s, 6H). LCMS $(M+H)^+$=285.3.

Step 2. 1-(3,8-diazabicyclo[3.2.1]octan-8-yl)-2-methyl-propan-2-ol

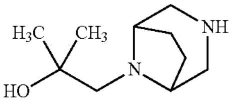

To a stirred solution of tert-butyl 8-(2-hydroxy-2-methyl-propyl)-3,8-diazabicyclo[3.2.1]octane-3-carboxylate (780 mg, 2.74 mmol) in DCM (4 mL) and methanol (0.5 mL) was added 4 M HCl in 1,4-dioxane (1.5 mL). The resulting solution was stirred at room temperature for 3 days, after which time the mixture was concentrated under reduced pressure to afford the title compound (600 mg crude) as a white solid. LCMS $(M+H)^+$=185.2.

Step 3. 2-chloro-5-[2-(4-methylsulfonylphenyl)ethynyl]pyridin-4-amine

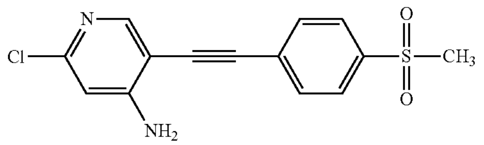 [SMILES: CS(=O)(=O)c1ccc(C#Cc2cnc(Cl)cc2N)cc1]

To a solution of 2-chloro-5-iodo-pyridin-4-amine (2 g, 7.86 mmol) in DMF (20 mL) were added 1-ethynyl-4-methylsulfonyl-benzene (1.7 g, 9.43 mmol), $Pd(PPh_3)_2Cl_2$ (550 mg, 0.79 mmol), CuI (150 mg, 0.79 mmol) and TEA (2.39 g, 23.58 mmol). The resulting solution was degassed three times with nitrogen and stirred at 100° C. After 3 h, the mixture was diluted with ammonium chloride solution (100 mL) and extracted with EtOAc (3×100 mL). The combined organic layers were dried over $Na_2SO_4$ and concentrated under reduced pressure. LCMS $(M+H)^+$=306.9.

Step 4. 6-chloro-2-(4-methylsulfonylphenyl)-1H-pyrrolo[3,2-c]pyridine

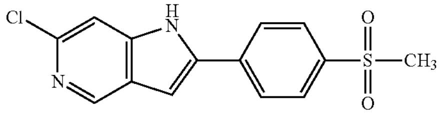 [SMILES: CS(=O)(=O)c1ccc(-c2cc3cnc(Cl)cc3[nH]2)cc1]

To a solution of 2-chloro-5-[2-(4-methylsulfonylphenyl)ethynyl]pyridin-4-amine (2.4 g, 7.82 mmol) in DMF (20 mL) was added t-BuOK (2.63 g, 23.47 mmol) at 0° C. The resulting solution was stirred at 80° C. for 1 hour, after which time the mixture was diluted with water (100 mL) and extracted with EtOAc (3×100 mL). The combined organic layers were washed with brine, dried over $Na_2SO_4$ and concentrated under reduced pressure. The crude product was applied on a silica gel column with petroleum ether/EtOAc (1:4) as eluent to afford the title compound (920 mg, 38.3% yield) as a light yellow solid. $^1$H NMR (400 MHz, DMSO-$d_6$) δ 12.38 (s, 1H), 8.70 (s, 1H), 8.16 (d, J=8.3 Hz, 2H), 8.04 (d, J=8.3 Hz, 2H), 7.44 (s, 1H), 7.32 (d, J=1.9 Hz, 1H), 3.27 (s, 3H). LCMS $(M+H)^+$=306.9.

Step 5. 6-chloro-1-cyclopropyl-2-(4-methylsulfonylphenyl)pyrrolo[3,2-c]pyridine

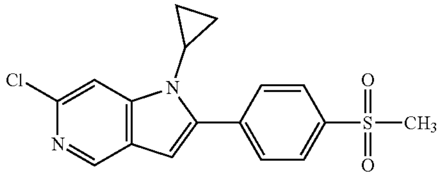 [SMILES: CS(=O)(=O)c1ccc(-c2cc3cnc(Cl)cc3n2C2CC2)cc1]

To a solution of 6-chloro-2-(4-methylsulfonylphenyl)-1H-pyrrolo[3,2-c]pyridine (500 mg, 1.63 mmol) in DCE (10 mL) were added $Na_2CO_3$ (518 mg, 4.89 mmol), cyclopropylboronic acid (420 mg, 4.89 mmol), $Cu(OAc)_2$ (388 mg, 2.44 mmol) and 2,2'-bipyridine (382 mg, 2.44 mmol). The resulting solution was stirred at 60° C. for 3 days. The mixture was then diluted with water (60 mL) and extracted with DCM (3×60 mL). The combined organic layers were dried over $Na_2SO_4$, concentrated under reduced pressure and purified by Flash-HPLC (Column: C18; Mobile Phase A: water (0.05% TFA), Mobile Phase B: ACN; Flow rate: 50 mL/min; Gradient: 10% B to 48% B in 20 min, 254/210 nm) to afford the title compound (230 mg, 40.7% yield) as a brown solid. $^1$H NMR (300 MHz, DMSO-$d_6$) δ 8.68 (d, J=1.1 Hz, 1H), 8.05 (s, 4H), 7.65 (s, 1H), 6.92 (d, J=1.1 Hz, 1H), 3.77 (dt, J=6.9, 3.3 Hz, 1H), 3.31 (s, 3H), 1.05 (dd, J=7.4, 5.4 Hz, 2H), 0.63-0.51 (m, 2H). LCMS $(M+H)^+$=347.1.

Step 6. 4-[1-cyclopropyl-2-(4-methylsulfonylphenyl)pyrrolo[3,2-c]pyridin-6-yl] benzaldehyde

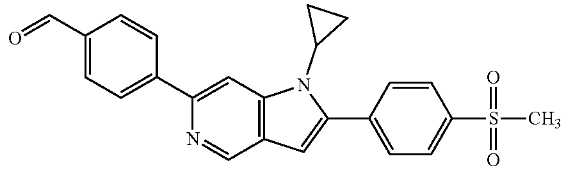 [SMILES: CS(=O)(=O)c1ccc(-c2cc3cnc(-c4ccc(C=O)cc4)cc3n2C2CC2)cc1]

To a solution of 6-chloro-1-cyclopropyl-2-(4-methylsulfonylphenyl)pyrrolo[3,2-c] pyridine (230 mg, 0.66 mmol) in 1,4-dioxane (4 mL) and water (0.8 mL) were added $K_3PO_4$ (422 mg, 1.99 mmol), 4-(4,4,5,5-tetramethyl-1,3,2-dioxaborolan-2-yl) benzaldehyde (308 mg, 1.33 mmol) and Xphos-Pd-G3 (56 mg, 0.07 mmol). The resulting solution was degassed three times with nitrogen and stirred at 90° C. for 1 h. The mixture was then diluted with water (50 mL) and extracted with DCM (3×50 mL). The combined organic layers were dried over $Na_2SO_4$, concentrated under reduced pressure and purified by Flash-HPLC (Column: C18 Column; Mobile Phase A: water (0.05% TFA), Mobile Phase B: ACN; Flow rate: 50 mL/min; Gradient: 5% B to 31% B in 12 min; Wave Length: 254/210 nm) to afford the title compound (135 mg, 47.8% yield) as a light yellow solid. $^1$H NMR (400 MHz, Methanol-$d_4$) δ 9.15 (s, 1H), 8.37 (s, 1H), 8.19-8.15 (m, 3H), 8.13-8.08 (m, 2H), 8.00-7.95 (m, 2H), 7.76 (d, J=8.1 Hz, 2H), 7.27 (s, 1H), 3.90 (tt, J=7.1, 3.8 Hz, 1H), 3.23 (s, 3H), 1.27-1.20 (m, 2H), 0.83-0.77 (m, 2H). LCMS $(M+H)^+$=417.2.

Step 7. Example 121

To a solution of 4-[1-cyclopropyl-2-(4-methylsulfonylphenyl)pyrrolo[3,2-c] pyridin-6-yl]benzaldehyde (50 mg, 0.12 mmol) in DCM (3 mL) were added 1-(3,8-diazabicyclo[3.2.1]octan-8-yl)-2-methyl-propan-2-ol (66 mg, 0.36 mmol) and acetic acid (0.01 mL). After stirring at room temperature for 3 hours, to the mixture was added $NaBH(OAc)_3$ (76 mg, 0.36 mmol). The resulting solution was stirred at room temperature for 1 hour. The reaction mixture was then diluted with saturated sodium bicarbonate solution and extracted with DCM (3×50 mL). The combined organic layers were dried over $Na_2SO_4$ and concentrated under reduced pressure. The crude product was purified by Prep-HPLC (Column: Kinetex EVO C18 Column, 21.2*150, Sum; Mobile Phase A: water (10 mmol/L $NH_4HCO_3$), Mobile Phase B: ACN; Flow rate: 20 mL/min; Gradient: 40% B to 60% B in 5.5 min, 60% B; Wave Length: 254/210 nm); to afford the title compound (8.6 mg, 11.6% yield) as an off-white solid. $^1$H NMR (300 MHz, Methanol-$d_4$) δ 8.85 (s, 1H), 8.06 (q, J=8.4 Hz, 4H), 7.99-7.83 (m, 3H), 7.46 (d, J=7.9 Hz, 2H), 6.89 (s, 1H), 3.86-3.66 (m, 1H), 3.55 (s, 2H), 3.30-3.11 (m, 5H), 2.64 (d, J=9.0 Hz, 2H), 2.40 (d, J=10.2 Hz, 2H), 2.28 (s, 2H), 2.00-1.81 (m, 4H), 1.25-1.11 (m, 8H), 0.71-0.63 (m, 2H). LCMS $(M+H)^+$=585.3.

| Ex. No. | Structure |
|---|---|
| 122 | 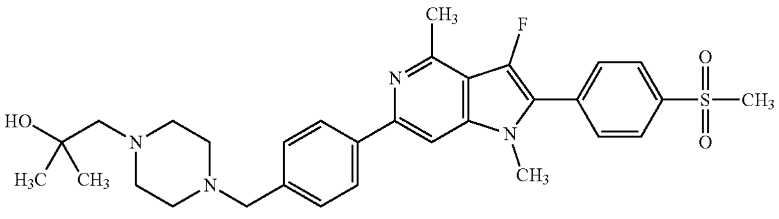 [SMILES: Cc1nc(-c2ccc(CN3CCN(CC(C)(C)O)CC3)cc2)cc2c1c(F)c(-c1ccc(S(C)(=O)=O)cc1)n2C] |
| 123 | 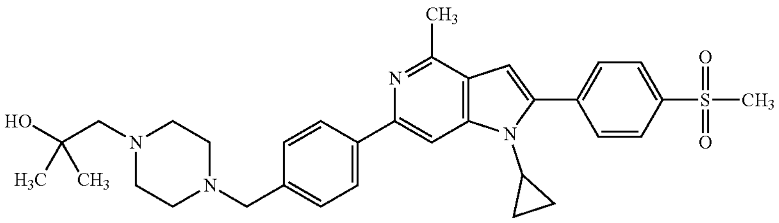 [SMILES: Cc1nc(-c2ccc(CN3CCN(CC(C)(C)O)CC3)cc2)cc2c1cc(-c1ccc(S(C)(=O)=O)cc1)n2C1CC1] |
| 124 | 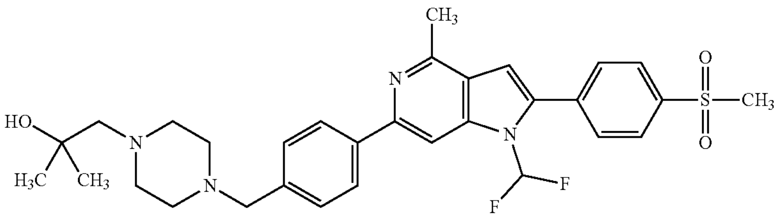 [SMILES: Cc1nc(-c2ccc(CN3CCN(CC(C)(C)O)CC3)cc2)cc2c1cc(-c1ccc(S(C)(=O)=O)cc1)n2C(F)F] |

-continued
| Ex. No. | Structure |
|---|---|
| 125 | 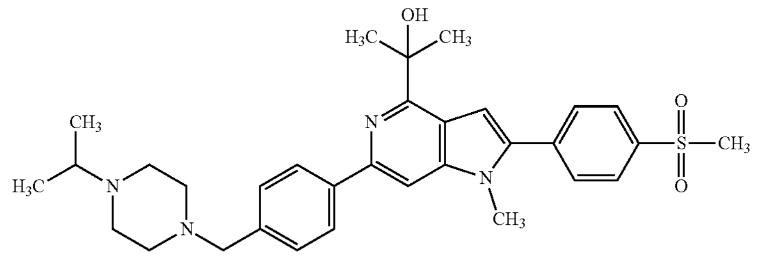 [SMILES: CC(C)N1CCN(Cc2ccc(-c3cc4c(cc(-c5ccc(S(C)(=O)=O)cc5)n4C)c(C(C)(C)O)n3)cc2)CC1] |
| 126 | 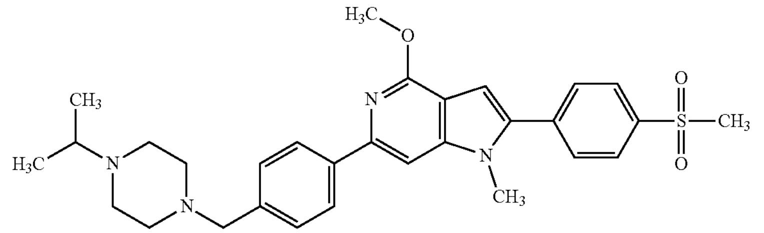 [SMILES: COc1nc(-c2ccc(CN3CCN(C(C)C)CC3)cc2)cc2c1cc(-c1ccc(S(C)(=O)=O)cc1)n2C] |
| 127 | 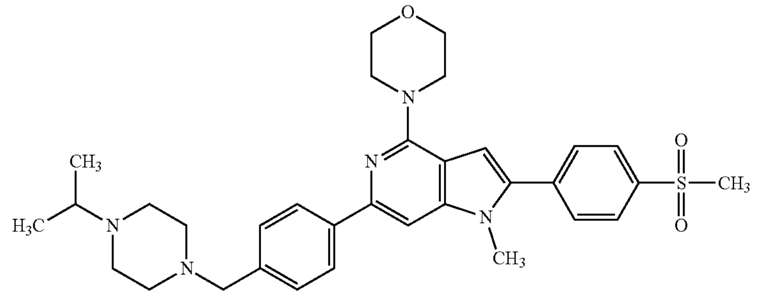 [SMILES: CC(C)N1CCN(Cc2ccc(-c3cc4c(cc(-c5ccc(S(C)(=O)=O)cc5)n4C)c(N4CCOCC4)n3)cc2)CC1] |
| 128 | 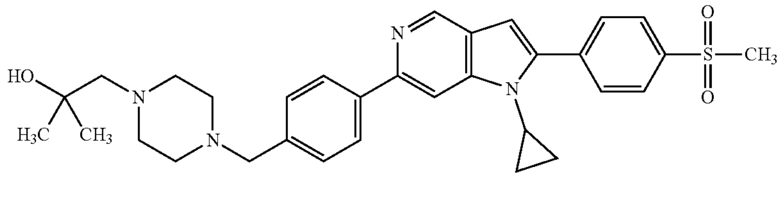 [SMILES: CC(C)(O)CN1CCN(Cc2ccc(-c3cc4c(cn3)cc(-c3ccc(S(C)(=O)=O)cc3)n4C3CC3)cc2)CC1] |
| 129 | 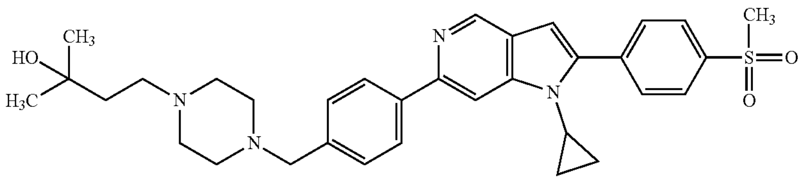 [SMILES: CC(C)(O)CCN1CCN(Cc2ccc(-c3cc4c(cn3)cc(-c3ccc(S(C)(=O)=O)cc3)n4C3CC3)cc2)CC1] |
| 130 | 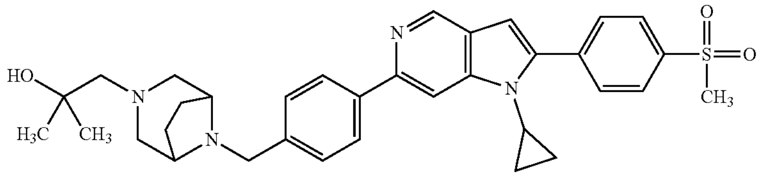 [SMILES: CC(C)(O)CN1CC2CCC(C1)N2Cc1ccc(-c2cc3c(cn2)cc(-c2ccc(S(C)(=O)=O)cc2)n3C2CC2)cc1] |

| | |
|---|---|
| 122 | LCMS $(M + H)^+$ = 565.1. $^1H$ NMR (400 MHz, Methanol-$d_4$) δ 8.15 (d, J = 8.8 Hz, 2H), 7.98 (d, J = 8.0 Hz, 2H), 7.88 (d, J = 8.2 Hz, 2H), 7.71 (d, J = 2.6 Hz, 1H), 7.47 (d, J = 8.0 Hz, 2H), 3.80 (s, 3H), 3.61 (s, 2H), 3.22 (s, 3H), 2.88 (s, 3H), 2.68 (s, 4H), 2.57 (s, 4H), 2.34 (s, 2H), 1.19 (s, 6H) |
| 123 | LCMS $(M + H)^+$ = 573.2. $^1H$ NMR (300 MHz, Methanol-$d_4$) δ 8.07 (q, J = 8.6 Hz, 4H), 7.98-7.84 (m, 2H), 7.80 (s, 1H), 7.49 (d, J = 8.0 Hz, 2H), 6.92 (s, 1H), 3.82-3.70 (m, 1H), 3.63 (s, 2H), 3.22 (s, 3H), 2.80 (s, 3H), 2.75-2.55 (m, 8H), 2.34 (s, 2H), 1.21-1.09 (m, 8H), 0.73-0.62 (m, 2H) |
| 124 | LCMS $(M + H)^+$ = 583.2. $^1H$ NMR (400 MHz, Methanol-$d_4$) δ 8.16 (d, J = 8.0 Hz, 2H), 8.00-7.52 (m, 6H), 7.49 (d, J = 7.9 Hz, 2H), 7.06 (s, 1H), 3.62 (s, 2H), 3.22 (s, 3H), 2.85 (s, 3H), 2.79-2.45 (m, 8H), 2.34 (s, 2H), 1.19 (s, 6H) |
| 125 | LCMS $(M + H)^+$ = 561.3. $^1H$ NMR (400 MHz, Chloroform-d) δ 8.20-7.92 (m, 4H), 7.77 (d, J = 8.4 Hz, 2H), 7.64 (d, J = 0.9 Hz, 1H), 7.45(d, J = 8.1 Hz, 2H), 6.80 (d, J = 0.9 Hz, 1H), 6.63 (s, 1H), 3.86 (s, 3H), 3.60 (s, 2H), 3.14 (s, 3H), 2.80-2.30 (m, 9H), 1.75 (s, 6H), 1.09 (d, J = 6.5 Hz, 6H) |
| 126 | LCMS $(M + H)^+$ = 533.2. $^1H$ NMR (400 MHz, DMSO-$d_6$) δ 8.17 (d, J = 8.4 Hz, 2H), 8.05 (d, J = 8.8 Hz, 2H), 7.94 (d, J = 8.4 Hz, 2H), 7.85 (s, 1H), 7.38 (d, J = 8.0 Hz, 2H), 6.82 (s, 1H), 4.11 (s, 3H), 3.89 (s, 3H), 3.49(s, 2H), 3.34 (s, 3H), 2.64-2.56 (m, 1H), 2.49-2.33 (m, 8H), 0.96 (d, J = 6.4 Hz, 6H) |
| 127 | LCMS $(M + H)^+$ = 588.3. $^1H$ NMR (400 MHz, DMSO-$d_6$) δ 8.10-7.90 (m, 6H), 7.42 (d, J = 8.0 Hz, 2H), 6.98 (s, 1H), 6.84 (s, 1H), 3.93-3.70 (m, 7H), 3.67-3.42 (m, 6H), 3.30 (s, 3H), 2.66-2.55 (m, 1H), 2.49-2.33 (m, 8H), 0.96 (d, J = 6.5 Hz, 6H) |
| 128 | LCMS $(M + H)^+$ = 559.3. $^1H$ NMR (400 MHz, DMSO-$d_6$) δ 8.94 (d, J = 1.0 Hz, 1H), 8.13-7.89 (m, 7H), 7.39 (d, J = 8.2 Hz, 2H), 6.91 (s, 1H), 4.03 (s, 1H), 3.85-3.79 (m, 1H), 3.51 (s, 2H), 3.31 (s, 3H), 2.68-2.50 (m, 4H), 2.49-2.32 (m, 4H), 2.18 (s, 2H), 1.15-1.07 (m, 8H), 0.63-0.60 (m, 2H) |
| 129 | LCMS $(M + H)^+$ = 573.4. $^1H$ NMR (400 MHz, DMSO-$d_6$) δ 8.94 (d, J = 1.0 Hz, 1H), 8.13-8.03 (m, 7H), 7.41 (d, J = 8.3 Hz, 2H), 6.91 (s, 1H), 4.65 (s, 1H), 3.85-3.79 (m, 1H), 3.51 (s, 2H), 3.29 (s, 3H), 2.52-2.50 (m, 2H), 2.41-2.32 (m, 8H), 1.51 (t, J = 7.3 Hz, 2H), 1.15-1.08 (m, 8H), 0.63-0.59 (m, 2H) |
| 130 | LCMS $(M + H)^+$ = 585.4. $^1H$ NMR (400 MHz, DMSO-$d_6$) δ 8.93 (s, 1H), 8.24-7.90 (m, 7H), 7.48 (d, J = 8.0 Hz, 2H), 6.91 (s, 1H), 3.99 (s, 1H), 3.90-3.70 (m, 1H), 3.52 (s, 2H), 3.31 (s, 3H), 3.04 (s, 2H), 2.66 (dd, J = 10.2, 3.0 Hz, 2H), 2.42 (d, J = 10.0 Hz, 2H), 2.15 (s, 2H), 2.00-1.65 (m, 4H), 1.28-0.90 (m, 8H), 0.75-0.50 (m, 2H) |

Biological Assays

The pharmacological properties of the compounds of this invention may be confirmed by a number of biological assays. The exemplified biological assays, which follow, have been carried out with compounds of the invention.

TLR7/8/9 Inhibition Reporter Assays

HEK-Blue™-cells (Invivogen) overexpressing human TLR7, TLR8 or TLR9 receptors were used for screening inhibitors of these receptors using an inducible SEAP (secreted embryonic alkaline phosphatase) reporter gene under the control of the IFN-β minimal promoter fused to five NF-κB and AP-1-binding sites. Briefly, cells are seeded into Greiner 384 well plates (15000 cells per well for TLR7, 20,000 for TLR8 and 25,000 for TLR9) and then treated with test compounds in DMSO to yield a final dose response concentration range of 0.05 nM-50 μM. After a 30 minute compound pre-treatment at room temperature, the cells are then stimulated with a TLR7 ligand (gardiquimod at a final concentration of 7.5 μM), TLR8 ligand (R848 at a final concentration of 15.9 μM) or TLR9 ligand (ODN2006 at a final concentration of 5 nM) to activate NF-κB and AP-1 which induce the production of SEAP. After a 22 hour incubation at 37° C., 5% $CO_2$, SEAP levels are determined with the addition of HEK-Blue™ Detection reagent (Invivogen), a cell culture medium that allows for detection of SEAP, according to manufacturer's specifications. The percent inhibition is determined as the % reduction in the HEK-Blue signal present in wells treated with agonist plus DMSO alone compared to wells treated with a known inhibitor.

| Ex. No. | TLR9 $IC_{50}$ (μM) | TLR7 $IC_{50}$ (μM) | TLR8 $IC_{50}$ (μM) |
|---|---|---|---|
| 1 | 0.161 | 1.7 | 21.0 |
| 2 | 0.157 | 2.7 | 29.0 |
| 3 | 0.082 | 3.3 | 37.7 |
| 4 | 0.243 | 9.5 | 23.5 |
| 5 | 0.133 | 8.2 | >50 |
| 6 | 0.296 | 8.0 | 23.3 |
| 7 | 0.111 | >50 | 5.2 |
| 8 | 0.058 | 6.8 | 25.9 |
| 9 | 0.021 | 2.9 | 1.5 |
| 10 | 0.066 | 13.8 | 5.2 |
| 11 | 0.020 | 1.5 | 21.4 |
| 12 | 0.036 | n.d. | n.d. |
| 13 | 0.191 | 17.3 | >50 |
| 14 | 0.313 | 8.2 | >50 |
| 15 | 0.039 | 14.0 | >50 |
| 16 | 0.084 | 5.7 | 47.9 |
| 17 | 0.019 | 2.3 | >50 |
| 18 | 0.194 | 13.6 | >50 |
| 19 | 0.130 | 5.2 | >50 |
| 20 | 0.153 | 9.2 | >50 |
| 21 | 0.603 | 26.0 | >50 |
| 22 | 1.570 | 9.7 | >50 |
| 23 | 1.110 | >50 | >50 |
| 24 | 0.059 | 3.2 | 3.8 |
| 25 | 0.197 | 4.5 | >50 |
| 26 | 0.009 | 7.3 | 1.2 |
| 27 | 0.045 | 2.6 | 1.5 |
| 28 | 0.269 | >50 | 20.5 |
| 29 | 0.399 | 14.4 | 8.2 |
| 30 | 0.579 | n.d. | n.d. |
| 31 | 0.072 | 1.5 | 1.7 |
| 32 | 0.170 | 1.4 | >50 |
| 33 | 0.027 | 3.2 | >50 |
| 34 | 0.010 | 2.2 | >50 |

-continued

| Ex. No. | TLR9 $IC_{50}$ (μM) | TLR7 $IC_{50}$ (μM) | TLR8 $IC_{50}$ (μM) |
|---|---|---|---|
| 35 | 0.71 | 16.8 | >25 |
| 36 | 0.059 | 4.7 | >25 |
| 37 | 0.057 | 11.7 | >25 |
| 38 | 0.056 | 2.6 | 11.8 |
| 39 | 0.672 | n.d. | n.d. |
| 40 | 0.098 | n.d. | n.d. |
| 41 | 0.236 | 4.9 | >16.7 |
| 42 | 0.346 | n.d. | n.d. |
| 43 | 0.079 | 6.2 | 2.7 |
| 44 | 0.096 | 0.64 | 1.2 |
| 45 | 0.068 | 0.75 | n.d. |
| 46 | 0.213 | n.d. | n.d. |
| 47 | 0.077 | 14.7 | >25 |
| 48 | 0.385 | 2.1 | >25 |
| 49 | 6.76 | n.d. | n.d. |
| 50 | 2.41 | n.d. | n.d. |
| 51 | 0.044 | n.d. | n.d. |
| 52 | 0.202 | n.d. | n.d. |
| 53 | 0.021 | >50 | >50 |
| 54 | 0.042 | 4.6 | >50 |
| 55 | 2.81 | 5.7 | >50 |
| 56 | 0.270 | 18.5 | 13.2 |
| 57 | 0.046 | 6.0 | 7.5 |
| 58 | 0.107 | 8.2 | 17.8 |
| 59 | 0.772 | 12.9 | 17.2 |
| 60 | 0.064 | 5.4 | 4.6 |
| 61 | 0.109 | 3.1 | 0.86 |
| 62 | 0.105 | n.d. | n.d. |
| 63 | 0.146 | n.d. | n.d. |
| 64 | 0.0064 | n.d. | n.d. |
| 65 | 0.136 | n.d. | n.d. |
| 66 | 0.136 | n.d. | n.d. |
| 67 | 0.025 | n.d. | n.d. |
| 68 | 0.299 | n.d. | n.d. |
| 69 | 0.078 | 23.7 | >25 |
| 70 | 0.260 | >25 | >25 |
| 71 | 0.003 | n.d. | n.d. |
| 72 | 0.411 | n.d. | n.d. |
| 73 | 0.359 | n.d. | n.d. |
| 74 | 0.058 | 1.6 | 19.4 |
| 75 | 0.075 | 2.2 | 9.6 |
| 76 | 0.053 | 0.6 | 18.3 |
| 77 | 0.126 | 1.9 | 19.2 |
| 78 | 0.147 | 2.7 | 9.4 |
| 79 | 0.035 | 2.7 | 9.5 |
| 80 | 7.28 | n.d. | n.d. |
| 81 | 0.670 | n.d. | n.d. |
| 82 | 0.329 | 6.4 | >50 |
| 83 | 2.30 | n.d. | n.d. |
| 84 | 0.626 | n.d. | n.d. |
| 85 | 2.40 | n.d. | n.d. |
| 86 | 1.07 | n.d. | n.d. |
| 87 | 0.073 | 2.2 | 4.0 |
| 88 | 0.114 | 6.5 | 10.5 |
| 89 | 0.226 | >50 | >50 |
| 90 | 0.141 | 7.8 | 22.1 |
| 91 | 0.735 | 30.8 | 1.3 |
| 92 | 0.109 | 7.0 | >50 |
| 93 | 1.43 | 9.9 | >50 |
| 94 | 0.143 | 3.6 | 2.5 |
| 95 | 0.537 | 3.2 | 2.7 |
| 96 | 0.162 | 2.9 | 4.1 |
| 97 | 0.202 | 3.8 | 5.3 |
| 98 | 0.212 | 0.7 | >50 |
| 99 | 0.250 | 1.5 | 6.0 |
| 100 | 0.184 | 7.1 | 1.3 |
| 101 | 0.116 | 5.7 | 5.1 |
| 102 | 0.127 | 5.5 | 1.0 |
| 103 | 0.296 | n.d. | n.d. |
| 104 | 0.161 | 2.2 | 2.1 |
| 105 | 0.052 | 1.1 | 0.2 |
| 106 | 0.047 | 1.5 | 0.7 |
| 107 | 0.018 | 2.1 | 2.7 |
| 108 | 0.204 | 1.7 | 1.5 |
| 109 | 0.188 | 1.3 | 1.1 |
| 110 | 0.058 | n.d. | n.d. |
| 111 | 0.113 | n.d. | n.d. |
| 112 | 0.087 | n.d. | n.d. |
| 113 | 0.153 | n.d. | n.d. |
| 114 | 0.047 | 14.2 | >50 |
| 115 | 0.615 | 16.0 | 2.1 |
| 116 | 0.059 | 3.2 | 19.0 |
| 117 | 0.557 | 7.8 | 16.7 |
| 118 | 0.057 | 1.7 | 8.1 |
| 119 | 0.543 | n.d. | n.d. |
| 120 | 0.553 | n.d. | n.d. |
| 121 | 0.129 | 0.6 | >50 |
| 122 | 0.103 | 17.1 | 3.7 |
| 123 | 0.085 | 3.7 | 17.6 |
| 124 | 0.451 | >50 | >50 |
| 125 | 0.133 | 3.1 | 11.3 |
| 126 | 1.260 | n.d. | n.d. |
| 127 | 0.422 | n.d. | n.d. |
| 128 | 0.115 | 2.8 | 7.9 |
| 129 | 0.118 | 3.6 | 5.6 |
| 130 | 0.092 | 1.9 | 6.4 |

n.d.: not determined

What is claimed is:

1. A compound of Formula (IIIb):

(III)

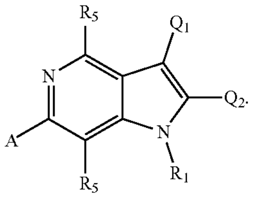

or salts thereof, wherein:

G is:

(i) phenyl substituted with 1 to 3 substituents independently selected from $—OCH_3$, $—S(O)_2CH_3$, $—S(O)_2N(CH_3)_2$, $—S(O)_2$(cyclopropyl), and $—S(O)(NH)N(CH_3)_2$;

(ii)

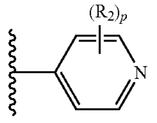

or

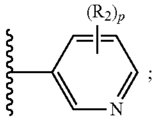

;

(iii)

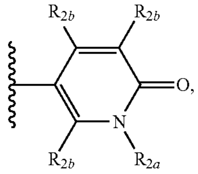

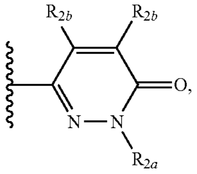

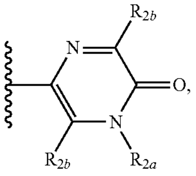

or

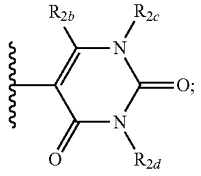

(iv) a 9-membered heterocyclic ring selected from:
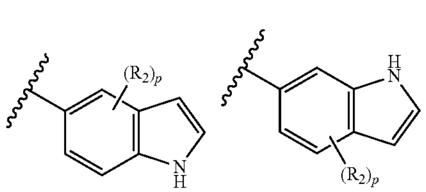
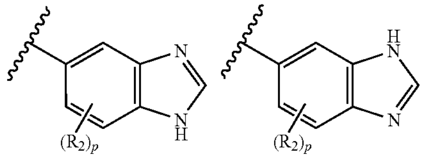
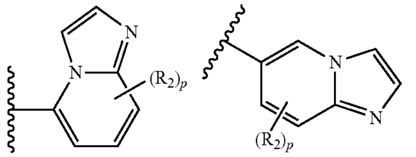
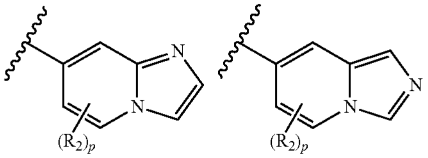
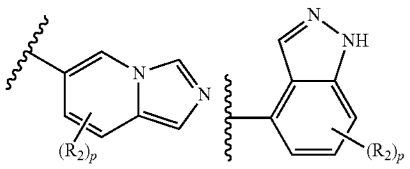
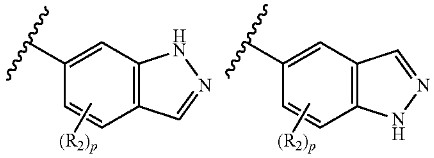
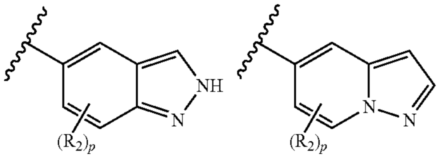
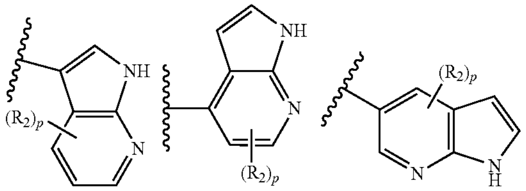
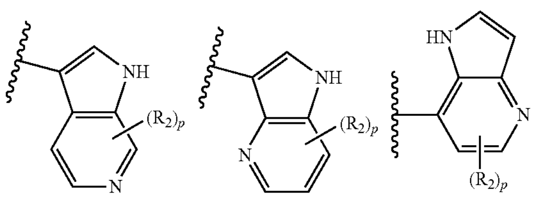
-continued
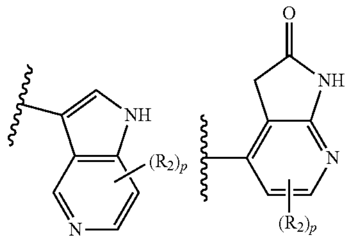
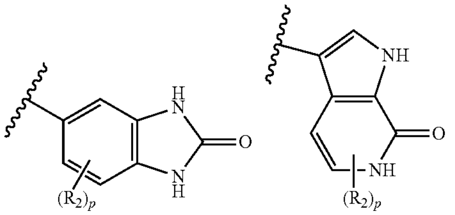
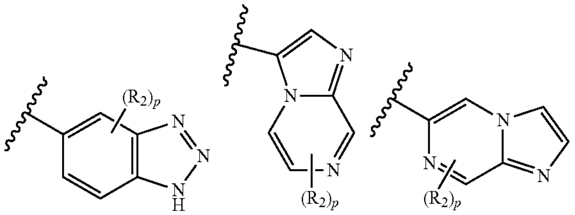
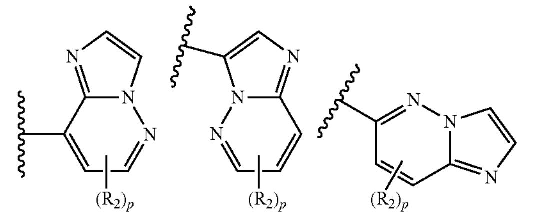
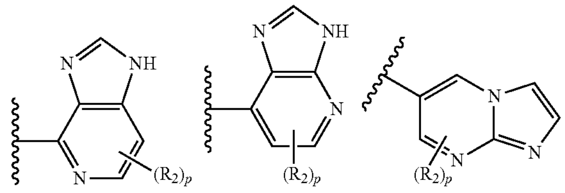
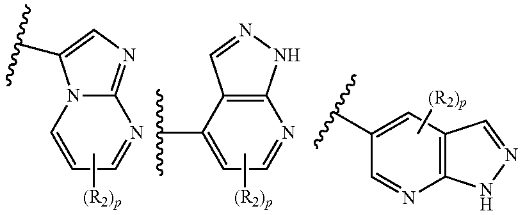
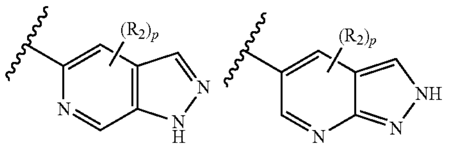
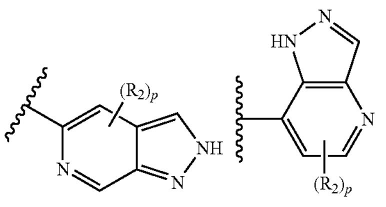

-continued
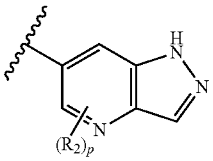
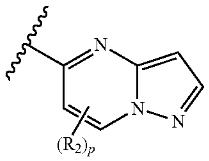
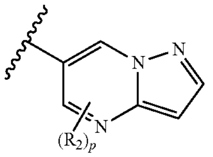
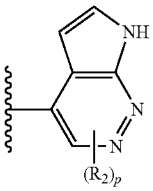
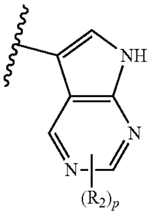
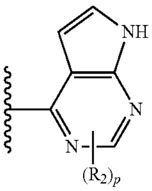
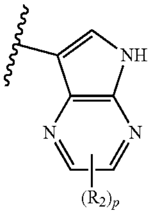
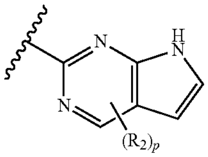
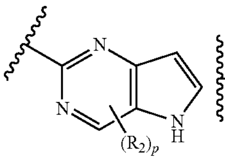
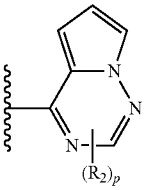
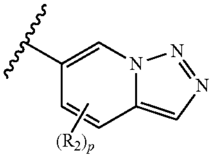
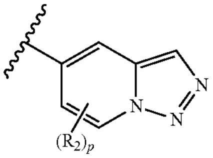
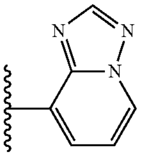
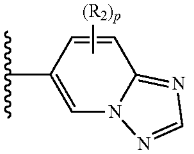
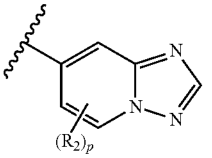
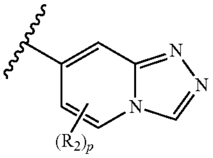
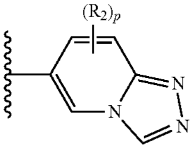
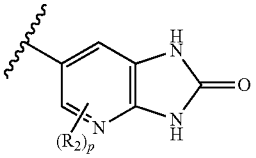
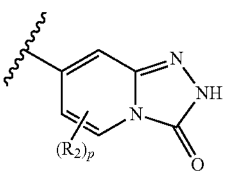
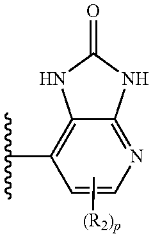
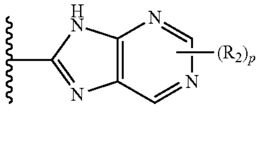
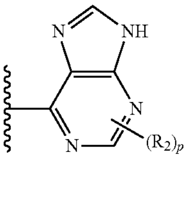
-continued
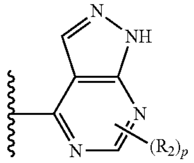
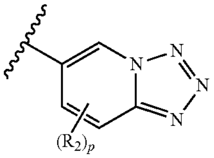
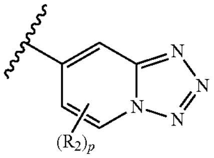
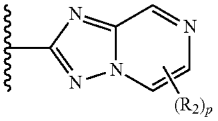
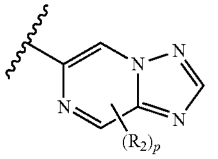
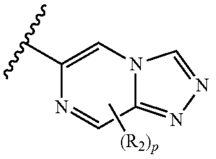
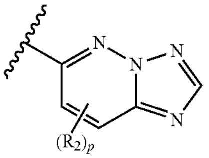
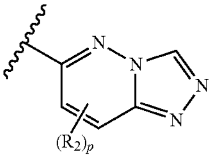
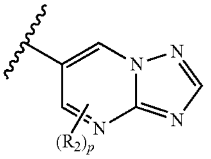
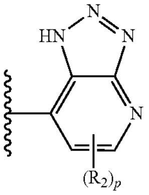
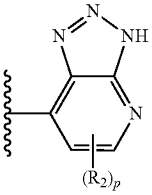
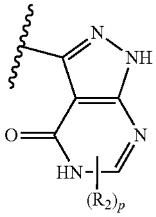
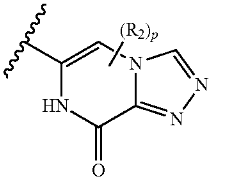
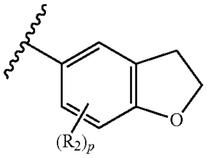
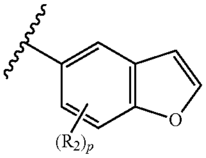
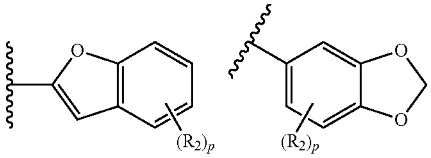
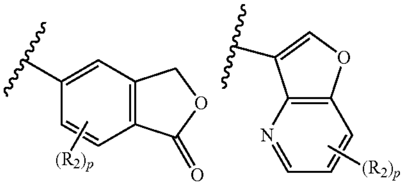
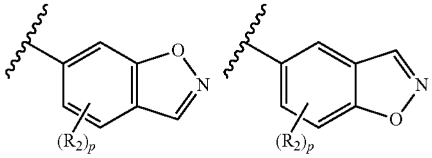

-continued

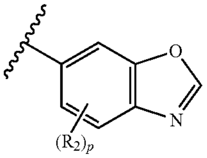
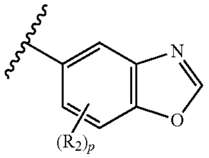
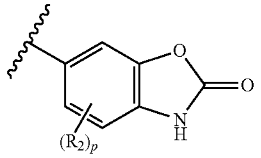
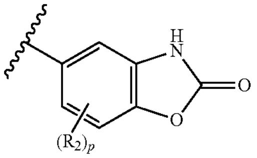
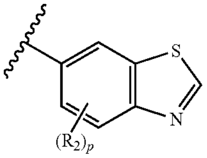
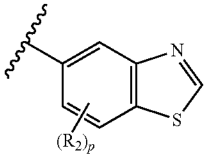
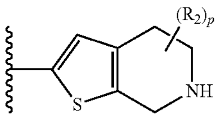
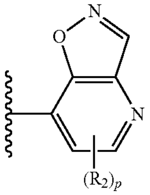
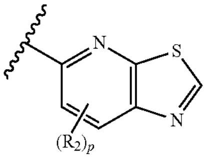
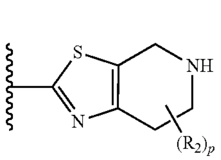
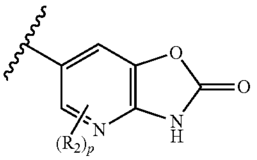

and

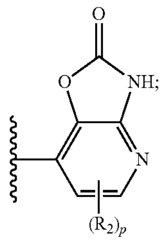

or (v) 10-membered heterocyclic ring selected from:

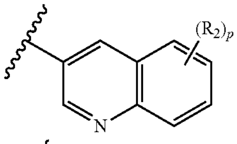
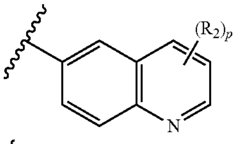
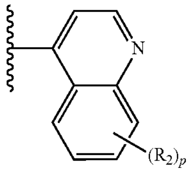
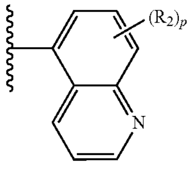
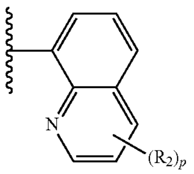
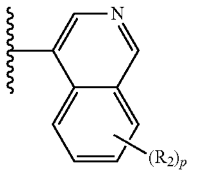

-continued

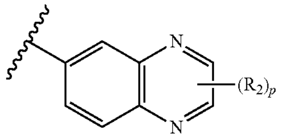
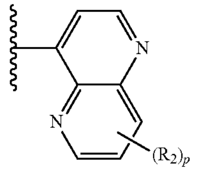
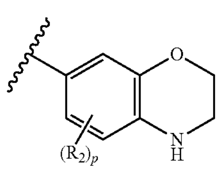

and

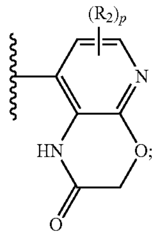

A is piperidinyl, phenyl, pyridinyl, pyrimidinyl, 6-azabicyclo[3.2.1]octanyl, or azabicyclo[3.2.1]octanyl, each substituted with $-L-R_4$ and zero to 2 $R_{4b}$;

L is a bond, $—CR_xR_x—$, or $—C(O)(CR_xR_x)_{0-2}—$;

$R_1$ is hydrogen, $C_{1-3}$ alkyl, $C_{1-2}$ fluoroalkyl, or $C_{3-4}$ cycloalkyl;

each $R_2$ is independently halo, —CN, —OH, $—NO_2$, $C_{1-4}$ alkyl, $C_{1-2}$ fluoroalkyl, $C_{1-2}$ cyanoalkyl, $C_{1-3}$ hydroxyalkyl, $C_{1-3}$ aminoalkyl, $—O(CH_2)_{1-2}OH$, $—(CH_2)_{0-4}O(C_{1-4}$ alkyl), $C_{1-3}$ fluoroalkoxy, $—(CH_2)_{1-4}O(C_{1-3}$ alkyl), $—O(CH_2)_{1-2}OC(O)(C_{1-3}$ alkyl), $—O(CH_2)_{1-2}NR_xR_x$, $—C(O)O(C_{1-3}$ alkyl), $—(CH_2)_{0-2}C(O)NR_yR_y$, $—C(O)NR_x(C_{1-5}$ hydroxyalkyl), $—C(O)NR_x(C_{2-6}$ alkoxyalkyl), $—C(O)NR_x(C_{3-6}$ cycloalkyl), $—NR_yR_y$, $—NR_y(C_{1-3}$ fluoroalkyl), $—NR_y(C_{1-4}$ hydroxyalkyl), $—NR_xCH_2$(phenyl), $—NR_xS(O)_2(C_{3-6}$ cycloalkyl), $—NR_xC(O)(C_{1-3}$ alkyl), $—NR_xCH_2(C_{3-6}$ cycloalkyl), $—S(O)_2(C_{1-3}$ alkyl), $—S(O)_2N(C_{1-3}$ alkyl$)_2$, $—S(O)(NH)N(C_{1-3}$ alkyl$)_2$, $—(CH_2)_{0-2}(C_{3-6}$ cycloalkyl), $—(CH_2)_{0-2}$(phenyl), morpholinyl, dioxothiomorpholinyl, dimethyl pyrazolyl, methylpiperidinyl, methylpiperazinyl, amino-oxadiazolyl, imidazolyl, triazolyl, or —C(O)(thiazolyl);

$R_{2a}$ is $C_{1-6}$ alkyl, $C_{1-3}$ fluoroalkyl, $C_{1-6}$ hydroxyalkyl, $C_{1-3}$ aminoalkyl, $—(CH_2)_{0-4}O(C_{1-3}$ alkyl), $C_{3-6}$ cycloalkyl, $—(CH_2)_{1-3}C(O)NR_xR_x$, $—CH_2(C_{3-6}$ cycloalkyl), $—CH_2$(phenyl), tetrahydrofuranyl, tetrahydropyranyl, or phenyl;

each $R_{2b}$ is independently H, halo, —CN, $—NR_xR_x$, $C_{1-6}$ alkyl, $C_{1-3}$ fluoroalkyl, $C_{1-3}$ hydroxyalkyl, $C_{1-3}$ fluoroalkoxy, $—(CH_2)_{0-2}O(C_{1-3}$ alkyl), $—(CH_2)_{0-3}C(O)NR_xR_x$, $—(CH_2)_{1-3}(C_{3-6}$ cycloalkyl), $—C(O)O(C_{1-3}$ alkyl), $—C(O)NR_x(C_{1-3}$ alkyl), $—CR_x{=}CR_xR_x$, or $—CR_x{=}CH(C_{3-6}$ cycloalkyl);

$R_{2c}$ is $R_{2a}$ or $R_{2b}$;

$R_{2d}$ is $R_{2a}$ or $R_{2b}$; provided that one of $R_{2c}$ and $R_{2d}$ is $R_{2a}$, and the other of $R_{2c}$ and $R_{2d}$ is $R_{2b}$;

$R_3$ is hydrogen, F, $C_{1-3}$ alkyl, or $C_{3-4}$ cycloalkyl;

$R_4$ is:

(i) $—N(CH_3)_2$;

(ii) morpholinyl, pyrrolidinyl, piperidinyl, piperazinyl, pyridinyl, dioxothiomorpholinyl, azaspiro[3.3]heptanyl, azabicyclo[3.2.1]octanyl, diazabicyclo[2.2.2]octanyl, or diazabicyclo[3.2.1]octanyl, each substituted with zero to 4 $R_{4a}$; or (iii)

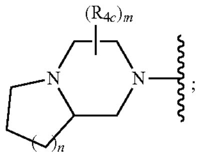

each $R_{4a}$ is independently —OH, $C_{1-6}$ alkyl, $C_{1-3}$ fluoroalkyl, $C_{3-6}$ cycloalkyl, —$CH_2$($C_{3-6}$ cycloalkyl), —C(O)($C_{1-4}$ alkyl), —C(O)($C_{3-6}$ cycloalkyl), —C(O)(phenyl), —C(O)$CH_2$($C_{3-6}$ cycloalkyl), —C(O)$CH_2$(phenyl), or —C(O)O($C_{1-4}$ alkyl);

each $R_{4b}$ is independently F, Cl, or —$CH_3$;

each $R_{4c}$ is independently —OH, $C_{1-6}$ alkyl, $C_{1-3}$ fluoroalkyl, —$CH_2$($C_{3-6}$ cycloalkyl), —C(O)($C_{1-4}$ alkyl), —C(O)(phenyl), —C(O)$CH_2$(phenyl), —C(O)$OCH_2CH_3$, or $C_{3-6}$ cycloalkyl;

each $R_5$ is independently hydrogen, F, Cl, $C_{1-3}$ alkyl, $C_{1-3}$ hydroxyalkyl, $C_{1-3}$ alkoxy, cyclopropyl, or morpholinyl;

each $R_x$ is independently H or —$CH_3$;

each $R_y$ is independently H or $C_{1-6}$ alkyl;

m is zero, 1, or 2;

n is zero, 1, or 2; and p is zero, 1, 2, 3, or 4.

2. The compound according to claim 1 or salts thereof, or a salt thereof, wherein:

G is phenyl substituted with 1 to 2 substituents independently selected from —$OCH_3$, —$S(O)_2CH_3$, —$S(O)_2N(CH_3)_2$, and —$S(O)_2$(cyclopropyl);

A is piperidinyl, phenyl, or pyridinyl, each substituted with -L-$R_4$ and zero to 2 $R_{4b}$;

L is a bond, —$CH_2$—, —C(O)—, —C(O)$CH_2$—, or —C(O)$CH_2CH_2$—;

$R_1$ is hydrogen, —$CH_3$, —$CHF_2$, or cyclopropyl;

$R_3$ is hydrogen, F, —$CH_3$, or cyclopropyl;

$R_4$ is:

(i) —$N(CH_3)_2$; or (ii) pyrrolidinyl, piperidinyl, piperazinyl, or pyridinyl, each substituted with zero to 4 $R_{4a}$;

each $R_{4a}$ is independently —OH, $C_{1-6}$ alkyl, $C_{1-3}$ fluoroalkyl, —$CH_2$($C_{3-6}$ cycloalkyl), —C(O)($C_{1-4}$ alkyl), —C(O)(phenyl), —C(O)$CH_2$(phenyl), —C(O)$OCH_2CH_3$, or $C_{3-6}$ cycloalkyl;

each $R_{4b}$ is independently F, Cl, or —$CH_3$;

each $R_{4c}$ is independently $C_{1-6}$ alkyl, $C_{1-3}$ fluoroalkyl, —$CH_2$($C_{3-6}$ cycloalkyl), —C(O)($C_{1-4}$ alkyl), —C(O)(phenyl), —C(O)$CH_2$(phenyl), —C(O)$OCH_2CH_3$, or $C_{3-6}$ cycloalkyl;

each $R_5$ is independently hydrogen, F, Cl, $C_{1-3}$ alkyl, $C_{1-3}$ hydroxyalkyl, $C_{1-2}$ alkoxy, cyclopropyl, or morpholinyl;

m is zero, 1, or 2; and n is zero, 1, or 2.

3. The compound according to claim 1 or salts thereof, wherein:

G is phenyl substituted with 1 to 2 substituents independently selected from —$OCH_3$, —$S(O)_2CH_3$, —$S(O)_2N(CH_3)_2$, and —$S(O)_2$(cyclopropyl);

A is piperidinyl, phenyl, or pyridinyl, each substituted with -L-$R_4$ and zero to 2 $R_{4b}$;

L is a bond, —$CH_2$—, —C(O)—, —C(O)$CH_2$—, or —C(O)$CH_2CH_2$—;

$R_1$ is hydrogen or —$CH_3$;

$R_3$ is hydrogen, F, —$CH_3$, or cyclopropyl;

$R_4$ is:

(i) —$N(CH_3)_2$; or (ii) pyrrolidinyl, piperidinyl, piperazinyl, or pyridinyl, each substituted with zero to 4 $R_{4a}$;

each $R_{4a}$ is independently —OH, —$CH_3$, —$CHCH_3$, —$CH(CH_3)_2$, —$CH_2CH(CH_3)_2$, —$C(CH_3)_3$, —$CH_2C(CH_3)_3$, —$CH_2CH_2C(CH_3)_3$, —$CF_3$, —$CH_2CH_2OH$, —$CH_2CH_2CH_2OH$, —$CH_2C(CH_3)_2OH$, —$CH_2CH_2C(CH_3)_2OH$, —$CH_2CH_2OCH_3$, —$CH_2$(cyclopropyl), —C(O)$CH_3$, —C(O)$CH(CH_3)_2$, —C(O)$CH_2CH_3$, —C(O)(phenyl), —C(O)$CH_2$(phenyl), —C(O)$OCH_2CH_3$, —C(O)O(phenyl), cyclopropyl, cyclobutyl, oxetanyl, tetrahydrofuranyl, tetrahydropyranyl, —$(CH_2)_{1-2}$(bromophenyl), or —$(CH_2)_{1-2}$(iodophenyl);

each $R_{4b}$ is F; and each $R_5$ is independently hydrogen, —$CH_3$, —$C(CH_3)_2OH$, —$OCH_3$, or morpholinyl.

4. The compound according to claim 1 salts thereof, wherein:

G is phenyl substituted with 1 to 2 substituents independently selected from —$OCH_3$, —$S(O)_2CH_3$, —$S(O)_2N(CH_3)_2$, and —$S(O)_2$(cyclopropyl);

A is piperidinyl, phenyl, or pyridinyl, each substituted with -L-$R_4$ and zero to 2 $R_{4b}$;

L is a bond, —$CH_2$—, —C(O)—, —C(O)$CH_2$—, or —C(O)$CH_2CH_2$—;

$R_1$ is hydrogen or —$CH_3$;

$R_3$ is hydrogen, F, —$CH_3$, or cyclopropyl;

$R_4$ is:

(i) —$N(CH_3)_2$; or (ii) pyrrolidinyl, piperidinyl, piperazinyl, or pyridinyl, each substituted with zero to 4 $R_{4a}$;

each $R_{4a}$ is independently —OH, —$CH_3$, —$CHCH_3$, —$CH(CH_3)_2$, —$CH_2CH(CH_3)_2$, —$C(CH_3)_3$, —$CH_2C(CH_3)_3$, —$CH_2CH_2C(CH_3)_3$, —$CF_3$, —$CH_2CH_2OH$, —$CH_2CH_2CH_2OH$, —$CH_2C(CH_3)_2OH$, —$CH_2CH_2C(CH_3)_2OH$, —$CH_2CH_2OCH_3$, —$CH_2$(cyclopropyl), —C(O)$CH_3$, —C(O)$CH(CH_3)_2$, —C(O)$CH_2CH_3$, —C(O)(phenyl), —C(O)$CH_2$(phenyl), —C(O)$OCH_2CH_3$, —C(O)O(phenyl), cyclopropyl, cyclobutyl, oxetanyl, tetrahydrofuranyl, tetrahydropyranyl, —$(CH_2)_{1-2}$(bromophenyl), or —$(CH_2)_{1-2}$(iodophenyl);

each $R_{4b}$ is F; and each $R_5$ is independently hydrogen, —$CH_3$, —$C(CH_3)_2OH$, —$OCH_3$, or morpholinyl.

5. The compound according to claim 1 or salts thereof, wherein:

G is phenyl substituted with 1 to 2 substituents independently selected from —$OCH_3$, —$S(O)_2CH_3$, —$S(O)_2N(CH_3)_2$, and —$S(O)_2$(cyclopropyl);

A is piperidinyl or phenyl, each substituted with -L-$R_4$ and zero to 2 $R_{4b}$;

L is a bond, —$CH_2$—, or —C(O)$CH_2$—;

$R_1$ is —$CH_3$;

$R_3$ is hydrogen, F, or cyclopropyl;

$R_4$ is morpholinyl, piperidinyl, piperazinyl, pyridinyl, dioxothiomorpholinyl, azabicyclo[3.2.1]octanyl, diazabicyclo[2.2.2]octanyl, or diazabicyclo[3.2.1]octanyl, each substituted with zero to 4 $R_{4a}$; or

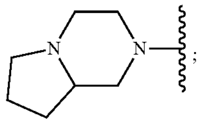

(iii)

each substituted with zero to 4 $R_{4a}$;

each $R_{4a}$ is independently —OH, —$CH_3$, —$CHCH_3$, —$CH(CH_3)_2$, —$CH_2CH(CH_3)_2$, —$C(CH_3)_3$, —$CF_3$, —$CH_2CH_2OH$, —$CH_2CH_2CH_2OH$, —$CH_2C(CH_3)_2OH$, —$CH_2CH_2C(CH_3)_2OH$, —$CH_2CH_2OCH_3$, —$CH_2$(cyclopropyl), —C(O)$CH_3$, —C(O)(phenyl), —C(O)O$CH_2CH_3$, cyclopropyl, cyclobutyl, oxetanyl, tetrahydrofuranyl, tetrahydropyranyl, —$(CH_2)_{1-2}$(bromophenyl), or —$(CH_2)_{1-2}$(iodophenyl);

each $R_{4b}$ is F; and each $R_5$ is independently hydrogen, —$CH_3$, —$C(CH_3)_2OH$, —$OCH_3$, or morpholinyl.

6. The compound according to claim 1 or salts thereof, wherein said compound is:

ethyl 4-(2-(3,4-dimethoxyphenyl)-1-methyl-1H-pyrrolo[3,2-c]pyridin-6-yl)-[1,4'-bipiperidine]-1'-carboxylate (7);

2-(3,4-dimethoxyphenyl)-1-methyl-6-(1-((6-methylpyridin-3-yl)methyl)piperidin-4-yl)-1H-pyrrolo[3,2-c]pyridine (8);

6-(4-(4-(cyclopropylmethyl)piperazin-1-yl)phenyl)-2-(3,4-dimethoxyphenyl)-1-methyl-1H-pyrrolo[3,2-c]pyridine (9);

6-(4-(4-cyclobutylpiperazin-1-yl)phenyl)-2-(3,4-dimethoxyphenyl)-1-methyl-1H-pyrrolo[3,2-c]pyridine (10);

6-(4-(4-isopropylpiperazin-1-yl)phenyl)-1,4-dimethyl-2-(4-(methylsulfonyl)phenyl)-1H-pyrrolo[3,2-c]pyridine (11);

6-(3-fluoro-4-(4-isopropylpiperazin-1-yl)phenyl)-1,4-dimethyl-2-(4-(methylsulfonyl)phenyl)-1H-pyrrolo[3,2-c]pyridine (12);

2-(3,4-dimethoxyphenyl)-6-(4-(4-isopropylpiperazin-1-yl)phenyl)-1-methyl-1H-pyrrolo[3,2-c]pyridine (24);

1-(4-(2-(3,4-dimethoxyphenyl)-1-methyl-1H-pyrrolo[3,2-c]pyridin-6-yl)piperidin-1-yl)-2-(piperidin-1-yl)ethan-1-one (25);

(4-(2-(3,4-dimethoxyphenyl)-1-methyl-1H-pyrrolo[3,2-c]pyridin-6-yl)-[1,4'-bipiperidin]-1'-yl)(phenyl)methanone (26);

2-(3,4-dimethoxyphenyl)-1-methyl-6-(4-(4-methylpiperazin-1-yl)phenyl)-1H-pyrrolo[3,2-c]pyridine (27);

2-(3,4-dimethoxyphenyl)-1-methyl-6-(1-((6-(trifluoromethyl)pyridin-3-yl)methyl) piperidin-4-yl)-1H-pyrrolo[3,2-c]pyridine (28);

(4-(4-(2-(3,4-dimethoxyphenyl)-1-methyl-1H-pyrrolo[3,2-c]pyridin-6-yl)phenyl) piperazin-1-yl)(phenyl)methanone (29);

1-(4-(4-(2-(3,4-dimethoxyphenyl)-1-methyl-1H-pyrrolo[3,2-c]pyridin-6-yl)phenyl) piperazin-1-yl)ethan-1-one (30);

2-(3,4-dimethoxyphenyl)-6-(6-(4-isopropylpiperazin-1-yl)pyridin-3-yl)-1-methyl-1H-pyrrolo[3,2-c]pyridine (31);

6-(4-(4-isobutylpiperazin-1-yl)phenyl)-1,4-dimethyl-2-(4-(methylsulfonyl)phenyl)-1H-pyrrolo[3,2-c]pyridine (34);

1,4-dimethyl-2-(4-(methylsulfonyl)phenyl)-6-(4-(4-(tetrahydro-2H-pyran-4-yl) piperazin-1-yl)phenyl)-1H-pyrrolo[3,2-c]pyridine (35);

3-(4-(4-(1,4-dimethyl-2-(4-(methylsulfonyl)phenyl)-1H-pyrrolo[3,2-c]pyridin-6-yl) phenyl)piperazin-1-yl)propan-1-ol (36);

1,4-dimethyl-2-(4-(methylsulfonyl)phenyl)-6-(4-(4-(tetrahydrofuran-3-yl)piperazin-1-yl)phenyl)-1H-pyrrolo[3,2-c]pyridine (37);

6-(4-(4-(2-methoxyethyl)piperazin-1-yl)phenyl)-1,4-dimethyl-2-(4-(methylsulfonyl) phenyl)-1H-pyrrolo[3,2-c]pyridine (38);

6-(4-(4-isopropylpiperazin-1-yl)phenyl)-1,4-dimethyl-2-(3-(methylsulfonyl)phenyl)-1H-pyrrolo[3,2-c]pyridine (39);

6-(4-(4-isobutylpiperazin-1-yl)phenyl)-1,4-dimethyl-2-(3-(methylsulfonyl)phenyl)-1H-pyrrolo[3,2-c]pyridine (40);

3-(4-(4-(1,4-dimethyl-2-(4-(methylsulfonyl)phenyl)-1H-pyrrolo[3,2-c]pyridin-6-yl) phenyl)piperidin-1-yl)propan-1-ol (41);

2-(4-(cyclopropylsulfonyl)phenyl)-6-(4-(4-isopropylpiperazin-1-yl)phenyl)-1,4-dimethyl-1H-pyrrolo[3,2-c] pyridine (42);

6-(2,5-difluoro-4-(piperazin-1-yl)phenyl)-1,4-dimethyl-2-(4-(methylsulfonyl) phenyl)-1H-pyrrolo[3,2-c]pyridine (43);

1-(4-(4-(1,4-dimethyl-2-(4-(methylsulfonyl)phenyl)-1H-pyrrolo[3,2-c]pyridin-6-yl) benzyl)piperazin-1-yl)-2-methylpropan-2-ol (44);

3-((1R,4R)-5-(4-(1,4-dimethyl-2-(4-(methylsulfonyl) phenyl)-1H-pyrrolo[3,2-c] pyridin-6-yl)benzyl)-2,5-diazabicyclo[2.2.2]octan-2-yl)-2,2-dimethylpropan-1-ol (45);

2-(4-(cyclopropylsulfonyl)phenyl)-6-(4-(4-isobutylpiperazin-1-yl)phenyl)-1,4-dimethyl-1H-pyrrolo[3,2-c]pyridine (46);

3-(4-(4-(2-(4-(cyclopropylsulfonyl)phenyl)-1,4-dimethyl-1H-pyrrolo[3,2-c]pyridin-6-yl)phenyl)piperazin-1-yl)propan-1-ol (47);

2-(4-(cyclopropylsulfonyl)phenyl)-6-(4-(4-(2-methoxyethyl)piperazin-1-yl)phenyl)-1,4-dimethyl-1H-pyrrolo[3,2-c]pyridine (48);

4-(6-(4-(4-isopropylpiperazin-1-yl)phenyl)-1,4-dimethyl-1H-pyrrolo[3,2-c]pyridin-2-yl)-N,N-dimethylbenzenesulfonamide (49);

4-(1,4-dimethyl-6-(4-(4-(oxetan-3-yl)piperazin-1-yl)phenyl)-1H-pyrrolo[3,2-c] pyridin-2-yl)-N,N-dimethylbenzenesulfonamide (50);

4-(6-(4-(4-(2-methoxyethyl)piperazin-1-yl)phenyl)-1,4-dimethyl-1H-pyrrolo[3,2-c] pyridin-2-yl)-N,N-dimethylbenzenesulfonamide (51);

4-(1,4-dimethyl-6-(4-(4-(tetrahydrofuran-3-yl)piperazin-1-yl)phenyl)-1H-pyrrolo[3,2-c]pyridin-2-yl)-N,N-dimethylbenzenesulfonamide (52);

6-(4-(4-isobutylpiperazin-1-yl)phenyl)-1-methyl-2-(4-(methylsulfonyl)phenyl)-1H-pyrrolo[3,2-c]pyridine (53);

6-(4-(4-isopropylpiperazin-1-yl)phenyl)-1-methyl-2-(4-(methylsulfonyl)phenyl)-1H-pyrrolo[3,2-c]pyridine (54);

3-(4-(4-(1,4-dimethyl-2-(4-(methylsulfonyl)phenyl)-1H-pyrrolo[3,2-c]pyridin-6-yl)-2,3-difluorophenyl)piperazin-1-yl)propan-1-ol (55);

3-(4-(4-(1,4-dimethyl-2-(4-(methylsulfonyl)phenyl)-1H-pyrrolo[3,2-c]pyridin-6-yl)-2,5-difluorophenyl)piperazin-1-yl)propan-1-ol (56);

6-(4-((4-isobutylpiperazin-1-yl)methyl)phenyl)-1,4-dimethyl-2-(4-(methylsulfonyl) phenyl)-1H-pyrrolo[3,2-c]pyridine (57);

3-(4-(4-(1,4-dimethyl-2-(4-(methylsulfonyl)phenyl)-1H-pyrrolo[3,2-c]pyridin-6-yl) benzyl)piperazin-1-yl)propan-1-ol (58);

1-(4-(1,4-dimethyl-2-(4-(methylsulfonyl)phenyl)-1H-pyrrolo[3,2-c]pyridin-6-yl) benzyl)-4-methylpiperidin-4-ol (59);

4-(4-(4-(1,4-dimethyl-2-(4-(methylsulfonyl)phenyl)-1H-pyrrolo[3,2-c]pyridin-6-yl) benzyl)piperazin-1-yl)-2-methylbutan-2-ol (60);

4-((1S,4S)-5-(4-(1,4-dimethyl-2-(4-(methylsulfonyl)phenyl)-1H-pyrrolo[3,2-c] pyridin-6-yl)benzyl)-2,5-diazabicyclo[2.2.2]octan-2-yl)-2-methylbutan-2-ol (61);

6-(4-(4-cyclopropylpiperazin-1-yl)phenyl)-1,4-dimethyl-2-(4-(methylsulfonyl) phenyl)-1H-pyrrolo[3,2-c]pyridine (62);

6-(4-(hexahydropyrrolo[1,2-a]pyrazin-2(1H)-yl)phenyl)-1,4-dimethyl-2-(4-(methylsulfonyl)phenyl)-1H-pyrrolo[3,2-c]pyridine (63);

6-(4-(8-isopropyl-3,8-diazabicyclo[3.2.1]octan-3-yl)phenyl)-1,4-dimethyl-2-(4-(methylsulfonyl)phenyl)-1H-pyrrolo[3,2-c]pyridine (64);

6-(3-fluoro-4-(hexahydropyrrolo[1,2-a]pyrazin-2(1H)-yl) phenyl)-1,4-dimethyl-2-(4-(methylsulfonyl)phenyl)-1H-pyrrolo[3,2-c]pyridine (65);

6-(3-fluoro-4-(4-(2-methoxyethyl)piperazin-1-yl)phenyl)-1,4-dimethyl-2-(4-(methylsulfonyl)phenyl)-1H-pyrrolo[3,2-c]pyridine (66);

6-(3-(4-isopropylpiperazin-1-yl)phenyl)-1,4-dimethyl-2-(4-(methylsulfonyl)phenyl)-1H-pyrrolo[3,2-c]pyridine (67);

6-(3-(4-cyclopropylpiperazin-1-yl)phenyl)-1,4-dimethyl-2-(4-(methylsulfonyl) phenyl)-1H-pyrrolo[3,2-c]pyridine (68);

2-(4-(4-(1,4-dimethyl-2-(4-(methylsulfonyl)phenyl)-1H-pyrrolo[3,2-c]pyridin-6-yl)-2-fluorophenyl)piperazin-1-yl)ethan-1-ol (69);

6-(3-fluoro-4-(4-(tetrahydrofuran-3-yl)piperazin-1-yl) phenyl)-1,4-dimethyl-2-(4-(methylsulfonyl)phenyl)-1H-pyrrolo[3,2-c]pyridine (70);

6-(3-fluoro-4-(4-(tetrahydro-2H-pyran-4-yl)piperazin-1-yl)phenyl)-1,4-dimethyl-2-(4-(methylsulfonyl)phenyl)-1H-pyrrolo[3,2-c]pyridine (71);

6-(3-fluoro-4-(4-isobutylpiperazin-1-yl)phenyl)-1,4-dimethyl-2-(4-(methylsulfonyl) phenyl)-1H-pyrrolo[3,2-c]pyridine (72);

6-(4-(8-isobutyl-3,8-diazabicyclo[3.2.1]octan-3-yl)phenyl)-1,4-dimethyl-2-(4-(methylsulfonyl)phenyl)-1H-pyrrolo[3,2-c]pyridine (73);

6-(4-(8-(2-methoxyethyl)-3,8-diazabicyclo[3.2.1]octan-3-yl)phenyl)-1,4-dimethyl-2-(4-(methylsulfonyl)phenyl)-1H-pyrrolo[3,2-c]pyridine (74);

6-(3-fluoro-4-(8-(2-methoxyethyl)-3,8-diazabicyclo[3.2.1]octan-3-yl)phenyl)-1,4-dimethyl-2-(4-(methylsulfonyl)phenyl)-1H-pyrrolo[3,2-c]pyridine (75);

3-(3-(4-(1,4-dimethyl-2-(4-(methylsulfonyl)phenyl)-1H-pyrrolo[3,2-c]pyridin-6-yl) phenyl)-3,8-diazabicyclo[3.2.1]octan-8-yl)propan-1-ol (76);

3-(3-(4-(1,4-dimethyl-2-(4-(methylsulfonyl)phenyl)-1H-pyrrolo[3,2-c]pyridin-6-yl)-2-fluorophenyl)-3,8-diazabicyclo[3.2.1]octan-8-yl)propan-1-ol (77);

6-(2,5-difluoro-4-(8-(2-methoxyethyl)-3,8-diazabicyclo[3.2.1]octan-3-yl)phenyl)-1,4-dimethyl-2-(4-(methylsulfonyl)phenyl)-1H-pyrrolo[3,2-c]pyridine (78);

3-(3-(4-(1,4-dimethyl-2-(4-(methylsulfonyl)phenyl)-1H-pyrrolo[3,2-c]pyridin-6-yl)-2,5-difluorophenyl)-3,8-diazabicyclo[3.2.1]octan-8-yl)propan-1-ol (79-80);

6-(2,5-difluoro-4-(4-(tetrahydro-2H-pyran-4-yl)piperazin-1-yl)phenyl)-1,4-dimethyl-2-(4-(methylsulfonyl) phenyl)-1H-pyrrolo[3,2-c]pyridine (81);

6-(2,3-difluoro-4-(4-isobutylpiperazin-1-yl)phenyl)-1,4-dimethyl-2-(4-(methylsulfonyl)phenyl)-1H-pyrrolo[3,2-c]pyridine (82);

6-(2,3-difluoro-4-(4-(tetrahydro-2H-pyran-4-yl)piperazin-1-yl)phenyl)-1,4-dimethyl-2-(4-(methylsulfonyl) phenyl)-1H-pyrrolo[3,2-c]pyridine (83);

6-(3,5-difluoro-4-(4-isobutylpiperazin-1-yl)phenyl)-1,4-dimethyl-2-(4-(methylsulfonyl)phenyl)-1H-pyrrolo[3,2-c]pyridine (84);

4-(4-(1,4-dimethyl-2-(4-(methylsulfonyl)phenyl)-1H-pyrrolo[3,2-c]pyridin-6-yl) phenyl)thiomorpholine 1,1-dioxide (85);

4-(4-(1,4-dimethyl-2-(4-(methylsulfonyl)phenyl)-1H-pyrrolo[3,2-c]pyridin-6-yl) phenyl)morpholine (86);

1-cyclopropyl-4-(4-(1,4-dimethyl-2-(4-(methylsulfonyl) phenyl)-1H-pyrrolo[3,2-c] pyridin-6-yl)phenyl)piperidin-4-ol (87);

4-(4-(1,4-dimethyl-2-(4-(methylsulfonyl)phenyl)-1H-pyrrolo[3,2-c]pyridin-6-yl) phenyl)-1-isopropylpiperidin-4-ol (88);

6-(3,5-difluoro-4-(4-(tetrahydro-2H-pyran-4-yl)piperazin-1-yl)phenyl)-1,4-dimethyl-2-(4-(methylsulfonyl) phenyl)-1H-pyrrolo[3,2-c]pyridine (89);

4-(4-(1,4-dimethyl-2-(4-(methylsulfonyl)phenyl)-1H-pyrrolo[3,2-c]pyridin-6-yl)-2-fluorophenyl)-1-isobutylpiperidin-4-ol (90);

(1R,3r,5S)-3-(4-(1,4-dimethyl-2-(4-(methylsulfonyl)phenyl)-1H-pyrrolo[3,2-c]pyridin-6-yl)-2-fluorophenyl)-8-isobutyl-8-azabicyclo[3.2.1]octan-3-ol (91);

4-(4-(1,4-dimethyl-2-(4-(methylsulfonyl)phenyl)-1H-pyrrolo[3,2-c]pyridin-6-yl)-2-fluorophenyl)-1-(2-methoxyethyl)piperidin-4-ol (92);

1-cyclopropyl-4-(4-(1,4-dimethyl-2-(4-(methylsulfonyl) phenyl)-1H-pyrrolo[3,2-c]pyridin-6-yl)-2-fluorophenyl)piperidin-4-ol (93);

4-(4-(1,4-dimethyl-2-(4-(methylsulfonyl)phenyl)-1H-pyrrolo[3,2-c]pyridin-6-yl)-2,5-difluorophenyl)-1-isobutylpiperidin-4-ol (94);

4-(4-(1,4-dimethyl-2-(4-(methylsulfonyl)phenyl)-1H-pyrrolo[3,2-c]pyridin-6-yl)-2,5-difluorophenyl)-1-(2-methoxyethyl)piperidin-4-ol (95);

1-cyclopropyl-4-(4-(1,4-dimethyl-2-(4-(methylsulfonyl) phenyl)-1H-pyrrolo[3,2-c]pyridin-6-yl)-2,5-difluorophenyl)piperidin-4-ol (96);

6-(2,5-difluoro-4-(hexahydropyrrolo[1,2-a]pyrazin-2(1H)-yl)phenyl)-1,4-dimethyl-2-(4-(methylsulfonyl) phenyl)-1H-pyrrolo[3,2-c]pyridine (97);

6-(3,5-difluoro-4-(hexahydropyrrolo[1,2-a]pyrazin-2(1H)-yl)phenyl)-1,4-dimethyl-2-(4-(methylsulfonyl) phenyl)-1H-pyrrolo[3,2-c]pyridine (98);

6-(2,3-difluoro-4-(hexahydropyrrolo[1,2-a]pyrazin-2(1H)-yl)phenyl)-1,4-dimethyl-2-(4-(methylsulfonyl) phenyl)-1H-pyrrolo[3,2-c]pyridine (99);

(1R,3r,5S)-3-(4-(1,4-dimethyl-2-(4-(methylsulfonyl)phenyl)-1H-pyrrolo[3,2-c] pyridin-6-yl)-2-fluorophenyl)-8-isopropyl-8-azabicyclo[3.2.1]octan-3-ol (100);

(1R,3r,5S)-3-(4-(1,4-dimethyl-2-(4-(methylsulfonyl)phenyl)-1H-pyrrolo[3,2-c]pyridin-6-yl)-2-fluorophenyl)-8-ethyl-8-azabicyclo[3.2.1]octan-3-ol (101);

(1R,3r,5S)-3-(4-(1,4-dimethyl-2-(4-(methylsulfonyl)phenyl)-1H-pyrrolo[3,2-c] pyridin-6-yl)-2-fluorophenyl)-8-methyl-8-azabicyclo[3.2.1]octan-3-ol (102);

(1R,3r,5S)-3-(4-(1,4-dimethyl-2-(4-(methylsulfonyl)phenyl)-1H-pyrrolo[3,2-c] pyridin-6-yl)-3-fluorophenyl)-8-isopropyl-8-azabicyclo[3.2.1]octan-3-ol (103);

1-(tert-butyl)-4-(4-(1,4-dimethyl-2-(4-(methylsulfonyl) phenyl)-1H-pyrrolo[3,2-c] pyridin-6-yl)-2-fluorophenyl)piperidin-4-ol (104);

(R)-4-(4-(1,4-dimethyl-2-(4-(methylsulfonyl)phenyl)-1H-pyrrolo[3,2-c]pyridin-6-yl)-2-fluorophenyl)-1-isopropyl-2,2-dimethylpiperidin-4-ol (105);

(S)-4-(4-(1,4-dimethyl-2-(4-(methylsulfonyl)phenyl)-1H-pyrrolo[3,2-c]pyridin-6-yl)-2-fluorophenyl)-1-isopropyl-2,2-dimethylpiperidin-4-ol (106);

4-(4-(1,4-dimethyl-2-(4-(methylsulfonyl)phenyl)-1H-pyrrolo[3,2-c]pyridin-6-yl)-2-fluorophenyl)-1-isopropylpiperidin-4-ol (107);

1-(tert-butyl)-4-(4-(1,4-dimethyl-2-(4-(methylsulfonyl) phenyl)-1H-pyrrolo[3,2-c] pyridin-6-yl)-3-fluorophenyl)piperidin-4-ol (108);

4-(4-(1,4-dimethyl-2-(4-(methylsulfonyl)phenyl)-1H-pyrrolo[3,2-c]pyridin-6-yl)-3-fluorophenyl)-1-isopropylpiperidin-4-ol (109);

6-(4-(4-(4-iodophenethyl)piperazin-1-yl)phenyl)-1,4-dimethyl-2-(4-(methylsulfonyl) phenyl)-1H-pyrrolo[3,2-c]pyridine (110);

6-(4-(4-(4-bromophenethyl)piperazin-1-yl)phenyl)-1,4-dimethyl-2-(4-(methylsulfonyl)phenyl)-1H-pyrrolo[3,2-c]pyridine (111);

6-(4-(4-(4-iodobenzyl)piperazin-1-yl)phenyl)-1,4-dimethyl-2-(4-(methylsulfonyl) phenyl)-1H-pyrrolo[3,2-c] pyridine (112);

6-(4-(4-(4-bromobenzyl)piperazin-1-yl)phenyl)-1,4-dimethyl-2-(4-(methylsulfonyl) phenyl)-1H-pyrrolo[3,2-c] pyridine (113);

6-(1-(8-isobutyl-8-azabicyclo[3.2.1]octan-3-yl)piperidin-4-yl)-1,4-dimethyl-2-(4-(methylsulfonyl)phenyl)-1H-pyrrolo[3,2-c]pyridine (114);

4-(4-(4-(3-fluoro-1,4-dimethyl-2-(4-(methylsulfonyl) phenyl)-1H-pyrrolo[3,2-c]pyridin-6-yl)benzyl)piperazin-1-yl)-2-methylbutan-2-ol (115);

4-[4-[[4-[1-cyclopropyl-4-methyl-2-(4-methylsulfonylphenyl)pyrrolo[3,2-c]pyridin-6-yl]phenyl]methyl] piperazin-1-yl]-2-methyl-butan-2-ol (116);

4-[4-[[4-[1-(difluoromethyl)-4-methyl-2-(4-methylsulfonylphenyl)pyrrolo[3,2-c] pyridin-6-yl]phenyl]methyl] piperazin-1-yl]-2-methyl-butan-2-ol (117);

2-[6-[4-(4-isopropylpiperazin-1-yl)phenyl]-1-methyl-2-(4-methylsulfonylphenyl) pyrrolo[3,2-c]pyridin-4-yl] propan-2-ol (118);

6-[4-(4-isopropylpiperazin-1-yl)phenyl]-4-methoxy-1-methyl-2-(4-methylsulfonylphenyl)pyrrolo[3,2-c]pyridine (119);

4-[6-[4-(4-isopropylpiperazin-1-yl)phenyl]-1-methyl-2-(4-methylsulfonylphenyl) pyrrolo[3,2-c]pyridin-4-yl] morpholine (120);

1-[3-[[4-[1-cyclopropyl-2-(4-methylsulfonylphenyl)pyrrolo[3,2-c]pyridin-6-yl] phenyl]methyl]-3,8-diazabicyclo[3.2.1]octan-8-yl]-2-methyl-propan-2-ol (121);

1-(4-(4-(3-fluoro-1,4-dimethyl-2-(4-(methylsulfonyl) phenyl)-1H-pyrrolo[3,2-c] pyridin-6-yl)benzyl)piperazin-1-yl)-2-methylpropan-2-ol (122);

1-(4-(4-(1-cyclopropyl-4-methyl-2-(4-(methylsulfonyl) phenyl)-1H-pyrrolo[3,2-c] pyridin-6-yl)benzyl)piperazin-1-yl)-2-methylpropan-2-ol (123);

1-(4-(4-(1-(difluoromethyl)-4-methyl-2-(4-(methylsulfonyl)phenyl)-1H-pyrrolo[3,2-c]pyridin-6-yl)benzyl)piperazin-1-yl)-2-methylpropan-2-ol (124);

2-(6-(4-((4-isopropylpiperazin-1-yl)methyl)phenyl)-1-methyl-2-(4-(methylsulfonyl) phenyl)-1H-pyrrolo[3,2-c]pyridin-4-yl)propan-2-ol (125);

6-(4-((4-isopropylpiperazin-1-yl)methyl)phenyl)-4-methoxy-1-methyl-2-(4-(methylsulfonyl)phenyl)-1H-pyrrolo[3,2-c]pyridine (126);

4-(6-(4-((4-isopropylpiperazin-1-yl)methyl)phenyl)-1-methyl-2-(4-(methylsulfonyl) phenyl)-1H-pyrrolo[3,2-c]pyridin-4-yl)morpholine (127);

1-(4-(4-(1-cyclopropyl-2-(4-(methylsulfonyl)phenyl)-1H-pyrrolo[3,2-c]pyridin-6-yl) benzyl)piperazin-1-yl)-2-methylpropan-2-ol (128);

4-(4-(4-(1-cyclopropyl-2-(4-(methylsulfonyl)phenyl)-1H-pyrrolo[3,2-c]pyridin-6-yl) benzyl)piperazin-1-yl)-2-methylbutan-2-ol (129); or 1-(8-(4-(1-cyclopropyl-2-(4-(methylsulfonyl)phenyl)-1H-pyrrolo[3,2-c]pyridin-6-yl) benzyl)-3,8-diazabicyclo[3.2.1]octan-3-yl)-2-methylpropan-2-ol (130).

7. A pharmaceutical composition comprising one or more compounds according claim 1 or pharmaceutically-acceptable salts thereof; and a pharmaceutically acceptable carrier.

8. A method of treating a disease of disorder, comprising administering to a mammalian patient a compound according to claim 1 or a pharmaceutically acceptable salt thereof, wherein said disease or disorder is pathological fibrosis.

9. The method according to claim 8 wherein said pathological fibrosis is liver fibrosis, renal fibrosis, biliary fibrosis, or pancreatic fibrosis.

10. A method of treating a disease of disorder, comprising administering to a mammalian patient a compound according to claim 1 or a pharmaceutically acceptable salt thereof, wherein said disease or disorder is nonalcoholic steatohepatitis (NASH), non-alcoholic fatty liver disease (NAFLD), chronic kidney disease, diabetic kidney disease, primary sclerosing cholangitis (PSC), or primary biliary cirrhosis (PBC).

11. A method of treating a disease of disorder, comprising administering to a mammalian patient a compound according to claim 1 or a pharmaceutically acceptable salt thereof, wherein said disease or disorder is idiopathic pulmonary fibrosis (IPF).

* * * * *